(12) United States Patent
Biesgen

(10) Patent No.: US 7,462,758 B2
(45) Date of Patent: Dec. 9, 2008

(54) METHODS FOR THE TRANSFORMATION OF VEGETAL PLASTIDS

(75) Inventor: Christian Biesgen, Quedlinburg (DE)

(73) Assignee: SunGene GmbH & Co. KGaA (DE)

( * ) Notice: Subject to any disclaimer, the term of this patent is extended or adjusted under 35 U.S.C. 154(b) by 444 days.

(21) Appl. No.: 10/499,518

(22) PCT Filed: Dec. 16, 2002

(86) PCT No.: PCT/EP02/14302

§ 371 (c)(1),
(2), (4) Date: Jun. 21, 2004

(87) PCT Pub. No.: WO03/054189

PCT Pub. Date: Jul. 3, 2003

(65) Prior Publication Data

US 2006/0253916 A1    Nov. 9, 2006

(30) Foreign Application Priority Data

Dec. 20, 2001 (DE) .................. 101 63 161

(51) Int. Cl.
*C12N 15/82* (2006.01)
*A01H 5/00* (2006.01)
(52) U.S. Cl. .............. 800/278; 800/298; 435/419
(58) Field of Classification Search .............. None
See application file for complete search history.

(56) References Cited

U.S. PATENT DOCUMENTS

| 5,451,513 | A | 9/1995 | Maliga et al. |
| 5,877,402 | A | 3/1999 | Maliga et al. |
| 5,932,479 | A | 8/1999 | Daniell et al. |
| 6,153,813 | A | 11/2000 | Reichert et al. |

FOREIGN PATENT DOCUMENTS

| EP | 251654 A2 | 1/1988 |
| WO | WO-95/15388 A1 | 6/1995 |
| WO | WO-96/14408 A1 | 5/1996 |
| WO | WO-97/32977 A1 | 9/1997 |
| WO | WO 99/10513 * | 3/1999 |
| WO | WO-99/10513 A1 | 3/1999 |
| WO | WO-00/07431 A1 | 2/2000 |
| WO | WO-00/20611 A1 | 4/2000 |
| WO | WO-00/28014 A2 | 5/2000 |
| WO | WO-00/32799 A1 | 6/2000 |
| WO | WO-00/39313 A1 | 7/2000 |
| WO | WO 01/29241 * | 4/2001 |
| WO | WO-01/29241 A2 | 4/2001 |
| WO | WO-01/42441 A2 | 6/2001 |
| WO | WO-01/64024 A1 | 9/2001 |

OTHER PUBLICATIONS

McFadden, G. I., "Chloroplast Origin and Integration", Plant Physiology, 2001, vol. 125, pp. 50-53.
Boynton, J. E., et al., "Chloroplast Transformation in *Chlamydomonas* with High Velocity Microprojectiles", Science, 1988, vol. 240, pp. 1534-1538.
Blowers, A. D., et al., "Studies on *Chlamydomonas* Chloroplast Transformation: Foreign DNA Can Be Stably Maintained in the Chromosome", The Plant Cell, 1989, vol. 1, pp. 123-132.
Svab, Z., et al., "Stable Transformation of Plastids in Higher Plants", Proc. Natl. Acad. Sci. USA, 1990, vol. 87, pp. 8526-8530.
Guda, C., et al., "Stable Expression of a Biodegradable Protein-Based Polymer in Tobacco Chloroplasts", Plant Cell Reports, 2000, vol. 19, pp. 257-262.
Bogorad, L., "Engineering Chloroplasts: An Alternative Site for Foreign Genes, Proteins, Reactions and Products", Tibtech, 2000, vol. 18, pp. 257-263.
Svab, Z., et al., "High-Frequency Plastic Transformation in Tobacco by Selection for a Chimeric *aadA* Gene", Proc. Natl. Acad. Sci. USA, 1993, vol. 90, pp. 913-917.
Kota, M., et al., "Overexpression of the *Bacillus thuringiensis* (Bt) Cry2Aa2 Protein in Chloroplasts Confers Resistance to Plants Against Susceptible and Bt-Resistant Insects", Proc. Natl. Acad. Sci. USA, 1999, vol. 96, pp. 1840-1845.
Ruf, S., et al., "Stable Genetic Transformation of Tomato Plastids and Expression of a Foreign Protein in Fruit", Nature Biotechnology, 2001, vol. 19, pp. 870-875.
Heifetz, P. B., et al., "Protein Expression in Plastids", Current Opinion in Plant Biology, 2001, vol. 4, pp. 157-161.
Yang, J., et al., "Efficient Integration of an Intron RNA into Double-Stranded DNA by Reverse Splicing", Nature, 1996, vol. 381, pp. 332-335.
Eickbush, T. H., "Mobile Introns: Retrohoming by Complete Reverse Splicing", Current Biology, 1999, vol. 9, pp. R11-R14.
Matsuura, M., et al., "A Bacterial Group II Intron Encoding Reverse Transcriptase, Maturase, and DNA Endonuclease Activities: Biochemical Demonstration of Maturase Activity and Insertion of New Genetic Information within the Intron", Genes & Development, 1997, vol. 11, pp. 2910-2924.
Cousineau, B., et al., "Retrohoming of a Bacterial Group II Intron: Mobility via Complete Reverse Splicing, Independent of Homologous DNA Recombination", Cell, 1998, vol. 94, pp. 451-462.
Mohr, G., et al., "Rules for DNA Target-Site Recognition by a Lactococcal Group II Intron Enable Retargeting of the Intron to Specific DNA Sequences", Genes & Development, 2000, vol. 14, pp. 559-573.
Guo, H., et al., "Group II Intron Endonucleases Use Both RNA and Protein Subunits for Recognition of Specific Sequences in Double-Stranded DNA", The EMBO Journal, 1997, vol. 16, No. 22, pp. 6835-6848.
Guo, H., et al., "Group II Introns Designed to Insert into Therapeutically Relevant DNA Target Sites in Human Cells", Science, 2000, vol. 289, pp. 452-457.
Sidorov, V., et al., "Stable Chloroplast Transformation in Potato: Use of Green Fluorescent Protein as a Plastid Marker", The Plant Journal, 1999, vol. 19, No. 2, pp. 209-216.

(Continued)

*Primary Examiner*—Anne R Kubelik
(74) *Attorney, Agent, or Firm*—Connolly Bove Lodge & Hutz LLP

(57) ABSTRACT

The present invention relates to novel methods for the generation of transgenic plants with genetically modified plastids, and to the transgenic plants generated with these methods.

16 Claims, 32 Drawing Sheets

OTHER PUBLICATIONS

Figure 1:
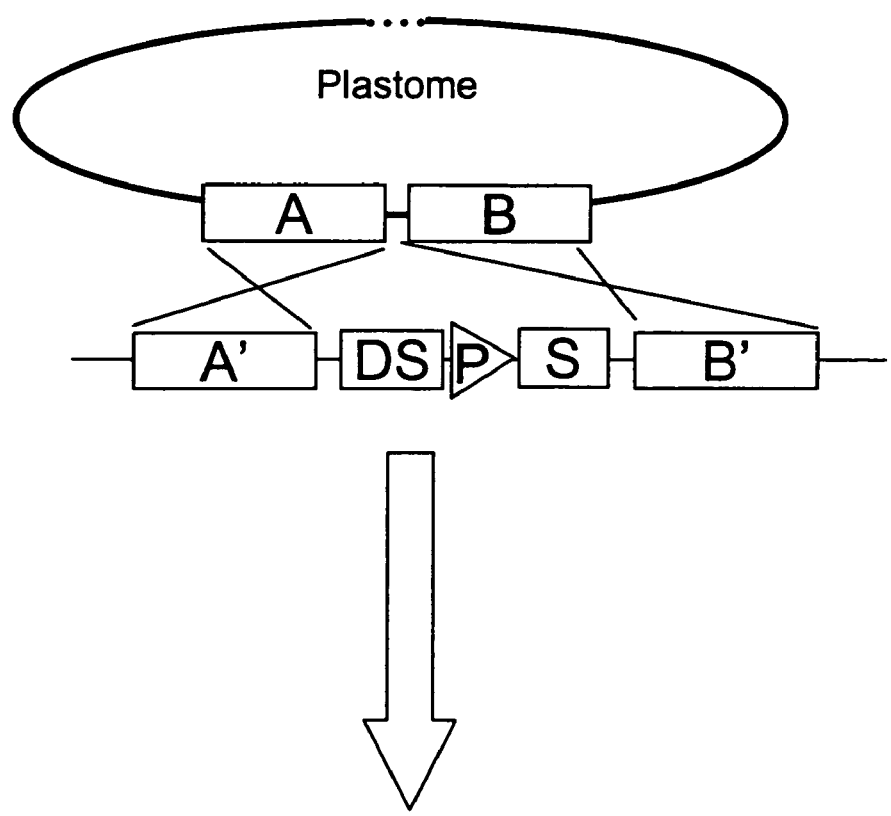
Figure 1:
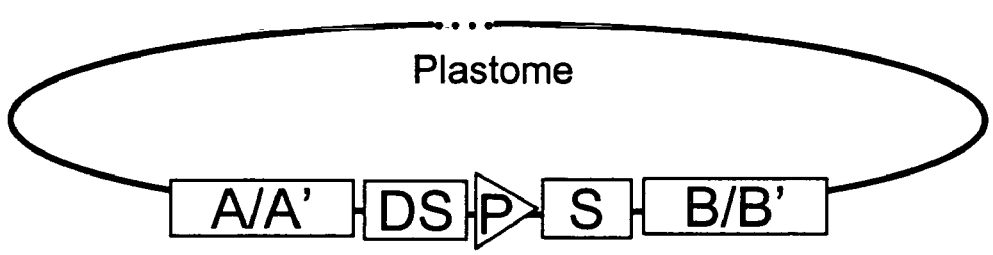

Khan, M. S., et al., "Fluorescent Antibiotic Resistance marker for Tracking Plastid Transformation in Higher Plants", Nature Biotechnology, 1999, vol. 17, pp. 910-915.

Sikdar, S. R., et al., "Plastid Transformation in *Arabidopsis thaliana*", Plant Cell Reports, 1998, vol. 18, pp. 20-24.

Puchta, H., "Use of I-Sce I to Induce DNA Double-Strand Breaks in *Nicotiana*", Methods in Molecular Biology, 1999, vol. 113, pp. 447-451.

Pósfai, G., et al., "Markerless Gene Replacement in *Escherichia coli* Stimulated by a Double-Strand Break in the Chromosome", Nucleic Acids Research, 1999, vol. 27, No. 22, pp. 4409-4415.

Kuzminov, A., "Recombinational Repair of DNA Damage in *Escherichia coli* and Bacteriophage λ", Microbiology and Molecular Biology Reviews, 1999, vol. 63, No. 4, pp. 751-813.

Vogel, J., et al., "Comparative Analysis of Splicing of the Complete Set of Chloroplast group II Introns in Three Higher Plants Mutants", Nucleic Acids Research, 1999, vol. 27, No. 19, pp. 3866-3874.

Jenkins, B. D., et al., "Nuclear Mutation That Block Group II RNA Splicing in Maize Chloroplasts Reveal Several Intron Classes with Distinct Requirements for Splicing Factors", The Plant Cell, 1997, vol. 9, pp. 283-296.

Eddy, S. R., et al., "Artificial Mobile DNA Element Constructed from the *Eco*RI Endonuclease Gene", Proc. Natl. Acad. Sci. USA, 1992, vol. 89, pp. 1544-1547.

Sato, N., "Was the Evolution of Plastid Genetic Machinery Discontinuous?", Trends in Plant Science, 2001, vol. 6, No. 4, pp. 151-155.

Kavanagh, T. A., et al., "Homeologous Plastid DNA Transformation in Tobacco Is Mediated by Multiple Recombination Events", Genetics, 1999, vol. 152, pp. 1111-1122.

Hagemann, R., "Plastid Genetics in Higher Plants", Chapter 2 in Cell Organelles, R.G. Herrmann (ed.), 1992, pp. 65-96.

Puchta, H., et al., "Homologous Recombination in Plant Cells in Enhanced by in vivo Induction of Double Strand Breaks into DNA by a Site-Specific Endonuclease", Nucleic Acids Research, 1993, vol. 21, No. 22, pp. 5034-5040.

Rong, Y. S., et al., "Gene Targeting by Homologous Recombination in *Drosophila*", Science, vol. 288, pp. 2013-2018.

Jasin, M., "Genetic Manipulation of Genomes with Rare-Cutting Endonucleases", TIG, 1996, vol. 12, No. 6, pp. 224-228.

Bock, R., et al., Extranuclear Inheritance: Plastid Genetics: Manipulation of Plastid Genomes and Biotechnological Applications, Genetics, 2000, vol. 61, pp. 76-90.

Maliga, P., et al., "Homologous Recombination and Integration of Foreign DNA in Plastids of Higher Plants", Chapter 5 in Homologous Recombination and Gene Silencing in Plants, J. Paszkowski (ed.), 1994, pp. 83-93.

Bock, R., et al., "Correct Splicing of a Group II Intron from a Chimeric Reporter Gene Transcript in Tobacco Plastids", Nucleic Acids Research, 1995, vol. 23, No. 13, pp. 2544-2547.

Dürrenberger, F., et al., "Double Strand Break-Induced Recombination in *Chlamydomonas reinhardtii* Chloroplasts", Nucleic Acids Research, 1996, vol. 24, No. 17, pp. 3323-3331.

Odom, O. W., et al., "Mobile Self-Splicing Group I Introns from the *psbA* Gene of *Chlamydomonas reinhardtii*: Highly Efficient Homing of an Exogenous Intron Containing Its Own Promoter", Molecular and Cellular Biology, 2001, vol. 21, No. 10, pp. 3472-3481.

Puchta, H., et al., "Two Different but Related Mechanisms are used in Plants for the Repair of Genomic Double-Strand Breaks by Homologous Recombination", Proc. Natl. Acad. Sci. USA, 1996, vol. 93, pp. 5055-5060.

Doetsch, N. A., et al., "Chloroplast Transformation in *Euglena gracilis*: Splicing of a Group III Twintron Transcribed from a Transgenic *psbK* Operon", Curr. Genet., 2001, vol. 39, pp. 49-60.

Turmel, M., et al., "Evolutionary Transfer of ORF-Containing Group I Introns Between Different Subcellular Compartments (Chloroplast and Mitochondrion)", Molecular Biology and Evolution, 1995, vol. 12, No. 4, pp. 533-545.

Xu, M.Q., et al., "Bacterial Origin of a Chloroplast Intron: Conserved Self-Splicing Group I Introns in Cyanobacteria", Science, 1990, vol. 250, pp. 1566-15-70.

\* cited by examiner

A

SEQ ID NO: 160

B

SEQ ID NO: 161

METHODS FOR THE TRANSFORMATION OF VEGETAL PLASTIDS

RELATED APPLICATIONS

This application is a national stage application (under 35 U.S.C. 371) of PCT/EP02/14302 filed Dec. 16, 2002, which claims the benefit of German Application 101 63 161.8 filed Dec. 20, 2001.

FIELD OF THE INVENTION

The contents of the following submission on compact discs are incorporated herein by reference in its entirety: two copies of the Sequence Listing (COPY 1 and COPY 2 REPLACEMENT Mar. 21, 2007) and a computer-readable form of the Sequence Listing (CRF COPY REPLACEMENT Mar. 21, 2007), all on CD-Rs, each containing: file name: Second Replacement Sequence list-13173-00013-US, date recorded: Mar. 21, 2007, size: 95 KB.

The present invention relates to novel methods for the generation of transgenic plants with genetically modified plastids and to the transgenic plants generated using these methods.

DESCRIPTION OF THE BACKGROUND

Biotechnological work carried out on plants aims at generating plants with advantageous novel properties, for example to increase agricultural productivity, to increase the quality in foodstuffs or for producing certain chemicals or pharmaceuticals.

Plastids are organelles within plant cells which have their own genome. They play an essential role in photosynthesis and in amino acid and lipid biosynthesis. The plastids' genome consists of a double-stranded, circular DNA with an average size of from 120 to 160 kb and is present—for example in leaf cells—as approximately 1900 to 50,000 copies per cell (Palmer (1985) Ann Rev Genet 19:325-54). A single plastid has a copy number of approximately from 50 to 100. The term plastids comprises chloroplasts, proplastids, etioplasts, chromoplasts, amyloplasts, leukoplasts and elaioplasts (Heifetz P (2000) Biochimie 82:655-666). The various forms can be converted into one another and all arise from the proplastids. This is why all manifested forms of the plastids comprise the same genetic information. Preference is given in the literature as starting material for the transformation of plastids, however, to green cells, which comprise the chloroplasts as the manifested form.

It is of great economic interest for plant biotechnologists to develop efficient methods for the transformation of plastids (McFadden G (2001) Plant Physiol. 125:50-53). The stable transformation of plastids of higher plants is one of the great challenges.

In the transformation of plastids, the technique of undirected (illegitimate) DNA insertion, which is frequently employed in insertion into the nuclear DNA, has the disadvantage that it is highly likely that an essential gene on the gene-dense plastidic genome is affected, which would frequently be lethal for the plant. The directed insertion of foreign DNA is therefore advantageous in plastids.

Various methods for the directed insertion into the plastidic genome have been described. The first to be described was plastid transformation in green algae (Boynton J E et al. (1988) Science 240: 1534-1538; Blowers A D et al. (1989) Plant Cell 1:123-132), followed later by higher plants such as tobacco (Svab Z et al. (1990) Proc Natl Acad Sci USA 87:8526-8530).

EP-A 0 251 654, U.S. Pat. Nos. 5,932,479, 5,451,513, 5,877,402, WO 01/64024, WO 00/20611, WO 01/42441, WO 99/10513, WO 97/32977, WO 00/28014, WO 00/39313 describe methods and DNA constructs for the transformation of plastids of higher plants, where the DNA to be transformed is introduced into the plastome (plastidic genome) via homologous recombination ("double crossover"). In general, homologous regions of 1000 bp or more on either side of the sequence to be inserted are employed. This rapidly gives rise to large vectors whose handling is not very convenient. Moreover, the transformation efficiency drops. The homologous recombination efficiency drops with the increasing length of the foreign DNA to be integrated. A further disadvantage is the fact that a homologous region which can be utilized for the process of DNA integration by means of double crossover must be identified for each plant species. WO 99/10513 claims the identification of an intergenic DNA sequence with supposedly sufficient homology between the genomes of the chloroplasts of many higher plants, which DNA sequence can thus act as a universal target sequence. However, it has not been demonstrated that this vector can be utilized successfully in species other than tobacco; rather, in WO 01/64024, the same inventor adapts the transformation vector to non-tobacco plant species by using homologous DNA sequences isolated from these plant species. Since only few recombination events result in all of the above-described methods, selection of the recombinant plastidic DNA molecules is required.

The plastid DNA of higher plants is present in the form of up to several thousand copies per cell. To ensure stable integration of foreign DNA, all copies of the plastidic DNA must be modified in the same manner. In plastid transformation, this is referred to as having reached the homotransplastomic state. This state is achieved by what is known as a segregation-and-sorting process, by exerting a continuous selection pressure on the plants. Owing to the continual selection pressure, those plastids in which many copies of the plastidic DNA have already been modified are enriched during cell and plastid division. The selection pressure is maintained until the homotransplastomic state is reached (Guda C et al. (2000) Plant Cell Reports 19:257-262). The modification of all of the copies of the plastidic genome in order to obtain homotransplastomic plants which have incorporated the foreign gene stably into their plastidic genome over generations without addition of a selection agent is a great challenge (Bogorad L (2000) TIBTECH 18:257-263). In addition to the continuous selection pressure, achieving the homotransplastomic state is, if appropriate, ensured by repeatedly regenerating tissue which has already been transformed (Svab Z and Maliga P (1993) Proc Natl Acad Sci USA 90:913-917). However, this procedure limits the plant material which is available for plastid transformation. Coupling, if appropriate, the transgene with another gene which is essential for the survival of the plant is therefore proposed.

In most cases, tissue culture techniques and selection processes cannot be applied universally to all plant species and constitute a substantial limitation of plastid transformation, in particular with regard to the applicability of the method to species other than tobacco. (Kota M et al. (1999) Proc Natl Acad Sci USA 96:1840-1845). A recently published transformation of tomato plastids is based on modifications in the regeneration and selection scheme (Ruf S et al. (2001) Nature Biotech 19:870-875), which, however, are expensive and time-consuming. Another approach aims at reducing the number of plastids per cell and the DNA molecules per plastid so that fewer DNA molecules have to be modified (Bogorad L (2000) TIBTECH 18:257-263). All of the selection and segregation processes are very time-consuming.

WO 99/10513 describes a method in which a plastidic ORI (origin of replication) is localized on the plasmid to be transformed in order to increase, in this manner, the number of copies of the vector to be transformed which are available for integration into the plastidic genome (Guda C et al. (2000) Plant Cell Reports 19:257-262).

The necessity of improving the plastid transformation technique is also mentioned in Heifetz and Tuttle (Heifetz P and Tuttle A M (2001) Curr Opin Plant Biol 4:157-161). WO 00/32799 teaches increasing the efficiency of plastid transformation by employing plants with enlarged plastids. This results in a large plastid surface, through which the DNA to be transformed can enter the plastids with greater ease. However, the mechanism of DNA integration relies, again, on conventional homologous recombination, as was the case in the above-described methods.

A variety of other methods for the sequence-specific integration of DNA—in particular into the nuclear DNA—have been described. A method based on self-splicing group II introns has been described. Self-splicing group II introns are capable of inserting in a sequence-specific fashion, for example into intron-free genes. The sequence-specific hydrolysis of the target DNA is catalyzed by an RNA-protein (ribonucleoprotein) complex. Here, the sequence specificity of the endonuclease function is determined in particular by base pairings being formed between the RNA moiety of the ribonucleoprotein complex and the target DNA. The use of group II introns as vectors for foreign DNA has been discussed. By modifying certain sequences of a group II intron, it was possible to modify the target specificity of the latter. Also, it was possible to insert further sequences into group II introns without destroying functions of the latter (Yang J et al. (1996) Nature 381:332-335; Eickbush T H (1999) Curr Biol 9:R11-R14; Matsuura M et al. (1997) Genes Develop 11:2910-2924; Cousineau B et al. (1998) Cell 94: 451-462). The adaptation to certain target sequences and the determination of the associated rules, however, is laborious and has as yet been elucidated in detail only for the L1.ltrB intron (Mohr G et al. (2000) Genes Develop 14:559-573). Moreover, the retrohoming efficiency was reduced significantly by the modification, and not every single one of the modified introns tested inserted into the desired target DNA. The disadvantage of the technique is that some positions in the nucleotide sequence are fixed, which limits the choice of the target region in the DNA to be transformed (Guo H et al. (1997) EMBO J. 16:6835-6848). Moreover, the efficiency of the retrohoming process with regard to that of the wild-type intron appears to be diminished. The efficiency of intron insertion at different sites on the genes investigated differed with regard to its level. The work aimed at providing an improved method for the directed insertion of DNA into the nuclear DNA of organisms which permit no efficient homologous recombination (Guo et al. (2000) Science 289:452-456). The experiments described have been carried out extrachromosomally both in the prokaryote E. coli and in human cells. The applicability to the chromosomal DNA of higher organisms or the applicability to plastidic DNA was neither described nor demonstrated. It was merely proposed to attempt the optimization of this system in such a way that insertion into chromosomal DNA of higher eukaryotes can take place. This system is supposed to be an alternative method for higher eukaryotes which lack efficient homologous recombination (Guo et al. (2000) Science 289:452-456). This does not apply to plastids of higher plants, where homologous recombination—at least in the case of individual plastidic DNA molecules—can usually be performed without problems.

Plastid transformation was demonstrated not only in tobacco, but also in potato (Sidorov V A et al. (1999) Plant J 19:209-216; WO 00/28014), petunia (WO 00/28014), rice (Khan M S and Maliga P (1999) Nature Biotech 17:910-915; WO 00/07431; U.S. Pat. No. 6,153,813), *Arabidopsis* (Sikdar S R et al. (1998) Plant Cell Reports 18: 20-24; WO 97/32977) and oilseed rape (WO 00/39313). (Review article: Bogorad L (2000) TIBTECH 18:257-263). Transplastomic tomato plants have also been described recently (Ruf S et al. (2001) Nature Biotech 19:870-875).

The generation of sequence-specific double-strand breaks with the aid of restriction enzymes in eukaryotic genomes, including plants, has been described (Puchta H (1999) Methods Mol Biol 113:447-451).

WO 96/14408 describes the homing restriction endonuclease I-SceI and various possibilities for its use. An application for inserting DNA sequences into plastidic DNA is not described.

Posfai et al. describe a method for the substitution of genes in the prokaryote *E. coli* (Posfai G et al. (1999) Nucleic Acids Res 27(22):4409-4415). Here, an intramolecular recombination between the endogenous and the mutated gene takes place in the *E. coli* genome, which combination is induced by cleaving with the restriction enzyme I-SceI. Recombinations in *E. coli* proceed markedly more efficiently and, presumably, following different mechanisms than is the case in the nucleus of higher eukaryotes (for example described by Kuzminov A (1999) Microbiol Mol Biol Rev. 63(4):751-813).

"Homing" refers to the phenomenon that two or more copies of a DNA sequence exist in one compartment, where at least one of these two sequences is interrupted by a further DNA sequence, and a copy of the interrupting DNA sequence is subsequently also introduced into the noninterrupted DNA sequence. This phenomenon usually takes the form of intron homing. Here, two or more alleles of one gene exist in one compartment, where at least one of these alleles has no intron. A copy of the intron is subsequently also introduced into the intron-free allele.

Introns in plastidic genes of higher plants have been described (Vogel J et al. (1999) Nucl Acids Res 27:3866-3874; Jenkins B D et al. (1997) Plant Cell 9:283-296; Xu M Q et al. (1990) Science 250: 1566-1570). The splicing of a homologous, unmodified intron with the natural exon regions at an ectopic locus in the plastidic genome has likewise been described (Bock R and Maliga P (1995) Nucl Acids Res 23(13):2544-2547). Experiments of introducing, into plastids of higher plants, heterologous introns which are additionally modified in such a way that they comprise additional genetic information and/or splice in a normatural sequence environment have not been carried out as yet.

Experiments carried out by Eddy and Gold into the homing process in *E. coli* have demonstrated that certain recombination systems are required. The type of the recombination system of the host is a key variable (Eddy S R and Gold L (1992) Proc Natl Acad Sci USA 89:1544-1547). It was therefore impossible to assume that the naturally occurring homing process of one organism can be applied at will to another organism, in particular when this process probably does not occur naturally in the latter organism.

Dürrenberger et al. describe the induction of an intrachromosomal recombination in chloroplasts of the single-celled green alga *Chlamydomonas reinhardtii* using the I-CreI homing endonuclease (Dürrenberger F et al. (1996) Nucleic Acid Res 24(17):3323-3331).

The recombination takes place between the endogenous 23S gene and a 23S-cDNA which is inserted into the chromosome of an I-CreI deletion strain and which comprises an I-CreI cleavage site. Double-strand breaks are induced by mating the relevant transgenic organism with an organism which naturally expresses I-CreI. At the point in time of the double-strand break, the foreign DNA is already inserted into the chromosomal DNA, and recombination takes place intramolecularly and not between two separate molecules.

It has been shown recently that a mobile intron which naturally occurs in *Chlamydomonas reinhardtii* and which also encodes a homing endonuclease can be transformed efficiently into an intron-free copy (Odom O W et al. (2001) Mol Cell Biol 21: 3472-3481). In this work, the increase of the transformation rate was dependent on the presence of the homing endonuclease. In the discussion, it is proposed in general terms and without specific suggestions regarding the implementation, to improve plastid transformation by inducing double-strand breaks. To this end, the recognition regions of rare nucleases were initially to be introduced in a first step, and the subsequent integration event was then to take place at the same locus. More detailed suggestions regarding the manner in which the recognition regions are to be introduced, the type of nucleases and recognition regions which can be used, the way in which the first step and the second step can be designed in actual reality, and the like, are not provided. All that has been shown to date is that the introduction of a homologous intron, into plastids of the alga *Chlamydomonas*, by means of the homing endonuclease naturally associated with the mobility of the intron did work. Moreover, the results were generated in an algal species. The abovementioned experiments by Eddy and Gold with *E. coli*, where no mobile group I introns are known, as is the case with the plastids of higher plants, demonstrate that an applicability to heterologous systems is not readily feasible. It is therefore by no means obvious for the skilled worker to apply the observations on the alga *Chlamydomonas* to higher plants. In contrast, there are a number of suggestions which make such an applicability rather doubtful:

1. Homing systems cannot be applied readily from one system to another (Eddy S R and Gold L (1992) Proc Natl Acad Sci USA 89:1544-1547). The applicability to higher plants is all the more dubious since no homing endonucleases have been identified in those plastidic genomes of higher plants which have already been sequenced (http://megasun.bch.umontreal.ca/ogmp/projects/other/cp_list.html). It can therefore be assumed that the introns found in the plastidic genome of higher plants are not mobile, and that no homing mechanism exists naturally in these genomes.
2. *Chlamydomonas* only has one plastid per cell, while in cells of higher plants up to 100 plastids are present per cell.
3. The efficiency of conventional plastid transformation in *Chlamydomonas* exceeds that in higher plants by several orders of magnitude, which suggests that these two systems cannot be compared directly with one another. As regards the regeneration of transplastomic algae or transplastomic plants, the fact that division of the algal plastids is synchronized with the cell cycle, while this is not the case for the plastids of the higher plants, might also play an important role (Sato N (2001) Trends Plant Science 6:151-155).
4. The mechanisms of DNA integration into plastids of *Chlamydomonas* and of higher plants appear to be fundamentally different. Thus, it has been found that inter-specific plastid transformation (where homologous regions are utilized instead of identical sequences) in *Chlamydomonas* leads to a marked reduction of the transformation efficiency, which was, however, not observed in tobacco. This also applies analogously to the distance of a molecular marker on the homologous DNA from the heterologous sequence on the transformation plasmid: the closer the molecular marker to the edge of the target region for integration by means of double crossover, the less frequently it is transferred when transformed into *Chlamydomonas* plastids. In tobacco, multiple recombination mechanisms were observed, but here even molecular markers which were close to the edge of the homologous regions were transferred efficiently into the plastidic genome during transformation (Kavanagh TA et al. (1999) Genetics 152: 1111-1122 and references cited therein).
5. In *Chlamydomonas*, the plastids of the two parents fuse during hybridization, even in the case of inter-specific hybridization. In *Chlamydomonas*, plastid fusion is a natural process, and the DNA of the plastids too is mixed and undergoes new recombination. This is why mobile introns in the organelles of these organisms make sense. In contrast, in most of the higher plants, the plastids are inherited uniparentally, so that neither mixing of the plastidic DNA results nor recombinations can occur between the maternal and the paternal plastidic DNA. Even in those plant species in which the plastids are inherited biparentally, no plastid fusion was observed. It can therefore be assumed that natural plastid fusion in higher plants can be ruled out (Hagemann R (1992) plastidic genetics in higher plants; in Cell organelles, editor: Herrmann R G, Springer Verlag, Vienna, pp. 65-96) and that mechanisms like intron homing are either not developed or even suppressed.

Increasing the homologous recombination efficiency within the nuclear DNA with the aid of rare endonucleases has been described for various organisms (Puchta H et al. (1993) Nucleic Acids Research. 21(22):5034-40; Puchta H et al. (1996) Proc Natl Acad Sci USA 93:5055-5060; Rong Y S and Golic K G (2000) Science 28:2013-2018; Jasin M (1996) Trends Genet 12: 224-229). In contrast to plastids, insertion by homologous recombination into the nuclear DNA is problematic and usually takes place owing to random illegitimate integration. This demonstrates that techniques which are established for the nuclear genome cannot necessarily be applied to the plastids. In contrast to the situation regarding the nucleus, integration in plastids of higher plants takes place virtually exclusively, and with high efficiency, via homologous recombination (Bock R and Hagemann R (2000) Progress in Botany 61:76-90; Maliga P et al. (1994) Homologous recombination and integration of foreign DNA in plastids of higher plants. In Homologous recombination and gene silencing in plants. Paszkowski J, ed. (Kluwer Academic publishers), pp. 83-93).

The homologous recombination efficiency for the integration of DNA into the plastome has generally not been thought of as a limiting factor and, in contrast, considered as not being critical. Accordingly, current research into the optimization of plastid transformation does not focus on the optimization of homologous recombination but for example on improved selection markers, improved selection and regeneration techniques and the like. Nevertheless, no essential breakthrough has been achieved to date.

SUMMARY OF THE INVENTION

As emphasized clearly by the above-described methods and problems in the transformation of plastids, providing novel methods for the generation of homotransplastomic plants is a long-existing, unmet need of plant biotechnology. A further need is the avoidance of antibiotic or herbicide selection markers for reasons of registration and consumer acceptance. To date, no plastid transformation method has been described which does away with the need for such a selection marker.

It is therefore an object to develop novel methods which ensure efficient integration of foreign DNA in all copies of the plastidic DNA and which make possible the efficient selection of corresponding homotransplastomic plants. Surprisingly, this object has been achieved by providing the integration/selection method according to the invention.

A first subject matter of the invention relates to a method for the integration of a DNA sequence into the plastidic DNA of a multi-celled plant or cell derived therefrom and for the selection of predominantly homotransplastomic cells or plants, wherein a) the plastidic DNA molecules of said multi-celled plant or cell derived therefrom comprise at least one recognition sequence for the directed induction of DNA double-strand breaks and b) at least one enzyme suitable for the induction of DNA double-strand breaks at the recognition sequence for the directed induction of DNA double-strand breaks and at least one transformation construct comprising an insertion sequence are combined in at least one plastid of said multi-celled plant or cell derived therefrom, and c) DNA double-strand breaks are induced at the recognition sequences for the directed induction of DNA double-strand breaks, and d) the insertion sequence inserts into the plastidic DNA, the functionality of the recognition sequence for the directed induction of DNA double-strand breaks being deactivated so that said recognition sequence is no longer capable of being cleaved by the enzyme suitable for the induction of DNA double-strand breaks, and e) plants or cells in which the insertion sequence has been inserted into the plastidic DNA molecules are isolated.

Surprisingly, the system makes possible a substantial increase of he efficiency in the generation of predominantly homotransplastomic plants. In this context, not only the efficacy of insertion into the plastidic DNA, but also the efficacy of the selection process of predominantly homotransplastomic plants are increased.

Other embodiments and advantages of the invention are set forth in part in the description, which follows, and in part, may be obvious from this description, or may be learned from the practice of the invention.

DESCRIPTION OF THE INVENTION

Application of the method according to the invention results in a selection pressure of incorporating the insertion sequence into all of the copies of the plastidic DNA. Ideally, the insertion sequence is spread independently of the selection markers, such as herbicide or antibiotic resistances. This has pronounced advantages with regard to registration and/or consumer acceptance. However, the use of such selection markers can further increase the efficiency. The method according to the invention for the generation of homoplastomic plants clearly outperforms the prior-art methods since it shows a more rapid, more efficient and therefore more economical route to obtain homotransplastomic plants. A further advantage of the system is that the size of the constructs employed for the transformation can be kept small since the homologous regions in the plastid transformation vector can be smaller in comparison with the integration by means of double crossover, or can be completely absent.

The transformation of plastids has a large number of advantages over the transformation of the nucleus. The following are to be mentioned inter alia:

a) While homologous recombination into the nuclear DNA can only be realized with difficulty, DNA in plastids can be integrated readily at a predefined locus by means of double crossover, a form of homologous recombination. Positional effects or gene silencing, which are encountered in transformations of the nucleus owing to the illegitimate integration at a non-predefined locus, are thus avoided.

b) Very high expression levels can be achieved, presumably owing to the high copy number of the plastidic DNA.

c) In higher plants, plastidic DNA is, as a rule, only subject to maternal inheritance so that the foreign DNA introduced cannot be spread via pollen and cross-pollination can thus be prevented effectively.

d) The prokaryotic nature of the plastids makes possible the expression of genes in the context of a polycistronic operon structure. It is therefore not necessary to equate each gene to be expressed with its own promoter and the like. This facilitates the introduction of a large number of genes in one pass, for example for introducing entire biosynthetic pathways into the plastids.

"Plastid" refers to the proplastids and to all organelles to which they give rise, such as, for example, chloroplasts, etioplasts, chromoplasts, amyloplasts, leukoplasts, dermaplasts and elaioplasts (Heifetz P (2000) Biochimie 82:655-666).

"Plastome" refers to the genome, i.e. the totality of the genetic information, of a plastid.

"Homotransplastomic" refers to a transplastomic and homoplastomic state.

With regard to, for example, a plant, cell, tissue, plastid or a plastidic DNA, "transplastomic" refers to all those forms of the above, realized by recombinant methods, which comprise a plastidic DNA which has been modified by recombinant methods, it being possible for the modification to comprise, for example, substitutions, additions, deletions, inversions or insertions of one or more nucleotide residues.

"Heteroplastomic" refers to the presence of a mixed population of a variety of plastidic DNAs within a single plastid or within a population of plastids within a plant cell or tissue.

"Homoplastomic" refers to a uniform population of plastidic DNA within a single plastid or within a population of plastids within a plant cell or tissue. Homoplastomic cells, tissues or plants are genetically stable since they only comprise one type of plastidic DNA, i.e. they generally remain homopolastomic even when the selection pressure ceases. Progeny obtained by selfing are likewise homoplastomic.

For the purposes of the present invention, "predominantly homoplastomic" or "predominantly homotransplastomic" refers to all those plants or cells in which the percentage of the desired plastidic DNA molecules which have been modified with regard to a trait—for example with the recognition sequence for the directed induction of DNA double-strand breaks or the inserted insertion sequence—amounts to at least 50%, preferably at least 70%, very especially preferably at least 90%, most preferably at least 95% of the totality of all plastidic DNA molecules in a plant or a tissue, cell or plastid of same. Predominantly homoplastomic or predominantly homotransplastomic plants can be converted into homoplastomic or homotransplastomic plants by continued maintenance of the selection pressure and, if appropriate, repeated regeneration steps. Owing to the homing process, however, a continuous selection pressure is not necessarily required. In a particular embodiment, a predominantly homoplastomic, or homotransplastomic, plant is therefore truly homoplastomic, or homotransplastomic. A plant which, with regard to a DSB recognition sequence, is predominantly homoplastomic or homotransplastomic, or truly homoplastomic or homotransplastomic, is subsequently referred to as "master plant". The percentage of the desired plastidic DNA molecules which have been modified with regard to a trait can be determined in the manner known to the skilled worker, for example by means of Southern analysis as described by way of example in Example 4. The ratio between the plastid starting DNA molecules and the plastidic DNA molecules which have been modified with regard to a trait can be determined by comparing the intensity of the bands in question.

"Multi-celled plant or cell derived therefrom" refers generally to all those cells, tissues, parts or propagation materials (such as seeds or fruits) of a plant which constitutes, or may constitute, a multi-celled organism in its adult state. Included for the purpose of the invention are all genera and species of higher and lower plants of the plant kingdom. Annual, perennial, monocotyledonous and dicotyledonous plants are preferred. Included are mature plants, seeds, shoots and seedlings, and parts derived therefrom, propagation material (for example tubers, seeds or fruits) and cultures, for example cell or callus cultures. "Mature plants" means plants at any developmental stage beyond the seedling stage. The term seedling means a young immature plant an early developmental stage.

Preferred plants are those from the following plant families: Amaranthaceae, Asteraceae, Brassicaceae, Carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanaceae, Sterculiaceae, Tetragoniaceae, The aceae, Umbelliferae.

Preferred monocotyledonous plants are selected in particular from the monocotyledonous crop plants such as, for example, the Gramineae family such as rice, maize, wheat or other cereal species such as barley, millet and sorghum, rye, triticale or oats, and sugar cane, and all grass species.

Preferred dicotyledonous plants are selected in particular from dicotyledenous crop plants, such as, for example, Asteraceae such as sunflower, tagetes or calendula and others, Compositae, especially the genus *Lactuca*, very particularly the species sativa (lettuce) and others, Cruciferae, particularly the genus *Brassica*, very particularly the species *napus* (oilseed rape), *campestris* (beet), *oleracea cv Tastie* (cabbage), *oleracea cv Snowball Y*(cauliflower) and *oleracea cv Emperor* (broccoli) and other cabbages; and the genus *Arabidopsis*, very particularly the species *thaliana*, and cress or canola and others, Cucurbitaceae such as melon, pumpkin/squash or zucchini and others, Leguminosae, particularly the genus *Glycine*, very particularly the species max (soybean), soybean, and alfalfa, pea, bean or peanut and others, Rubiaceae, preferably the subclass Lamiidae such as, for example, *Coffea arabica* or *Coffea liberica* (coffee bush) and others, Solanaceae, particularly the genus *Lycopersicon*, very particularly the species *esculentum* (tomato), the genus *Solanum*, very particularly the species *tuberosum* (potato) and *melongena* (aubergine) and tobacco or paprika and others, Sterculiaceae, preferably the subclass Dilleniidae such as, for example, *Theobroma cacao* (cacao bush) and others, Theaceae, preferably the subclass Dilleniidae such as, for example, *Camellia sinensis* or *Thea sinensis* (tea shrub) and others, Umbelliferae, particularly the genus *Daucus* (very particularly the species *carota* (carrot)) and *Apium* (very particularly the species *graveolens dulce* (celery)) and others; and the genus *Capsicum*, very particularly the genus *annuum* (pepper) and others, and linseed, soybean, cotton, hemp, flax, cucumber, spinach, carrot, sugar beet and the various tree, nut and grapevine species, in particular banana and kiwi fruit.

Also encompassed are ornamental plants, useful or ornamental trees, flowers, cut flowers, shrubs or turf. Plants which may be mentioned by way of example but not by limitation are angiosperms, bryophytes such as, for example, *Hepaticae* (liverworts) and *Musci* (mosses); pteridophytes such as ferns, horsetails and clubmosses; gymnosperms such as conifers, cycads, ginkgo and Gnetatae, the families of the Rosaceae such as rose, Ericaceae such as rhododendron and azalea, Euphorbiaceae such as poinsettias and *croton*, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geranium, Liliaceae such as dracena, Moraceae such as *ficus*, Araceae such as philodendron and many others.

Most preferred are *Arabidopsis thaliana, Nicotiana tabacum, Tagetes* and *Brassica napus* and all those genera and species which are used as foods or feeds, such as the above-described cereal species, or which are suitable for the production of oils, such as oil plants, nut species, soybean, sunflower, pumpkin/squash and peanut.

"Enzyme suitable for inducing DNA double-strand breaks at the recognition sequence for the directed induction of DNA double-strand breaks" (hereinbelow referred to as "DSBI enzyme" for "double strand-break inducing enzyme") generally refers to all those enzymes which are capable of generating, in a sequence-specific manner, double-strand breaks in double-stranded DNA. The following may be mentioned by way of example, but not by limitation:

1. Restriction endonucleases, preferably type II restriction endonucleases, especially preferably homing endonucleases as described in detail hereinbelow.
2. Artificial nucleases such as described in detail hereinbelow, such as, for example, chimeric nucleases, mutated restriction or homing endonucleases, or RNA protein particles derived from mobile group II introns.

Both natural and artificially generated DSBI enzymes are suitable. Preferred are all those DSBI enzymes whose recognition sequence is known and which can be obtained either in the form of their proteins (for example by purification) or which can be expressed using their nucleic acid sequence.

The DSBI enzyme, whose specific recognition sequence is known, is preferably selected in such a way that it has no further functional recognition regions in the plastidic genome, in addition to the target recognition sequence. Homing endonucleases are therefore very especially preferred (review: Belfort M and Roberts R J (1997) Nucleic Acids Res 25:3379-3388; Jasin M (1996) Trends Genet 12:224-228; website: http://rebase.neb.com/rebase/rebase.homing.html; Roberts R J and Macelis D (2001) Nucleic Acids Res 29: 268-269). These meet this requirement owing to their long recognition sequences. Owing to the small size of the plastome, however, it is also feasible that DSBI enzymes with shorter recognition sequences (for example restriction endonucleases) can be employed successfully.

In addition to the above-described preferred embodiment, where only a singular recognition sequence for the DSBI enzyme is present in the plastidic DNA, cases where further, functionally identical, recognition sequences can be employed advantageously are also feasible. This is the case in particular when the plastome comprises duplicated genes (for example in the form of inverted repeats). Here, integration into all copies is to take place, so that cleavage in all copies is likewise desirable.

The sequences which encode such homing endonucleases can be isolated for example from the chloroplast genome of *Chlamydomonas* (Turmel M et al. (1993) J Mol Biol 232: 446-467). They are small (18 to 26 kD), but have, in their open reading frame (ORF), a "coding usage" which is directly suitable for expression in the nucleus or plastids of higher plants (Monnat R J Jr et al. (1999) Biochem Biophys Res Com 255:88-93).

Further homing endonucleases are mentioned in the above-mentioned website; homing endonucleases which may be mentioned are, for example, F-SceI, F-SceII, F-SuvI, F-TevI, F-TevII, I-AmaI, I-AniI, I-CeuI, I-CeuAIIP, I-ChuI, I-CmoeI, I-CpaI, I-CpaII, I-CreI, I-CrepsbIP, I-CrepsbIIP, I-CrepsbIIIP, I-CrepsbIVP, I-CsmI, I-CvuI, I-CvuAIP, I-DdiII, I-DirI, I-DmoI, I-HspNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PpbIP, I-PpoI, I-SPBetaIP, I-ScaI, I-SceI, I-SceII, I-SceIII, I-SceIV, I-SceV, I-SceVI, I-SceVII, I-SexIP, I-SneIP, I-SpomCP, I-SpomIP, I-SpomIIP, I-SquIP, I-Ssp6803I, I-SthPhiJP, I-SthPhiST3P, I-SthPhiS3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP, PI-MtuHIIP, PI-PfuI, PI-PfuII, PI-PkoI, PI-PkoII, PI-PspI, PI-Rma438121P, PI-SPBetaIP, PI-SceI, PI-TfuI, PI-TfuII, PI-ThyI, PI-TliI, PI-TliII.

Preferred in this context are those homing endonucleases whose gene sequences are already known, such as, for example, F-SceI, I-CeuI, I-ChuI, I-DmoI, I-CpaI, I-CpaII, I-CreI, I-CsmI, F-TevI, F-TevII, I-TevI, I-TevII, I-AniI, I-CvuI, I-LlaI, I-NanI, I-MsoI, I-NitI, I-NjaI, I-PakI, I-PorI, I-PpoI, I-ScaI, I-SceI, I-Ssp6803I, PI-PkoI, PI-PkoII, PI-PspI, PI-TfuI, PI-TliI.

Homing endonucleases which are especially preferably used are those which are found as such naturally, especially preferably those which are found naturally in organelles. Most preferably, the homing endonucleases originate from organisms which live at similar temperatures to plants. Those which are of particular interest in this contest are the homing endonucleases identified in yeast and *Chlamydomonas* species. Naturally, it is also feasible to utilize homing endonucleases which are isolated from extremophilic organisms, as long as they are active in the plastids of the plant to be transformed.

The following are very especially preferred:

I-CeuI (Cote M J and Turmel M (1995) Curr Genet 27:177-183.; Gauthier A et al. (1991) Curr Genet 19:43-47; Marshall (1991) Gene 104:241-245; GenBank Acc. No.: Z17234 nucleotides 5102 to 5758), I-ChuI (Cote V et al. (1993) Gene 129:69-76; GenBank Acc. No.: L06107, nucleotides 419 to 1075), I-CmoeI (Drouin M et al. (2000) Nucl Acids Res 28: 4566-4572), I-CpaI from *Chiamydomonas pallidostigmatica* (GenBank Acc. No.: L36830, nucleotides 357 to 815; Turmel M et al. (1995) Nucleic Acids Res 23:2519-2525; Turmel, M et al. (1995) Mol Biol Evol 12:533-545; see also SEQ ID NO: 13 and 14)

I-CpaII (Turmel M et al. (1995) Mol Biol Evol 12:533-545; GenBank Acc. No.: L39865, nucleotides 719 to 1423), I-CreI (Wang J et al. (1997) Nucleic Acids Res 25: 3767-3776; Dürrenberger, F and Rochaix J D (1991) EMBO J. 10:3495-3501; GenBank Acc. No.: X01977, nucleotides 571 to 1062), I-CsmI (Ma D P et al. (1992) Plant Mol Biol 18:1001-1004)

I-NanI (Elde M et al. (1999) Eur J. Biochem. 259:281-288; GenBank Acc. No.: X78280, nucleotides 418 to 1155), I-NitI (GenBank Acc. No.: X78277, nucleotides 426 to 1163), I-NjaI (GenBank Acc. No.: X78279, nucleotides 416 to 1153), I-PpoI encodes on the extrachromosomal DNA in the nucleus of *Physarum polycephalum* (Muscarella D E and Vogt V M (1989) Cell 56:443-454; Lin J and Vogt V M (1998) Mol Cell Biol 18:5809-5817; GenBank Acc. No.: M38131, nucleotides 86 to 577). In addition, the longer sequence encoding I-PpoI, which originates from an alternative start codon, may also be used. This sequence comprises the nucleotides 20 to 577 in the sequence of GenBank Acc. No. M38131. It is preferred to use the shorter sequence; however, it can be substituted at any location by the corresponding, longer one. A sequence which is especially preferred for the purposes of the present invention is an artificial sequence which encodes for the same amino acid as the sequence of the nucleotides 86 to 577 of the sequence of GenBank Acc. No.: M38131 (see also SEQ ID NO: 5, 11, 12, 70 or 71), I-PspI (GenBank Acc. No.: U00707, nucleotides 1839 to 3449), I-ScaI (Monteilhet C et al. (2000) Nucleic Acids Res 28: 1245-1251; GenBank Acc. No.: X95974, nucleotides 55 to 465)

I-SceI from the mitochondria of bakers' yeast (WO 96/14408; U.S. Pat. No. 5,962,327 Seq ID NO: 1 therein), Endo SceI (Kawasaki et al. (1991) J Biol Chem 266:5342-5347, identical with F-SceI; GenBank Acc. No.: M63839, nucleotides 159 to 1589), I-SceII (Sarguiel B et al. (1990) Nucleic Acids Res 18:5659-5665), I-SceIII (Sarguiel B et al. (1991) Mol Gen Genet. 255:340-341), I-Ssp68031 (GenBank Acc. No.: D64003, nucleotides 35372 to 35824), I-TevI (Chu et al. (1990) Proc Natl Acad Sci USA 87:3574-3578; Bell-Pedersen et al. (1990) Nucleic Acids Res 18:3763-3770; GenBank Acc. No.: AF158101, nucleotides 144431 to 143694), I-TevII (Bell-Pedersen et al. (1990) Nucleic Acids Res 18:3763-3770; GenBank Acc. No.: AF158101, nucleotides 45612 to 44836), I-TevIII (Eddy et al. (1991) Genes Dev. 5:1032-1041), Commercially available homing endonucleases such as I-CeuI, I-SceI, I-PpoI, PI-PspI or PI-SceI are very especially preferred. Most preferred are I-SceI and I-PpoI. While the gene encoding I-PpoI can be used in its natural form, the gene encoding I-SceII contains an editing locus. Since, in contrast to yeast mitochondria, the editing in question is not performed in the plastids of higher plants, an artificial sequence which encodes the I-SceI protein must be employed for the heterologous expression of this enzyme (U.S. Pat. No. 5,866, 361).

In addition to the above-stated homing endonucleases, there are further intron-encoded enzymes which can be found at homologous locations of the genomes of related organisms. As a rule, these homing endonucleases have similar sequence specificity and are therefore equally suited as DSBI enzyme for the introduction of a DSB into the plastome at the DSB recognition sequence. The corresponding sequence is thus also recognized by Sob2593c, Clu2593c, Col2593c, Ciy2593c, Hla2593c, Cag2593c, I-CvuI, I-PakI, Tmu2593c, Msp2593c, I-MsoI, Sdu2593c, Mvi2593m, Nol2593m or Aca2593m, in addition to I-CreI. Corresponding sequence is also recognized by I-CecI, I-CmoI, I-CeII, I-CpaIII, I-CmuI, I-CluI, I-SobI or I-AstI, in addition to I-CeuI. A corresponding sequence is also recognized by Cbr1931c, Cfr1931c, Cme1931c, Cge1931c, Pcr1931c, Msp1931c, Mso1931C, Ptu1931c, Cvu1931m, Msp1931m, Msol931m, Nol1931m, Acal931m or Sne1931b, in addition to I-CpaI. Moreover, introns exist which are inserted at position 1951 of the 23S rDNA (numbering refers to homologous position in the 23S rDNA of E. coli). These introns, again, encode putative homing endonucleases which can be used as. DSBI enzymes for the specific cleavage of the plastidic DNA. They include, for example, Cbr1951c, Msp1951c, Mso1951c, Cvu1951m or Acal951m (Lucas P et al. (2001) Nucl Acids Res 29:960-969).

Most preferred are the homing endonucleases of the protein sequences described by SEQ ID NO: 5, 12 or 14. When preparing corresponding expression cassettes, accordingly, nucleic acid sequences are employed which encode a protein as shown in SEQ ID NO: 5, 12 and 14, respectively; especially preferred in this context is the use of the nucleic acid sequences as shown in SEQ ID NO: 11 and 13 or of an expression cassette as shown in SEQ ID NO: 4.

The enzymes can be isolated from their source organisms in the manner with which the skilled worker is familiar and/or the nucleic acid sequence encoding them can be cloned. The sequences of a variety of enzymes have been deposited at GenBank (see above).

Examples of artificial DSBI enzymes by way of example are chimeric nucleases which are composed of an unspecific nuclease domain and a sequence-specific DNA binding domain (for example consisting of zinc fingers) (Smith J et al. (2000) Nucl Acids Res 28(17):3361-3369; Bibikova M et al. (2001) Mol Cell Biol. 21:289-297). Thus, for example, the catalytic domain of the restriction endonuclease FokI has been fused with zinc finger binding domains, whereby the specificity of the endonuclease has been defined (Chandrasegaran S & Smith J (1999) Biol Chem 380:841-848; Kim Y G & Chandrasegaran S (1994) Proc Natl Acad Sci USA 91:883-887; Kim Y G et al. (1996) Proc Natl Acad Sci USA 93:1156-1160). The catalytic domain of the yeast Ho endonuclease, too, has already been conferred a predefined specificity, using the above-described technique, by fusing it with the zinc finger domain of transcription factors (Nahon E & Raveh D (1998) Nucl Acids Res 26:1233-1239).

As mentioned, zinc finger proteins are particularly suitable as DNA binding domain for the purpose of chimeric nucleases. These DNA-binding zinc finger domains can be adapted to match any desired DNA sequence. Suitable methods for the preparation of such zinc finger domains are described and known to the skilled worker (Beerli R R et al. (2000) Proc Natl Acad Sci USA 97(4):1495-1500; Beerli R R et al. (2000) J Biol Chem 275(42):32617-32627; Segal D J and Barbas C F 3rd. (2000) Curr Opin Chem Biol 4(1):34-39; Kang J S and Kim J S (2000) J Biol Chem 275(12):8742-8748; Beerli R R et al. (1998) Proc Natl Acad Sci USA 95(25):14628-14633; Kim J S et al. (1997) Proc Natl Acad Sci USA 94(8):3616-3620; Klug A (1999) J Mol Biol 293(2):215-218; Tsai S Y et al. (1998) Adv Drug Deliv Rev 30(1-3):23-31; Mapp A K et al. (2000) Proc Natl Acad Sci USA 97(8):3930-3935; Sharrocks A D et al. (1997) Int J Biochem Cell Biol 29(12):1371-1387; Zhang L et al. (2000) J Biol Chem 275(43):33850-33860). Methods for the preparation and selection of zinc finger DNA binding domains with high sequence specificity have been described (WO 96/06166, WO 98/53059, WO 98/53057). Fusing a DNA binding domain thus obtained with the catalytic domain of an endonuclease (such as, for example, the FokI or Ho endonuclease) allows the preparation of chimeric nucleases with any desired specificity which can be employed advantageously as DSBI enzymes for the purposes of the present invention.

Artificial DSBI enzymes with modified sequence specificity can also be prepared by mutating known restriction endonucleases or homing endonucleases by methods known to the skilled worker. The mutagenesis of maturases with the purpose of obtaining a modified substrate specificity is of particular interest, besides the mutagenesis of homing endonucleases. Frequently, maturases share many features with homing endonucleases and, if appropriate, they can be converted into nucleases by carrying out few mutations. This has been shown, for example, for the maturase in the bakers' yeast bi2 intron. Only two mutations in the maturase-encoding open reading frame (ORF) sufficed to confer a homing endonuclease activity to this enzyme (Szczepanek & Lazowska (1996) EMBO J 15:3758-3767).

Further artificial nucleases can be generated with the aid of mobile group II introns and the proteins encoded by them, or parts of these proteins. Many mobile group II introns, together with the proteins encoded by them, form RNA-protein particles which are capable of recognizing, and cleaving, DNA in a sequence-specific manner. Here, the sequence specificity can be adapted to suit the needs by mutating certain intron regions (see hereinbelow) (WO 97/10362).

The skilled worker is familiar with various methods for introducing a DSBI enzyme into plastids or expressing it therein.

The following may be mentioned by way of example, but not by limitation:

a) Nuclear expression using plastidic transit peptides

An expression cassette encoding a DSBI enzyme fusion protein can be constructed in the manner known to the skilled worker, introduced into the nucleus and—optionally—integrated stably into the chromosomal DNA. For transport into the plastids, the DSBI enzyme is preferably expressed in fusion with a plastid localization sequence (PLS). Methods for the direct transportation, into the plastids, of proteins which per se are not localized in the plastids, and a variety of PLS sequences, have been described (Klosgen R B and Weil J H (1991) Mol Gen Genet 225(2):297-304; Van Breusegem F et al. (1998) Plant Mol Biol 38(3):491-496). Preferred are those PLS which, after translocation of the DSBI enzyme into the plastids, are cleaved enzymatically from the DSBI enzyme moiety. Especially preferred is the PLS which is derived from the plastidic *Nicotiana tabacum* transketolase or from another transit peptide (for example the transit peptide of the small Rubisco subunit or of the ferredoxin NADP oxidoreductase, and also isopentenyl-pyrophosphate isomerase-2) or its functional equivalent. Promoters which are suitable for expression in the nucleus are, in principle, all those which make possible an expression in plants. Examples can be found further below. Preferred are constitutive promoters such as the CaMV 35S promoter or the nitrilase-1 promoter of the *Arabidopsis* nit1 gene (GenBank Acc. No.: Y07648.2, nucleotides 2456 to 4340; Hillebrand H et al. (1998) Plant Mol Biol 36 (1):89-99; Hillebrand H et al. (1996) Gene 170(2):197-200).

Preferred PLS Sequences Are:
i) the *Arabidopsis* isopentenyl isomerase (IPP) transit peptide (GenBank Acc. No.: NC 003074; nucleotides 604657-604486)
ii) transit peptides derived from the small subunit (SSU) of ribulose-bisphosphate carboxylase (Rubisco ssu) from, for example, pea, maize, sunflower or *Arabidopsis*.
  *Arabidopsis thaliana*: GenBank Acc. No.: for example AY054581, AY054552;
  pea, GenBank Acc. No.: for example X00806, nucleotides 1086 to 1256; X04334, X04333 (Hand JM (1989) EMBO J 8(11):3195-206). Especially preferred in this context are: expression cassette and transit peptide (pea, rbcS3A) from vector pJIT117 (Guerineau F (1988) Nucleic Acids Res 16(23):11380. Especially preferred is the peptide sequence as shown in SEQ ID NO: 35. Most preferred for the use in constructing suitable expression constructs is the nucleic acid sequence as shown in SEQ ID NO: 34.
  maize, GenBank Acc. No.: for example S42568, S42508
  sunflower, GenBank Acc. No.: Y00431, nucleotides 301 to 465.
iii) transit peptides derived from plant fat biosynthesis genes, such as the transit peptide of the plastid acyl carrier protein (ACP) (for example the *Arabidopsis thaliana* beta-ketoacyl-ACP synthetase 2; GenBank Acc. No.: AF318307), stearyl-ACP desaturase, β-ketoacyl-ACP synthase or acyl-ACP thioesterase (for example *A. thaliana* mRNA for acyl-(acyl carrier protein)thioesterase: GenBank Acc. No.: Z36911).
iv) the GBSSI (starch granule bound synthase I) transit peptide
v) the transit peptide of the LHCP II genes.
Especially preferred is the PLS of the plastidic tobacco transketolase (SEQ ID NO: 36). To express corresponding fusion proteins, different PLS nucleic acid cassettes can be used in the three reading frames as KpnI/BamHI fragments for the purposes of the present invention (the translation start (ATG codon) is localized in the NcoI cleavage site) (pTP09 SEQ ID NO: 37; pTP10 SEQ ID NO: 38; pTP11 SEQ ID NO: 39).
A further example of a PLS to be employed advantageously is the transit peptide of the plastidic *Arabidopsis thaliana* isopentenyl-pyrophosphate isomerase-2 (IPP-2) (SEQ ID NO: 40). The nucleic acid sequences encoding three cassettes (corresponding to the three reading frames) of the PLS from the *Arabidopsis thaliana* isopentenyl-pyrophosphate isomerase-2 (IPP-2) can be used very especially preferably (EcoRV/SalI cassettes with ATG; IPP-9 SEQ ID NO: 41; ipp-10 SEQ ID NO: 42; IPP-11 SEQ ID NO: 43).
The nucleic acids according to the invention can be of synthetic origin or have been obtained naturally or comprise a mixture of synthetic and natural nucleic acid components, or else consist of various heterologous gene segments from a variety of organisms.
The sequence encoding the transit peptide can comprise all or part of the peptide sequence of the original protein. An accurate determination of the amino acid residues which are essential for the transport is not required as long as the functionality of the PLS—which is the transport into the plastid—is ensured and the function of the DSBI enzyme is not entirely destroyed. Very especially preferred are the following PLS sequences:
PLS1: N-MASSSSLTLSQAILSRSVPRHG-SASSSQLSPSSLTFSGLKSNPNITTSRRR TPSSAAAAAVVRSPAIRASAATETIEKTETAGS-C (SEQ ID NO: 36). Corresponds to the PLS of the tobacco plastidic transketolase.
PLS2: N-MSASSLFNLPLIRLRSLALSSSFSSFR-FAHRPLSSISPRKLPNFRAFSGTA MTDTKDG-SRVDM-C (SEQ ID NO: 40). Corresponds to the PLS of isopentenyl-pyrophosphate isomerase-2 (IPP-2), the last methionine preferably being the start methionine of the DSBI enzyme.
The homing endonuclease as shown in SEQ ID NO: 69 is a preferred fusion protein of the native I-Ppo I nuclease and the IPP plastid localization sequence. This protein is preferably encoded by the sequence with the SEQ ID NO: 68.
For the purposes of the present invention, fusion proteins of PLS and DSBI enzyme come under the term "DSBI enzyme". If a DSBI enzyme is expressed in the nucleus, the DSBI enzyme is preferably understood as meaning a fusion protein of PLS and DSBI enzyme.
The invention furthermore relates to fusion proteins of DSBI enzymes with plastid localization sequence (PLS), sequences and expression cassettes comprising a fusion protein of a plastid localization sequence (PLS) and a DSBI enzyme under the control of a promoter which is functional in the plant nucleus. Such suitable promoters are known to the skilled worker and described further below. The expression cassette can comprise further elements such as, for example, transcription terminators and/or selection markers.

b) Expression in plastids
An expression in plastids can also take place by the direct introduction of an expression cassette for the DSBI enzyme into plastids, if appropriate integration into the plastidic DNA, and expression of the DSBI enzyme. In a preferred embodiment, this expression cassette is present in the transformation construct which comprises the insertion sequence.
Promoters which can be employed are, firstly, specific plastid or chromoplast promotors as detailed hereinbelow. However, a directed expression in plastids can also be achieved by using for example a viral, bacterial or bacteriophage promoter, introducing the resulting expression cassette into the plastidic DNA, and then inducing expression by the corresponding viral, bacterial or bacteriophage RNA polymerase. The corresponding RNA polymerase, in turn, can be introduced into the plastids in various ways, preferably by nuclear transformation in the form of a fusion protein with a PLS. Suitable methods have been described (WO 95/16783, WO 97/06250, U.S. Pat. No. 5,925,806). It is preferably introduced into plastids by microinjection, especially preferably by means of particle bombardment.

c) Introduction in the form of RNA
The DSBI enzyme can also be introduced into plastids by introducing the mRNA—for example mRNA which has been generated in vitro—which encodes the DSBI enzyme via, for example, microinjection, particle bombardment (biolistic methods), or polyethylene glycol- or liposome-mediated transfection. This embodiment is advantageous since no DSBI-enzyme-encoding sequences remain in the plastome or genome in this case. Preferably, the RNA encoding the DSBI enzyme is generated by in-vitro transcription in the manner with which the skilled worker is familiar.

d) Introduction in the form of the protein
The DSBI enzyme can be introduced into plastids directly, for example via microinjection, particle bombardment (biolistic methods) or polyethylene glycol transfection or liposome-mediated transfection. This embodiment is advantageous since no DSBI-enzyme-encoding sequences remain in the plastome or genome. Such a method is described, for example, by Segal D J et al. (1995) Proc Natl Acad Sci USA 92:806-810.

The DSBI enzyme can be introduced into plant cells as a fusion protein with the VirE2 or VirF protein of an *agrobacterium* and a PLS. Such methods have been described for example for Cre recombinase (Vergunst AC et al. (2000) Science 290:979-982). This embodiment is advantageous since no DSBI enzyme-encoding sequences remain in the genome.

Of course, combinations of the above-described possibilities are also feasible.

The expression cassette for the DSBI enzyme is preferably present on the insertion sequence or on the transformation construct.

The DSBI enzyme is preferably introduced, or activated, simultaneously with, or after, the introduction of the insertion sequence into the plastids. Expression and/or activation at the correct site and the correct point in time can be ensured by various approaches:

a) Inducible expression

The expression of a DSBI enzyme can be controlled using an inducible promoter, preferably a chemically inducible promoter. To this end, for example, the expression cassette which encodes the DSBI enzyme can be transformed stably into the plastidic or nuclear DNA of a master plant. If it is transformed into the nuclear genome, the subcellular localization must be ensured— as described above—by suitable PLS transit peptides. Shortly before or during the transformation with the insertion sequence or the transformation construct, the expression of the DSBI enzyme will then be switched on by applying a suitable inductor, which depends on the choice of the inducible system. The skilled worker is familiar with a variety of methods or promoters for induced expression. Chemical compounds or else physical stimuli such as, for example, increased temperature or wounding and the like can act as stimulus. Various examples are described further below.

b) Inducible activity

The DSBI enzyme can already exist in the plastids of the master plant when the activity is induced by suitable techniques at the selected point in time only, for example by addition of chemical compounds. Such methods have been described for sequence-specific recombinases (Angrand P O et al. (1998) Nucl Acids Res 26(13):3263-3269; Logie C and Stewart A F (1995) Proc Natl Acad Sci USA 92(13):5940-5944; Imai T et al. (2001) Proc Natl Acad Sci USA 98(1):224-228). Fusion proteins of the DSBI enzyme and the ligand binding domain of a steroid hormone receptor (for example the human androgen receptor, or mutated variants of the human estrogen receptor as described therein) are employed in these methods. Induction can be effected with ligands such as, for example, estradiol, dexamethasone, 4-hydroxytamoxifen or raloxifen.

Some of the DSBI enzymes are active in the form of the dimer (homo- or heterodimer) (1-CreI forms a homodimer; I-PpoI forms a homodimer, Flick K E et al. (1998) Nature 394: 96-101). In general, enzymes of the LAGLIDADG family tend to form homodimers when only one LAGLIDADG motif is present per monomer (Jurica M S & Stoddard B L (1999) Cell Mol Life Sci 55:1304-1326; I-CeuI may be mentioned by way of example). A dimerization can be designed to be inducible, for example by substituting the natural dimerization domains by the binding domain of a low-molecular-weight ligand. Addition of a dimeric ligand then brings about the dimerization of the fusion protein. Such inducible dimerization methods are described, as is the preparation of the dimeric ligands (Amara J F et al. (1997) Proc Natl Acad Sci USA 94(20): 10618-10623; Muthuswamy S K et al. (1999) Mol Cell Biol 19(10): 6845-6857; Schultz L W and Clardy J (1998) Bioorg Med Chem Lett 8(1):1-6; Keenan T et al. (1998) Bioorg Med. Chem. 6(8):1309-1335).

c) Cotransfection

The expression cassette encoding the DSBI enzyme is preferably introduced into the plastids simultaneously with the insertion sequence. In this context, the expression cassette for the DSBI enzyme and the insertion sequence may be present on one DNA molecule or else on two separate DNA molecules. Preferably, the two sequences are present together on one DNA molecule, so that the expression cassette is present in the transformation construct comprising the insertion sequence.

In an especially preferred embodiment, the sequence encoding the DSBI enzyme is removed from the genome of the transformed plasmids after homoplastomic plants have been regenerated. The skilled worker is familiar with a variety of methods for doing so which are detailed further below.

Some of the above-described DSBI enzymes (in particular homing endonucleases) can have recognition sequences in the intermediate host *E. coli*, which is preferably used. Since, moreover, some expression cassettes for expression in plastids are also functional in *E. coli*, it is preferred to prevent expression of the DSBI enzyme in *E. coli* in various ways with which the skilled worker is familiar in order to avoid any disadvantageous effects on *E. coli* during amplification of the expression cassette. Thus, for example, several consecutive codons which occur rarely in *E. coli* (for example the codons AGA and AGG, which encode arginine) can be inserted into the reading frame of the DSBI enzyme. This prevents expression in *E. coli*, but—owing to the different codon usage— continues to make possible expression in the plastids. As an alternative, promoters which are not active in *E. coli*, but are active in the plastids of higher plants can be used (for example promoters of the nuclear encoded plastidic RNA polymerases [NEP promoters; see hereinbelow]). A preferred method is the use of promoters which are recognized neither by the plastids nor by *E. coli* (for example viral promoters or bacteriophage promoters) and which only become functional by the simultaneous presence of the corresponding viral/bacteriophage RNA polymerase. Such methods are known to the skilled worker and described hereinbelow. Furthermore, it is feasible to destroy the relevant DSB recognition sequences in *E. coli* or to use a different host which has no DSB recognition sequences for the DSBI enzyme in question. Moreover, it is feasible and advantageous to have the coding region of the DSBI enzyme in promoterless form for amplification in *E. coli*. In this case, the sequence which encodes the DSBI enzyme is preferably present on a plasmid which is capable of integration into the plastidic genome of the plant to be transformed. Here, the integration site can be chosen in such a way that the gene encoding the DSBI enzyme comes under the control of a promoter which is naturally present in the plastome or has been inserted artificially into the plastome, thus resulting in expression of the DSBI enzyme in the plastids. A further preferred embodiment ensures that the gene encoding the DSBI enzyme can later be deleted from the plastome (see hereinbelow). In addition, it is possible to create a linkage between a promoter and a DSBI enzyme by adding such a promoter in vitro upstream of the open reading frame by means of PCR techniques with which the skilled worker is familiar. The PCR product can then be used for introduction into the plant plastids. Moreover, nonfunctional parts of an expression cassette for a DSBI enzyme can be generated and amplified in *E. coli* when these parts undergo recombination with one another after introduction into plant plastids (for example by means of homologous recombination in overlapping regions of the nonfunctional moieties of the expression cassette), thus giving rise to a functional expression cassette.

"Recognition sequence for the directed induction of DNA double-strand breaks" (hereinbelow "DSB recognition sequence" for double-strand break recognition sequence) generally refers to those sequences which permit recognition and cleavage by a DSBI enzyme under the conditions in the plastids of the plant cell or plant used in each case. Especially preferred are DSB recognition sequences for-homing endonucleases which are encoded naturally in mitochondria or the nucleus of other organisms. Also, it is possible to use DSB recognition sequences of homing endonucleases which are derived from plastids (for example from green algae). Preferably, the DSB recognition sequence is singular in the plastidic DNA, i.e. a double-strand break is only generated at the location thus predefined. However, cases where more than one DSB recognition sequence is present in the plastome are also feasible. This is the case in particular when the DSB recognition sequence is localized in duplicated genes (for example in inverted repeats). In the latter case, more than one identical DSB recognition sequence exist, but their context is identical, so that, again, directed insertion takes place. Indeed, it is preferred that integration into all copies takes place, which also requires cleavage in all copies. DSB recognition sequences which, while occurring more than once in one plastome, are localized in the same plastomic context (for example in repeats or in gene duplications) come under the term "singular DSB recognition sequences" for the purposes of the present invention.

Preferably, the plant employed, or the cell derived therefrom, is predominantly homoplastomic or homotransplastomic with regard to the DSB recognition sequence, i.e. the predominant number of the plastidic DNA molecules present in the plastid contain this DSB recognition sequence. For the purposes of the present invention, such plants are also referred to as master plants.

In principle, two types of DSB recognition sequences can be used:

a) Natural, endogenous DSB recognition sequences

As has been demonstrated within the scope of the present invention, the plastomes of higher plants comprise various sequences which can act as recognition sequences for DSBI enzymes (for example homing endonucleases), even though no such endonucleases have been demonstrated in higher plants to date. Such DSB recognition sequences can be identified by screening the plastidic DNA sequence using the known DSB recognition sequences (for example those described in Table 2). The plastidic genome of various plants is known (http://megasun.bch.umontreal.ca/ogmp/projects/other/cp_list.html). The sequences of the plastomes of the following have been reported:

*Arabidopsis thaliana* (Sato S et al. (1999) DNA Res. 6 (5):283-290) (GenBank Acc. No.: AP000423; NCBI Acc. No. NC_000932)

*Epifagus virginiana* (Beechdrops; Wolfe K H et al. (1992) J Mol Evol 35(4):304-317; NCBI Acc. No.: NC_001568; GenBank Acc. No.: M81884)

*Lotus japonicus* (Kato T et al. (2000) DNA Res 7(6): 323-330; NCBI Acc. No.: NC_002694; GenBank Acc. No.:AP002983)

*Oryza sativa* (rice) (Hiratsuka J et al. (1989) Mol Gen Genet 217(2-3):185-194; NCBI Acc. No.: NC_001320; GenBank Acc. No: X15901), Marchantia polymorpha (Liverwort; Ohyama K et al. (1988) J Mol Biol 203(2):281-298; Yamano Y et al. (1984) Nucl Acids Res 12(11):4621-4624; GenBank Acc. No.: X04465 and Y00686; NCBI Acc. No.: NC_001319)

*Nicotiana tabacum* (tobacco) (GenBank Acc. No.: Z00044 and S54304; NCBI Acc. No.: NC_001879; Shinozaki K et al. (1986) EMBO J 5:2043-2049)

*Oenothera elata* ssp. *hookeri* (Monterey evening primrose; GenBank Acc. No.: AJ271079; NCBI Acc. No.: NC_002693; Hupfer H et al. (2000) Mol Gen Genet 263(4):581-585)

*Medicago truncatula* (Gen Bank Acc. No.: AC093544)

*Pinus thunbergii* (black pine; Tsudzuki J et al. (1994) Curr Genet 26(2):153-158; NCBI Acc. No.:NC_001631; GenBank Acc. No.: D17510)

*Spinacia oleracea* (GenBank Acc. No.: AJ400848 J01442 M12028 M16873 M16878 M27308 M55297 X00795 X00797 X01724 X04131 X04185 X05916 X06871)

*Triticum aestivum* (wheat; GenBank Acc. No.: AB042240; NCBI Acc. No.: NC_002762) and

*Zea mays* (GenBank Acc. No.: X86563; NCBI Acc. No.: NC_001666)

In addition, further plastomes can be sequenced in order to identify DSB recognition sites therein. In general, it suffices to isolate highly-conserved regions from the plastome by PCR methods with which the skilled worker is familiar and to sequence these regions only.

Furthermore, it is possible to determine natural, endogenous DSB recognition sites experimentally, for example by isolating the plastidic DNA (for example by the method of Mariac P et al. (2000) BioTechniques 28:110-113), amplifying the plastidic genome fragments to be taken into consideration by means of PCR or by using synthetic fragments and carrying out a restriction analysis with the DSBI enzyme in question. This restriction analysis is preferably carried out under conditions as they prevail in the plastid of a higher plant.

Moreover, the endogenous DSB recognition sequences for natural homing endonucleases which have been identified and described in Table 1 within the scope of the present invention are located in the conserved regions of the plastome so that—in particular taking into consideration the given variability, with regard to their respective recognition sequences, of the homing endonucleases mentioned in each case—it can be assumed that these recognition sequences are found virtually universally in all the plastomes of higher plants. The positions shown in Table 1 reveal in each case the sequence stated and the reverse-complementary sequence, since all of the recognition regions shown in Table 1 are localized in the inverted repeat of the plastidic genome. Homing endonucleases which are especially preferred among those mentioned in Table 1 are I-CpaI, I-CeuI, I-ChuI, I-CpaII and I-CreI.

The recognition sequences identified thus can be used for the insertion of foreign DNA by generating a double-strand break by introducing the corresponding DSBI enzyme. If the DSB recognition sequence were to be located in a highly-conserved region within a gene of the organelle genome, the foreign DNA is preferably inserted in the form of a self-splicing intron, which allows the reconstitution of the mRNA of the affected gene (see hereinbelow).

The skilled worker is furthermore familiar with methods in which any endogenous sequence can act as recognition sequence for chimeric, mutated or artificial endonucleases, by subjecting their DNA recognition region to directed modification, for example by modification of a zinc finger domain fused to an endonuclease domain, or by modification of the RNA sequence of a group II intron RNA/protein complex (see hereinabove; WO 96/06166, Bibikova M et al. (2001) Mol Cell Biol 21:289-297).

Tab 1: Preferred endogenous cleavage sites in the plastidic genomes of tobacco, wheat, rice, maize and *Arabidopsis*. c=complementary. Acc. No: GenBank Accession Number (http://www.ncbi.nlm.nih.gov/).

Singular cleavage sites of restriction endonucleases also exist in the plastidic genome. However, they are usually located in less highly-conserved regions and can therefore not necessarily be exploited universally in all plant species. The following may be mentioned by way of example:

a) With the sequence GGCCTTTATGGCC the enzyme SfiI has a singular recognition site in the plastidic genome of *Arabidopsis* (GenBank Acc. No.: AP000423) at position 40846-40858.

b) In the plastidic genome of maize (GenBank Acc. No.: X86563), there is a singular cleavage site for the enzyme AscI at position 42130-42137, with the sequence GGCGCGCC.

| DSBI enzyme | Published DSB recognition sequence | Sequence in the plastome | Position in the tobacco plastome Acc. Z00044 | Position in the wheat plastome Acc. AB042240 |
|---|---|---|---|---|
| I-DmoI | ATGCGCGCCGGAACT TACCCGGCAAGGCAT | GTGCGGGTCGGAACT TACCCGACAAGGAAT | c(108281-108310) 134316-134345 | 118010-118039 c(96855-96884) |
| I-CpaI | CGATCCTAAGGTAGC GAAATTCA | CGGTCCTAAGGTAGC GAAATTCC | 108263-108285 c(134341-134363) | 96837-96859 c(118035-118057) |
| I-CeuI | CGTAACTATAACGGT CCTAAGGTAGCGAA | CGTAACTATAACGGT CCTAAGGTAGCGAA | c(134346-134374) 108252-108280 | c(118040-118068) 96826-96854 |
| I-ChuI | GAAGGTTTGGCACCT CGATGTCGGCTCATC | GAAGGTTTGGCACCT CGATGTCGGCTCTTC | 108832-108861 c(133765-133794) | 97405-97434 c(117460-117489) |
| I-CpaII | CCCGGCTAACTCTGT GCCAG | ATCGGCTAACTCTGT GCCAG | c(139398-139417) 103209-103228 | c(123374-123393) 91501-91520 |
| I-CreI | CTGGGTTCAAAACGT CGTGAGACAGTTTGG | CTGGGTTCAGAACGT CGTGAGACAGTTCGG | 108925-108954 c(133672-133701) | 97498-97527 c(117367-117396) |
| I-SceI | TACCCTGTTATCCCT AGCGTAACT | CAGCCTGTTATCCCTA GAGTAACT | c(108804-108781) 133822-133845 | c(97377-97354) 117516-117540 |

| DSBI enzyme | Position in the rice plastome Acc. X159019 | Position in the maize plastome Acc. X86563 | Position in the *Arabidopsis* plastome Acc. AP000423 |
|---|---|---|---|
| I-DmoI | 117846-117875 c(97243-97272) | 121617-121646 c(101091-101120) | 131977-132006 c(106643-106672) |
| I-CpaI | 97224-97246 c(117871-117893) | 101073-101095 c(121642-121664) | 106625-106647 c(132002-132024) |
| I-CeuI | c(117876-117904) 97214-97242 | 101062-101090 c(121647-121675) | c(132007-132035) 106614-106642 |
| I-ChuI | 97792-97821 c(117297-117326) | 101641-101670 c(121067-121096) | 107194-107223 c(131426-131455) |
| I-CpaII | c(123351-123370) 91748-91767 | c(127108-127127) 95610-95629 | c(137169-137188) 101461-101480 |
| I-CreI | 97885-97914 c(117204-117233) | deviating sequence: ctgggttcagaac gtcgtgagacgttcgg c(120975-121003) 101734-101762 | 107287-107316 c(131333-131362) |
| I-SceI | c(97741-97764) 117354-117377 | c(101590-101613) 121124-121147 | c(107143-107166) 131483-131506 | c) In the plastidic genome of rice (GenBank Acc. No.: X159019), there is a singular cleavage site for the enzyme SgfI at position 77309-77316, with the sequence GCGATCGC, and for the enzyme AscI at position 39776-39783 with the sequence GGCGCGCC.

d) In the plastidic genome of tobacco (Accession Z00044), there is in each case a singular cleavage site for the enzyme SfiI at position 42475-42487, with the sequence GGCCTTTATGGCC, for the enzyme SgrI at position 78522-78529, with the sequence CACCG-GCG, and for the enzyme PmeI at position 120895-120902, with the sequence GTTTAAAC.

e) In the plastidic genome of wheat (Accession AB042240), there is in each case a singular cleavage site for the enzyme PmeI at position 59331-59338, with the sequence GTTTAAAC, a singular cleavage site for the enzymes NarI, KanI, EheI and BbeI at position 41438-41443, with the recognition sequence GGCGCC, and a recognition region for the enzyme SfiI at position 112656-112668, with the sequence GGCCCAGGGGGCC.

All these plants with endogenous, natural DSB recognition sequences constitute, in a manner of speaking, naturally occurring master plants. In them, the DSB recognition sequence is naturally present in homoplastomic form. This eliminates the need for the introduction and selection of artificial DSB recognition sequences.

b) Artificially Introduced DSB Recognition Sequences

The skilled worker realizes that the recognition region for a rare enzyme introduced into a master plant need not be of natural origin. In principle, any recognition sequence of any DSBI enzyme can be inserted at any position of the plastidic DNA. The preparation is preferably carried out using a construct for inserting the DSB recognition sequence (hereinbelow DSBR construct). Preferably, the DSBR construct comprises a selection marker to facilitate the selection of transplastomic plants with the successfully inserted DSB recognition sequence, which selection is required for generating suitable master plants. The skilled worker is familiar with a variety of selection markers which make possible selection of plastids (see hereinbelow). aada, nptII or BADH are preferred, with aadA being especially preferred. Selection is carried out for example with the aid of the "segregation and sorting" process, with which the skilled worker is familiar (described by way of example in Example 4). The selection marker is preferably constructed in such a way that a subsequent deletion from the plastome is made possible. Such methods are known to the skilled worker and described hereinbelow.

Thus, it is preferred first to generate a plant which is homotransplastomic with regard to the inserted DSB recognition sequence and which has a DSB recognition sequence in all or the predominant number of the plastids of the plant in question. Such plants can advantageously be employed as master plants.

In addition to the selection marker, the DSBR construct may comprise further sequences. These may contain for example further regulatory elements for the expression of the insertion sequences to be introduced subsequently. In a preferred embodiment, the selection marker introduced within the construct for insertion of the DSB recognition sequence is deleted after obtaining the homoplastomic master plant by methods known to the skilled worker (see hereinbelow).

In a preferred embodiment, the DSBR construct comprises, for making possible a site-specific insertion, further flanking sequences at least one, preferably at both sides of the DSB recognition sequence, which flanking sequences have sufficient length and homology with corresponding target sequences in the plastome to ensure site-specific insertion by means of homologous recombination.

Owing to the large number of the DSBI enzymes with defined recognition sequences which have been described in the prior art, it is possible, and preferred, to generate master plants which have a plurality of different singular DSB recognition sequences incorporated into their plastidic genome.

The recognition sequences for the respective DSBI enzymes listed are mentioned hereinbelow in Table 2 by way of example, but not by limitation.

TABLE 2

Recognition sequences and source organism of the DSBI enzymes ("^" shows the cleavage site of the DSBI enzyme within a recognition sequence.)

| DSBI enzyme | Source organism | Recognition sequence |
|---|---|---|
| I-AniI | *Aspergillus nidulans* | 5'-TTGAGGAGGTT^TCTCTGTAAATAANNNNNNNNNNNNNNN<br>3'-AACTCCTCCAAAGAGACATTTATTNNNNNNNNNNNNNNN^ |
| I-CvuI | *Chlorella vulgaris* | 5'-CTGGGTTCAAAACGTCGTGA^GACAGTTTGG<br>3'-GACCCAAGTTTTGCAG^CACTCTGTCAAACC |
| I-CsmI | *Chlamydomonas smithii* | 5'-GTACTAGCATGGGGTCAAATGTCTTTCTGG |
| I-CmoeI | *Chlamydomonas moewusii* | 5'-TCGTAGCAGCT^CACGGTT<br>3'-AGCATCG^TCGAGTGCCAA |
| I-CreI | *Chlamydomonas reinhardtii* | 5'-CTGGGTTCAAAACGTCGTGA^GACAGTTTGG<br>3'-GACCCAAGTTTTGCAG^CACTCTGTCAAACC |
| I-ChuI | *Chlamydomonas humicola* | 5'-GAAGGTTTGGCACCTCG^ATGTCGGCTCATC<br>3'-CTTCCAAACCGTG^GAGCTACAGCCGAGTA |

TABLE 2-continued

Recognition sequences and source organism of the DSBI enzymes ("^" shows the cleavage site of the DSBI enzyme within a recognition sequence.)

| DSBI enzyme | Source organism | Recognition sequence |
|---|---|---|
| I-CpaI | *Chlamydomonas pallido-stigmatica* | 5'-CGATCCTAAGGTAGCGAA^ATTCA<br>3'-GCTAGGATTCCATC^GCTTTAAGT |
| I-CpaII | *Chlamydomonas pallido-stigmatica* | 5'-CCCGGCTAACTC^TGTGCCAG<br>3'-GGGCCGAT^TGAGACACGGTC |
| I-CeuI | *Chlamydomonas eugametos* | 5'-CGTAACTATAACGGTCCTAA^GGTAGCGAA<br>3'-GCATTGATATTGCCAG^GATTCCATCGCTT |
| I-DmoI | *Desulfurococcus mobilis* | 5'-ATGCCTTGCCGGGTAA^GTTCCGGCGCGCAT<br>3'-TACGGAACGGCC^CATTCAAGGCCGCGCGTA |
| I-SceI | *Saccharomyces cerevisiae* | 5'-AGTTACGCTAGGGATAA^CAGGGTAATATAG<br>3'-TCAATGCGATCCC^TATTGTCCCATTATATC<br>5'-TAGGGATAA^CAGGGTAAT<br>3'-ATCCC^TATTGTCCCATTA ("Core" sequence) |
| I-SceII | *Saccharomyces cerevisiae* | 5'-TTTTGATTCTTTGGTCACCC^TGAAGTATA<br>3'-AAAACTAAGAAACCAG^TGGGACTTCATAT |
| I-SceIII | *Saccharomyces cerevisiae* | 5'-ATTGGAGGTTTTGGTAAC^TATTTATTACC<br>3'-TAACCTCCAAAACC^ATTGATAAATAATGG |
| I-SceIV | *Saccharomyces cerevisiae* | 5'-TCTTTTCTCTTGATTA^GCCCTAATCTACG<br>3'-AGAAAAGAGAAC^TAATCGGGATTAGATGC |
| I-SceV | *Saccharomyces cerevisiae* | 5'-AATAATTTTCT^TCTTAGTAATGCC<br>3'-TTATTAAAAGAAGAATCATTA^CGG |
| I-SceVI | *Saccharomyces cerevisiae* | 5'-GTTATTTAATG^TTTTAGTAGTTGG<br>3'-CAATAAATTACAAAATCATCA^ACC |
| I-SceVII | *Saccharomyces cerevisiae* | 5'-TGTCACATTGAGGTGCACTAGTTATTAC |
| PI-SceI | *Saccharomyces cerevisiae* | 5'-ATCTATGTCGGGTGC^GGAGAAAGAGGTAAT<br>3'-TAGATACAGCC^CACGCCTCTTTCTCCATTA |
| F-SceI | *Saccharomyces cerevisiae* | 5'-GATGCTGTAGGC^ATAGGCTTGGTT<br>3'-CTACGACA^TCCGTATCCGAACCAA |
| F-SceII | *Saccharomyces cerevisiae* | 5'-CTTTCCGCAACA^GTAAAATT<br>3'-GAAAGGCG^TTGTCATTTTAA |
| I-LlaI | *Lactococcus lactis* | 5'-CACATCCATAAC^CATATCATTTTT<br>3'-GTGTAGGTATTGGTATAGTAA^AAA |
| I-MsoI | *Monomastix species* | 5'-CTGGGTTCAAAACGTCGTGA^GACAGTTTGG<br>3'-GACCCAAGTTTTGCAG^CACTCTGTCAAACC |
| I-NanI | *Naegleria andersoni* | 5'-AAGTCTGGTGCCA^GCACCCGC<br>3'-TTCAGACC^ACGGTCGTGGGCG |
| I-NitI | *Naegleria italica* | 5'-AAGTCTGGTGCCA^GCACCCGC<br>3'-TTCAGACC^ACGGTCGTGGGCG |
| I-NjaI | *Naegleria jamiesoni* | 5'-AAGTCTGGTGCCA^GCACCCGC<br>3'-TTCAGACC^ACGGTCGTGGGCG |
| I-PakI | *Pseudendoclonium akinetum* | 5'-CTGGGTTCAAAACGTCGTGA^GACAGTTTGG<br>3'-GACCCAAGTTTTGCAG^CACTCTGTCAAACC |
| I-PorI | *Pyrobaculum organotrophum* | 5'-GCGAGCCCGTAAGGGT^GTGTACGGG<br>3'-CGCTCGGGCATT^CCCACACATGCCC |

TABLE 2-continued

Recognition sequences and source organism of the DSBI enzymes ("^" shows the cleavage site of the DSBI enzyme within a recognition sequence.)

| DSBI enzyme | Source organism | Recognition sequence |
|---|---|---|
| I-PpoI | *Physarum polycephalum* | 5'-TAACTATGACTCTCTTAA^GGTAGCCAAAT<br>3'-ATTGATACTGAGAG^AATTCCATCGGTTTA<br>"Core sequence":<br>    CTCTCTTAA^GGTAGC<br>    GAGAG^AATTCCATCG |
| I-ScaI | *Saccharomyces capensis* | 5'-TGTCACATTGAGGTGCACT^AGTTATTAC<br>3'-ACAGTGTAACTCCAC^GTGATCAATAATG |
| I-Ssp6803I | *Synechocystis* species | 5'-GTCGGGCT^CATAACCCGAA<br>3'-CAGCCCGAGTA^TTGGGCTT |
| PI-PfuI | *Pyrococcus furiosus* Vc1 | 5'-GAAGATGGGAGGAGGG^ACCGGACTCAACTT<br>3'-CTTCTACCCTCC^TCCCTGGCCTGAGTTGAA |
| PI-PfuII | *Pyrococcus furiosus* Vc1 | 5'-ACGAATCCATGTGGAGA^AGAGCCTCTATA<br>3'-TGCTTAGGTACAC^CTCTTCTCGGAGATAT |
| PI-PkoI | *Pyrococcus kodakaraensis* KOD1 | 5'-GATTTTAGAT^CCCTGTACC<br>3'-CTAAAA^TCTAGGGACATGG |
| PI-PkoII | *Pyrococcus kodakaraensis* KOD1 | 5'-CAGTACTACG^GTTAC<br>3'-GTCATG^ATGCCAATG |
| PI-PspI | *Pyrococcus* sp. | 5'-AAAATCCTGGCAAACAGCTATTAT^GGGTAT<br>3'-TTTTAGGACCGTTTGTCGAT^AATACCCATA |
| PI-TfuI | *Thermococcus fumicolans* ST557 | 5'-TAGATTTTAGGT^CGCTATATCCTTCC<br>3'-ATCTAAAA^TCCAGCGATATAGGAAGG |
| PI-TfuII | *Thermococcus fumicolans* ST557 | 5'-TAYGCNGAYACN^GACGGYTTYT<br>3'-ATRCGNCT^RTGNCTGCCRAARA |
| PI-ThyI | *Thermococcus hydro-thermalis* | 5'-TAYGCNGAYACN^GACGGYTTYT<br>3'-ATRCGNCT^RTGNCTGCCRAARA |
| PI-TliI | *Thermococcus litoralis* | 5'-TAYGCNGAYACNGACGG^YTTYT<br>3'-ATRCGNCTRTGNC^TGCCRAARA |
| PI-TliII | *Thermococcus litoralis* | 5'-AAATTGCTTGCAAACAGCTATTACGGCTAT |
| I-TevI | Bacteriophage T4 | 5'-AGTGGTATCAAC^GCTCAGTAGATG<br>3'-TCACCATAGT^TGCGAGTCATCTAC |
| I-TevII | Bacteriophage T4 | 5'-GCTTATGAGTATGAAGTGAACACGT^TATTC<br>3'-CGAATACTCATACTTCACTTGTG^CAATAAG |
| F-TevI | Bacteriophage T4 | 5'-GAAACACAAGA^AATGTTTAGTAAANNNNNNNNNNNNNN<br>3'-CTTTGTGTTCTTTACAAATCATTTNNNNNNNNNNNNNN^ |
| F-TevII | Bacteriophage T4 | 5'-TTTAATCCTCGCTTC^AGATATGGCAACTG<br>3'-AAATTAGGAGCGA^AGTCTATACCGTTGAC |

Also comprised are deviations (degenerations) of the recognition sequence which nevertheless continue to make possible recognition and cleavage by the DSBI enzyme in question. Such deviations—also in connection with different framework conditions such as, for example, calcium or magnesium concentrations—have been described (Argast G M et al. (1998) J Mol Biol 280: 345-353). Furthermore comprised are core sequences of these recognition sequences. It is known that the inner portions of the recognition sequences also suffice for an induced double-strand break and that the outer portions are not necessarily relevant, but may have an effect on the cleavage efficiency. Thus, for example, an 18 bp core sequence can be defined for I-SceI. The term "DSB recognition sequence" thus also comprises all essentially identical recognition sequences. Essentially identical recognition sequences refers to those recognition sequences which, while deviating from the recognition sequence identified as being optimal for the enzyme in question, still permit cleavage by the same.

Various localization sites (in the case of already existing endogenous DSB recognition sequences) or integration sites (in the case of artificially generated DSB recognition sequences) are possible for the DSB recognition sequence. Examples which may be mentioned are:

a) Localization (integration)-in a transcriptionally silent region

Localization (integration) of the DSB recognition sequence in a transcriptionally silent region of the plastidic genome (intergenic region) is the preferred embodiment. In this manner, an adverse effect on the plastids' functions can be largely ruled out. In this context, it must be noted that, if appropriate, suitable regulatory elements such as promoters and the like must also be introduced for expression to take place.)

b) Localization (integration) in a transcriptionally active but noncoding (intercistronic) region The advantage of this localization (integration) is that the insertion sequence to be introduced is thereby ultimately encoded in a plastidic operon and promoter(s)/terminator(s) need not be introduced separately, but those present endogenously at this locus can, but do not have to, be utilized. In such a case, only ribosome binding sites should be present at a suitable distance upstream of the coding region of the foreign genes to be introduced. However, it is also feasible that an intergenic region is not entirely transcriptionally silent, for example because transcriptional termination from an adjacent gene or operon is only inefficient.)

c) Localization (integration) in a transcriptionally active coding region.

The localization (integration) described under a) and b) of the DSB recognition sequence at a noncoding locus has the advantage that the insertion of the foreign DNA is highly likely not to affect the function of the plastidic genome. However, noncoding regions are less well conserved than coding regions. In order to have available as universal a method as possible which works in many plant species, the DSB recognition sequence (and therefore the insertion sequence) is, in an especially preferred embodiment, localized in the coding sequence of an existing gene. Destruction of the gene function by introducing the DSB recognition sequence (in the case of an artificially generated DSB recognition sequence), or the introduction of the insertion sequence, is prevented inventively, in a preferred variant of this embodiment, by introducing the DSB recognition sequence, or the insertion sequence, within an intron. In this manner, the complete coding mRNA is regenerated at the site of integration by splicing the pre-RNA of the gene.

DSB recognition sequences which do not occur naturally in the plastidic DNA can be introduced into the plastidic DNA in various ways. Examples which may be mentioned are:

a) Integration by means of double crossover

Integration into the plastidic genome is preferably carried out with the aid of the above-described methods with which the skilled worker is generally familiar (double crossover).

b) Integration using natural, endogenous DSB recognition sequences c) Integration using recombinases and corresponding recognition sequences.

Even though the procedure for inserting an artifical DSB recognition sequence into the plastidic DNA is relatively complicated and, in case a), corresponds to the plastid transformation method currently described in the prior art, this complicated procedure only has to be carried out once. The resulting homotransplastomic master plant can then be employed for any number of different subsequent transformations using the method according to the invention, which makes possible a substantial increase in the transformation efficiency: instead of having to carry out the conventional selection process for a homotransplastomic plant every single time, it only has to be carried out once in the present context.

"Deactivation of the functionality" of a DSB recognition sequence means that, owing to insertion of the insertion sequence at or near the position of the double-strand break, the DSB recognition sequence is destroyed, i.e. the corresponding DSBI enzyme no longer recognizes the region and, accordingly, no longer induces a double-strand break at this position.

Construction of the transformation construct with the insertion sequence

Using one of the above-described master plants or cells derived from them which contain a natural and/or an artificially generated DSB recognition sequence in the plastome, the insertion sequence is inserted into said DSB recognition sequence within a transformation process. This is effected with the simultaneous presence of a DSBI enzyme, which recognizes one of the DSB recognition sequences in the plastome.

In its simplest form, the transformation construct consists only of the insertion sequence itself, for example of an expression cassette which is to ensure the expression of a certain gene in the plastids. The sequence-specific induction of double-strand breaks suffices to ensure that this insertion sequence is placed at this position and thus to bring about the deactivation of the DSB recognition sequence.

In a preferred embodiment, the insertion sequence comprises at least one nucleic acid sequence to be expressed. To ensure expression (transcription and/or translation), they are to be provided with regulatory elements, depending on the embodiment and the insertion site. If insertion takes place at a transcriptionally active locus, no promoter sequences are required, as described above. The sequences to be expressed are advantageously provided in any case with ribosome binding sites at a suitable distance upstream of the open reading frame, or are already equipped naturally with such sites. These regulatory sequences or parts thereof can, however, also be present naturally in the plastome or introduced into the plastidic DNA together with the DSB recognition sequence as early as in the first step, i.e. in the generation of a nonnatural master plant.

An increase of the insertion efficiency and insertion accuracy can be brought about by flanking the insertion sequence present in the transformation construct and the DSB recognition sequence by homologous sequence regions which, owing to the induced double-strand break, ensure homologous recombination. In a preferred embodiment, the insertion sequence comprises flanking homology sequences A' and B', the sequence to be introduced into the plastidic DNA being located between A' and B'. The DSB recognition sequence is flanked by homology sequences A and B, respectively, the DSB recognition sequence being located between A and B. A and B can be of natural origin or have been introduced in context with the insertion of nonnatural DSB recognition sequences. A and A' and B and B', respectively, are sufficiently long and sufficiently homologous to one another to ensure a homologous recombination between A and A', and B and B', respectively.

In a further embodiment, the DSB recognition sequence is flanked merely by a homologous sequence A which has sufficient homology to a sequence A' which flanks the insertion sequence unilaterally.

With regard to the homology sequences, "sufficient length" preferably means sequences with a length of at least 20 base pairs, preferably at least 50 base pairs, especially preferably at least 100 base pairs, very especially preferably at least 250 base pairs, most preferably at least 500 base pairs.

With regard to the homology sequences A and A', and B and B', respectively, "sufficient homology" preferably means sequences which have at least 70%, preferably 80%, by preference at least 90%, especially preferably at least 95%, very especially preferably at least 99%, most preferably 100% homology within these homology sequences over a length of at least 20 base pairs, preferably at least 50 base pairs, especially preferably at least 100 base pairs, very especially preferably at least 250 base pairs, most preferably at least 500 base pairs.

Homology between two nucleic acids is understood as meaning the identity of the nucleic acid sequence over in each case the entire sequence length which is calculated by alignment with the aid of the program algorithm GAP (Wisconsin Package Version 10.0, University of Wisconsin, Genetics Computer Group (GCG), Madison, USA), setting the following parameters:

Gap Weight: 12 Length Weight: 4

Average Match: 2,912 Average Mismatch: −2,003

Since homologous recombination is promoted by the induced double-strand break, the requirements regarding length and homology of the sequences are markedly less than is the case for example in the case of conventional homologous recombination. In this context, the homologous regions can also be markedly smaller than 250 bp. The advantage of using homology sequences is that, when A' and B' are different, or when only one homology sequence A' is being used, a directed insertion of the insertion sequence into the plastidic DNA can take place.

The transformation construct or the insertion sequence preferably comprises a selection marker which makes possible the selection of transplastomic plastids (see hereinbelow), especially preferably aada, BADH or a binding-type marker. The selection marker is preferably constructed in such a way that subsequent deletion from the plastome is made possible. Such methods are known to the skilled worker and described hereinbelow.

The insertion sequence or the transformation construct preferably has the structure and sequence of an intron. As a rule, the naturally occurring introns are modified in such a manner for this purpose that they meet the requirements of the method according to the invention. Such artificial introns are especially preferred when they are to be inserted into a transcriptionally active or even coding region, for example, using a natural, endogenous DSB recognition sequence. Preferably, insertion takes place in such a way that the inserted sequence is removed completely by splicing the pre-mRNA. The RNA which has been spliced out (that is to say the artificial intron) now constitutes the mRNA, for example for the translation of proteins encoded on it. This method has further advantages:

The introns utilized show pronounced secondary folding so that a relatively stable RNA results. The genes of interest which are encoded in the intron can therefore be expressed at a particularly high level, as has been demonstrated, for example, in *E. coli* (Chan K Y W et al. (1988) Gene 73:295-304).

When the intron is integrated into a gene, the transcription of the intron is subject to the regulatory control of the gene into which the intron has been integrated. This is why all regulatory elements upstream or downstream of the gene(s) of interest can be dispensed with in the intron. The constructs can thus be kept correspondingly small, and it is certain that transcription does indeed work, including in the species under investigation. The utilization of heterologous regulatory elements involves the residual risk that these elements are not functional in the investigated plastids of the plant species in question. The utilization of homologous sequences can, owing to the sequence duplication, lead to spontaneous recombination events with the endogenous sequences and thus to instability of the organelle genome. Owing to the possibility of largely being able to dispense with the introduction of regulatory elements—for example by encoding the gene of interest in an intron which is inserted into a transcriptionally active plastome region—many other disadvantages of conventional plastid transformation can be avoided with the method according to the invention in this embodiment, in addition to increasing the insertion and distribution ability of the transformation constructs.

Moreover, all introns can be used when the relevant factors which mediate splicing are simultaneously expressed in the plastids or imported into them. Preferably, the splicing factors are encoded in the intron itself. Group II introns, which themselves encode at least one of the splice factors, are especially preferred in this embodiment. They include the *Lactococcus* Ll.ltrB intron. Likewise preferred introns are those which naturally occur in the plastids of higher plants, especially group II introns, very especially preferably introns which encode a protein, most preferably introns of the trnK genes of the plastidic genome. In the latter case, the introns from the trnk genes of the plastids from the species *Arabidopsis*, maize and tobacco are especially preferred.

Preferred introns are those which have a self-splicing activity which does not depend on further protein factors, or introns which utilize general factors for splicing which are universally present, and therefore also in plastids, and also introns which themselves encode factors required for splicing. These introns include, for example, a) the group I intron from Tetrahymena (GenBank Acc. No.: X54512; Kruger K et al. (1982) Cell 31:147-157; Roman J and Woodson S A (1998) Proc Natl Acad Sci USA 95:2134-2139)

b) the group II rII intron from Scenedesmus obliquus (GenBank Acc. No.: X17375.2 nucleotides 28831 to 29438; Holländer V and Kück U (1999) Nucl Acids Res 27: 2339-2344; Herdenberger F et al. (1994) Nucl Acids Res 22: 2869-2875; Kück U et al. (1990) Nucl Acids Res 18:2691-2697).

c) the Ll.LtrB intron (GenBank Acc. No.: U50902 nucleotides 2854 to 5345)
d) the *Arabidopsis* trnK intron (GenBank Acc. No.: AP000423, complementary nucleotides 1752 to 4310)
e) the maize trnK intron (GenBank Acc. No.: X86563, complementary nucleotides 1421 to 3909)
f) the tobacco trnK intron (GenBank Acc. No.: Z00044, complementary nucleotides 1752 to 4310).

Not only heterologous introns, but also introns which naturally occur in the plastids of the plant in question can be utilized. Heterologous introns—for example heterologous trnk introns—are preferred to avoid instabilities brought about by sequence duplication. In a preferred embodiment, introns which occur naturally in the plastids of the plant in question are modified in such a way that they have a sequence homology of less than 95%, preferably 80%, especially preferably 70% with the sequence of the starting intron, while still being able to retain their function.

In a further preferred embodiment, a factor which brings about splicing of the intron in question is available in trans, i.e. it is not encoded in the intron itself. If this factor is not naturally present in the plastid in question, but first has to be introduced into it, such a procedure can be effected in various ways with which the skilled worker is familiar. Examples which may be mentioned are the introduction of a suitable coding sequence, which is capable of expression, into the plastome or the introduction into the nuclear DNA; in the latter case, the factor is preferably fused with a PLS.

Especially preferred introns are those which naturally encode a DSB enzyme (in particular a homing endonuclease). Especially preferred is the intron Cp.LSU2 from *Chlamydomonas pallidostigmatica*, which encodes the enzyme I-CpaI (Turmel M et al. (1995) Mol Biol Evol 12:533-545). Also preferred are the group-II introns from yeast mitochondria.

In a preferred embodiment, the intron sequence is adapted to suit the insert site so that they can splice at this locus. In the case of group I introns, this adaptation can relate to the internal guide sequence (IGS) and in the case of the group II introns the exon binding sequence (EBS) I and/or II.

In the case of the maize trnK intron, it must be noted that the protein encoded by the trnK intron, which also comprises the maturase function, is probably not functional in its naturally encoded form without editing. It has been demonstrated that editing (His420Tyr) of the corresponding mRNA takes place in barley plastids (Vogel J et al. (1997) J Mol Biol 270:179-187). Tyrosine at position 420 of the matK protein is highly conserved. In the monocots rice and maize, too, a codon encoding His has been found at the corresponding position in the coding DNA. It can therefore be assumed that the matK transcript is also edited in those plants, as is the case in barley. Since, however, other plant species may, if appropriate, not be able to provide such RNA editing, a preferred embodiment provides that the matK gene in the maize trnk intron is already modified at DNA level by a suitable His/Tyr substitution, so that RNA editing is no longer required. For example, the sequence CATTATCATAGTGGAT of the maize trnk intron can be mutated into CATTATTATAGTGGAT.

In the case of group I introns, the splicing site is determined by the pairing of IGS with the exon of the corresponding transcript, which exon is located 5' and/or 3' relative to the intron (Lambowitz A M & Belfort M (1993) Annu Rev Biochem 62:587-622). Using techniques which are known to the skilled worker, such as PCR or the synthetic generation of nucleotide sequences, the IGS can be matched to any group I introns in such a way that splicing takes place at the predefined insertion site within the DSB recognition region. The modified IGS is designed in such a way that it can undergo—at least partial—base pairing with the sequences of the transcript 5' and 3' of the insertion site. The *C. pallidostigmatica* CpLSU2 intron, which encodes the homing endonuclease I-CpaI, is preferably utilized. If this intron is utilized in connection with the expression of the DSBI enzyme I-CpaI, whereby insertion of the DNA to be transformed into the 23S rDNA of the plastidic genome of higher plants results, no adaptation of the intron is necessary. Insertion takes place at a locus in the plastidic genome of higher plants which is homologous to the locus at which the intron is naturally present in *C. pallidostigmatica*. This intron is therefore already designed in such a way that pairings with the 5' and 3' exon can be undergone and that correct splicing in this nucleotide environment takes place. Furthermore preferred is the group I intron from Tetrahymena thermophila, where, as a 413 bp intervening sequence (IVS), it interrupts the 26S rRNA coding region (Accession V01416 J01235 nucleotides 53 to 465). The IGS with the sequence 5'-ggaggg-3' which can be found naturally (Waring R B et al. 1985 Cell 40: 371-380; Been, M D & Cech, T R 1986 Cell 47: 207-216) can be adapted to the new insertion site by techniques with which the skilled worker is familiar. If, for example, integration into the DSB recognition site of the I-CpaI enzyme at the position identified by ^ (cggtcct^aaggagcgaaattc) is desired, the mutated, adapted IGS can, for example, have the following sequence: 5'-gggacc-3'.

In group II introns, which are mobile, further activities in addition to maturase are frequently encoded in the protein moiety of the ribonucleoprotein complex. However, these are not necessarily required for the method described and can therefore be deleted. Indeed, deletion is preferred since it makes the construct in question smaller and easier to handle. The skilled worker is familiar with a variety of options for removing such activities from the protein moiety. For example, this can be effected by generating a synthetic gene which comprises only the desired regions, or by suitable PCR methods.

Self-splicing group II introns have a conserved structure and generally consist of 6 different domains. Domain I comprises the exon binding sites (EBS1 and EBS2) which, during the splicing procedure, interact with the exon located 5' from the intron. In addition, an interaction between the "δ region" (located immediately 5' of EBS1) and the "δ' region" at the 3' exon takes place (Lambowitz A M & Belfort M (1993) Annu Rev Biochem 62:587-622; Michel F & Ferat J L (1995) Annu Rev Biochem 64:435-461). These sequences can be adapted by techniques with which the skilled worker is familiar, such as synthetic generation of the introns or suitable PCR methods, in each case in such a way that correct choice of the splicing sites at the insert site chosen in the DSB recognition region is ensured. This is done in such a way that the regions mentioned are modified so that base pairings with the corresponding sequences upstream (intron binding sequences, IBS) and downstream (δ') of the artificial insertion sequence can be undergone. If, for example, cggtcctaaggt^agcgaaattc is chosen as insertion site (^) for the Ll.LtrB intron in the I-CpaI recognition region, the δ region and the EBS1 region can, for example, adopt the sequence TCGCTACCTTAG (natural sequence: TTATGGTTGTG), and EBS2 for example the sequence GACCG (natural sequence: ATGTG). If the *Arabidopsis thaliana* trnK intron is selected, the δ region and the EBS1 region can, for example, adopt the sequence CGCTACCTTAGG (natural sequence: AATGTTAAAAA), assuming the same insertion site as indicated for the Ll.LtrB intron.

If the DSB recognition sequence takes the form of a natural, endogenous recognition sequence of a homing endonuclease, a selected intron is preferably inserted at the site of the DSB recognition region at which the intron belonging to the homing endonuclease in question can also be found naturally.

The artificial insertion site of an intron in the DSB recognition site is preferably chosen such that 5' and 3' of the intron inserted as many bases as possible correspond to those of the natural insertion site of the intron in question and that the DSB recognition sequence is no longer functional after insertion of the intron. Very especially preferably, the nucleotide located in each case immediately upstream or downstream of the insert site of the intron corresponds to that at the natural insertion site.

In an especially preferred embodiment, the intron is flanked by homology sequences in order to make possible a directed insertion. Here, the homology sequences are—as described above—homologous to the sequences flanking the DSB recognition sequence and thus make possible an accurate insertion.

The invention therefore furthermore also relates to DNA constructs comprising at least one nucleic acid and intron sequence elements which are capable of ensuring, in a ribonucleic acid sequence derived from said DNA construct, the deletion of the ribonucleic acid fragment encoding said nucleic acid sequence, where said nucleic acid sequence is heterologous with regard to said intron sequence elements.

In a preferred embodiment, the nucleic acid sequence is flanked at least by a splice acceptor sequence and a splice donor sequence.

In a further embodiment, the DNA construct comprises, at the 5' and the 3' end, sequences H1 and H2, respectively, which have sufficient length and homology with plastid sequences H1' and H2', respectively, to ensure homologous recombination between H1 and H1', and H2 and H2', respectively, and thus insertion of the H1- and H2-flanked sequence into the plastome.

The invention furthermore relates to a transgenic plastidic DNA comprising at least one nucleic acid sequence and intron sequence elements which are capable of ensuring, in a ribonucleic acid sequence derived from said transgenic plastidic DNA, the deletion of said ribonucleic acid fragment encoding said nucleic acid sequence, where said nucleic acid sequence is heterologous with regard to said intron sequence elements. In a preferred embodiment, the nucleic acid sequence is flanked by at least one splice acceptor sequence and one splice donor sequence.

To construct a transformation vector, the insertion sequence or the transformation construct can be cloned into a standard vector such as pBluescript or pUC18. In a preferred embodiment, the insertion sequence or the transformation construct is applied as a linear or linearized DNA molecule.

Preferably, only the portion of transformation vector which comprises the insertion sequence or the transformation construct with, if appropriate, homology sequences, selection marker and/or the expression cassette for the DSBI enzyme is applied. If all or some of the homology sequences are dispensed with, the linearized DNA molecule is preferably obtained by digestion with restriction endonucleases which generate single-stranded DNA overhangs at one or at both ends which are compatible with those generated by the DSBI enzyme in the plastidic DNA.

In a preferred embodiment, the transformation vector can comprise elements (for example a plastidic ORI (origin of replication)), which make it possible for the vector autonomously to replicate in the plastid or stably to exist in the plastids as extrachromosomal DNA molecule, before being integrated into the plastidic DNA. Such methods are known to the skilled worker (U.S. Pat. No. 5,693,507; U.S. Pat. No. 5,932,479; WO 99/10513). This method is preferred since it increases the copy number of the insertion sequences which is available for integration in the plastid.

One of the above-described constructs can be introduced into the plastids of a suitable master plant using one of the methods described. Microinjection is preferred, particle bombardment is particularly preferred.

Cloning, Expression, Selection and Transformation Methods

"Expression cassette" means—for example regarding the expression cassette for the DSBI enzyme—those constructions in which the DNA to be expressed is in operable linkage with at least one genetic control element which makes possible or regulates its expression (i.e. transcription and/or translation). In this context, expression can be, for example, stable or transient, constitutive or inducible. A variety of direct methods (for example transfection, particle bombardment, microinjection) or indirect methods (for example agrobacterial infection, viral infection) stated hereinbelow is available to the skilled worker for the introduction, and these methods will be stated hereinbelow.

An operable linkage is generally understood as meaning an arrangement in which a genetic control sequence can exert its function with regard to a nucleic acid sequence, for example encoding a DSBI enzyme. Function, in this context, can mean for example the control of the expression, i.e. transcription and/or translation, of the nucleic acid sequence, for example encoding a DSBI enzyme. Control, in this context, comprises for example initiating, increasing, governing or suppressing the expression, i.e. transcription and, if appropriate, translation. Governing, in turn, can be tissue and/or timing-specific. It may also be inducible, for example by certain chemicals, stress, pathogens and the like.

An operable linkage is understood as meaning for example the sequential arrangement of a promoter, of the nucleic acid sequence to be expressed—for example encoding a DSBI enzyme—and, if appropriate, further regulatory elements such as, for example, a terminator in such a way that each of the regulatory elements can fulfill its function upon expression of the nucleic acid sequence, for example encoding a DSBI enzyme. In this context, operable linkage need not necessarily exist on the transformation constructs themselves. Operable linkage can also result as a consequence of the insertion into the nuclear or plastidic DNA, where the regulatory elements are already present in the nuclear or plastidic DNA. In this respect, the regulatory elements can be naturally present or else introduced in a preceding step, for example when introducing an artificial DSB recognition sequence.

Direct linkage in the chemical sense is not necessarily required in this context. Genetic control sequences such as, for example, enhancer sequences, can also exert their function on the target sequence from positions which are further away, or indeed from other DNA molecules. Preferred arrangements are those in which the nucleic acid sequence to be expressed—for example encoding a DSBI enzyme—is positioned behind a sequence which acts as promoter, so that the two sequences are bonded covalently with one another. Preferably, the distance between the promoter sequence and the nucleic acid sequence—for example encoding a DSBI enzyme—is less than 200 base pairs, especially preferably less than 100 base pairs, very especially preferably less than 50 base pairs.

The skilled worker is familiar with a variety of routes to obtain one of the transformation constructs according to the invention, vectors comprising them or one of the expression cassettes. They can be prepared by means of customary recombination and cloning techniques as are described for example in Maniatis T, Fritsch E F and Sambrook J, Molecular Cloning: A Laboratory Manual, Cold Spring Harbor Laboratory, Cold Spring Harbor, N.Y. (1989) and in Silhavy T J, Berman M L and Enquist L W, Experiments with Gene Fusions, Cold Spring Harbor Laboratory, Cold Spring Harbor, N.Y. (1984) and in Ausubel F M et al., Current Protocols in Molecular Biology, Greene Publishing Assoc. and Wiley Interscience (1987). The direct fusion of a nucleic acid sequence which acts as promoter and a nucleotide sequence to be expressed—for example encoding a DSBI enzyme—is preferred.

The term "genetic control sequences" is to be understood in the broad sense and refers to all those sequences which influence the generation or the function of an expression cassette or transformation vector. Genetic control sequences ensure transcription and, if appropriate, translation in the nucleus (or cytoplasm) or plastids. Preferably, the expression cassettes according to the invention comprise a promoter 5' upstream of the respective nucleic acid sequence to be expressed and a terminator sequence as additional genetic control sequence 3' downstream, and, if appropriate, further customary regulatory elements, in each case in operable linkage with the nucleic acid sequence to be expressed.

Genetic control sequences are described, for example, by "Goeddel; Gene Expression Technology: Methods in Enzymology 185, Academic Press, San Diego, Calif. (1990)" or "Gruber and Crosby, in: Methods in Plant Molecular Biology and Biotechnolgy, CRC Press, Boca Raton, Fla., eds.: Glick and Thompson, Chapter 7, 89-108" and the references cited therein.

Examples of such control sequences are sequences to which the inductors or repressors bind and thus regulate the expression of nucleic acid. The natural regulation of these sequences may still be present before the actual structural genes, in addition to these novel control sequences or instead of these sequences, and, if appropriate, can have been genetically modified so that the natural regulation has been switched off and gene expression enhanced. However, the expression cassette can also be simpler in structure, that is to say no additional regulatory signals are inserted before the abovementioned genes and the natural promoter together with its regulation is not removed. Instead, the natural control sequence is mutated in such a way that regulation no longer takes place and gene expression is enhanced. These modified promoters can also be placed by themselves before the natural genes in order to increase the activity.

Depending on the host organism or the starting organism described in greater detail hereinbelow, which is converted into a genetically modified or transgenic organism by the introduction of the expression cassettes or vectors, different control sequences are suitable.

Promoters which are suitable for nuclear expression (for example of a viral/bacteriophage RNA polymerase or of a DSBI enzyme with plastidic transit peptide) are, in principle, all those which are capable of governing the expression of genes, in particular foreign genes, in plants.

Suitable promoters are those which make possible constitutive expression in plants (Benfey et al. (1989) EMBO J. 8:2195-2202). In particular, a plant promoter or a promoter derived from a plant virus is used by preference. Especially preferred is the promoter of the cauliflower mosaic virus 35S transcript (Franck et al. (1980) Cell 21:285-294; Odell et al. (1985) Nature 313:810-812; Shewmaker et al. (1985) Virology 140:281-288; Gardner et al. 1986, Plant Mol. Biol. 6, 221-228) or the 19S CaMV promoter (U.S. Pat. No. 5,352, 605 and WO 84/02913). As is known, this promoter comprises different recognition sequences for transcriptional effectors which, in their totality, lead to largely permanent and constitutive expression of the gene introduced (Benfey et al. (1989) EMBO J 8:2195-2202). A further suitable constitutive promoter is the "Rubisco small subunit (SSU)" promotor (U.S. Pat. No. 4,962,028). A further example of a suitable promoter is the leguminB promoter (GenBank Acc. No.: X03677). Examples of further preferred constitutive promoters are the *Agrobacterium* nopaline synthase promoter, the TR dual promoter, the *Agrobacterium* OCS (octopine synthase) promoter, the ubiquitin promoter (Holtorf S et al. (1995) Plant Mol Biol 29:637-649), the promoters of the vacuolar ATPase subunits, the FBPaseP promoter (WO 98/18940) or the promoter of a proline-rich protein from wheat (WO 91/13991). Other suitable constitutive promoters which are preferred for the purposes of the present invention are the Super promoter (Ni M et al. (1995) Plant J 7:661-676; U.S. Pat. No. 5,955,646) and the nitrilase-1 promoter of the *Arabidopsis* nit1 gene (GenBank Acc. No.: Y07648.2, nucleotides 2456 to 4340; Hillebrand H et al. (1998) Plant Mol Biol 36 (1):89-99; Hillebrand H et al. (1996) Gene 170(2):197-200).

Promoters which are preferred are inducible promoters, especially preferably chemically inducible promoters (Aoyama T and Chua N H (1997) Plant J 11:605-612; Caddick M X et al. (1998) Nat. Biotechnol 16:177-180; Review: Gatz (1997) Annu Rev Plant Physiol Plant Mol Biol 48:89-108) by means of which expression can be controlled at a particular point in time. Examples which may be mentioned are the PRP1 promoter (Ward et al. (1993) Plant Mol Biol 22:361-366), a salicylic-acid-inducible promoter (WO 95/19443), a benzenesulfonamide-inducible promoter (EP-A-0388186), a tetracyclin-inducible promoter (Gatz et al. (1992) Plant J 2:397-404), an abscisic-acid-inducible promoter (EP-A 335 528), an ethanol-inducible promoter (Salter MG et al. (1998) *Plant J.* 16:127-132), the heavy-metal-inducible metallothionein I promoter (Amini S et al. (1986) Mol Cell Biol 6:2305-2316), the steroid-inducible MMTV LTR promoter (Izant J G et al. (1985) Science 229:345-352) and a cyclohexanone-inducible promoter (WO 93/21334). Especially preferred is the inducible expression of a PLS/DSBI enzyme fusion protein in the nucleus. Inducible promoters also comprise those which are capable of regulation by certain repressor proteins (for example tet, lac). Such repressor proteins can be translocated into the plastids in fusion with PLS, where they regulate the expression of certain genes under the control of suitable promoters. In the plastids, the repressor binds to an artificial repressor binding site which has been introduced into the plastome and can thus repress the expression of the downstream gene (cf. WO 95/25787). In this manner it is possible, for example, to induce the expression of a plastid-encoded DSBI enzyme when required, or to repress it until the point in time at which expression is desired.

Other promoters which are preferred are those which are induced by biotic or abiotic stress such as, for example, the pathogen-inducible promoter of the PRP1 gene (Ward et al., Plant Mol Biol 1993, 22: 361-366), the heat-inducible tomato hsp70 promoter or hsp80 promoter (U.S. Pat. No. 5,187,267), the chill-inducible potato alpha-amylase promoter (WO 96/12814) or the wounding-induced pinII promoter (EP-A 0 375 091).

In an especially preferred embodiment, the nucleic acid which encodes the DSBI enzyme is, above all, expressed under the control of an inducible promoter. A controlled expression capable of being governed is thus obtained, and any problems caused by expressing a DSBI enzyme constitutively are avoided.

Advantageous control sequences for the expression cassettes or vectors according to the invention comprise viral, bacteriophage or bacterial promoters such as cos, tac, trp, tet, phoA, tat, lpp, lac, laciq, T7, T5, T3, gal, trc, ara, SP6, λ-PR or λ-PL promoter. They are preferably employed in combination with the expression of the respective, corresponding RNA polymerase.

The expression in plastids can be effected using plastid promoters and/or transcription regulation elements. Examples which may be mentioned, but not by way of limitation, are the RNA polymerase promoter (WO 97/06250) or the promoters described in WO 00/07431, U.S. Pat. No. 5,877,402, WO 97/06250, WO 98/55595, WO 99/46394, WO 01/42441 and WO 01/07590. The rpo B promoter element, the atpB promoter element, the clpP promoter element (see also WO 99/46394) or the 16S rDNA promoter element should be mentioned. In this context, the promoter can also have a polycistronic "operon" assigned to it (EP-A 1 076 095; WO 00/20611). Systems in which a nonplant (for example viral) RNA polymerase is imported into the plastid using plastidic transit peptides and specifically induces, in the plastid, the expression transgenic sequences which are under the control of the RNA polymerase recognition sequences and have previously been inserted into the plastidic DNA have also been described (WO 95/16783; U.S. Pat. No. 5,925,806; U.S. Pat. No. 5,575,198).

In addition to the abovementioned promoters, the following can also be preferably used:
a) the PrbcL promoter (SEQ ID NO: 44)
b) the Prps16 promoter (SEQ ID NO: 50)
c) the Prrn16 promoter (SEQ ID NO: 46)

In an especially preferred embodiment, NEP promoters are employed. These are promoters which are functional in plastids and are recognized by the nuclear-encoded plastidic RNA polymerases (NEP). The following are preferred: Prrn-62; Pycf2-1577; PatpB-289; Prps2-152; Prps16-107; Pycf1-41; PatpI-207; PclpP-511; PclpP-173 and PaccD-129 (wo 97/06250; Hajdukiewicz P T J et al. (1997) EMBO J 16:4041-4048).

The following are especially preferred:
a) the PaccD-129 promoter of the tobacco accD gene (WO 97/06250; SEQ ID NO: 47)
b) the PclpP-53 promoter of the clpP gene as highly active NEP promoter in chloroplasts (WO 97/06250; SEQ ID NO: 48)
c) the Prrn-62 promoter of the rrn gene (SEQ ID NO: 49)
d) the Prps16-107 promoter of the rps16 gene (SEQ ID NO: 45)
e) the PatpB/E-290 promoter of the tobacco atpB/E gene (Kapoor S et al. (1997) Plant J 11:327-337) (SEQ ID NO: 51)
f) the PrpoB-345 promoter of the rpoB gene (Liere K & Maliga P (1999) EMBO J 18: 249-257) (SEQ ID NO: 52)

In general, all those promoters which belong to class III (Hajdukiewicz PTJ et al. (1997) EMBO J 16:4041-4048) and all fragments of the class II promoters which control the initiation of transcription by NEP can be utilized in this preferred embodiment. Such promoters or promoter moieties are not particularly highly conserved. ATAGAATAAA (SEQ ID NO: 162) is given as consensus near the transcription initiation site of NEP promoters (Hajdukiewicz PTJ et al (1997) EMBO J 16:4041-4048).

Normally, genes are surrounded by regulatory sequences which originate from the plastids of the organism to be transformed. Thus, sequence duplications which can lead to instabilities owing to spontaneous, intrachromosomal homologous recombination events are generated (Heifetz P B (2000) Biochimie 82(6-7):655-666). To overcome this problem, it has been proposed to utilize heterologous regulatory sequences or to exploit regulatory units which already exist endogenously in the plastidic genome (WO 99/46394; WO 01/42441). A reduction of the homology by mutagenesis of the endogenous promoter sequence has also been described (WO 01/07590).

In principle, all natural promoters together with their regulatory sequences, such as those mentioned above, can be used for the method according to the invention. Especially preferred promoters-are those which have been isolated from prokaryotes. Very especially preferred are promoters isolated from *Synechocystis* or *E. coli*. In addition, synthetic promoters such as, for example, a synthetic promoter derived from the *E. coli* consensus sequence for σ70 promoters

5'-TTGACA $N_{16-19}$ TATAAT $N_3$ CAT-3', (SEQ ID NO: 163)

where N represents any nucleotide (that is to say A, G, C or T) can additionally also be used advantageously. It is obvious to the skilled worker that individual or few base substitutions in the conserved regions stated are also possible without destroying the function of the promoter. The variable design of these synthetic promoters by using a variety of sequential sequences makes it possible to generate a multiplicity of promoters which lack extensive homologies, which increases the stability of the expression cassettes in the plastome in particular in the event that several promoters are required. The following, particularly preferred promoter sequences, which are derived from the abovementioned consensus sequence, may be mentioned by way of example, but not by limitation:

(SEQ ID NO: 53)
a) 5'-TTGACATTCACTCTTCAATTATCTATAATGATACA-3'

(SEQ ID NO: 72)
b) 5'-TTGACAATTTTCCTCTGAATTATATAATTAACAT-3'

It is obvious to the skilled worker that these synthetic promoters can control the expression of any genes. For example, they can be utilized for driving the expression of a selection marker, also in order to be able to select under regenerative conditions for transplastomic plants with the aid of said selection system. Examples of selection markers are enumerated further below. In addition, such synthetic promoters can be linked with any gene, for example with genes encoding antibodies, antigens or enzymes. Preferably, the expression cassettes consisting of such promoters also comprise 5'-untranslated regions (or ribosome binding sites) or 3'-noncoding regions which are detailed hereinbelow.

The invention furthermore relates to expression cassettes comprising a nucleic acid sequence encoding a DSBI enzyme under the control of a promoter which is functional in plant plastids, for example one of the above-described promoters. The expression cassette can comprise further elements such as, for example, transcription terminators and/or selection markers.

Genetic control sequences also comprise further promoters, promoter elements or minimal promoters which are capable of modifying the expression-controlling properties. Genetic control sequences furthermore also comprise the 5'-untranslated region (5'-UTR) or the noncoding 3' region (3'-UTR) of genes (Eibl C (1999) Plant J 19: 1-13). It has been demonstrated that these can exert significant functions in regulating the gene expression in plastids of higher plants. In the nucleus, too, genetic control elements such as 5'-UTR, introns or 3'-UTR, can exert a function in gene expression. Thus, for example, it has been demonstrated that 5'-untranslated sequences can enhance the transient expression of heterologous genes. They can furthermore promote tissue specificity (Rouster J et al., Plant J. 1998, 15: 435-440.).

5'-UTRs and 3'-UTRs which are preferably employed in plastids are:
a) 5'psbA (from tobacco) (SEQ ID NO: 54)
b) 5'rbcL including 5' portions from the coding region of the rbcL gene (from tobacco) (SEQ ID NO: 55); the sequence described as SEQ ID NO: 55 has been mutated in comparison with the native sequence in order to introduce a PagI and an NcoI cleavage site.
c) 5'rbcLs (SEQ ID NO: 56); the sequence described by SEQ ID NO: 56 has been mutated in comparison with the native sequence in order to introduce a PagI cleavage site.
d) 3'psbA-1 from *Synechocystis* (SEQ ID NO: 57)
e) 3'psbA from tobacco (SEQ ID NO: 58)
f) 3'rbcL from tobacco (SEQ ID NO: 59)

Genetic control sequences, especially for expression in plastids, also comprise in particular ribosome binding sequences for initiating translation. They are usually present in the 5'-UTRs. This is especially preferred when suitable sequences are not provided by the nucleic acid sequence to be expressed or when such sequences are compatible with the expression system. Especially preferred is the use of a synthetic ribosome binding site (RBS) with the sequence 5'-GGAGG(N)$_{3-10}$ATG-3', preferably 5'-GGAGG(N)$_5$ATG-3' (SEQ ID NO: 60), particularly preferably 5'-GGAGGATCTCATG-3' (SEQ ID NO: 61).

The expression cassette can advantageously comprise one or more what are known as enhancer sequences in operable linkage with the promoter; these enhancer sequences make possible an enhanced transgenic expression of the nucleic acid sequence. Additional advantageous sequences, such as further regulatory elements or terminators, may also be inserted at the 3' end of the nucleic acid sequences to be expressed recombinantly. One or more copies of the nucleic acid sequences to be expressed recombinantly may be present in the gene construct.

It is furthermore possible to insert, after the start codon, what is known as a downstream box, which enhances expression in general (translation enhancer WO 00/07431; WO 01/21782).

Polyadenylation signals which are suitable as genetic control sequences, above all in the transformation of the nucleus, are plant polyadenylation signals, preferably those which correspond essentially to T-DNA polyadenylation signals from *Agrobacterium tumefaciens*, in particular of gene 3 of the T-DNA (octopine synthase) of the Ti plasmid pTiACH5 (Gielen et al., EMBO J. 3 (1984), 835 et seq.) or functional equivalents thereof. Examples of especially suitable terminator sequences are the OCS (octopine synthase) terminator and the NOS (nopaline synthase) terminator.

The transformation vectors and insertion sequences according to the invention may comprise further nucleic acid sequences. Such nucleic acid sequences can preferably constitute expression cassettes. The following may be mentioned by way of example of the DNA sequences to be expressed in the expression constructs, but not by limitation:

1. Selection Markers

"Selection markers" means all those nucleic acid or protein sequences whose expression (i.e. transcription and, if appropriate, translation) confers a phenotype to a cell, tissue or organism which differs from that of an untransformed cell, tissue or organism. Selection markers comprises for example those nucleic acids or protein sequences whose expression confers an advantage (positiver selection marker) or disadvantage (negative selection marker) on a cell, tissue or organism in comparison with cells which do not express this nucleic acid or protein. For example, positive selection markers act by detoxifying a substance which has an inhibitory effect on the cell (for example resistance to antibiotics/herbicides), or by forming a substance which makes possible improved regeneration or enhanced growth of the plant under the selected conditions (for example nutritive markers, hormone-producing markers such as ipt; see hereinbelow). Another form of positive selection markers comprises mutated proteins or RNAs which are insensitive to a selective agent (for example 16S rRNA mutants, which are insensitive to spectinomycin). Negative selection markers act for example by catalyzing the formation of a toxic substance in the transformed cells (for example the codA gene). Moreover, selection marker can also comprise reporter proteins as long as they are suitable for differentiating transformed from untransformed cells, tissues or organs (for example by coloration or another detectable phenotype).

The following selection markers may be mentioned by way of example, but not by limitation:

1.1 Positive Selection Markers:

The selectable marker introduced into the nucleus or the plastids together with the expression cassette confers resistance to a biocide (for example a herbicide such as phosphinothricin, glyphosate or bromoxynil), a metabolic inhibitor such as 2-deoxyglucose-6-phosphate (WO 98/45456) or an antibiotic such as, for example, tetracyclins, ampicillin, kanamycin, G 418, neomycin, bleomycin or hygromycin, to the successfully transformed cells. The selection marker permits the selection of the transformed cells from untransformed cells (McCormick et al., Plant Cell Reports 5 (1986), 81-84; Dix PJ & Kavanagh TA (1995) Euphytica 85: 29-34).

Especially preferred selection markers are those which confer resistance to herbicides. Selection markers which may be mentioned by way of example are:

DNA sequences which encode phosphinothricin acetyltransferases (PAT), which acetylate the free amino group of the glutamine synthase inhibitor phosphinothricin (PPT) and thus detoxify the PPT (de Block et al. 1987, EMBO J. 6, 2513-2518) (also referred to as Bialophos® resistance gene (bar)). The bar gene encoding a phosphinothricin acetyltransferase (PAT) can be isolated for example from *Streptomyces hygroscopicus* or S. viridochromogenes. Such sequences are known to the skilled worker (from *Streptomyces hygroscopicus* GenBank Acc. No.: X17220 and X05822, from *Streptomyces* viridochromogenes GenBank Acc. No.: M 22827 and X65195; U.S. Pat. No. 5,489,520). Synthetic genes are further described for example for expression in plastids. A synthetic PAT gene is described in Becker et al. (1994) The Plant J. 5:299-307. The genes confer resistance to the herbicide bialaphos or glufosinate and are widely used markers in transgenic plants (Vickers J E et al. (1996). Plant Mol Biol Reporter 14:363-368; Thompson C J et al. (1987) EMBO J 6:2519-2523).

5-Enolpyruvylshikimate-3-phosphate synthase genes (EPSP synthase genes), which confer resistance to glyphosate (N-(phosphonomethyl)glycin). The nonselective herbicide glyphosate has 5-enolpyruvyl-3-phosphoshikimate synthase (EPSPS) as molecular target. This enzyme has a key function in the biosynthesis of aromatic amino acids in microbes and plants, but not in mammals (Steinrucken H C et al. (1980) Biochem. Biophys. Res. Commun. 94:1207-1212; Levin J G and Sprinson D B (1964) J. Biol. Chem. 239: 1142-1150; Cole D J (1985) Mode of action of glyphosate a literature analysis, p. 48-74. In: Grossbard E and Atkinson D (eds.). The herbicide glyphosate. Buttersworths, Boston.). Glyphosate-tolerant EPSPS variants are preferably used as selection markers (Padgette S R et al. (1996). New weed control opportunities: development of soybeans with a Roundup Ready™ gene. In: Herbicide Resistant Crops (Duke, S.O., ed.), pp. 53-84. CRC Press, Boca Raton, Fla.; Saroha M K and Malik V S (1998) J Plant Biochemistry and Biotechnology 7:65-72). The EPSPS gene of *Agrobacterium* sp. strain CP4 has a natural tolerance to glyphosate which can be transferred to corresponding transgenic plants. The CP4 EPSPS gene has been cloned from *Agrobacterium* sp. strain CP4 (Padgette S R et al. (1995) Crop Science 35(5):1451-1461). Sequences of 5-enolpyrvylshikimate-3-phosphate synthases which are glyphosate-tolerant, such as, for example, those described in U.S. Pat. No. 5,510,471; U.S. Pat. No. 5,776,760; U.S. Pat. No. 5,864,425; U.S. Pat. No. 5,633,435; U.S. Pat. No. 5,627,061; U.S. Pat. No. 5,463,175; EP 0 218 571, are described in the patents and also deposited in GenBank. Further sequences are described under GenBank Accession X63374. The aroA gene (M10947 *S. typhimurium* aroA locus 5-enolpyruvylshikimate-3-phosphate synthase (aroA protein) gene) is furthermore preferred.

the gox gene (glyphosate oxidoreductase), which encodes the Glyphosato® degrading enzyme. GOX (for example the glyphosate oxidoreductase from *Achromobacter* sp.) catalyzes the cleavage of a C—N bond in glyphosate, which is thus converted into aminomethylphosphonic acid (AMPA) and glyoxylate. GOX can thereby confer resistance to glyphosate (Padgette S R et al. (1996) J Nutr. 1996 March; 126(3):702-16; Shah D et al. (1986) Science 233: 478-481).

the deh gene (encoding a dehalogenase which inactives Dalapon®), (GenBank Acc. No.: AX022822, AX022820 and WO 99/27116)

bxn genes, which encode bromoxynil-degrading nitrilase enzymes, for example the *Klebsiella ozaenae* nitrilase. Sequences can be found in GenBank for example under the Acc. No: E01313 (DNA encoding bromoxynil specific nitrilase) and J03196 (*K. pneumoniae* bromoxynil-specific nitrilase (bxn) gene, complete cds).

Neomycin phosphotransferases confer resistance to antibiotics (aminoglycosides) such as neomycin, G418, hygromycin, paromomycin or kanamycin, by reducing their inhibitory action by means of a phosphorylation reaction. Especially preferred is the nptII gene. Sequences can be obtained from GenBank (AF080390 minitransposon mTn5-GNm; AF080389 minitransposon mTn5-Nm, complete sequence). Moreover, the gene is already a component in a large number of expression vectors and can be isolated from them using methods with which the skilled worker is familiar (such as, for example, polymerase chain reaction) (AF234316 pCAMBIA-2301; AF234315 pCAMBIA-2300, AF234314 pCAMBIA-2201). The NPTII gene encodes an aminoglycoside 3'-O-phosphotransferase from *E. coli*, Tn5 (GenBank Acc. No: U00004 position 1401-2300; Beck et al. (1982) Gene 19-327-336). Moreover, the Acinetobacter baumannii aphA-6 gene, which encodes an aminoglycoside phospho-transferase, may also be utilized as selection marker (Huang et al. (2002) Mol Genet Genomics 268:19-27)

the DOG$^R$1 gene. The gene DOG$^R$1 was isolated from the yeast *Saccharomyces cerevisiae* (EP 0 807 836). It encodes a 2-deoxyglucose-6-phosphate phosphatase, which confers resistance to 2-DOG (Randez-Gil et al. 1995, Yeast 11, 1233-1240; Sanz et al. (1994) Yeast 10:1195-1202, sequence: GenBank Acc. No.: NC001140 chromosome VIII, *Saccharomyces cervisiae* position 194799-194056).

Sulfonylurea- and imidazolinone-inactivating acetolactate synthases, which confer resistance to imidazolinone/sulfonylurea herbicides. Examples which may be mentioned of imidazolinone herbicides are the active substances imazamethabenz-methyl, imazamox, imazapyr, imazaquin and imazethapyr. Examples of sulfonylurea herbicides which may be mentioned are amidosulforon, azimsulfuron, chlorimuronethyl, chlorsulfuron, cinosulfuron, imazosulfuron, oxasulfuron, prosulfuron, rimsulfuron, sulfosulfuron. The skilled worker is familiar with a large number of further active substances from the abovementioned classes. Nucleic acid sequences such as, for example, the sequence for the *Arabidopsis thaliana* Csr 1.2 Gen (EC 4.1.3.18) which has been deposited under the GenBank Acc No.: X51514, are suitable (Sathasivan K et al. (1990) Nucleic Acids Res. 18(8):2188). Acetolactate synthases, which confer resistance to imidazolinone herbicides, are furthermore described under the GenBank Acc. Nos.:

a) AB049823 *Oryza sativa* ALS mRNA for acetolactate synthase, complete cds, herbicide resistant biotype b) AF094326 *Bassia scoparia* herbicide resistant acetolactate synthase precursor (ALS) gene, complete cds c) X07645 Tobacco acetolactate synthase gene, ALS SuRB (EC 4.1.3.18)

d) X07644 Tobacco acetolactate synthase gene, ALS SuRA (EC 4.1.3.18)

e) A19547 Synthetic nucleotide mutant acetolactate synthase f) A19546 Synthetic nucleotide mutant acetolactate synthase g) A19545 Synthetic nucleotide mutant acetolactate synthase h) 105376 Sequence 5 from patent EP 0257993 i) 105373 Sequence 2 from patent EP 0257993 j) AL133315

Hygromycin phosphotransferases (X74325 *P. pseudomallei* gene for hygromycin phosphotransferase) which confer resistance to the antibiotic hygromycin. The gene is a component of a large number of expression vectors and can be isolated from them using methods with which the skilled worker is familiar (such as, for example, polymerase chain reaction) (AF294981 pINDEX4; AF234301 pCAMBIA-1380; AF234300 pCAMBIA-1304; AF234299 pCAMBIA-1303; AF234298 pCAMBIA-1302; AF354046 pCAMBIA-1305.; AF354045 pCAMBIA-1305.1)

genes for resistance to a) chloramphenicol (chloramphenicol acetyltransferase), b) tetracyclin, various resistance genes have been described, for example X65876 S. ordonez genes class D tetA and tetR for tetracyclin resistance and repressor proteins X51366 *Bacillus cereus* plasmid pBC16 tetracyclin resistance gene. Moreover, the gene is already a component of a large number of expression vectors and can be isolated therefrom using methods known to the skilled worker (such as, for example polymerase chain reaction)

c) Streptomycin; various resistance genes have been described, for example with the GenBank Acc. No.: AJ278607 *Corynebacterium acetoacidophilum* ant gene for streptomycin adenylyltransferase.

d) Zeocin; the corresponding resistance gene is a component of a large number of cloning vectors (for example L36849 cloning vector pZEO) and can be isolated from these using methods known to the skilled worker (such as, for example, polymerase chain reaction).

e) Ampicillin (β-lactamase gene; Datta N, Richmond M H. (1966) Biochem J. 98(1):204-9; Heffron F et al. (1975) J. Bacteriol 122: 250-256; the Amp gene was first cloned for generating the *E. coli* vector pBR322; Bolivar F et al. (1977) Gene 2:95-114). The sequence is a component of a large number of cloning vectors and can be isolated from them using methods known to the skilled worker (such as, for example, polymerase chain reaction).

Genes such as the isopentenyl transferase from *Agrobacterium tumefaciens* (strain:PO22) (Genbank Acc. No.: AB025109). The ipt gene is a key enzyme of cytokinin biosynthesis. Its overexpression facilitates the regeneration of plants (for example selection on cytokinin-free medium). The method for utilizing the ipt gene has been described (Ebinuma H et al. (2000) Proc Natl Acad Sci USA 94:2117-2121; Ebinuma, H et al. (2000) Selection of marker-free transgenic plants using the oncogenes (ipt, rol A, B, C) of *Agrobacterium* as selectable markers, In Molecular Biology of Woody Plants. Kluwer Academic Publishers).

Various other positive selection markers which confer a growth-related advantage to the transformed plants over the nontransformed plants, and methods for their use, have been described, inter alia, in EP-A 0 601 092. Examples which may be mentioned are β-glucuronidase (in conjunction with, for example, cytokinin glucuronide), mannose-6-phosphate isomerase (in conjunction with mannose), UDP-galactose 4-epimerase (in conjunction with, for example, galactose), with mannose-6-phosphate isomerase in conjunction with mannose being especially preferred.

Preferred for a selection marker which is functional in plastids are, in particular, those which confer resistance to spectinomycin, streptomycin, kanamycin, lincomycin, gentamycin, hygromycin, methotrexate, bleomycin, phleomycin, blasticidin, sulfonamide, phosphinothricin, chlorsulfuron, bromoxynil, glyphosate, 2,4-D, atrazine, 4-methyltryptophan, nitrate, S-aminoethyl-L-cysteine, lysine/threonine, aminoethyl-cysteine or betaine aldehyde. Especially preferred are the genes aadA, nptII, BADH, FLARE-S (a fusion of aadA and GFP, described by Khan M S & Maliga P, 1999 Nature Biotech 17: 910-915).

As selection marker which is functional in plastids, it is mainly the aadA gene which has been described (Svab Z and Maliga P (1993) Proc Natl Acad Sci USA 90:913-917). Also described are modified 16S rDNA, the nptII gene (kanamycin resistance) and the bar gene (phosphinothricin resistance). Owing to the preference given to the selection marker aadA, the latter is preferably recycled, i.e. deleted from the genome, or plastome, following its use (Fischer N et al. (1996) Mol Gen Genet 251:373-380; Corneille S et al. (2001) Plant J 27:171-178), so that aada can be reused as selection marker in further transformations of an already transplastomic plant. The betaine-aldehyde dehydrogenase (BADH) from spinach has been described as a further possible selection marker (Daniell H et al. (2001) Trends Plant Science 6:237-239; Daniell H et al. (2001) Curr Genet 39:109-116; WO 01/64023; WO 01/64024; WO 01/64850). Lethal agents such as, for example, glyphosate, can also be utilized in connection with correspondingly detoxifying or resistant enzymes (WO 01/81605).

Binding type markers may also be utilized. To utilize the DBS recognition sequence of the homing endonuclease I-CpaI in the gene of the 23S rRNA, which sequence is preferred as insertion site, at least the 3' end of the insertion sequence (preferably an artificial intron) is surrounded by homologous sequences of the target region. Thus, sequences of the 23S rDNA are incorporated into the transformation vector. Point mutations can be introduced at one position (position 2073 or 2074 of the tobacco 23S rRNA, sequence: AAAGACCCTATGAAG becomes sequence: GGAGACCCTATGAAG), which point mutations confer resistance to lincomycin to the ribosomes derived from a 23S rDNA which has been mutated thus (Cseplö A et al. (1988) Mol Gen Genet 214:295-299). Further point mutations comprise those in the tobacco 16S rRNA which confer resistance to spectinomycin (mutation underlined):

a) 5'-GGAAGGTGAGGATGC-3'    (A in native sequence)

Other mutations confer resistance to streptomycin:

b) 5'-GAATGAAACTA-3'    (C in native sequence)

1.2 Negative Selection Markers

Negative selection markers make possible for example the selection of organisms with successfully deleted sequences which comprise the marker gene (Koprek T et al. (1999) The Plant Journal 19(6):719-726). For example, sequences which encode selection markers or DSBI enzymes can be deleted from the genome/plastome after successful application of the method according to the invention.

When carrying out a negative selection, for example a compound which otherwise has no disadvantageous effect on the plant is converted into a compound which is disadvantageous, for example owing to the negative selection marker introduced into the plant.

Genes which have a disadvantageous effect per se are furthermore also suitable, such as, for example, TK thymidine kinase (TK) and diphtheria toxin A fragment (DT-A), the coda gene product encoding a cytosine deaminase (Gleave A P et al. (1999) Plant Mol Biol 40(2):223-35; Perera R J et al. (1993) Plant Mol Biol 23(4): 793-799; Stougaard J (1993) Plant J 3:755-761), the cytochrome P450 gene (Koprek et al. (1999) Plant J. 16:719-726), genes encoding a haloalkane dehalogenase (Naested H (1999) Plant J. 18:571-576), the iaaH gene (Sundaresan V et al. (1995) Genes & Development 9:1797-1810) or the tms2 gene (Fedoroff N V & Smith D L (1993) Plant J 3:273-289).

The concentrations of the antibiotics, herbicides, biocides or toxins which are used in each case to carry out the selection must be adapted to the respective test-conditions or organisms. Examples which may be mentioned in context with plants are: kanamycin (Km) 50 to 100 mg/l, hygromycin B 40 mg/l, phosphino-thricin (Ppt) 6 to 20 mg/l, spectinomycin (Spec) 15 to 500 mg/l.

Furthermore, it is possible to express functional analogs of the abovementioned nucleic acids encoding selection markers. Functional analogs means, in the present context, all those sequences which have essentially the same function, i.e. which are capable of selecting transformed organisms. In this context, it is quite feasible that the functional analog differs with regard to other characteristics. For example, it can have a higher or lower activity, or else have further functionalities.

Functional analogs means furthermore sequences which encode fusion proteins consisting of one of the preferred selection markers and another protein, for example a further preferred selection marker, one of the reporter proteins mentioned hereinbelow or a PLS. By way of example, a fusion of the GFP (green fluorescent protein) and the aada gene may be mentioned (Sidorov V A et al. (1999) Plant J 19:209-216).

2. Reporter Genes

Reporter genes encode readily quantifiable proteins which, via their color or enzyme activity, allow an assessment of the transformation efficiency, the site or time of expression or the identification of transgenic plants. Very especially preferred in this context are genes encoding reporter proteins (see also Schenborn E, Groskreutz D. Mol Biotechnol. 1999; 13(1): 29-44) such as "green fluorescent protein" (GFP). (Chui W L et al., Curr Biol 1996, 6:325-330; Leffel S M et al., Biotechniques. 23(5):912-8, 1997; Sheen et al. (1995) Plant Journal 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228).

Chloramphenicol transferase,

Luciferase (Millar et al., Plant Mol Biol Rep 1992 10:324-414; Ow et al. (1986) Science, 234:856-859); allows detection via bioluminescence.

β-Galactosidase, encodes an enzyme for which a variety of chromogenic substrates are available.

β-Glucuronidase (GUS) (Jefferson et al., EMBO J. 1987, 6, 3901-3907) or the uida gene, which encodes an enzyme for a variety of chromogenic substrates.

R-Locus gene product: protein which regulates the production of anthocyanin pigments (red coloration) in plant tissue and thus makes possible the direct analysis of the promoter activity without addition of further auxiliary substances or chromogenic substrates (Dellaporta et al., In: Chromosome Structure and Function: Impact of New Concepts, 18th Stadler Genetics Symposium, 11:263-282, 1988).

β-Lactamase (Sutcliffe (1978) Proc Natl Acad Sci USA 75:3737-3741), enzyme for a variety of chromogenic substrates (for example PADAC, a chromogenic cephalosporin).

xylE gene product (Zukowsky et al. (1983) Proc Natl Acad Sci USA 80:1101-1105), catechol dioxygenase capable of converting chromogenic catechols.

Alpha-amylase (Ikuta et al. (1990) Bio/technol. 8:241-242).

Tyrosinase (Katz et al. (1983) J Gen Microbiol 129:2703-2714), enzyme which oxidizes tyrosine to DOPA and dopaquinone, which subsequently form melanin, which can be detected readily.

Aequorin (Prasher et al. (1985) Biochem Biophys Res Commun 126(3):1259-1268), can be used in the calcium-sensitive bioluminescence detection.

The selection marker, or the reporter gene, is preferably encoded on the transformation construct, especially preferably on the insertion sequence. However, it can also be encoded on an independent transformation construct which is introduced into the nucleus or the plastids of a plant cell in the form of a cotransformation together with the transformation construct of interest.

The transformation vectors and insertion sequences according to the invention may comprise further functional elements. The concept of further functional elements is to be understood in the broad sense. Preferably, it is understood as meaning all those elements which influence the generation, multiplication, function, use or value of the insertion sequences, transformation constructs or transformation vectors used within the scope of the present invention. The following may be mentioned by way of example of further functional elements, but not by limitation:

i. Replication origins (ORI) which make possible an amplification of the expression cassettes or vectors according to the invention in, for example, E. coli or else in plastids. Examples of E. coli ORIs which may be mentioned are the pBR322 ori, the P15A ori (Sambrook et al.: Molecular Cloning. A Laboratory Manual, 2nd ed. Cold Spring Harbor Laboratory Press, Cold Spring Harbor, N.Y., 1989) or the colE1 ORI, for example from pBLUESCRIPT. Plastidic ORIs are described in U.S. Pat. No. 5,693,507, U.S. Pat. No. 5,932,479 or WO 99/10513.

ii. Multiple cloning regions (MCRs) permit and facilitate the insertion of one or more nucleic acid sequences.

iii. Sequences which make possible the homologous recombination or insertion into the genome or plastome of a host organism.

iv. Elements, for example border sequences, which make possible the Agrobacterium-mediated transfer into plant cells for the transfer and integration into the plant genome, such as, for example, the right or left border of the T-DNA or the vir region.

An insertion sequence or an expression construct for a DSBI enzyme can be inserted advantageously using vectors into which these constructs, or cassettes, are inserted. Vectors can be plasmids, cosmids, phages, viruses, retroviruses or else agrobacteria, by way of example.

In an advantageous embodiment, the expression cassette is inserted by means of plasmid vectors. Preferred vectors are those which make possible a stable integration of the expression cassette into the host genome or plastome.

The generation of a transformed organism or a transformed cell requires introducing the DNA in question into the host cell in question, or into the plastids thereof. A multiplicity of methods is available for this procedure, which is referred to as transformation (see also Keown et al. (1990) Methods in Enzymology 185:527-537). Thus, for example, the DNA can be introduced directly by microinjection, electroporation or by bombardment with DNA-coated microparticles. Also, the cell can be permeabilized chemically, for example with polyethylene glycol, so that the DNA can penetrate the cell by diffusion. Transformation can also be effected by fusion with other DNA-comprising units such as minicells, cells, lysosomes or liposomes. Others which must additionally be mentioned are transfection using calcium phosphate, DEAE dextran or cationic lipids, transduction, infection, the incubation of dry embryos in DNA-comprising solution, sonication, and the transformation of intact cells or tissue by microinjection or macroinjection into tissue or embryos, or tissue electroporation, or the vacuum infiltration of seeds. The skilled worker is familiar with such methods. In the case of injection or electroporation of DNA into plant cells, the plasmid used need not meet any particular requirements. Simple plasmids such as those from the pUC series can be used. If intact plants are to be regenerated from the transformed cells, the presence of an additional, selectable marker gene on the plasmid is useful. Methods for the regeneration of plants from plant tissues or plant cells have also been described.

There are several options for introducing DNA into the plastids. The only decisive aspect for the present invention is that the DNA is introduced into the plastids. However, the present invention is not limited to a specific method. Any method which permits the introduction of the DNA to be transformed into the plastids of a higher plant is suitable. The stable transformation of plastids is a method with which the skilled worker is familiar; it has been described for higher plants (inter alia by Svab Z and Maliga P (1993) Proc Natl Acad Sci USA 90(3):913-917). For example, the methods are based on transformation by means of the particle gun and insertion into the plastidic genome by homologous recombination under selection pressure. Further methods are described in U.S. Pat. No. 5,877,402. In EP-A 0 251 654, the DNA is introduced by *Agrobacterium tumefaciens* (see De Block M et al. (1985) EMBO J 4:1367-1372; Venkateswarlu K and Nazar R N (1991) Bio/Technology 9:1103-1105). It has furthermore been demonstrated that DNA can be introduced into isolated chloroplasts by means of electroporation, thus bringing about transient expression (To KY et al. (1996) Plant J 10:737-743). Transformation by means of a direct DNA transfer into plastids of protoplasts, for example using PEG (polyethylene glycol) is preferred (Koop H U et al. (1996) Planta 199:193-201; Kofer W et al. (1998) In Vitro Cell Dev Biol Plant 34:303-309; Dix P J and Kavanagh T A (1995) Euphytica. 85:29-34; EP-A 0 223 247). Most preferred are biolistic transformation methods. Here, the DNA to be transformed is applied to, for example gold or tungsten particles. These particles are subsequently accelerated towards the explant to be transformed (Dix P J and Kavanagh T A (1995) Euphytica. 85:29-34; EP-A 0 223 247). Thereafter, transplastomic plants are regenerated under selection pressure on suitable medium in the manner with which the skilled worker is familiar. Such methods have been described (for example U.S. Pat. No. 5,451,513; U.S. Pat. No. 5,877,402; Svab Z et al. (1990) Proc Natl Acad Sci USA 87:8526-8530; Svab Z and Maliga P (1993) Proc Natl Acad Sci USA 90:913-917). Moreover, the DNA can be introduced into the plastids by means of microinjection. A specific microinjection method has been described recently (Knoblauch M et al. (1999) Nature Biotech 17:906-909; van Bel AJE et al. (2001) Curr Opin Biotechnol 12:144-149). This method is particularly preferred for the present invention. It is also possible to introduce, by means of protoplast fusion, the plastids from one species into a different species, to transform them in the latter and subsequently to return them to the original species by protoplast fusion (WO 01/70939).

Besides these "direct" transformation techniques, transformation can also be carried out by bacterial infection by means of *Agrobacterium tumefaciens* or *Agrobacterium rhizogenes* (Horsch R B (1986) Proc Natl Acad Sci USA 83(8):2571-2575; Fraley et al. (1983) Proc Natl Acad Sci USA 80:4803-4807; Bevans et al. (1983) Nature 304:184-187). The expression cassette for, for example, the DSBI enzyme is preferably intergrated into specific plasmids, either into a shuttle, or intermediate, vector or into a binary vector. Binary vectors are preferably used. Binary vectors are capable of replication both in *E. coli* and in *Agrobacterium* and be transformed directly into *Agrobacterium* (Holsters et al. (1978) Mol Gen Genet 163:181-187). Various binary vectors are known; some of them are commercially available such as, for example, pBIN19 (Clontech Laboratories, Inc. USA; Bevan et al. (1984) Nucl Acids Res 12:8711). The selection marker gene permits the selection of transformed *agrobacteria* and is, for example, the nptII gene, which confers resistance to kanamycin. The binary plasmid can be transferred into the agrobacterial strain for example by electroporation or other transformation methods (Mozo & Hooykaas 1991, Plant Mol. Biol. 16, 917-918). The plant explants are generally cocultured with the agrobacterial strain for two to three days. The *agrobacterium* which, in this case, acts as the host organism, should already comprise a plasmid with the vir region. Many *Agrobacterium tumefaciens* strains are capable of transferring genetic material, such as, for example, the strains EHA101[pEHA101] (Hood E E et al. (1996) J Bacteriol 168(3):1291-1301), EHA105[pEHA105] (Hood et al. (1993) Transgenic Research 2:208-218), LBA4404[pAL4404] (Hoekema et al. (1983) Nature 303:179-181), C58C1 [pMP90] (Koncz and Schell (1986) Mol Gen Genet 204:383-396) and C58C1[pGV2260] (Deblaere et al. (1985) Nucl Acids Res 13: 4777-4788).

To transfer the DNA to the plant cell, plant explants are cocultured with *Agrobacterium tumefaciens* or *Agrobacterium rhizogenes*. Starting from infected plant material (for example leaf, root or stem portions, but also protoplasts or suspensions of plant cells), intact plants can be regenerated using a suitable medium which may comprise, for example, antiobiotics or biocides for selecting transformed cells. A cotransformed selection marker permits the selection of transformed cells from untransformed cells (McCormick et al. (1986) Plant Cell Reports 5:81-84). The plants obtained can be bred, selfed and hybridized in the customary manner. Two or more generations should be grown to ensure that the genomic integration is stable and hereditary. The abovementioned methods are described in, for example, Jenes B et al. (1993) Techniques for Gene Transfer, in: Transgenic Plants, Vol. 1, Engineering and Utilization, edited by Kung S D and Wu R, Academic Press, pp. 128-143 and in Potrykus (1991) Ann Rev Plant Physiol Plant Molec Biol 42:205-225).

The *Agrobacterium*-mediated transformation is best suited to dicotyledonous plant cells, whereas the direct transformation techniques are suitable for any cell type.

The *Agrobacterium*-mediated transformation is especially preferably employed for the transformation of the nucleus, while the direct transformation techniques are especially preferably employed for the transformation of plastids.

As soon as a predominanly homotransplastomic plant cell has been generated by the method according to the invention, an intact plant can be obtained using methods with which the skilled worker is familiar. The starting material for this purpose is, for example, callus cultures. The development of shoot and root can be induced in the known manner in this as yet undifferentiated biomass. The shoots obtained can be planted out and used for breeding.

Deletion Methods

In the above-described methods according to the invention, it is advantageous, at various levels, to remove certain sequences which have previously been introduced (for example sequences for selection-markers and/or DSBI enzymes) from the plastome or genome of the plant or cell. Thus, it is advantageous, but not necessarily required, to remove the selection marker which has been introduced for example during the insertion of a normatural DSB recognition sequence, from the master plant since the same selection marker can then be utilized in a subsequent transformation (for example with the insertion sequence). Deletion is particularly advantageous since the selection marker is no longer necessarily required after the selection phase, and therefore superfluous. Moreover, deletion increases the consumer acceptance and is desirable for registration purposes. Moreover, the protein synthesis apparatus of the plastid is not unnecessarily burdened by the synthesis of the marker protein, which has potentially advantageous effects on the characteristics of the plant in question.

The skilled worker is familiar with a variety of methods for the directed deletion of sequences. One which should be mentioned by way of example, but not by limitation, is the excision by means of recombinases. Various sequence-specific recombination systems have been described, such as the Cre/lox system of bacteriophage P1 (Dale E C and Ow D W (1991) Proc Natl Acad Sci USA 88:10558-10562; Russell S H et al. (1992) Mol Gen Genet 234: 49-59; Osborne B I et al. (1995) Plant J. 7, 687-701), the yeast FLP/FRT system (Kilby N J et al. (1995) Plant J 8:637-652; Lyznik L A et al. (1996) Nucleic Acids Res 24:3784-3789), the Gin recombinase of the phage Mu, the Pin recombinase from *E. coli* or the R/RS system of the plasmid pSR1 (Onouchi H et al. (1995) Mol Gen Genet 247:653-660; Sugita K et al. (2000) Plant J 22:461-469). These methods can be utilized not only for deleting DNA sequences from the nuclear genome, but also from the plastome (Corneille et al. (2001) Plant J 27: 171-178; Hajdukieicz et al. (2001) Plant J 27:161-170). Further recombinases which can be employed are, for example, PhiC31 (Kuhstoss & Rao (1991) J Mol Biol 222:897-908), TP901 (Christiansen et al. (1996) J Bacteriol 178:5164-5173), xisF from Anabaena (Ramaswamy et al. (1997) Mol Microbiol 23:1241-1249), integrase from phage PhiLC3 (Lillehaug et al. (1997) Gene 188:129-136) or the recombinase encoded by the sre gene of the R4 phage (Matsuura et al. (1996) J Bacteriol 178:3374-3376).

In a preferred embodiment, however, the deletion is effected by intrachromosomal recombination owing to suitably introduced sequence duplications. The efficiency of the latter can be enhanced by the directed introduction of double-strand breaks near the sequence duplications (cf. FIG. 8). To this end, the sequence to be deleted is flanked bilaterally by homology sequences H1 and H2 which have sufficient length and homology to undergo recombination with one another. Recombination is induced by the induction of at least one sequence-specific double-strand break of a further DSB recognition sequence located near one of the two homology sequences (but preferably different from the first one). This DSB recognition sequence is preferably localized between the two homology sequences. To induce the double-strand break, it is preferred to express or introduce a second DSBI enzyme which differs from the first one. This method is especially preferably utilized for deleting selection markers from the plastome.

The invention furthermore relates to the transplastomic, predominantly homoplastomic, plants generated using the method according to the invention, and to parts of these plants, such as leaves, roots, seeds, fruits, tubers, pollen or cell cultures, callus and the like which are derived from such plants.

The invention furthermore relates to the plants employed in the method according to the invention which comprise an expression cassette according to the invention for a DSBI enzyme or a fusion protein of PLS and DSBI enzyme. In this context, the expression cassette for the fusion protein of PLS and DSBI enzyme is—especially preferably—stably integrated in the nuclear DNA under the control of a promoter which is functional in the plant nucleus. The expression cassette encoding a DSBI enzyme under the control of a promoter which is active in plant plastids is preferably stably integrated into the plastome. Comprised are furthermore parts of same such as leaves, roots, seeds, tubers, fruits, pollen or cell cultures, callus and the like which are derived from the abovementioned plants.

Genetically modified plants according to the invention which can be consumed by humans and animals can also be used as foods or feeds, for example directly or following processing known per se.

The invention furthermore relates to the use of the above-described transplastomic, predominantly homoplastomic, plants according to the invention and of the cells, cell cultures, parts—such as, for example, the roots, leaves and the like in the case of transgenic plant organisms—and transgenic propagation material such as seeds or fruits which are derived from them for the production of foods or feeds, pharmaceuticals or fine chemicals.

Fine chemicals refers to enzymes such as, for example, the industrial enzymes mentioned hereinbelow, vitamins such as, for example, tocopherols and tocotrienols (for example vitamin E) and vitamin B2, amino acids such as, for example, methionine, lysine or glutamate, carbohydrates such as, for example, starch, amylose, amylopectin or sucrose, fatty acids such as, for example, saturated, unsaturated and polyunsaturated fatty acids, natural and synthetic flavorings, aroma chemicals such as, for example linalool, menthol, borneone (camphor), pinene, limonene or geraniol, and colorants such as, for examle, retinoids (for example vitamin A), flavonoids (for example quercetin, rutin, tangeretin, nobiletin) or carotenoids (for example β-carotene, lycopene, astaxanthin). The production of tocopherols and tocotrienoles and of carotenoids is especially preferred. Growing the transformed host organisms, and isolation from the host organisms or the growth medium, are carried out using methods with which the skilled worker is familiar. The production of pharmaceuticals such as, for example, antibodies or vaccines has been described (Hood E E, Jilka J M. (1999) Curr Opin Biotechnol. 10(4):382-386; Ma J K and Vine N D (1999) Curr Top Microbiol Immunol. 236:275-92).

The method according to the invention is particularly suitable for producing industrial enzymes within what is known as "phytofarming". Examples of industrial enzymes which may be mentioned, but not by way of limitation, are lipases, esterases, proteases, nitrilases, acylases, epoxyhydrolases, amidases, phosphatases, xylanases, alcohol dehydrogenases, amylases, glucosidases, galactosidases, pullulanases, endocellulases, glucanases, cellulases, nucleases, chitin deacetylases, monoaminooxidases, lysozymes and laccases.

Embodiments which are especially preferred for the purposes of the invention are described in greater detail hereinbelow within the explanations of the figures.

Sequences

1. SEQ ID NO: 1
   pCB42-94 Basic vector for plastid transformation.
2. SEQ ID NO:2
   Nucleic acid sequence inserted into the multiple cloning site of pCB42-94 (SEQ ID NO: 1). Resulting vector: pCB199-3.
3. SEQ ID NO:3
   Nucleic acid sequence inserted into the multiple cloning site of pCB42-94 (SEQ ID NO: 1). Resulting vector: pCB401-20
4. SEQ ID NO:4
   Expession cassette from pCB289-13 for the expression of the I-PpoI homing endonuclease in plastids.

5. SEQ ID NO:5
   Amino acid sequence of the I-PpoI homing endonuclease encoded by the expression cassette from pCB289-13.
6. SEQ ID NO:6
   XhoI/BglII fragment employed for generating the vector pCB304-25.
7. SEQ ID NO:7
   Nucleic acid sequence inserted into the multiple cloning site of pGEMTeasy. Resulting vector: pCB220-17
8. SEQ ID NO:8
   Nucleic acid sequence inserted into the multiple cloning site of pBluescript. Resulting vector: pCB270-1
9. SEQ ID NO:9
   Sequence from vector pCB315-1: LacZ gene with inserted intron for detecting splicing.
10. SEQ ID NO: 10
    Ll.LtrB intron from vector pCB345-34.
11. SEQ ID NO: 11
    Synthetic sequence of the homing endonuclease I-PpoI (ORF: 16 to 507)
12. SEQ ID NO: 12
    Protein sequence of the homing endonuclease I-PpoI
13. SEQ ID NO: 13
    Nucleic acid sequence of the homing endonuclease I-CpaI from *Chlamydomonas pallidostigmatica* (modification of the published sequence at position 69. An NcoI cleavage site was introdued at ATG (ORF: 4 to 462)
14. SEQ ID NO: 14
    Protein sequence of the homing endonuclease I-CpaI
15. SEQ ID NO: 15
    Sequence comprising the CpLSU2 intron
16. SEQ ID NO: 16: Oligonucleotide primer p19

5'-TAAGGCCCTCGGTAGCAACGG-3'

17. SEQ ID NO: 17: Oligonucleotide primer p20

5'-GGGGTACCAAATCCAACTAG-3'

18. SEQ ID NO: 18: Oligonucleotide primer p21:

5'-GGAGCTCGCTCCCCCGCCGTCGTTC-3'

19. SEQ ID NO: 19: Oligonucleotide primer p22

5'-GATGCATGATGACTTGACGGCATCCTC-3'

20. SEQ ID NO: 20: Oligonucleotide primer p190

5'-GTCGACAGATCTTTAA-3'

21. SEQ ID NO: 21: Oligonucleotide primer p191

5'-AGATCTGTCGACTTAA-3'

22. SEQ ID NO: 22: Oligonucleotide primer p199

5'-GATCTCCAGTTAACTGGGGTAC-3'

23. SEQ ID NO: 23: Oligonucleotide primer p200

5'-CCCAGTTAACTGGA-3'

24. SEQ ID NO: 24: Oligonucleotide primer p218

5'-TTAAGCCAGTTAACTGGGCGGAGCT-3'

25. SEQ ID NO: 25: Oligonucleotide primer p219

5'-CCGCCCAGTTAACTGGC-3'

26. SEQ ID NO: 26: Oligonucleotide primer p276

5'-TCGAGAAGATCAGCCTGTTATCCCTAGAGTAACT-3'

27. SEQ ID NO: 27: Oligonucleotide primer p277

5'-CTAGAGTTACTCTAGGGATAACAGGCTGATCTTC-3'

28. SEQ ID NO: 28: Oligonucleotide primer p91

5'-AGAAGACGATCCTAAGG-3'

29. SEQ ID NO: 29: Oligonucleotide primer p92

5'-TGAAGACTTGACAAGGAATTTCGC-3'

30. SEQ ID NO: 30: Oligonucleotide primer p102

5'-AGAAGACGATCCTAAATAGCAATATTTACCTTTGGGACCAAAAGTTATCAGGCATG-3

31. SEQ ID NO: 31: Oligonucleotide primer p103

5'TGAAGACTTGACAAGGAATTTCGCTACCTTCGAGTACTCCAAAACTAATC-3'

32. SEQ ID NO: 32: Oligonucleotide primer p207

5'-GAGAAGACATTCCTAACACATCCATAACGTGCG-3'

33. SEQ ID NO: 33: Oligonucleotide primer p208

5'-TGAAGACTTGACATTTGATATGGTGAAGTAGG-3'

34. SEQ JD NO: 34
    Nucleic acid sequence encoding the transit peptide of the small subunit (SSU) of ribulose bisphosphate carboxylase (Rubisco ssu) from pea
35. SEQ ID NO: 35
    Transit peptide of the small subunit (SSU) of ribulose bisphosphate carboxylase (Rubisco ssu) from pea
36. SEQ ID NO: 36
    Transit peptide of the tobacco plastidic transketolase.
37. SEQ ID NO: 37
    Nucleic acid sequence encoding the transit peptide of the tobacco plastidic transketolase (reading frame 1; pTP09)
38. SEQ ID NO: 38
    Nucleic acid sequence encoding the transit peptide of the tobacco plastidic transketolase (reading frame 2; pTP10)
39. SEQ ID NO: 39
    Nucleic acid sequence encoding the transit peptide of the tobacco plastidic transketolase (reading frame 3; pTP11)

40. SEQ ID NO: 40
   Transit peptide of the plastidic isopentenyl-pyrophosphate isomerase-2 (IPP-2) from *Arabidopsis thaliana*.
41. SEQ ID NO: 41
   Nucleic acid sequence encoding the transit peptide of the plastidic isopentenyl-pyrophosphate isomerase-2 (IPP-2) from *Arabidopsis thaliana* (reading frame 1; IPP-9)
42. SEQ ID NO: 42
   Nucleic acid sequence encoding the transit peptide of the plastidic isopentenyl-pyrophosphate isomerase-2 (IPP-2) *Arabidopsis thaliana* (reading frame 2; IPP-10)
43. SEQ ID NO: 43
   Nucleic acid sequence encoding the transit peptide of the plastidic isopentenyl-pyrophosphate isomerase-2 (IPP-2) from *Arabidopsis thaliana* (reading frame 3; IPP-11)
44. SEQ ID NO: 44
   Nucleic acid sequence encoding the tobacco PrbcL promoter.
45. SEQ ID NO: 45
   Nucleic acid sequence encoding the tobacco Prps16-107 promoter.
46. SEQ ID NO: 46
   Nucleic acid sequence encoding the tobacco Prrn16 promoter.
47. SEQ ID NO: 47
   Nucleic acid sequence encoding the tobacco PaccD-129 promoter.
48. SEQ ID NO: 48
   Nucleic acid sequence encoding the tobacco PclpP-53 promoter.
49. SEQ ID NO: 49
   Nucleic acid sequence encoding the tobacco Prrn-62 promoter.
50. SEQ ID NO: 50
   Nucleic acid sequence encoding the tobacco Prps16 promoter.
51. SEQ ID NO: 51
   Nucleic acid sequence encoding the tobacco PatpB/E-290 promoter.
52. SEQ ID NO: 52
   Nucleic acid sequence encoding the tobacco PrpoB-345 promoter.
53. SEQ ID NO: 53
   Nucleic acid sequence encoding a promoter derived from the consensus sequence of the *E. coli* σ70 promoters.
54. SEQ ID NO: 54
   Nucleic acid sequence encoding the 5'-untranslated region of the tobacco psbA gene (5'psbA)
55. SEQ ID NO: 55
   Nucleic acid sequence encoding the 5'-untranslated region including 5' portions from the coding region of the tobacco rbcL gene (5'rbcL).
56. SEQ ID NO: 56
   Nucleic acid sequence encoding the 5'-untranslated region of the tobacco rbcLs gene.
57. SEQ ID NO: 57
   Nucleic acid sequence encoding the 3'-untranslated region of the *Synechocystis* psbA-1 gene (3'psbA-1)
58. SEQ ID NO: 58
   Nucleic acid sequence encoding the 3'-untranslated region of the tobacco psbA gene (3'psbA)
59. SEQ ID NO: 59
   Nucleic acid sequence encoding the 3'-untranslated region of the tobacco rbcL gene (3'rbcL)
60. SEQ ID NO: 60
   Nucleic acid sequence encoding synthetic ribosome binding sites (RBS)
61. SEQ ID NO: 61
   Nucleic acid sequence encoding synthetic ribosome binding sites (RBS)
62. SEQ ID NO: 62
   Complete insert of the vector pCB304-25
63. SEQ ID NO: 63
   BglII/MunI fragment of the vector pCB320-192.
64. SEQ ID NO: 64: Oligonucleotide primer p93

5'-AAAGATCTCCTCACAAAGGGGTCG-3'

65. SEQ ID NO: 65: Oligonucleotide primer p97

5'-TCGAAGACTTAGGACCGTTATAG-3'

66. SEQ ID NO: 66: Oligonucleotide primer p98

5'-AGGAAGACCTTGTCGGGTAAGTTCCG-3'

67. SEQ ID NO: 67: Oligonucleotide primer p95:

5'-CTCAATTGGGGTCTCTCTGTCCAGGTGCAGG-3'

68. SEQ ID NO: 68: Nucleic acid sequence encoding fusion proteins from the native I-Ppo-I nuclease and the IPP plastid localization sequence (ORF for I-PpoI: 181-672; IPP transit peptide: 1-180; native sequence from 1-172).
69. SEQ ID NO: 69: Fusion proteins of the native I-Ppo-I nuclease and the IPP-plastid localization sequence.
70. SEQ ID NO: 70: Nucleic acid sequence encoding long version of the I-Ppoi homing endonuclease.
71. SEQ ID NO: 71: Amino acid sequence encoding long version of the I-PpoI homing endonuclease.
72. SEQ ID NO: 72: Nucleic acid sequence encoding a promoter sequence derived from the consensus sequence of the σ70 promoters from *E. coli*.
73. SEQ ID NO: 73: Nucleic acid sequence encoding the artificial intron TetIVS2a.
74. SEQ ID NO: 74: Insert of vector pCB459-1
75. SEQ ID NO: 75: Insert of vector pCB478-3
76. SEQ ID NO: 76: Insert of vector pCB492-25
77. SEQ ID NO: 77: Oligonucleotide primer p396

5'-TAGTAAATGACAATTTTCCTCTGAATTATATAATTAACATGGCGACTGTTTACCAAAAAC-3

78. SEQ ID NO: 78: Oligonucleotide primer p95 5'-CTCAATTGGGGTCTCTCTGTCCAGGTGCAGG-3'
79. SEQ ID NO: 79: Nucleic acid sequence encoding PCR product Prom-TetIVS2a-Cpa
80. SEQ ID NO: 80: Insert of vector pCB435-45
81. SEQ ID NO: 81: Nucleic acid sequence encoding probe for Southern blot analysis (directed against portions of the 16SrDNA).
82. SEQ ID NO: 82: Nucleic acid sequence encoding probe for Southern blot analysis (directed against portions of the 23SrDNA).
83. SEQ ID NO: 83: Insert of vector pCB456-2
84. SEQ ID NO: 84: Insert of vector pCB528-2 from KpnI to SacI

Figures

Within the method according to the invention, particularly the embodiments detailed in the figures hereinbelow are especially preferred. The following abbreviations are generally used in the figures:

A, A' Pair of homologous sequences A and A'
A/A' Result of a homologous recombination between A and A' and/or a substitution of A by A' caused by repair synthesis.
B, B' Pair of homologous sequences B and B'
B/B' Result of a homologous recombination between B and B' and/or a substitution of B by B' caused by repair synthesis.
H1, H2: Pair of homologous sequences H1 and H2
H1/2: Sequence as the result of the homologous recombination of H1 and H2
DS Functional DSB recognition sequence
nDS nonfunctional half of a DSB recognition sequence
E: DSBI enzyme
P: Promoter
I: Further nucleic acid sequence (gene of interest)
S, S' Positive selection markers
NS Negative selection marker
IS Intron sequences. The intron in total is marked as a box. The box comprises all elements required for a functional intron.

As already described above, A/A' and B/B' are the result of a homologous recombination and/or a substitution brought about by repair synthesis. The resulting sequence, in turn, can be the starting sequence for further homologous recombinations or repair syntheses. For the sake of simplicity, this sequence (A/A' and B/B') is again referred to as A and B, respectively, in the steps which follow.

1. FIG. 1: Introduction of a DSB Recognition Sequence into the Plastome by Means of Double Cross-Over In an especially preferred embodiment 1, a DSBR construct is first introduced into plastids of a higher plant. In this embodiment, the DSBR construct is preferably equipped with homologous target regions and with an expressible selection marker (promoter—5'UTR—selection marker—3'UTR) and, in this embodiment, preferably comprises a recognition region for a DSBI enzyme which preferably has no natural recognition sequence in the plastidic genome of the (untransformed) plant in question. The DSBR construct can optionally already encode further genes of interest. Predominantly homoplastomic master plants are generated (FIG. 1).

2. FIG. 2A-E: Introduction of an Insert Sequence with an Expression Cassette for a DSBI Enzyme and, if Appropriate, Selection Markers and Further Genes of Interest Explants of the master plants generated in embodiment 1 are utilized for a further transformation with a transformation construct according to the invention. Preferably, the transformation construct according to the invention has regions which are homologous to the sequences surrounding the insertion site of the DSBR construct, which regions are preferably located on both sides (FIGS. 2A, 2B) or on one side (FIGS. 2C, 2D) of the insertion sequence. Insertion now takes place via homologous recombination (for example crossover) or via repair synthesis.

Figure 2A:
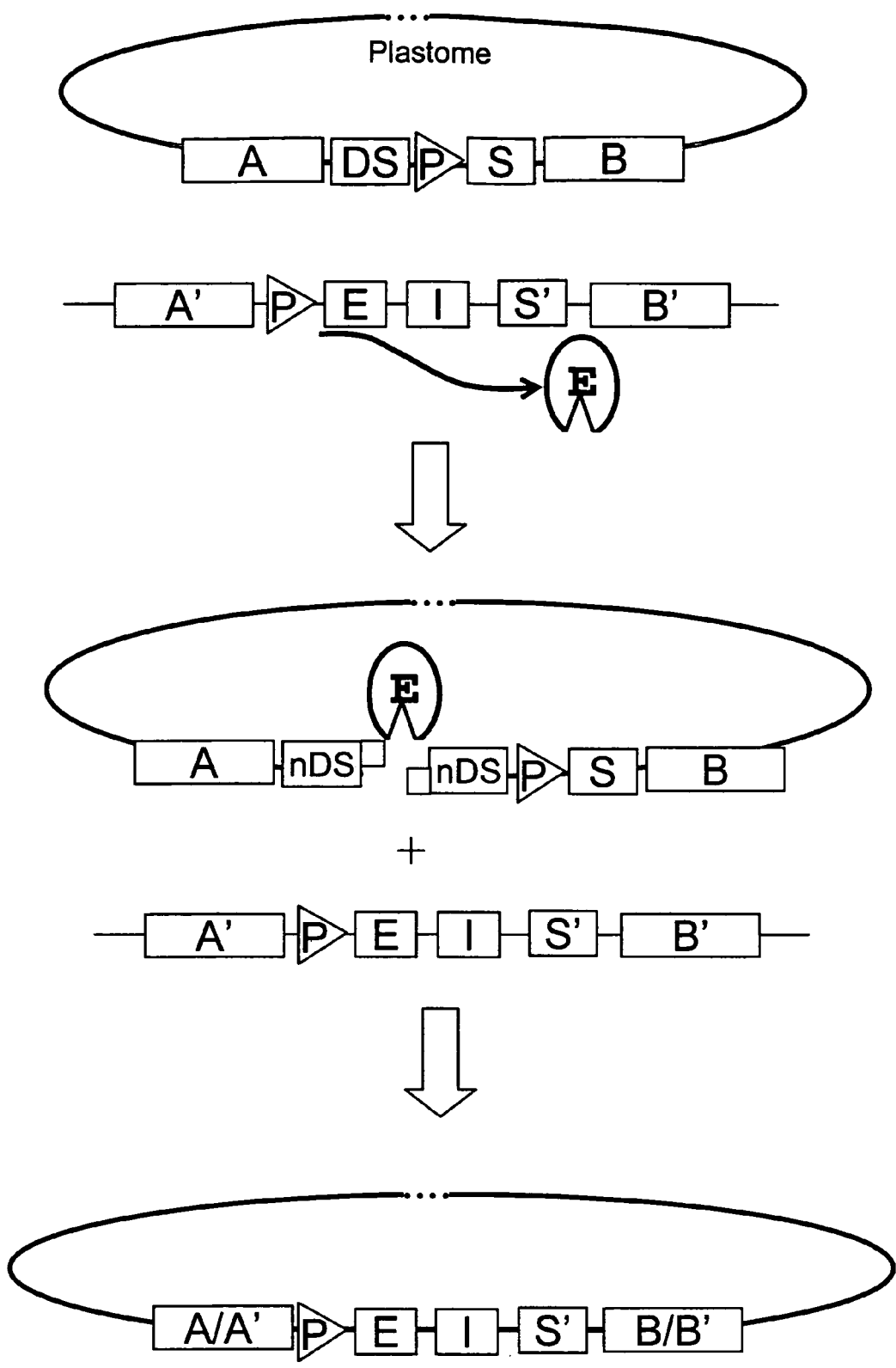
Figure 2B:
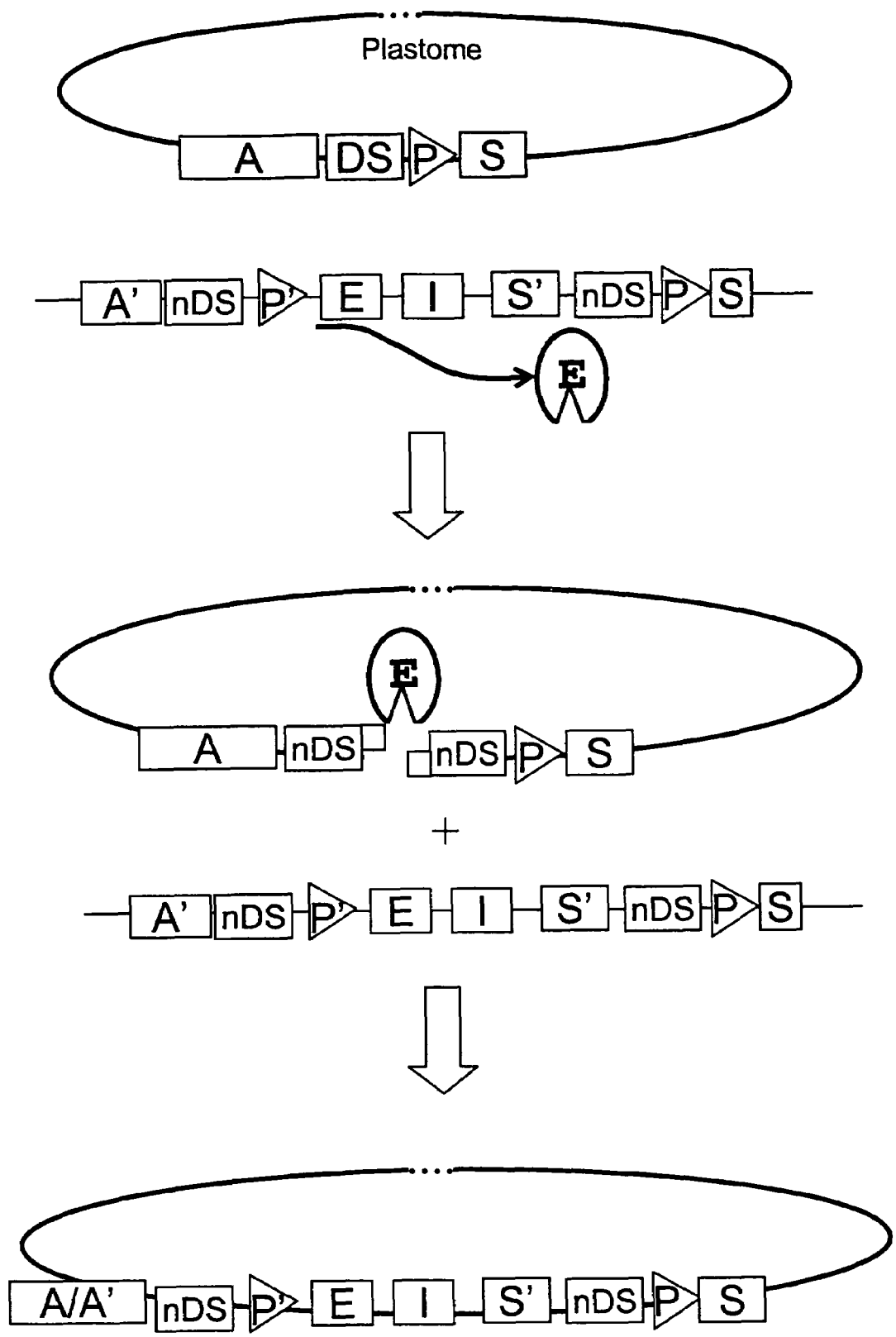
Figure 2C:
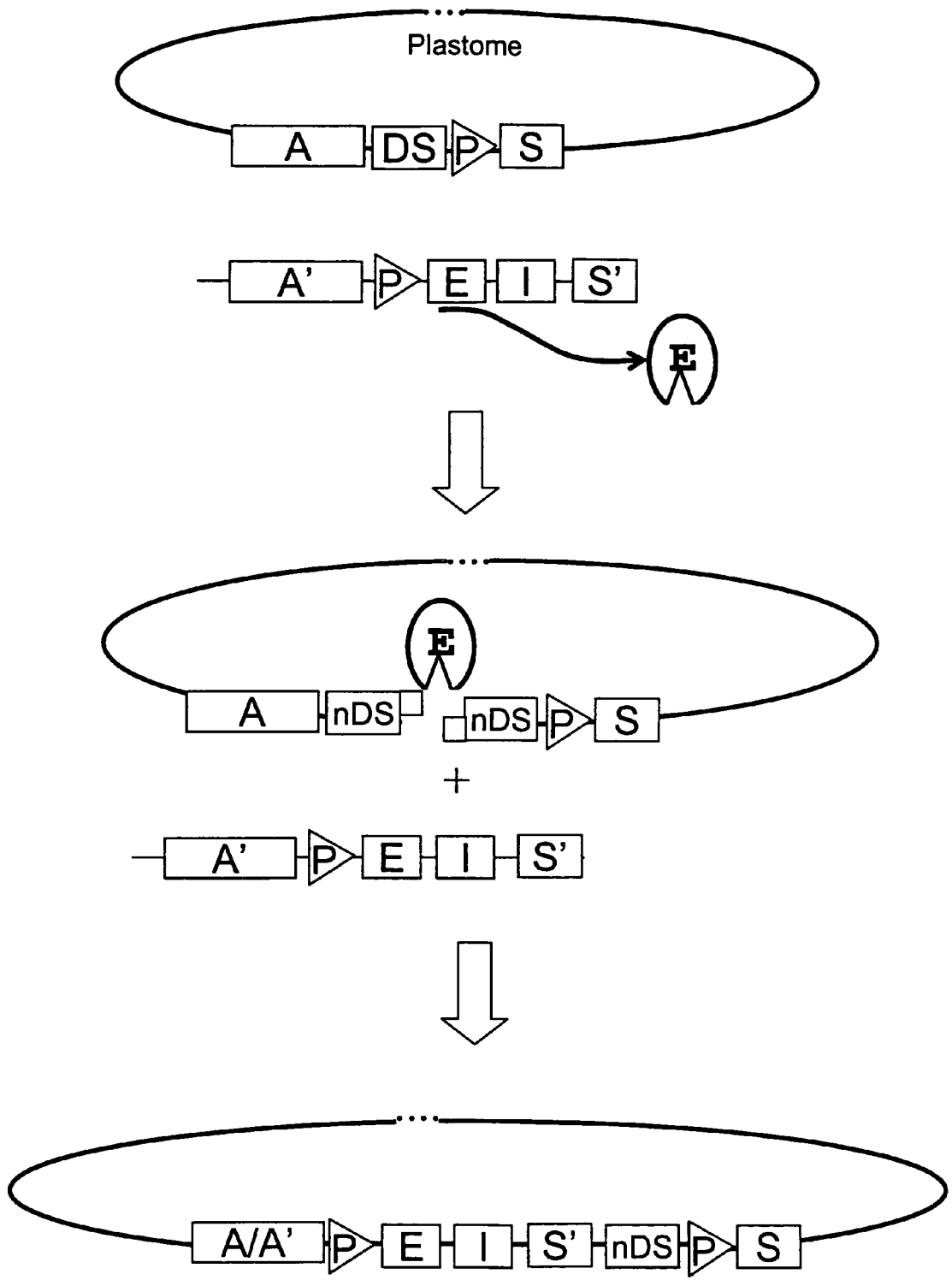

The sequences to be inserted are especially preferably—following the homology sequences inwardly—flanked by portions of the DSB recognition sequence (nDS) which correspond to the portions originating as the consequence of cleavage with the DSBI enzyme (FIG. 2B). The insertion sequence thus comprises sequences which correspond in detail to the ends which are the result of a cleavage in the plastome and thus ensure a particularly efficient incorporation.

Figure 2D:
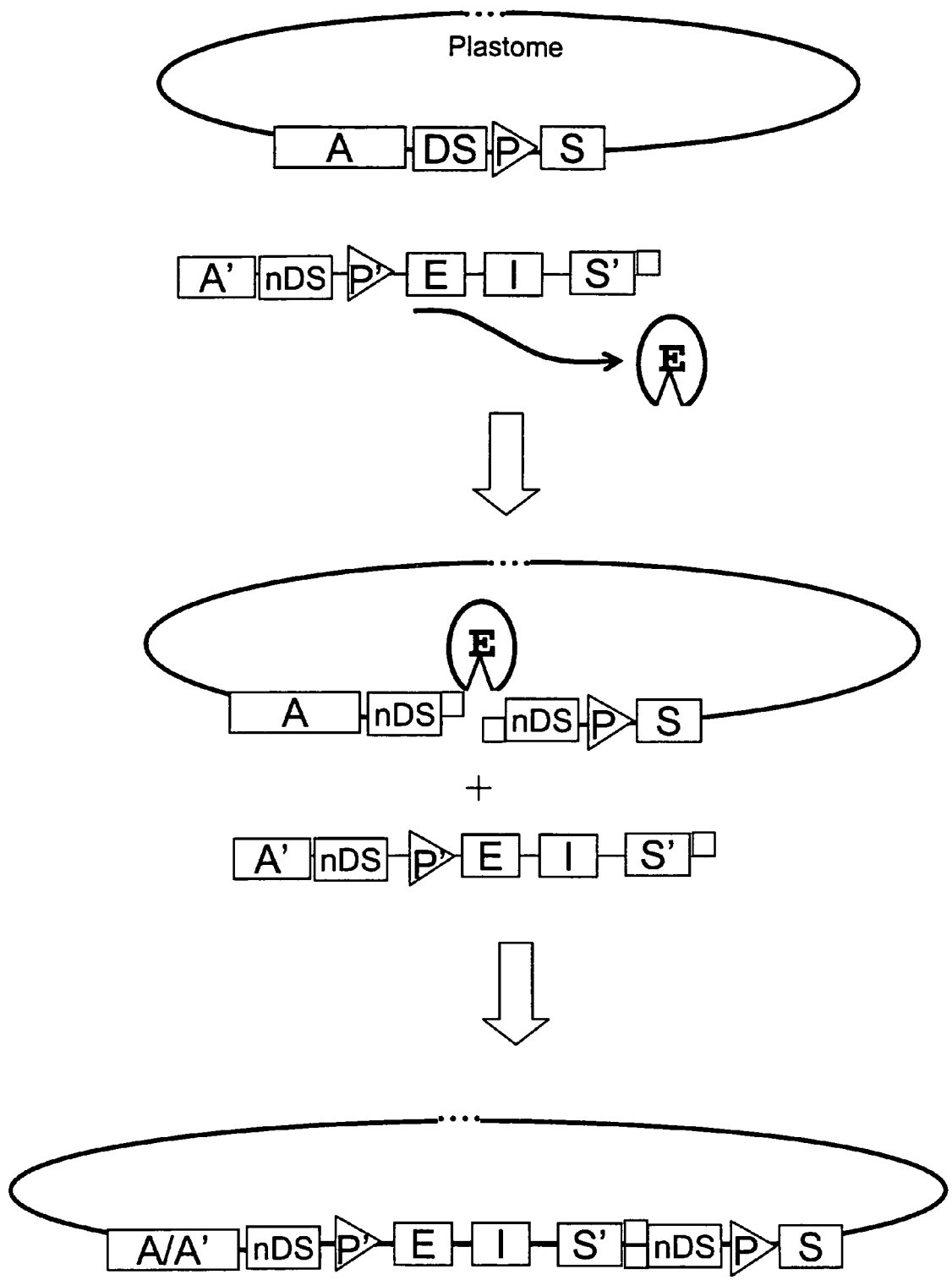
Figure 2E:
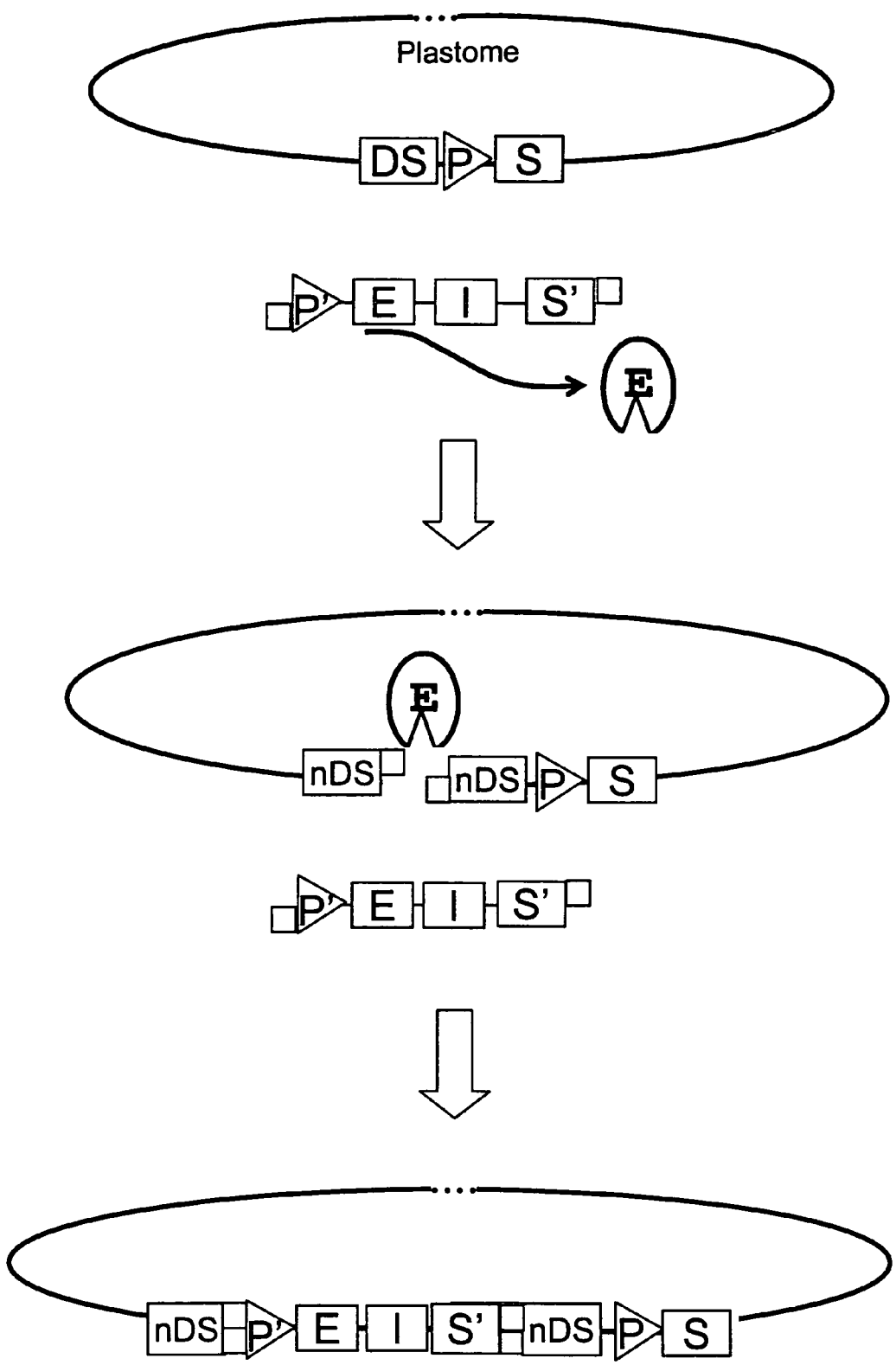

If the transformation construct, or the insertion sequence, has no such homologous regions, the insertion sequence is preferably provided, at these ends, with overhangs which are also generated by the DSBI enzyme after cleavage of the master plant plastome (FIG. 2E).

If only one homology sequence is present, this sequence borders, in an especially preferred embodiment, an nDS sequence (see hereinabove as described for FIG. 2B), while the other side of the insertion sequence is provided with overhangs which correspond to those generated by the DSBI enzyme in the plastome of the master plant (FIG. 2D).

The insertion sequence optionally codes for a further expressible selection marker which differs functionally from that of the DSBR construct, if appropriate one or more expressible genes of interest and the expressible DSBI enzyme, which cleaves the recognition sequence introduced by the DSBR construct at the insert site in the plastidic genome of the master plant. The insertion sequence of the transformation construct is inserted, in this context, in such a way at a position that said recognition region is no longer functional after the insertion.

Figure 3:
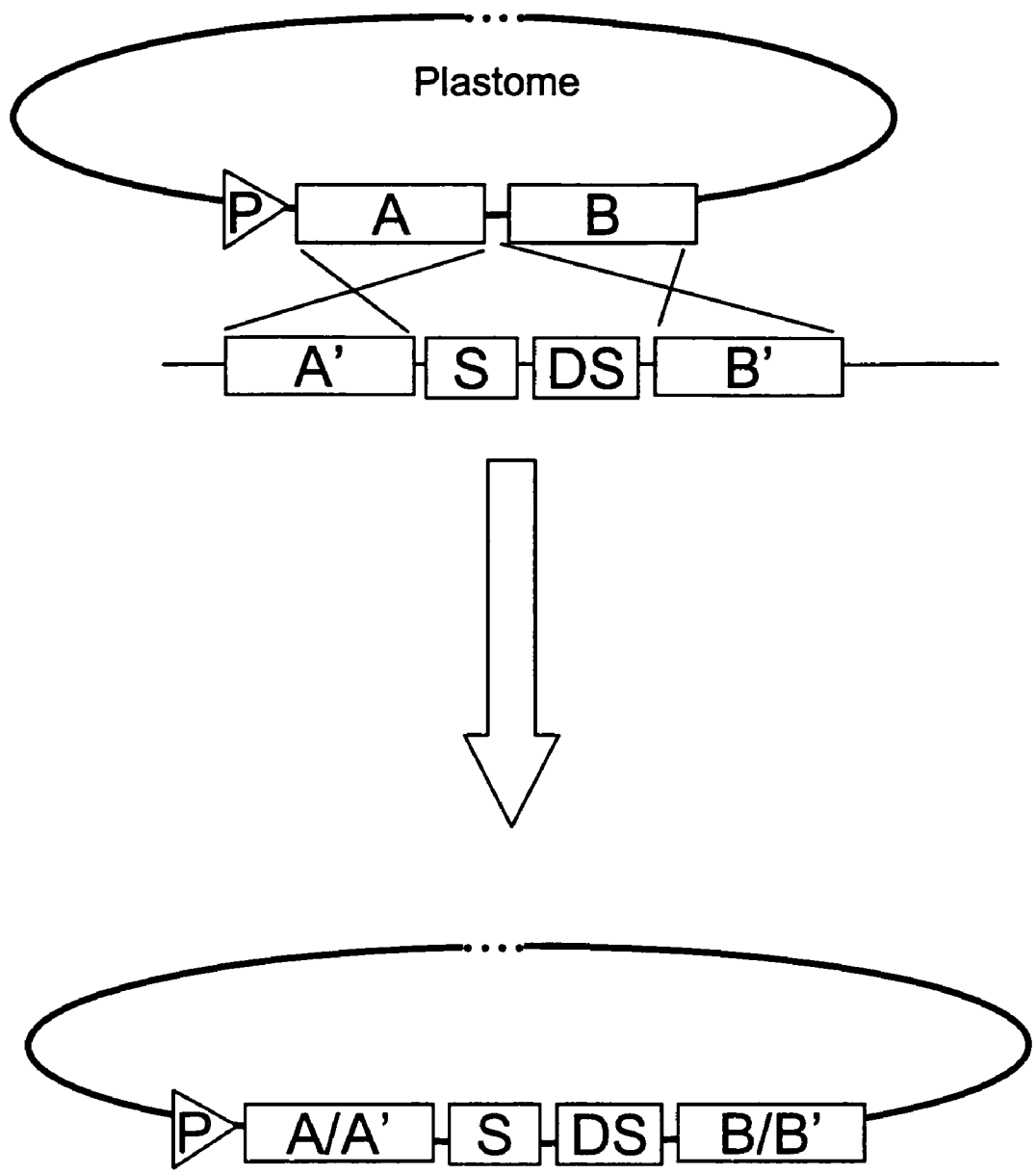

3. FIG. 3: Introduction of a DSB Recognition Sequence into the Plastome by Means of Double Cross-Over in a Transcriptionally Active Region In a further, especially preferred embodiment 2, a DSBR construct is initially introduced into plastids of a higher plant. In this embodiment, the DSBR construct is preferably equipped with homologous target regions and with an expressible selection marker, an endogenous promoter of the plastome being utilized, and it preferably additionally comprises a recognition sequence for a DSBI enzyme which preferably has no natural recognition sequence in the plastidic genome of the (nontransformed) plant in question. The DSBR construct may already encode genes of interest. Predominantly homoplastomic master plants are generated (FIG. 3).

Figure 4A:
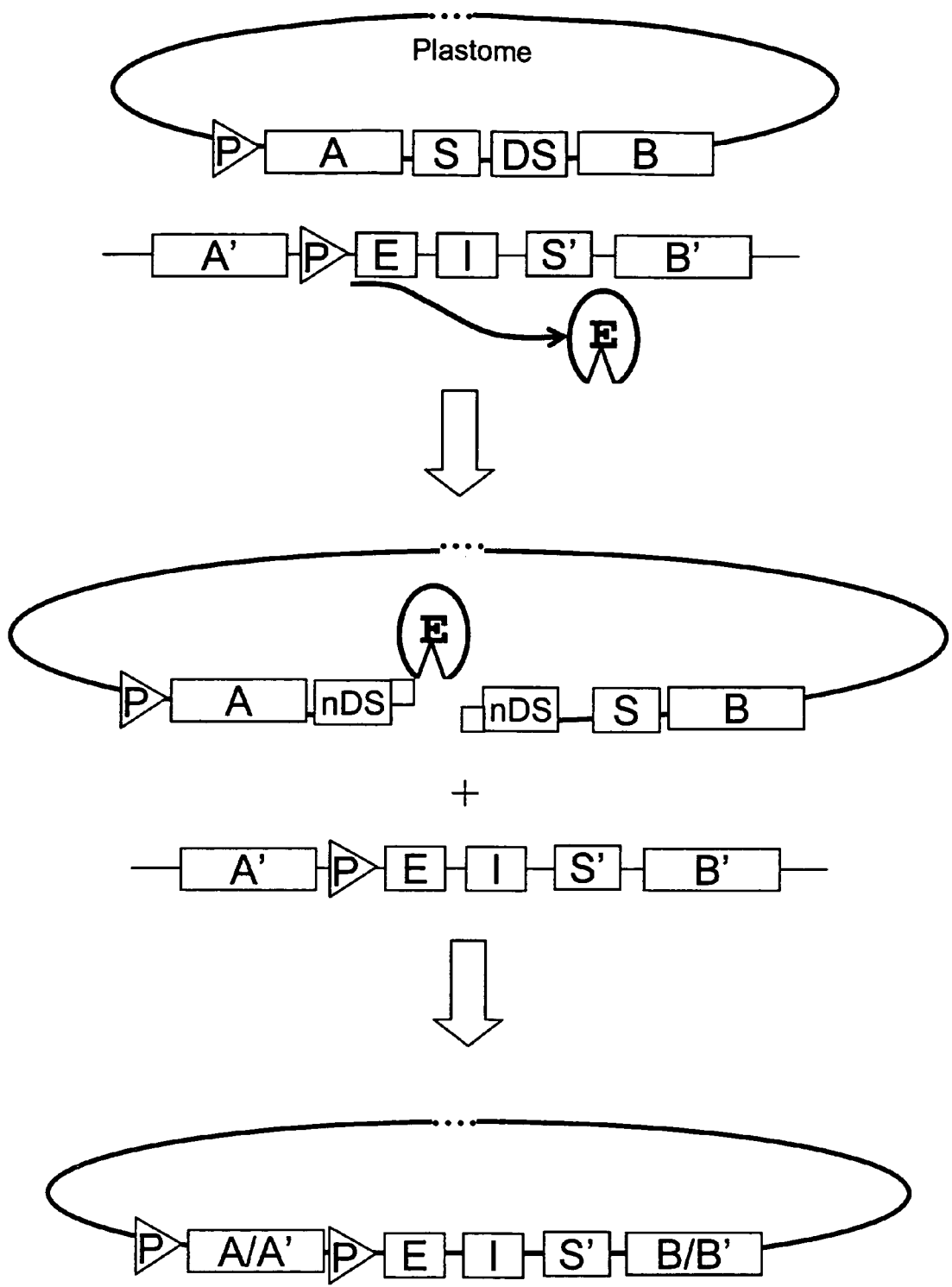
Figure 4B:
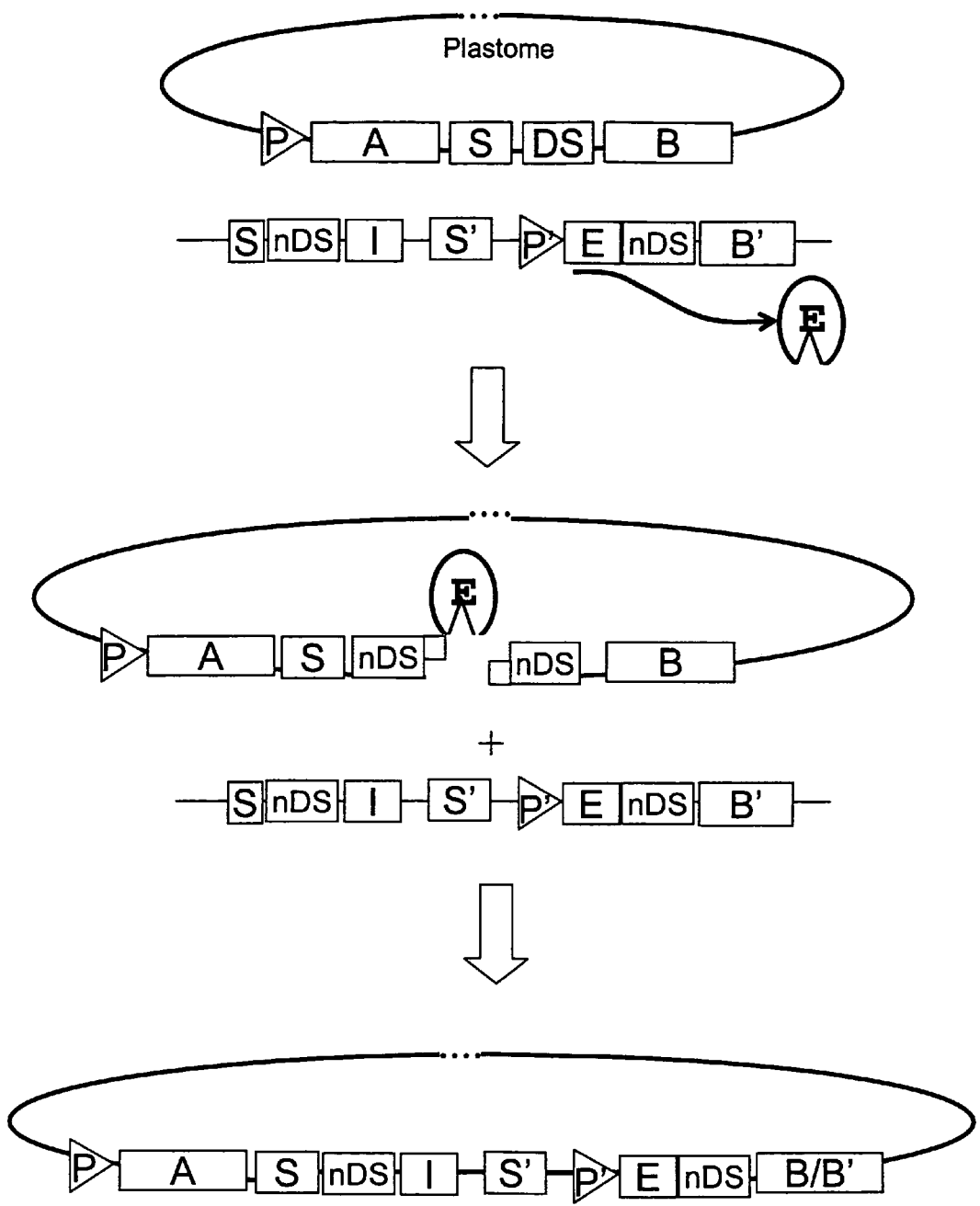
Figure 4C:
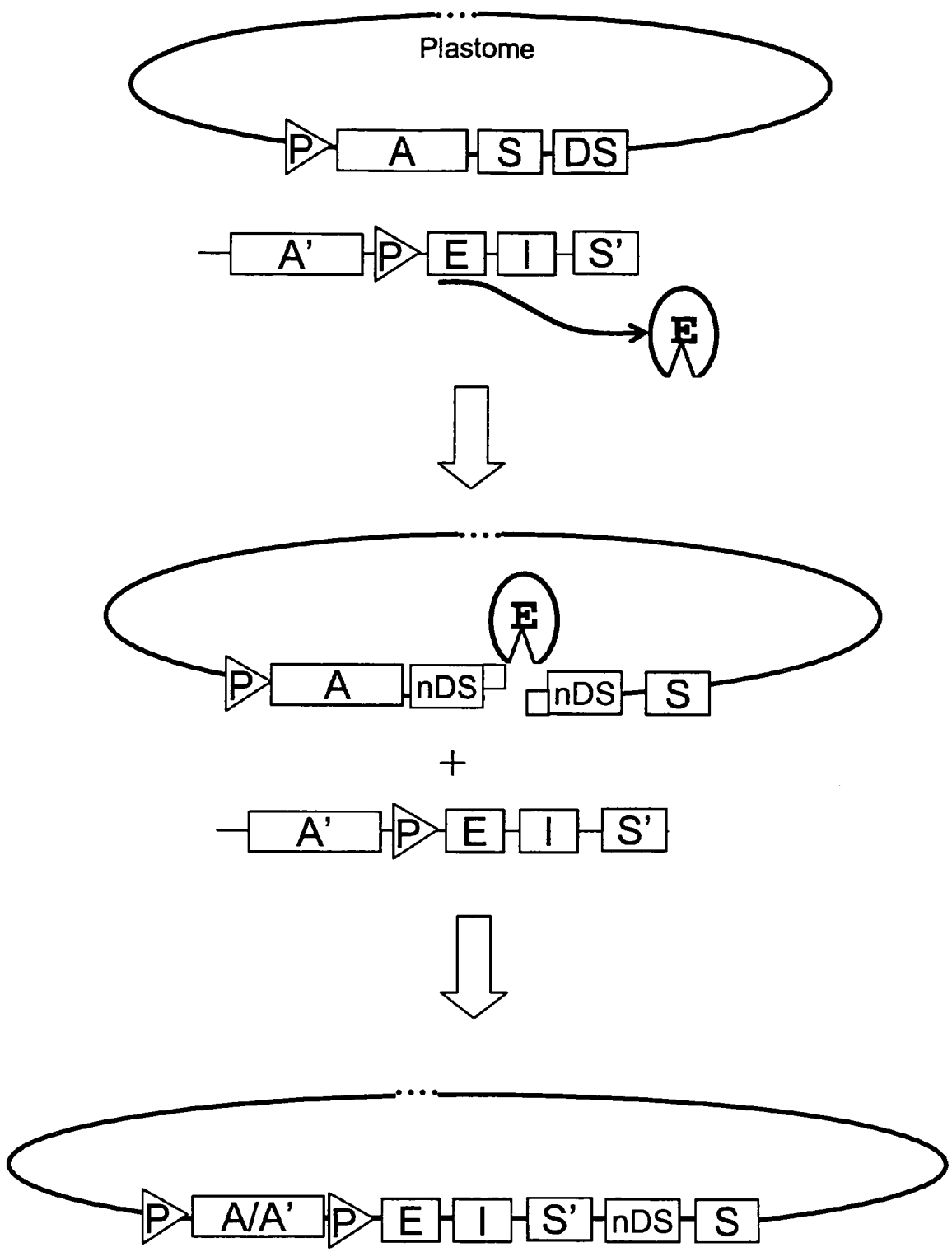

4. FIG. 4A-E: Introduction of an Isertion Sequence with a Cassette Encoding a DSBI Enzyme and, if Appropriate, a Selection Marker and Further Genes of Interest Explants of the master plants generated in embodiment 2 are utilized for a further transformation with a transformation construct according to the invention. Preferably, the transformation construct according to the invention has regions which are homologous to the sequences surrounding the insertion site of the DSBR construct, which regions are preferably located on both sides (FIGS. 4A, 4B) or on one side (FIGS. 4C, 4D) of the insertion sequence. Insertion now takes place via homologous recombination (for example crossover) or via repair synthesis. The sequences to be inserted are especially preferably—following the homology sequences inwardly—flanked by portions of the DSB recognition sequence (nDS) which correspond to the portions originating as the consequence of cleavage with the DSBI enzyme (FIG. 4B). The insertion sequence thus comprises sequences which correspond in detail to the ends which are the result of a cleavage in the plastome and thus ensure a particularly efficient incorporation.

Figure 4D:
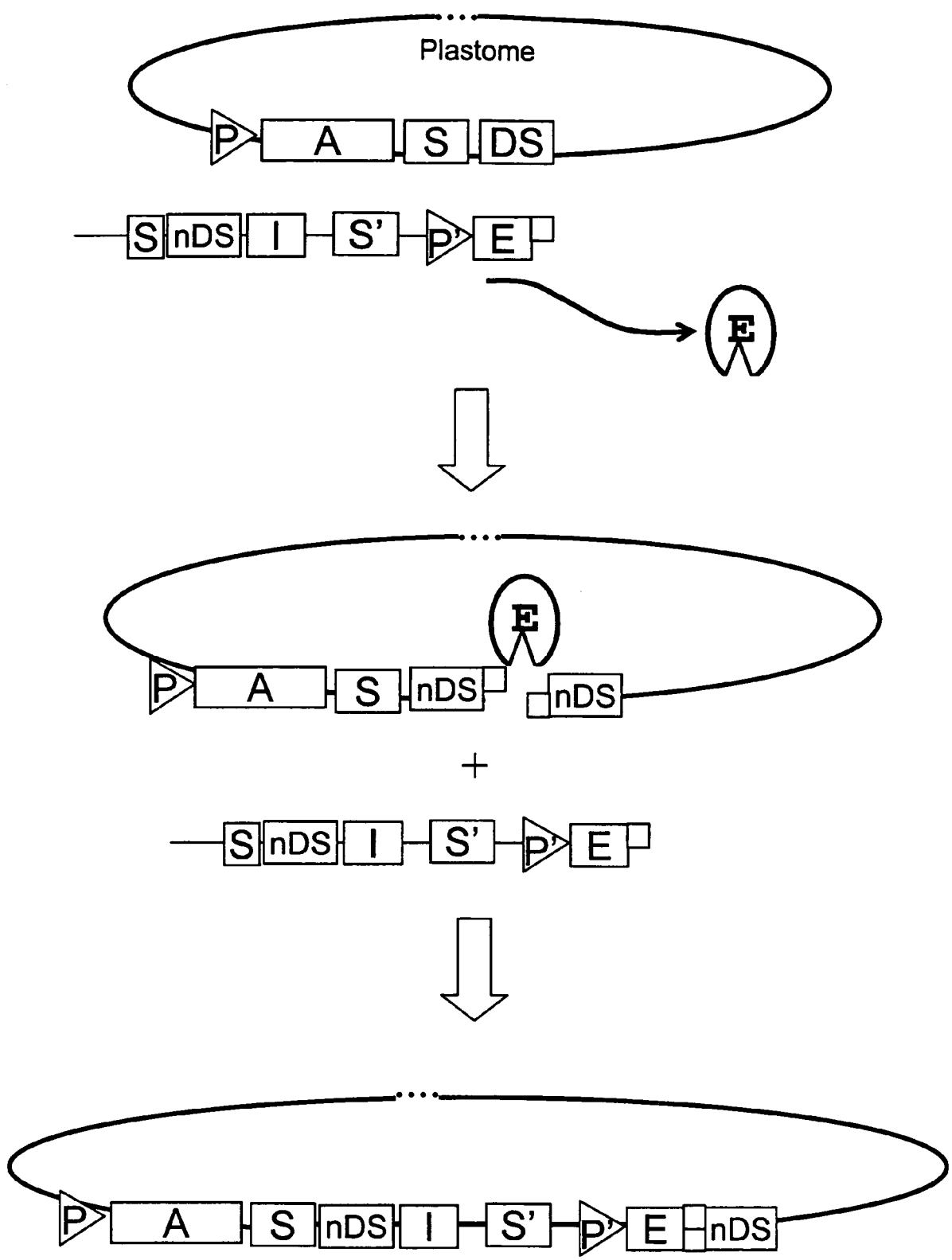
Figure 4E:
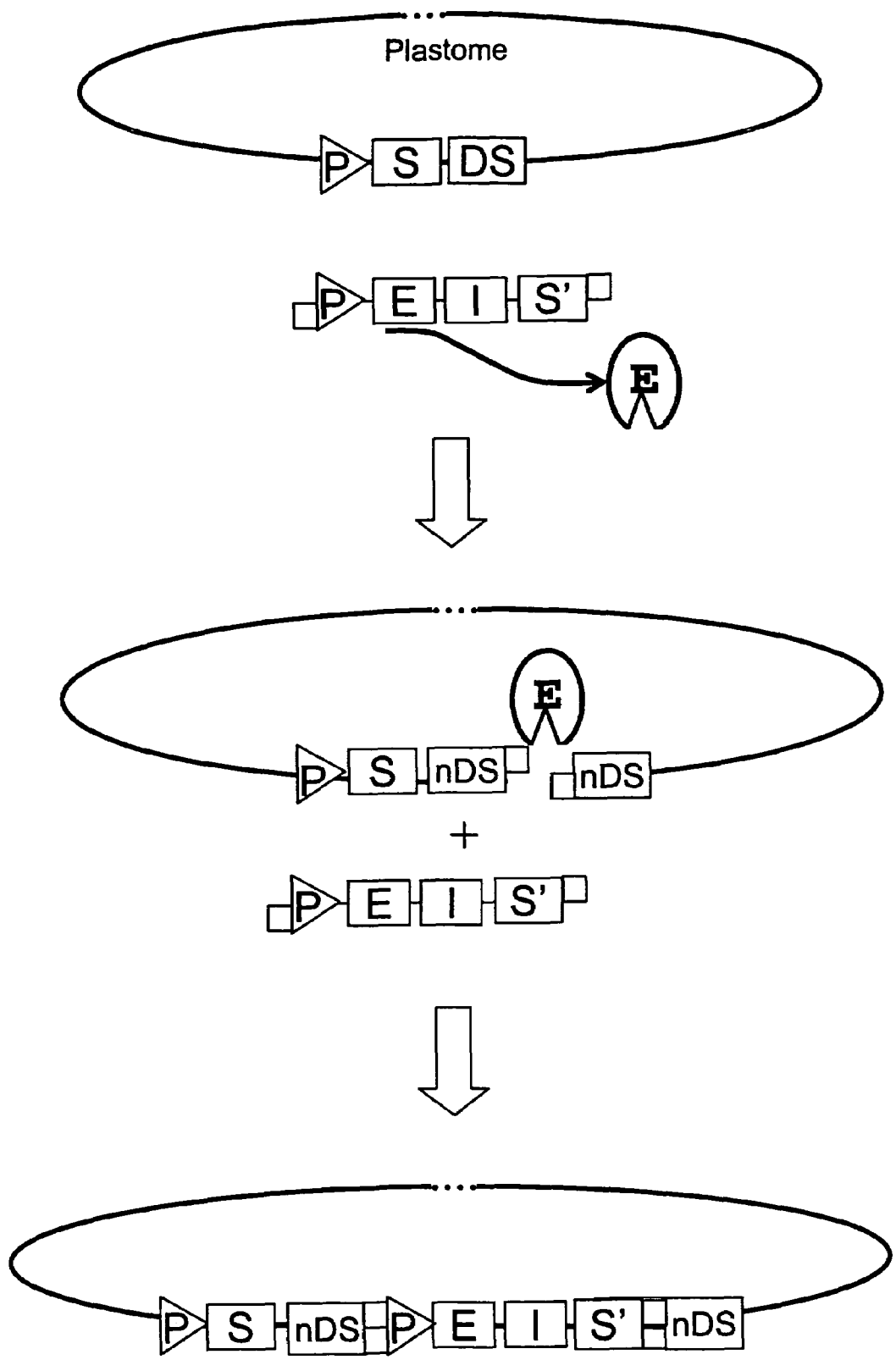

If the transformation construct, or the insertion sequence, has no such homologous regions, the insertion sequence is preferably provided, at these ends, with overhangs which are also generated by the DSBI enzyme after cleavage of the master plant plastome (FIG. 4E).

If only one homology sequence is present, this sequence borders, in an especially preferred embodiment, an nDS sequence (see hereinabove as described for FIG. 4B), while the other side of the insertion sequence is provided with overhangs which correspond to those generated by the DSBI enzyme in the plastome of the master plant (FIG. 4D).

The insertion sequence optionally codes for a further expressible selection marker which differs functionally from that of the DSBR construct, if appropriate one or more expressible genes of interest and the expressible DSBI enzyme, which cleaves the recognition sequence introduced by the DSBR construct at the insert site in the plastidic genome of the master plant. The insertion sequence of the transformation construct is inserted, in this context, in such a way at a position that said recognition region is no longer functional after the insertion.

5. FIG. 5A-E: Introduction of an Insertion Sequence with a Cassette Encoding a DSBI Enzyme and, if Appropriate, Selection Markers and Further Genes of Interest Utilizing Natural, Endogenous DSB Recognition Sequences In a further, very especially preferred embodiment 3, a transformation construct according to the invention comprises an expressible DSBI enzyme which has an endogenous, natural recognition sequence in the plastome of the plant in question.

Explants of these natural master plants are utilized for a transformation with a transformation construct according to the invention. Preferably, the transformation construct according to the invention has regions which are homologous to the sequences surrounding the insertion site of the DSBR construct, which regions are preferably located on both sides (FIGS. 5A, 5B) or on one side (FIGS. 5C, 5D) of the insertion sequence. Insertion now takes place via homologous recombination (for example cross-over) or via repair synthesis.

Figure 5A:
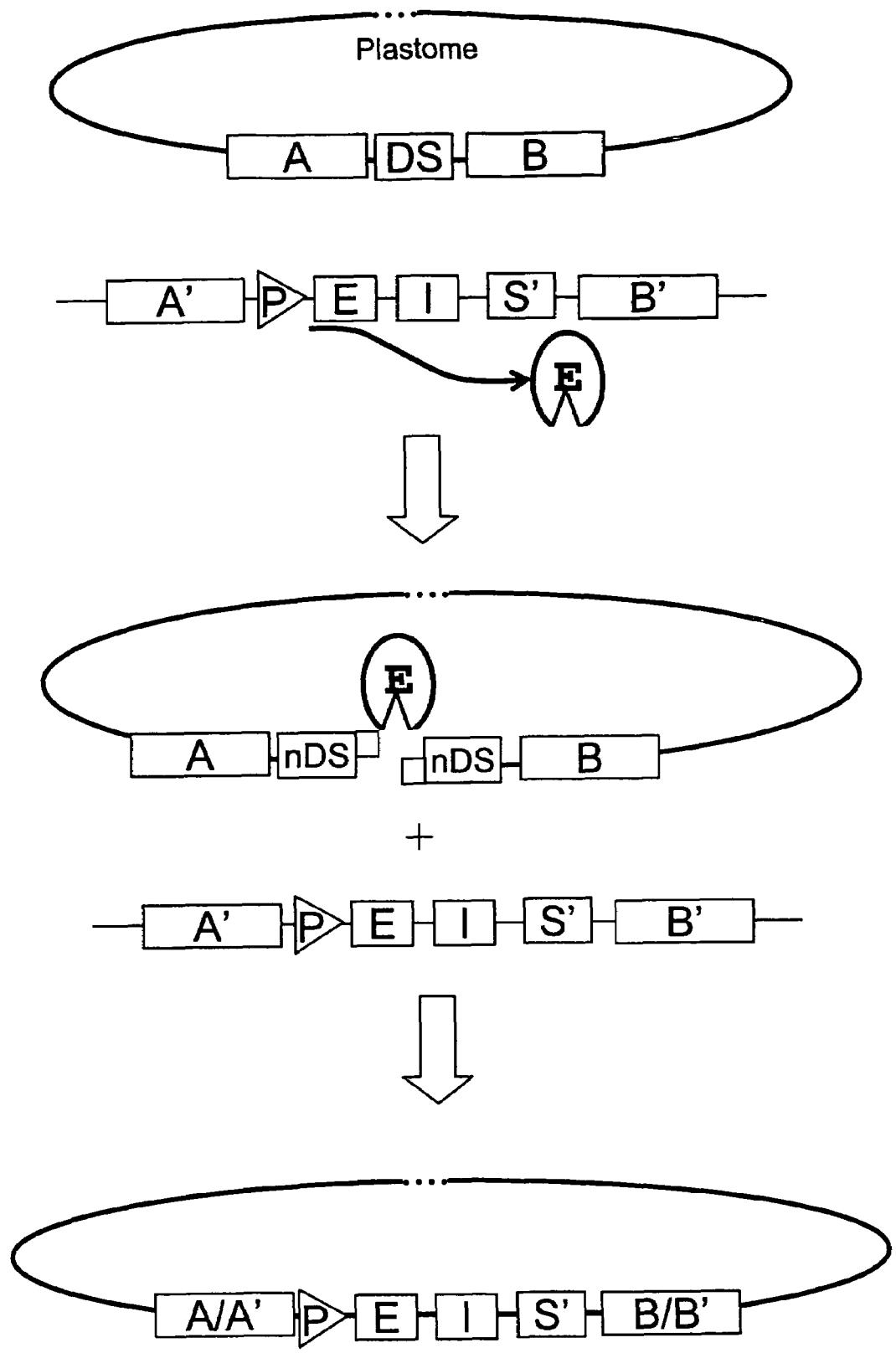
Figure 5B:
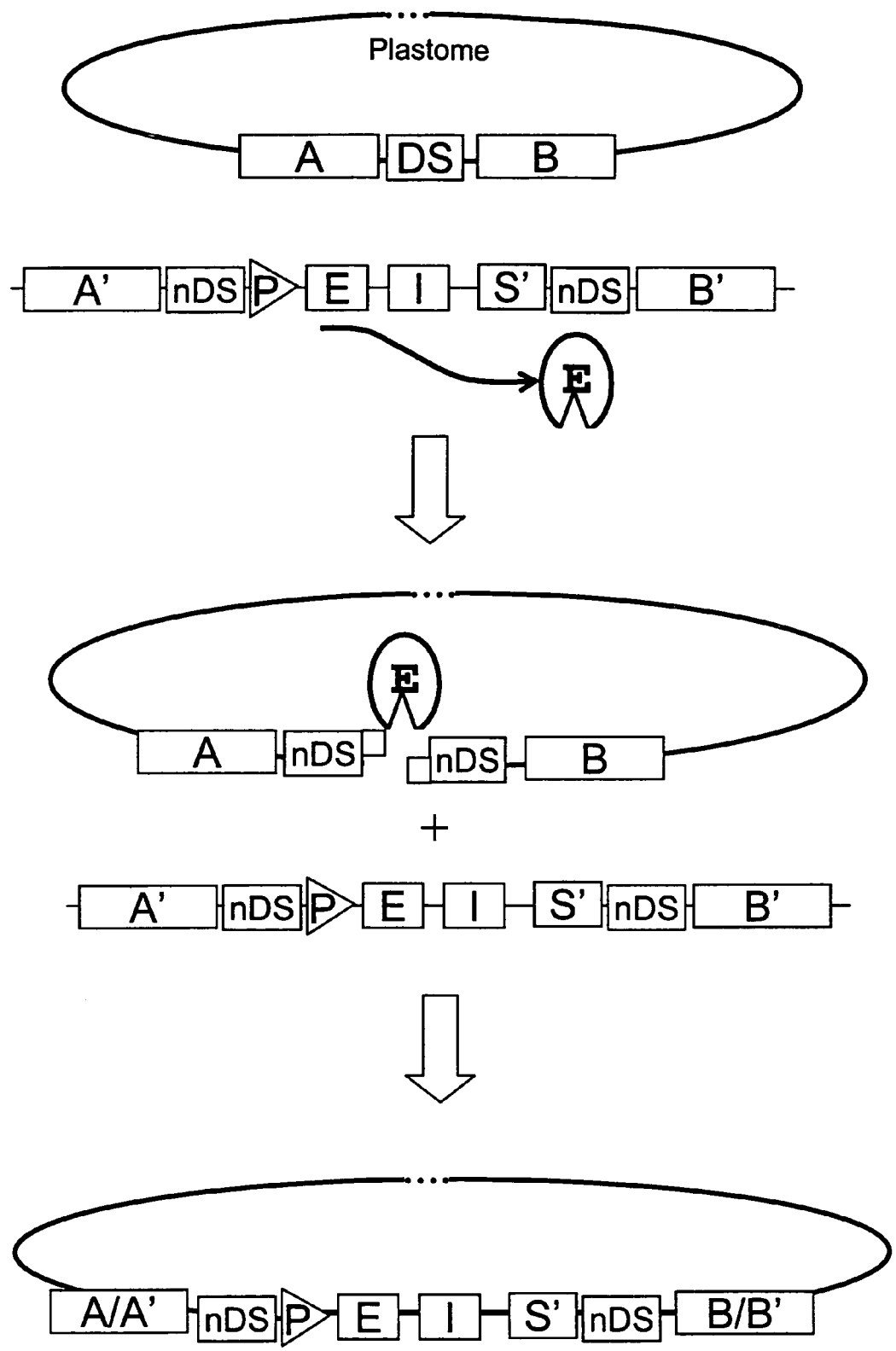
Figure 5C:
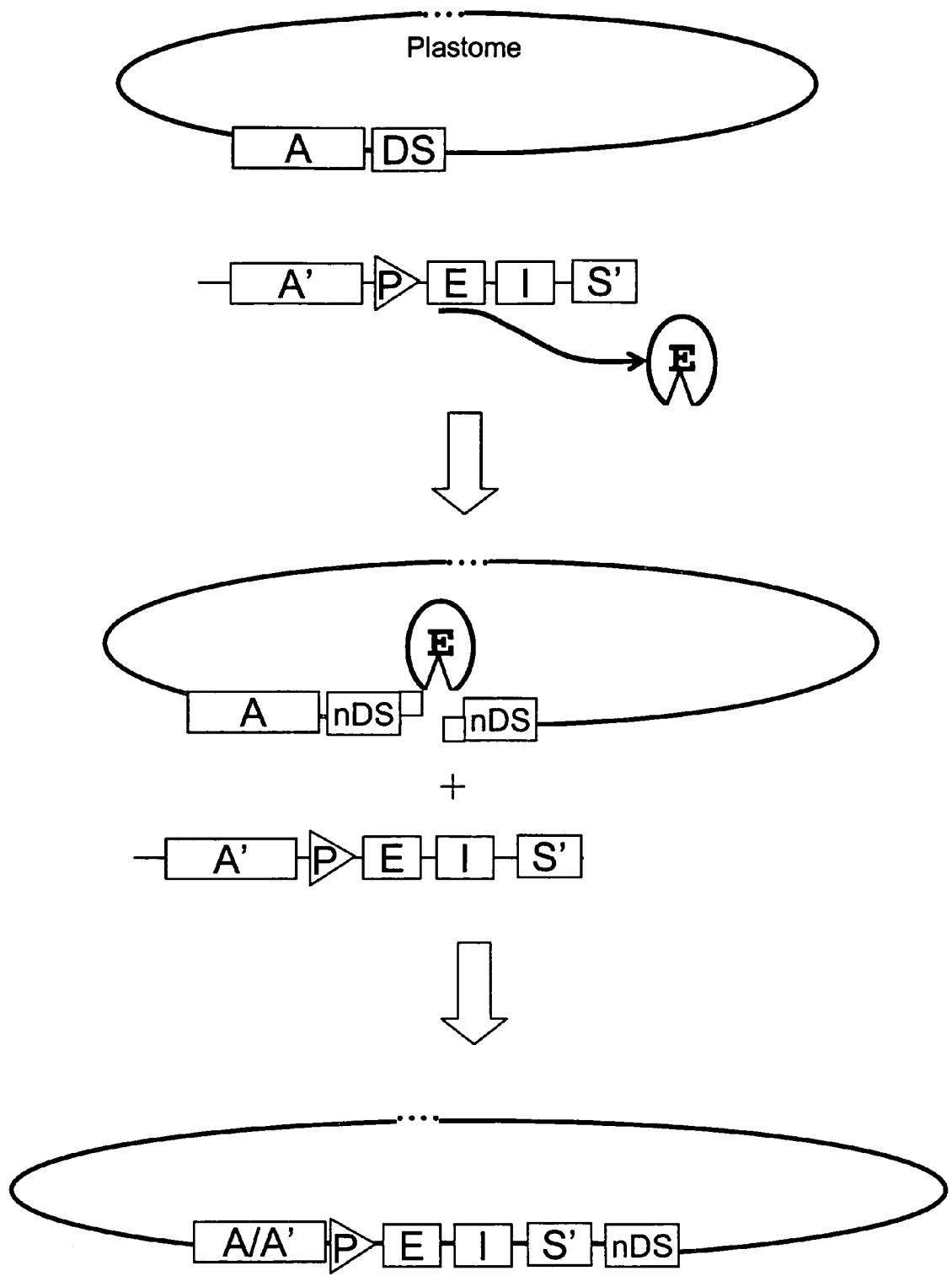

The sequences to be inserted are especially preferably—following the homology sequences inwardly—flanked by portions of the DSB recognition sequence (nDS) which correspond to the portions originating as the consequence of cleavage with the DSBI enzyme (FIG. 5B). The insertion sequence thus comprises sequences which correspond in detail to the ends which are the result of a cleavage in the plastome and thus ensure a particularly efficient incorporation.

Figure 5D:
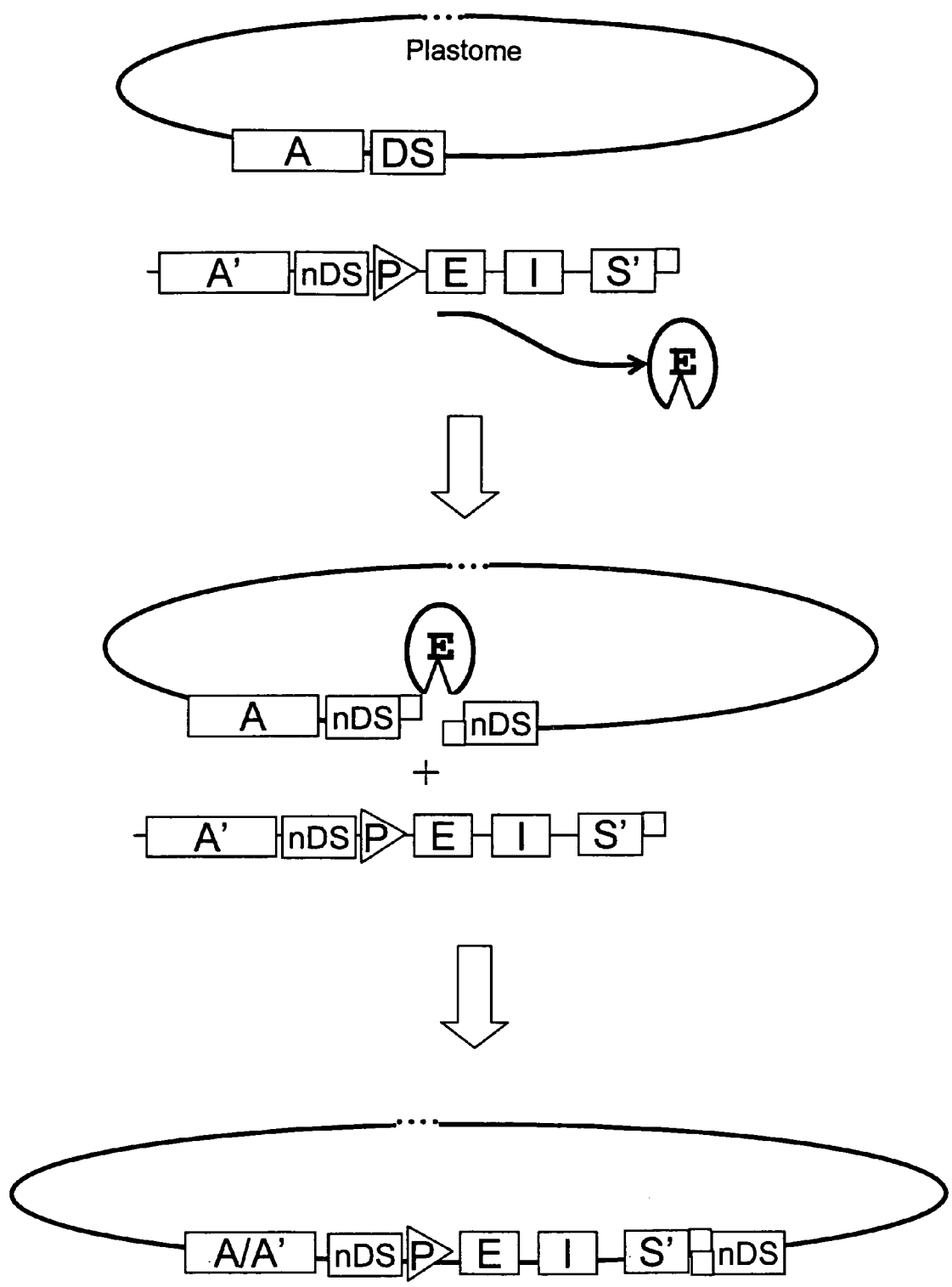
Figure 5E:
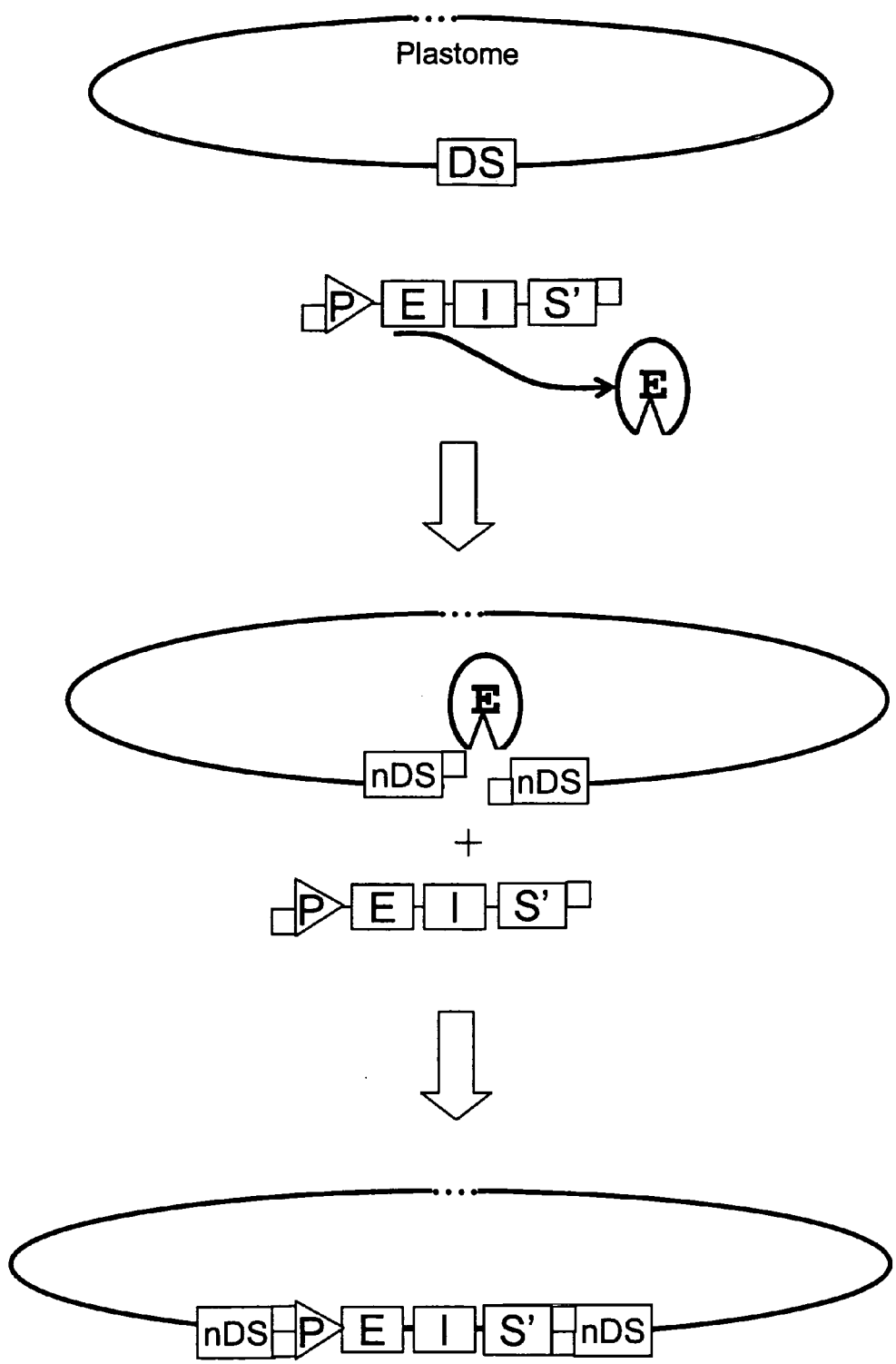

If the transformation construct, or the insertion sequence, has no such homologous regions, the insertion sequence is preferably provided, at these ends, with overhangs which are also generated by the DSBI enzyme after cleavage of the master plant plastome (FIG. 5E).

If only one homology sequence is present, this sequence borders, in an especially preferred embodiment, an nDS sequence (see hereinabove as described for FIG. 5B), while the other side of the insertion sequence is provided with overhangs which correspond to those generated by the DSBI enzyme in the plastome of the master plant (FIG. 5D).

The insertion sequence of the tranformation construct is, in this context, preferably inserted at a position in such a way that said recognition region is no longer functional after the insertion. The insertion sequence preferably encodes an expressible selection marker (S'), one or more genes of interest, and the expressible DSBI enzyme. The selection marker is optional.

6. FIG. 6A-E: Introduction of an Insertion Sequence with a Cassette Encoding Genes of Interest and, if Appropriate, Selection Markers, and Introduction of a DSBI Enzyme in Trans In further preferred embodiments 4, the DSBI enzyme is not encoded by the transformation construct, but either expressed in trans (in plastids or as PLS fusion protein in the nucleus) or transfected into the plastids in the form of RNA or protein. The DSBI enzyme recognizes either an artificially introduced DSB recognition sequence (FIGS. 6A, 6B) or a natural DSB recognition sequence (FIGS. 6C, 6D). This embodiment is especially preferred when the transformation construct comprises no promoter elements, and expression of the coded genes is only realized after insertion into the plastome, using plastidic, endogenous promoters.

As was the case in the embodiments which have already been described above, the transformation construct preferably has regions bilaterally (FIGS. 6A, 6B) or unilaterally (not shown) of the insertion sequence which are homologous to the sequences surrounding the insertion site of the DSBR construct. Insertion now takes place via homologous recombination (for example cross-over) or repair synthesis.

Figure 6A:
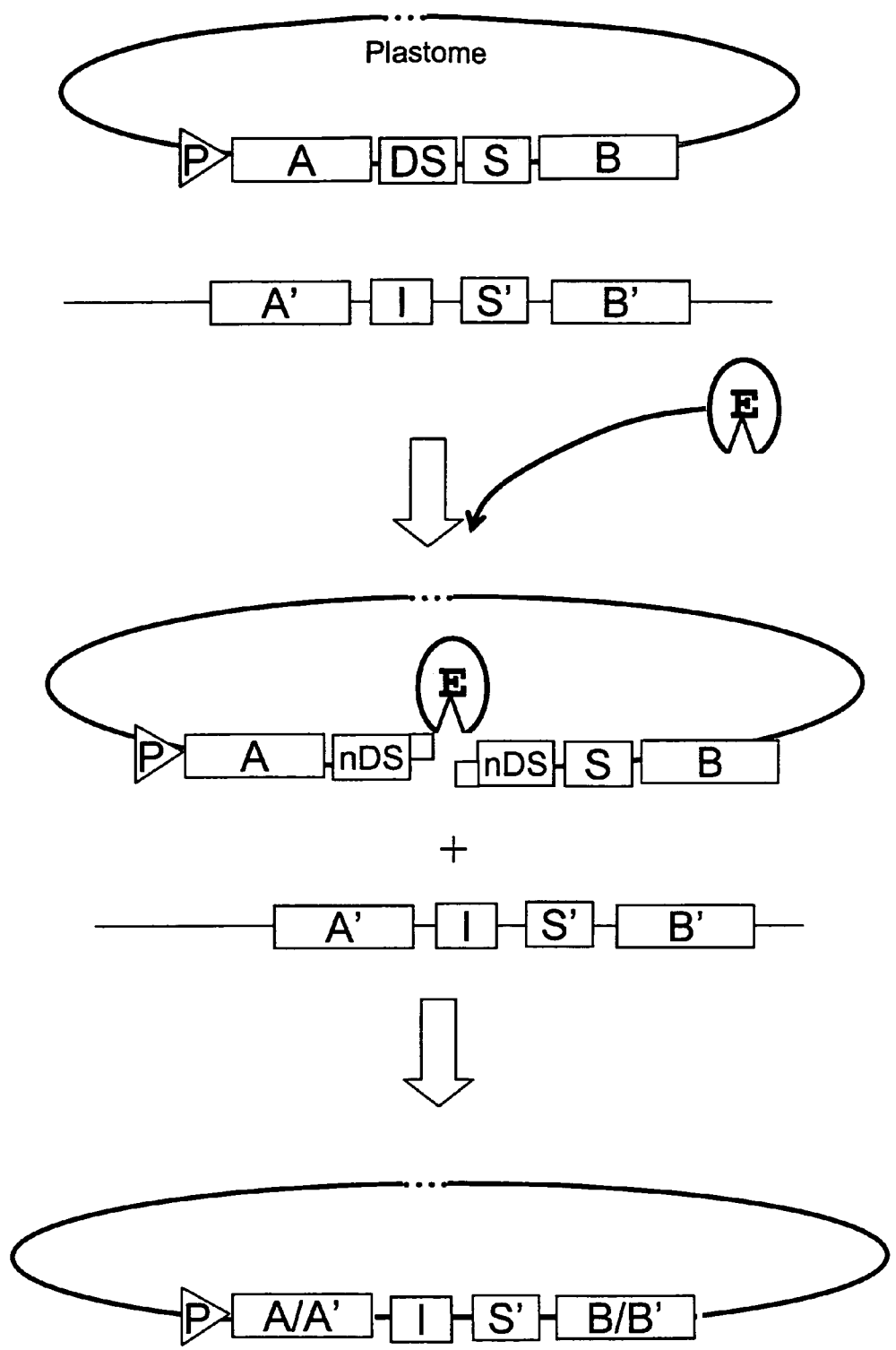
Figure 6B:
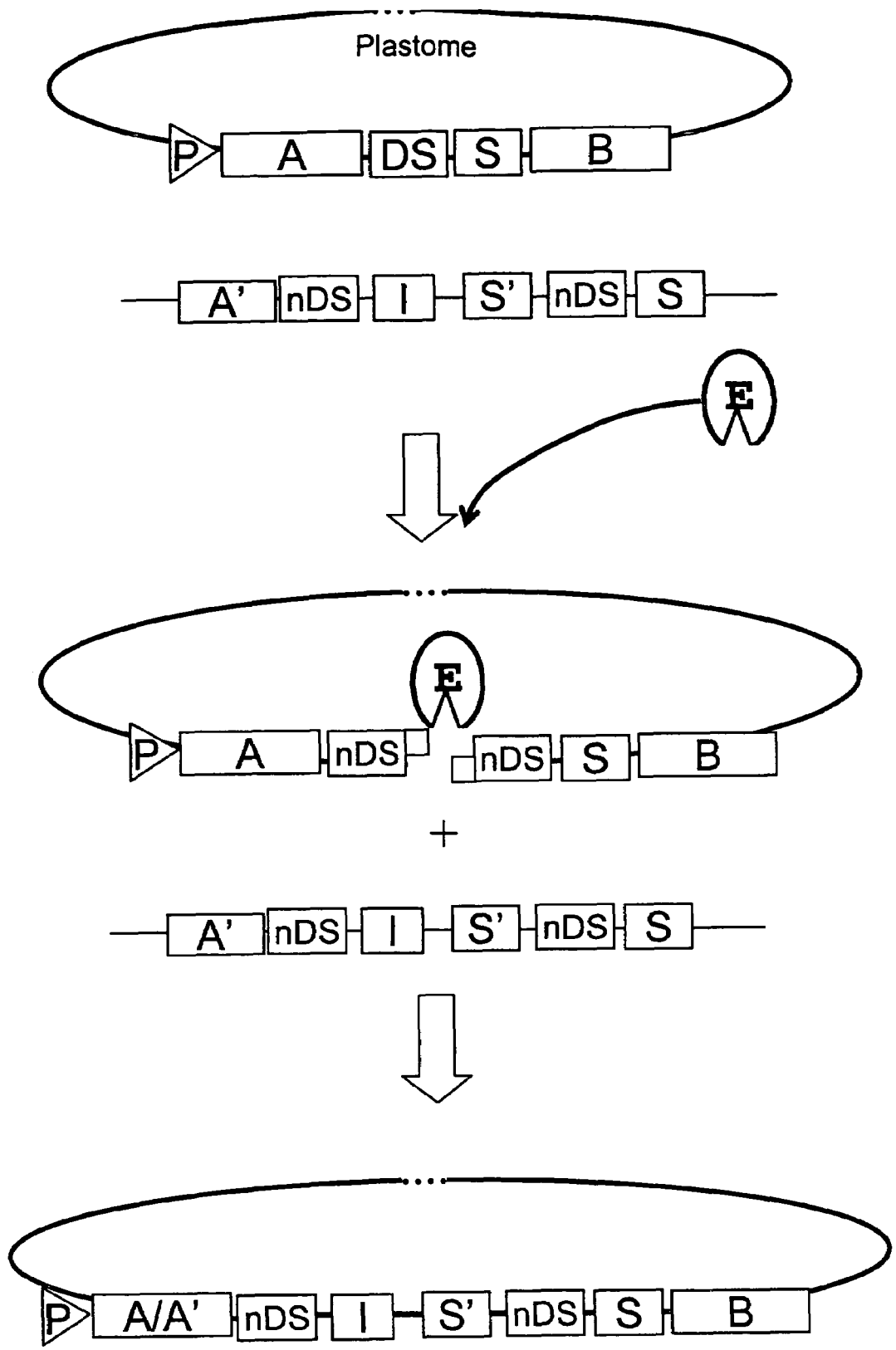
Figure 6C:
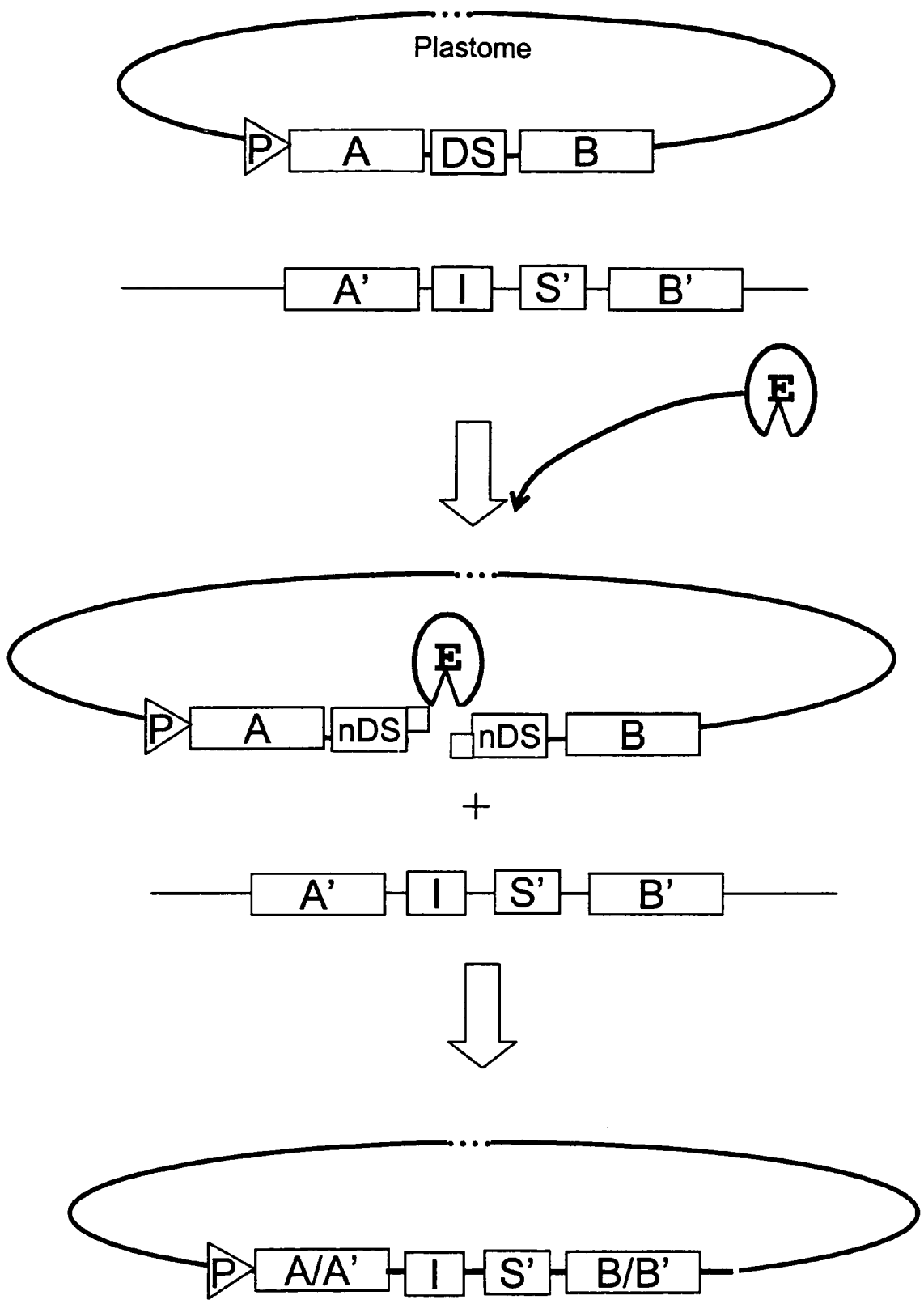
Figure 6D:
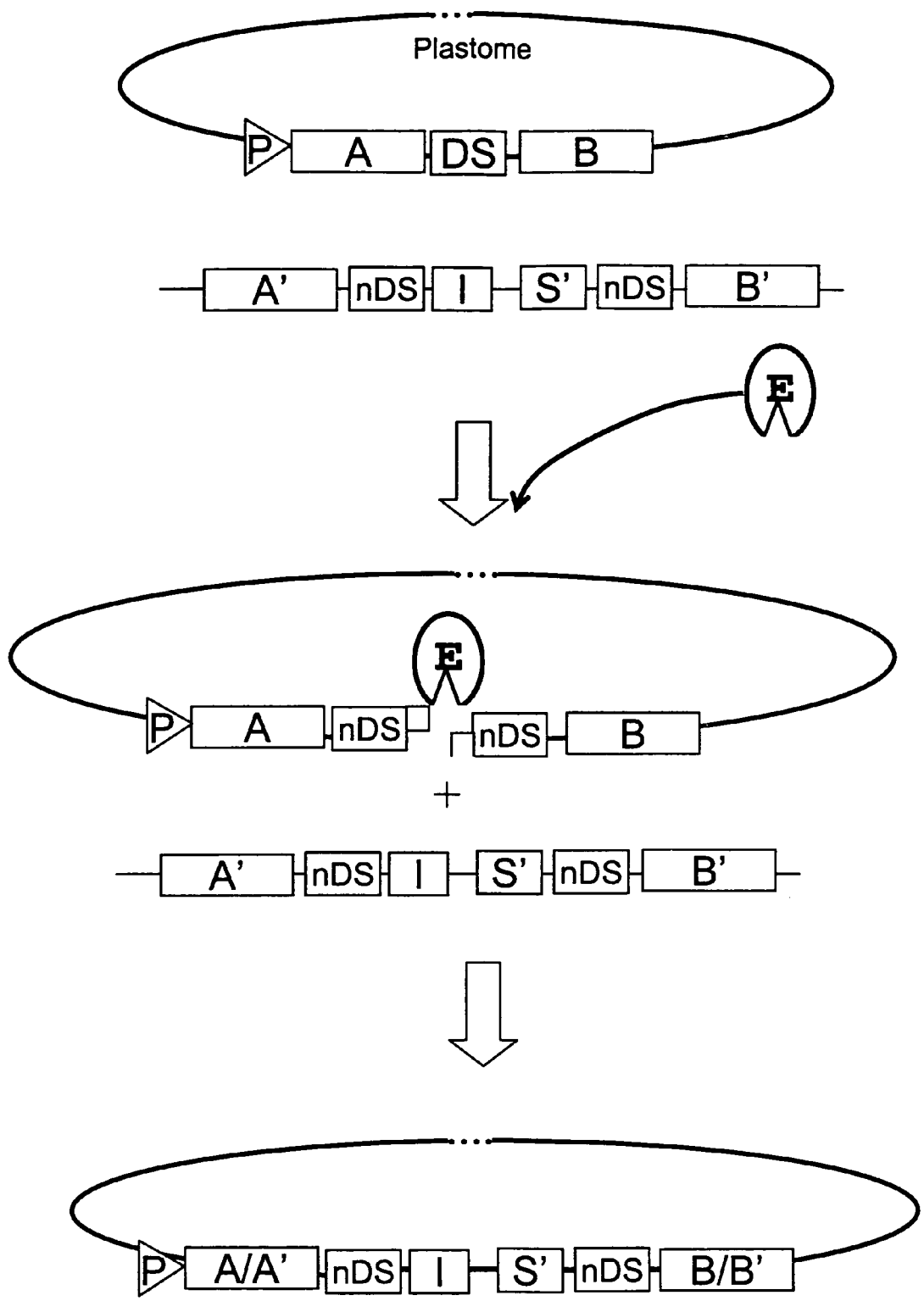

The sequences to be inserted are especially preferably—following the homology sequences inwardly—flanked by portions of the DSB recognition sequence (nDS) which correspond to the portions originating as the consequence of cleavage with the DSBI enzyme (FIGS. 6B, 6D). The insertion sequence thus comprises sequences which correspond in detail to the ends which are the result of a cleavage in the plastome and thus ensure a particularly efficient incorporation.

Figure 6E:
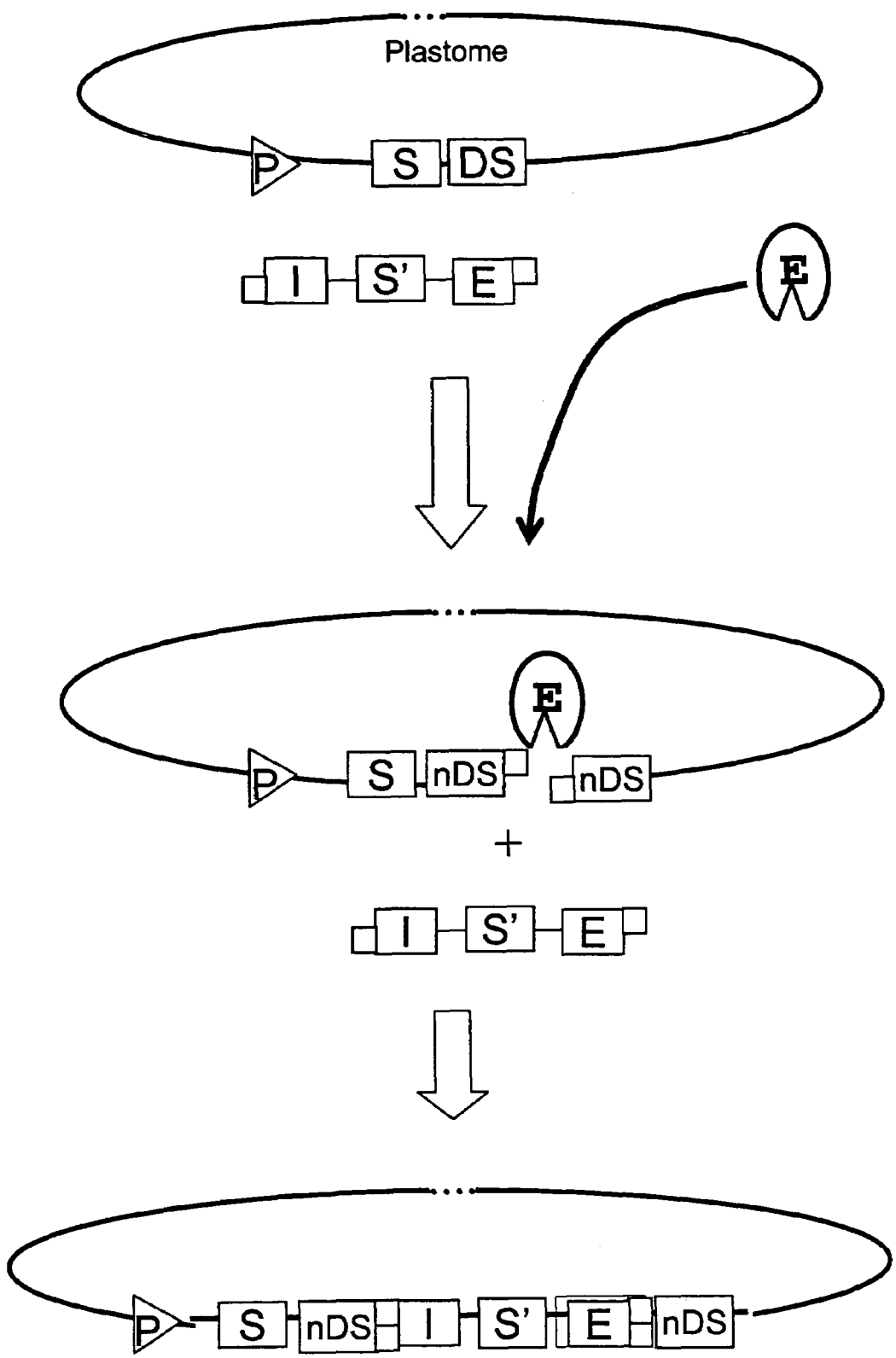

If the transformation construct, or the insertion sequence, has no such homologous regions, the insertion sequence is preferably provided, at these ends, with overhangs which are also generated by the DSBI enzyme after cleavage of the master plant plastome (FIG. 6E). The transformation construct can additionally comprise a sequence encoding a DSBI enzyme. However, expression only takes place after successful insertion into the plastome, so that it is desirable that a first amount of functional RNA or protein of a DSBI enzyme is provided.

If only one homology sequence is present, it borders, in an especially preferred embodiment, an nDS sequence (see above as described for FIGS. 6B, 6D), while the other side of the insertion sequence is provided with overhangs which correspond to those generated by the DSBI enzyme in the plastome of the master plant (not shown).

In this context, the insertion sequence of the transformation construct is preferably inserted at a position in such a way that said recognition region is no longer functional after the insertion.

7. FIG. 7A-E: Introduction of an Insertion Sequence Comprising an Intron Sequence with a Cassette Encoding Genes of Interest and, if Appropriate, Selection Markers or DSBI Enzymes In a further, very especially preferred embodiment 5, the gene of interest (and optionally a selection marker S' and/or the DSBI enzyme) is/are encoded within an intron which is functional at the insertion site selected, i.e. which can splice out of the transcript formed therein.

Preferably, the transformation construct according to the invention has regions which are homologous to the sequences surrounding the insertion site of the DSBR construct, which regions are preferably located on both sides (FIGS. 7A, 7B) or one one side (not shown) of the insertion sequence. Insertion now takes place via homologous recombination (for example cross-over) or via repair synthesis.

If the transformation construct or the insertion sequence has no such homologous regions, the insertion sequence is preferably provided, at these ends, with overhangs which are also generated by the DSBI enzyme after cleaving the plastome of the master plant (not shown).

Figure 7A:
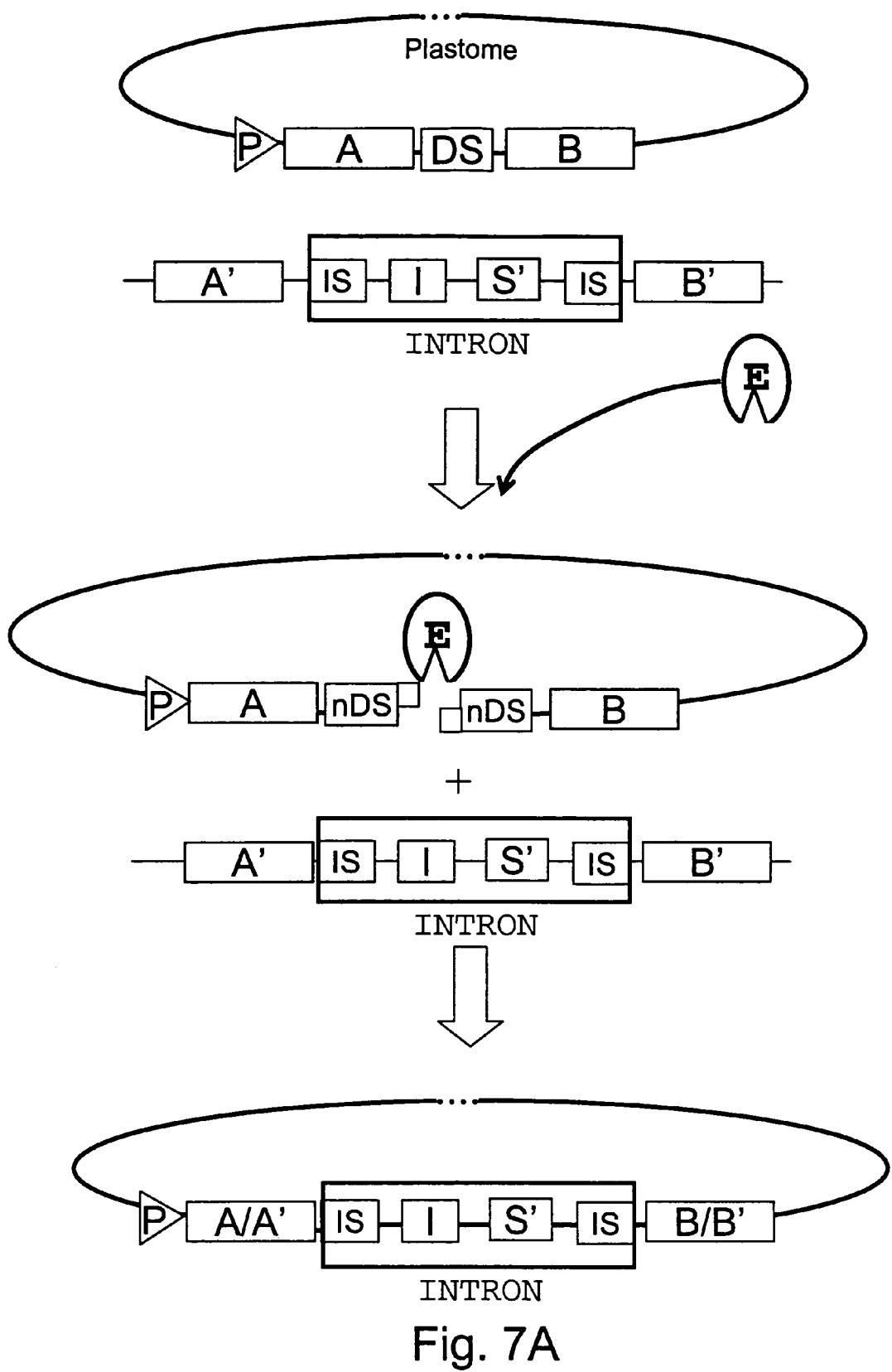
Figure 7B:
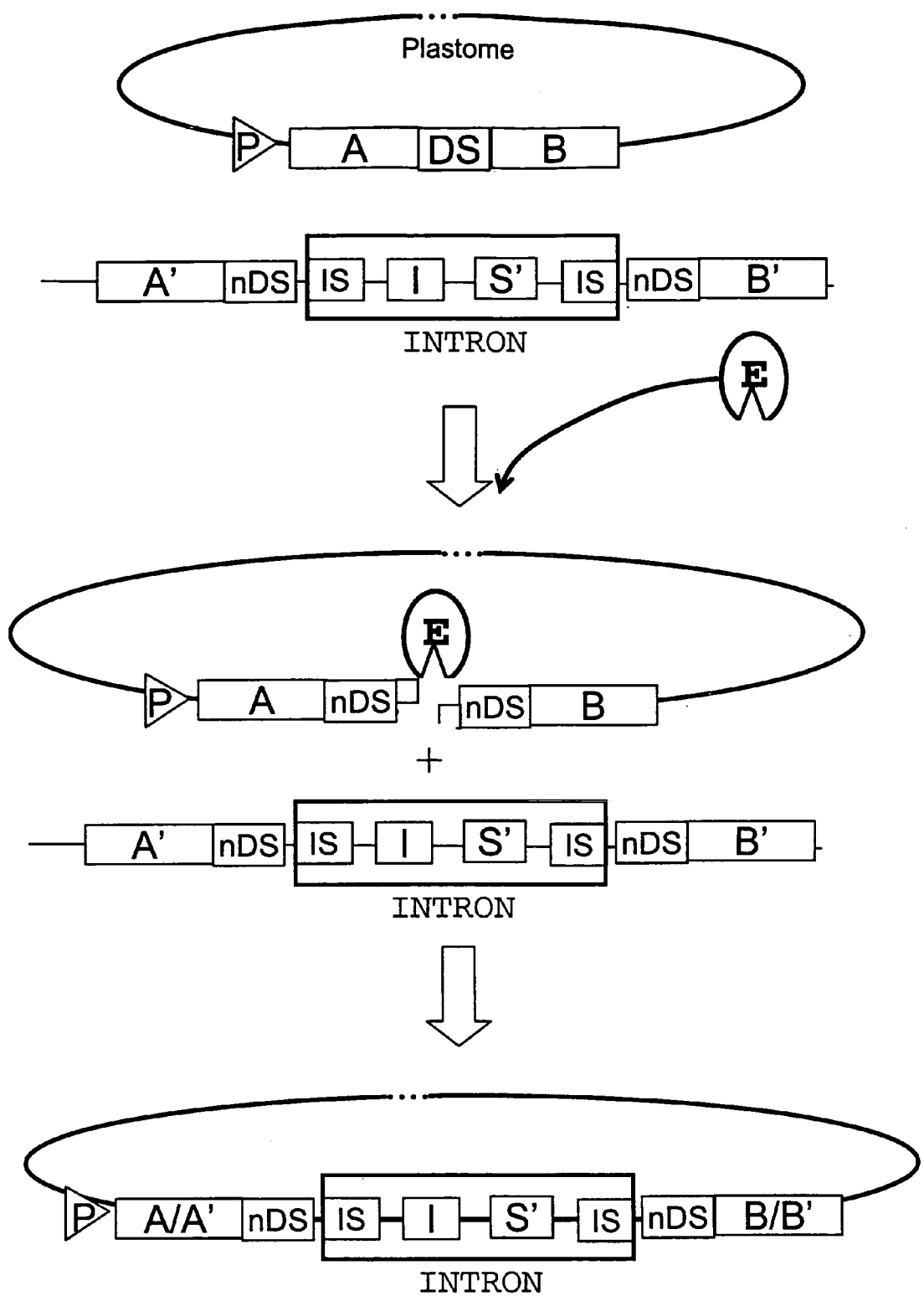
Figure 7C:
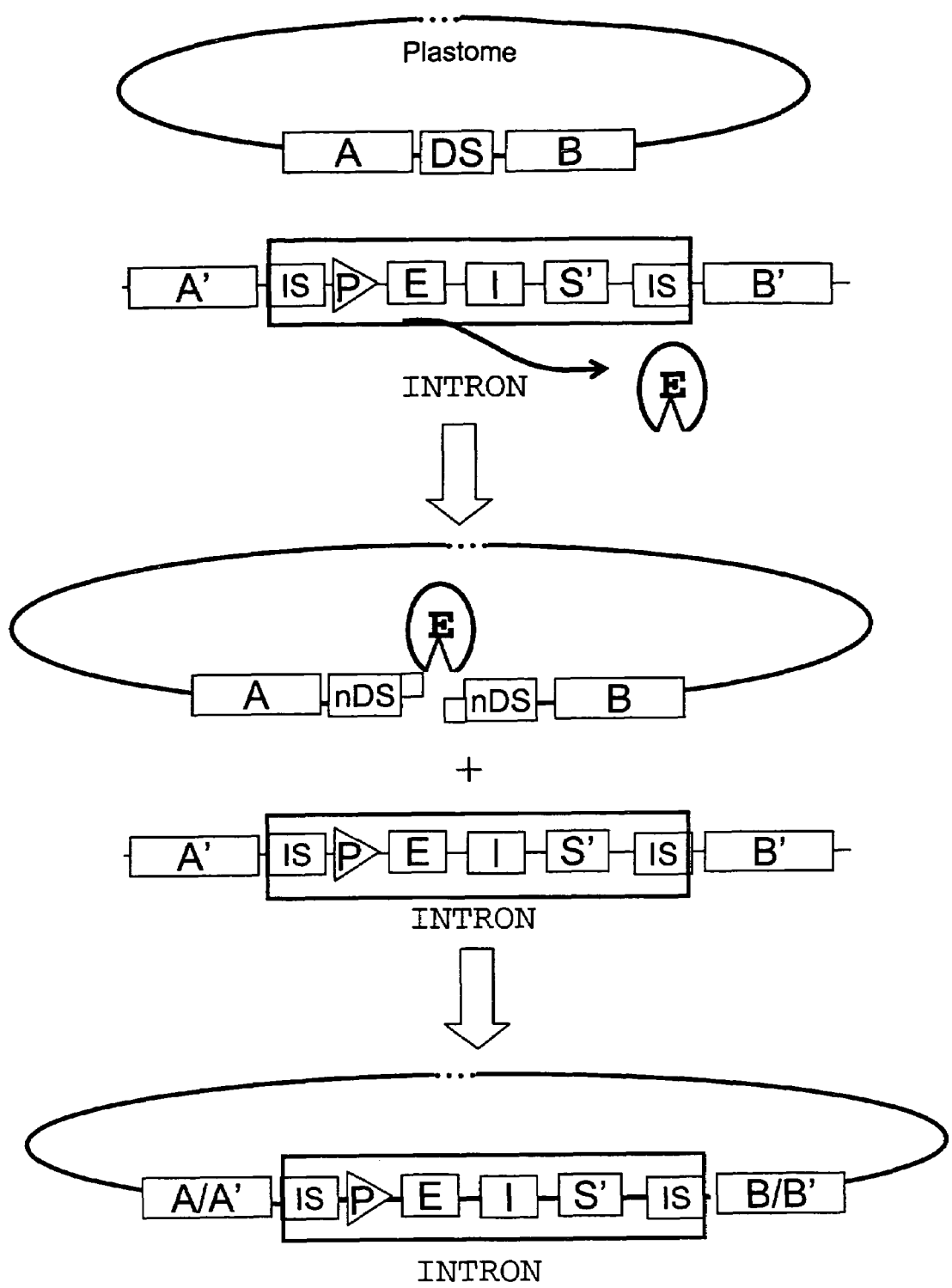
Figure 7D:
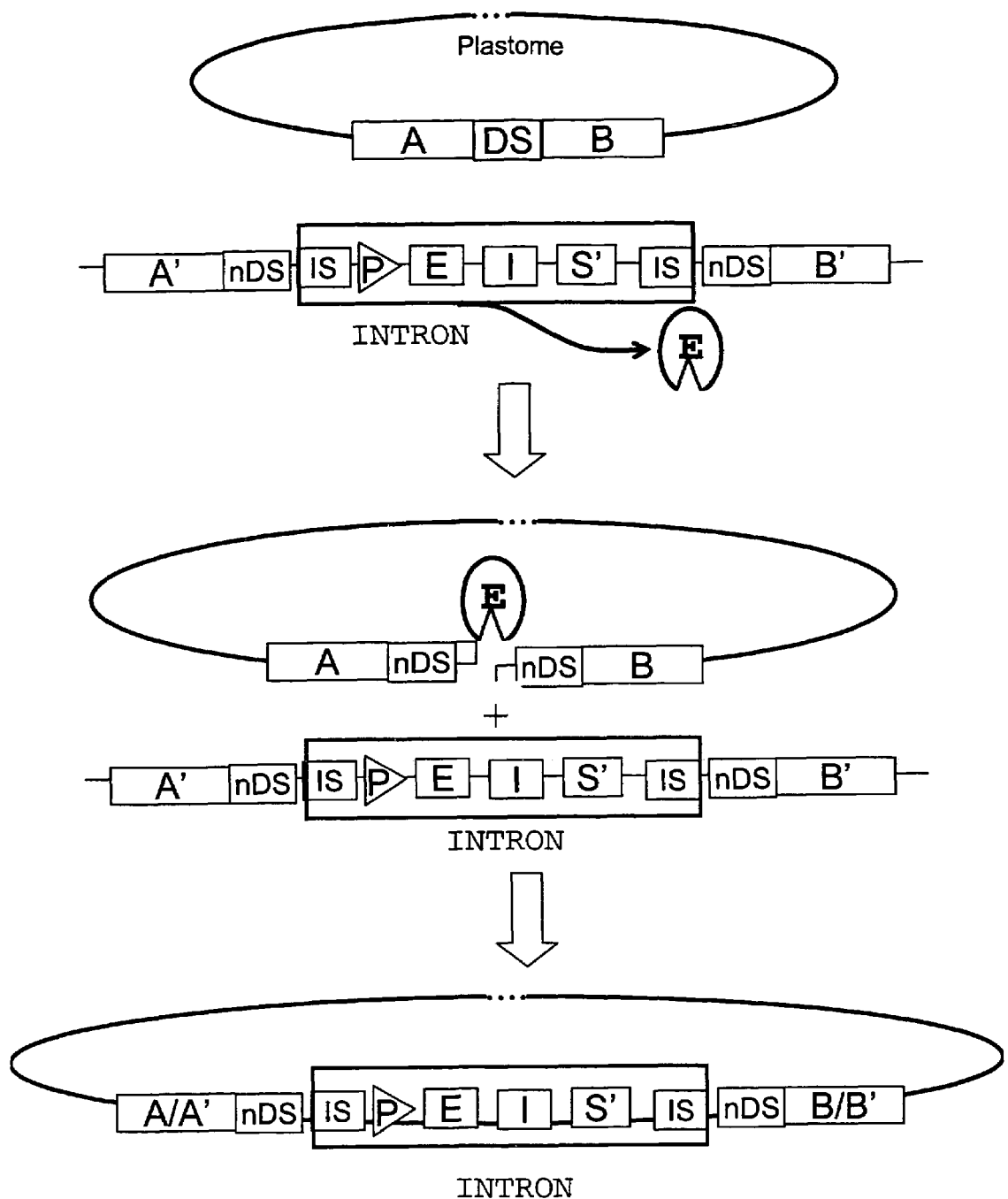
Figure 7E:
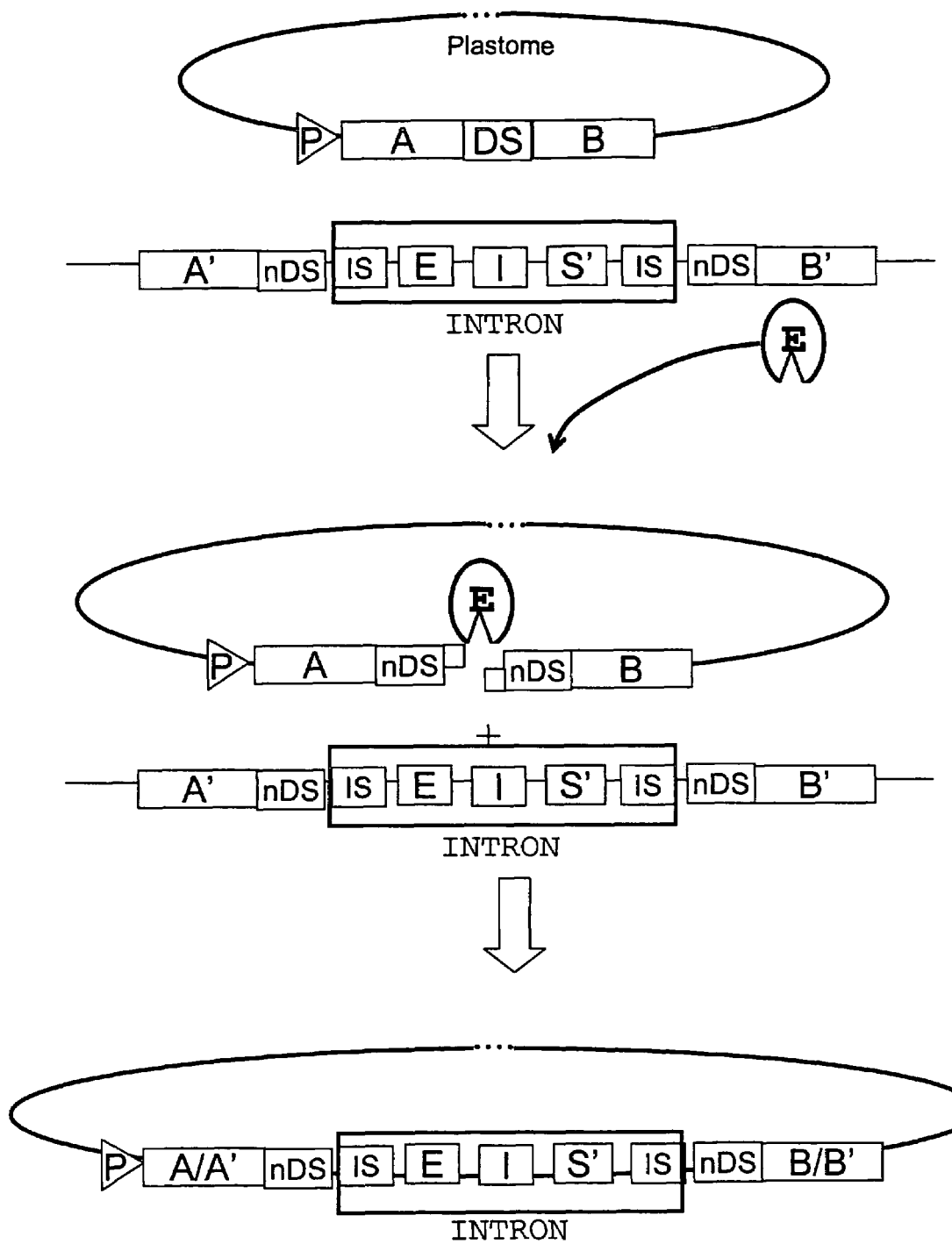

Expression can be controlled by means of a promoter which is present on the transformation construct (FIG. 7B) or an endogenous, plastidic promoter (FIG. 7A). In the first case, the DSBI enzyme is preferably present on the transformation construct (FIG. 7B), while, in the latter case, it is either expressed (at least in parallel) in trans (in plastids or as PLS fusion protein in the nucleus) or transfected into the plastids in the form of RNA or protein (FIG. 7A).

In this context, the insertion sequence of the transformation construct is preferably inserted at a position in such a way that said recognition region is no longer functional after the insertion. The transformation construct can additionally optionally comprise a sequence encoding a DSBI enzyme. However, expression only takes place after successful insertion into the plastome, so that it is desirable that a first amount of functional RNA or protein of a DSBI enzyme is provided.

Figure 8:
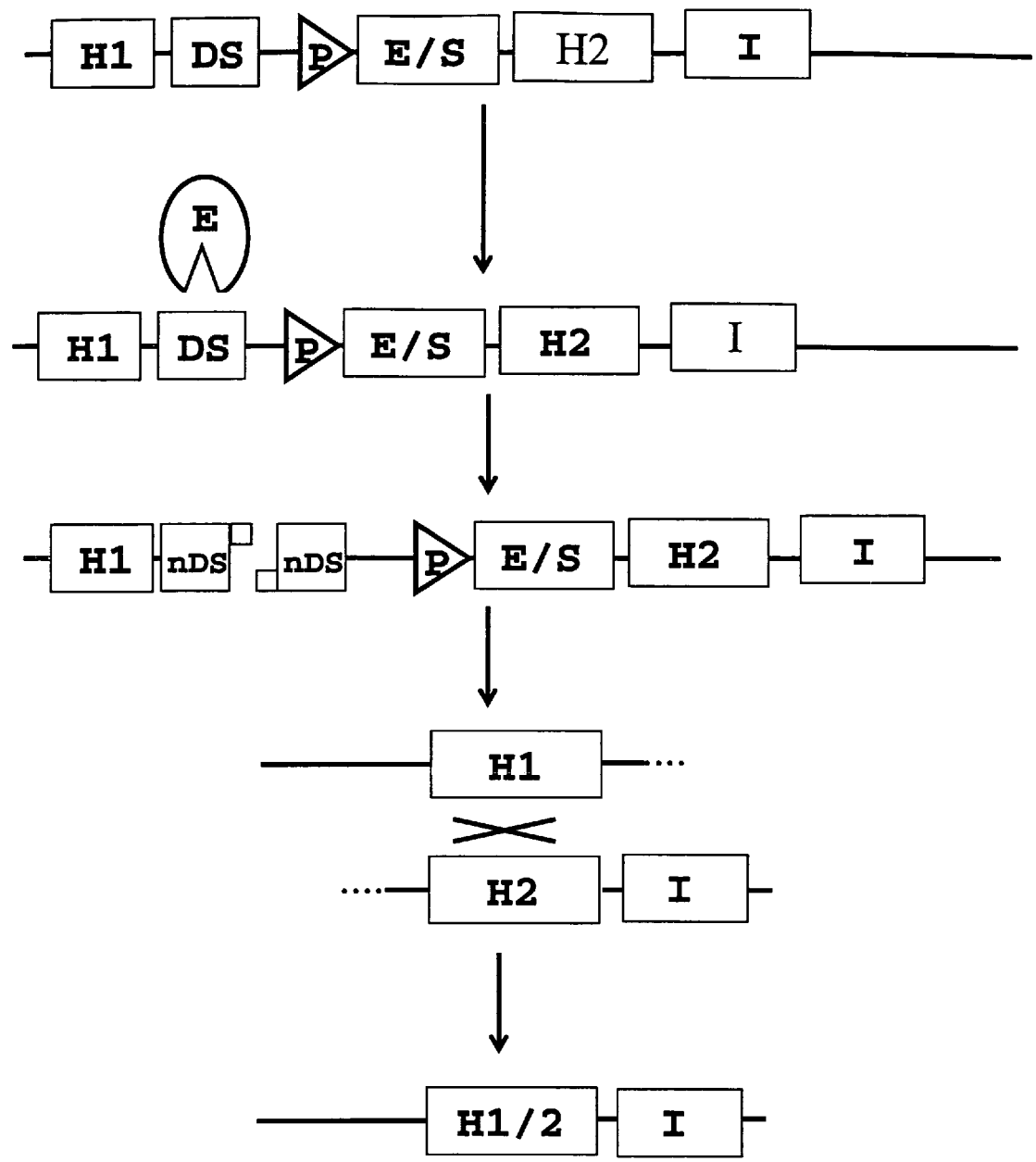

8. FIG. 8: Deletion of Sequences by Means of Intramolecular Homologous Recombination Induced by Sequence-Specific Double-Strand Breaks In all of the above-described embodiments, sequences—for example those encoding selection markers or DSBI enzymes—are preferably flanked by homology sequences H1 and H2 with sufficient length and homology to undergo recombination with one another. The recombination is induced by the induction of at least one double-strand break in the DSB recognition sequence located between the two homology sequences. To induce the double-strand break, it is preferred to transiently express or introduce a DSBI enzyme (FIG. 8).

The skilled worker realizes that the sequence of the genes expressed in an operon is exchangeable and can thus vary in the above-described embodiments. Also, when using only one homology sequence for inserting the insertion sequence, this homology sequence may be localized at the 5' side (as shown in the figures) or the 3' side of the double-strand break. In principle, the DSBI enzyme can be expressed on the transformation construct and/or separately (in the nucleus or the plastids) and introduced differently into—plastids, for example by transfection with RNA or protein.

Figure 9:
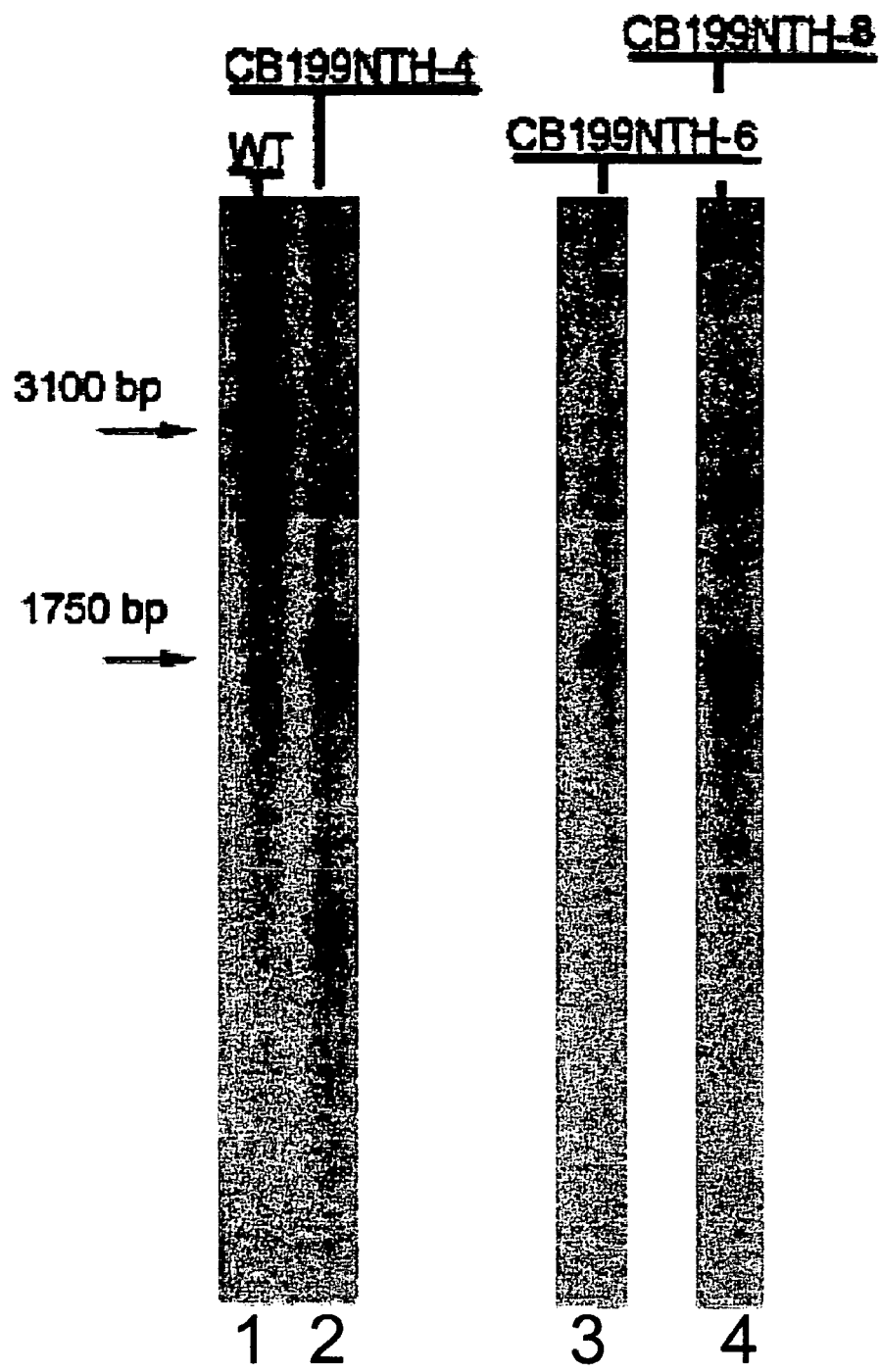

9. FIG. 9: Southern Analysis of Predominantly Homotransplastomic Plants

Wild-type and predominantly homotransplastomic master plants were analyzed with regard to the modification (introduction of a DSB recognition sequence; cf. Example 4). Owing to the modification, a 1750 bp band was detected (lanes 2, 3 and 4 corresponding to lines CB199NTH-4, -6 and -8), while a 3100 bp band was detected in the unmodified wild-type plant (lane 1).

Figure 10:
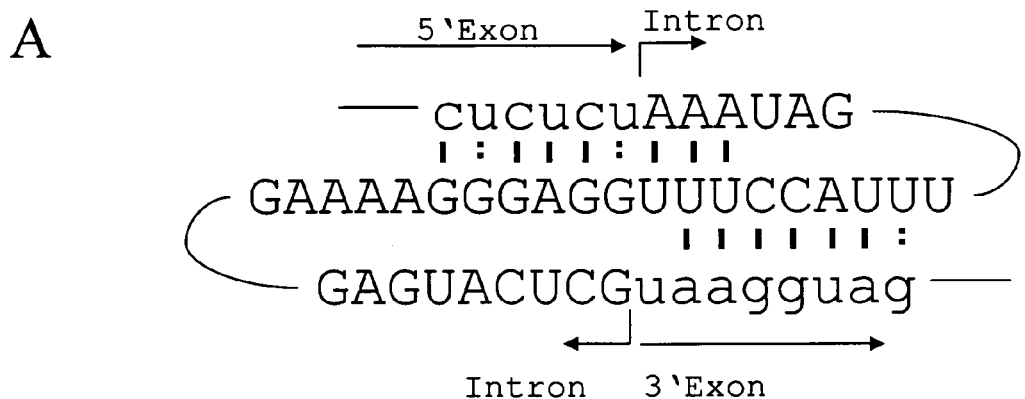
Figure 10:
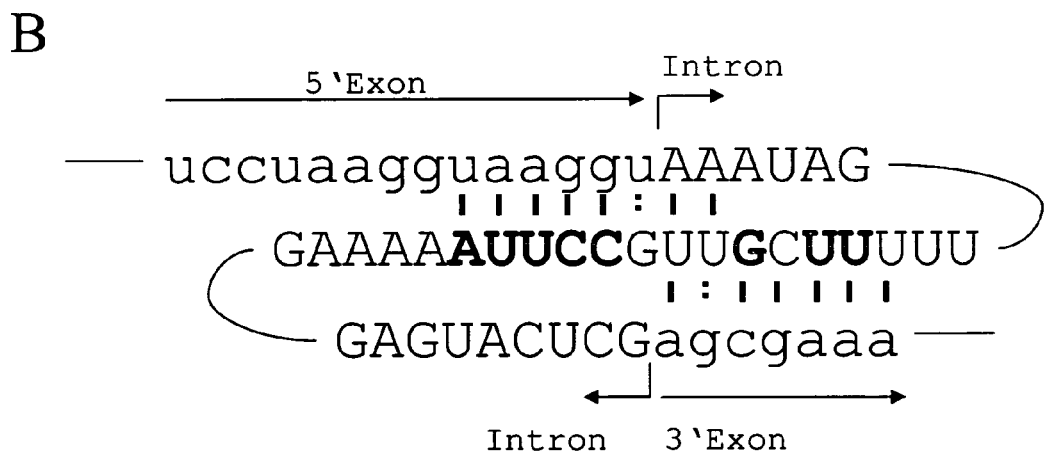

10. FIG. 10: Modification of the IGS of the Tetrahymena LSU Intron.

Capital letters indicate the sequence of the intron, while lower-case letters represent the sequence of the surrounding exons. The flanking exon sequences, the 5' and 3' portion of the intron or intron derivative, and the sequence comprising the IGS are shown. Bars between the bases indicate possible base pairings which can be formed for initiating the splicing procedure.

A: The abovementioned sequence segments of the naturally occurring Tetrahymena LSU intron in its natural exon environment are shown (SEQ ID NO: 160).
B: The abovementioned sequence segments of the Tetrahymena LSU intron derivative generated within the scope of the present invention (TetIVS2a) in the above-defined exon environment, as is found in the CpLSU5 intron within the DSB recognition sequence of the DSBI enzyme I-CpaI are shown (SEQ ID NO: 161). Letters in bold represent the mutations carried out in comparison with the natural sequence.

Figure 11:
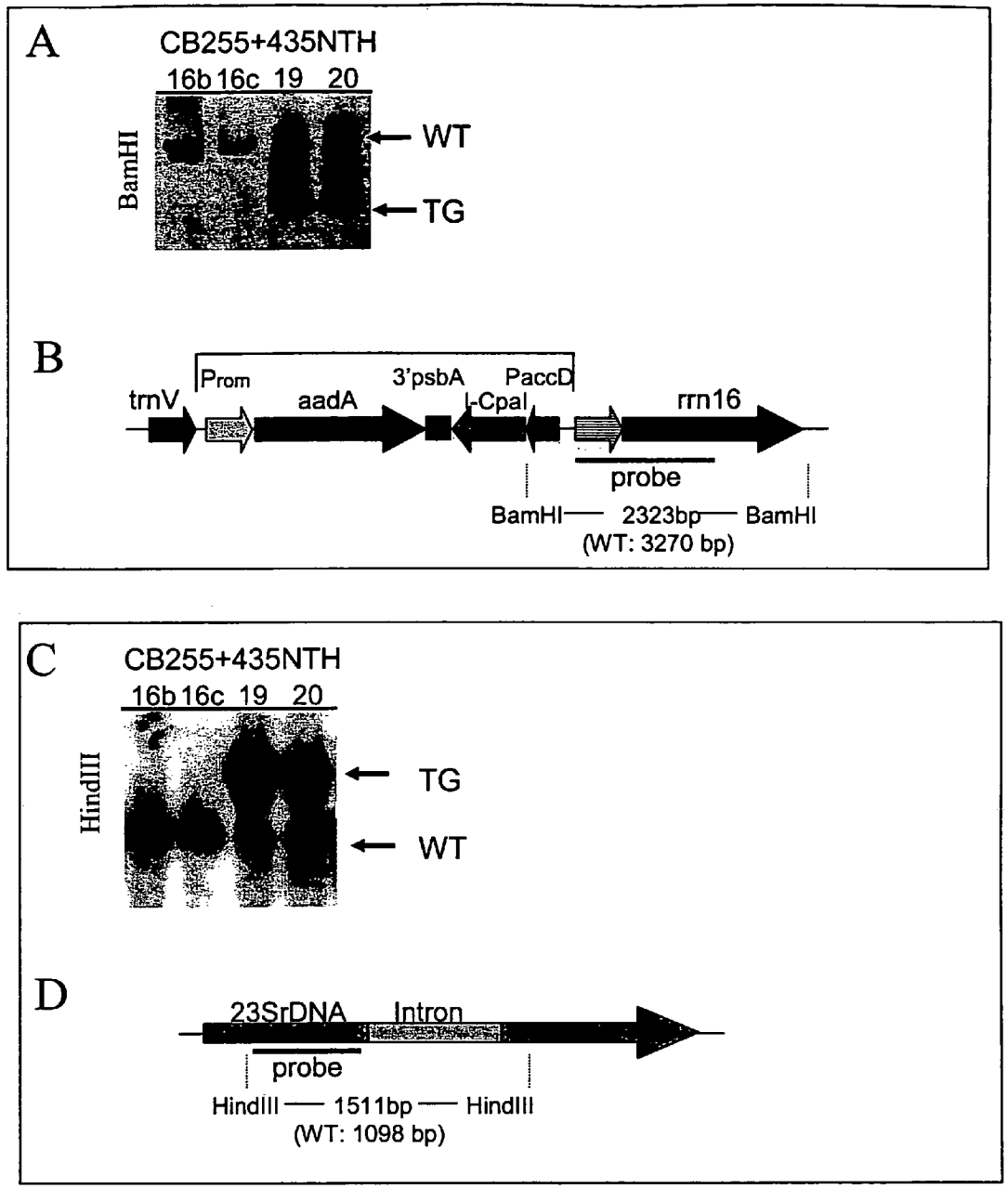

11. FIG. 11:
A: Southern analysis with BamHI-cut total DNA from the tobacco lines CB255+435NTH-16b, -16c, -19 and -20. A region of the 16Sr DNA was used as probe. The bands representing plastome copies which correspond to the wild type (WT; approx. 3.2 kb band detected) and those which bear the transgene (TG; approx. 2.3 kb band detected) are identified by arrows.
B: Schematic representation of transplastomic tobacco plants which have originated by the insertion of the insertion sequence from pCB435-45; and the bands to be expected in a corresponding Southern analysis (cf. A).
C: Southern analysis with HindIII-cut total DNA from the tobacco lines CB255+435NTH-16b, -16c, -19 and -20. A region of the 23Sr DNA was used as probe. The bands representing plastome copies which correspond to the wild type (WT; approx. 1.1 kb band detected) and those which bear the transgene (TG; approx. 1.5 kb band detected) are identified by arrows.
D: Schematic representation of transplastomic tobacco plants which have originated by the insertion of the insertion sequence from pCB255-1; and the bands to be expected in a corresponding Southern analysis (cf. C).

Figure 12:
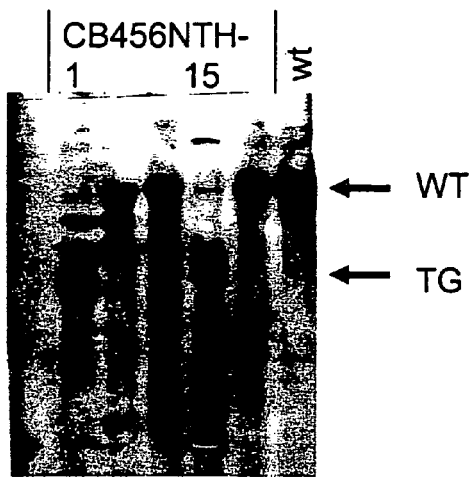
Figure 12:
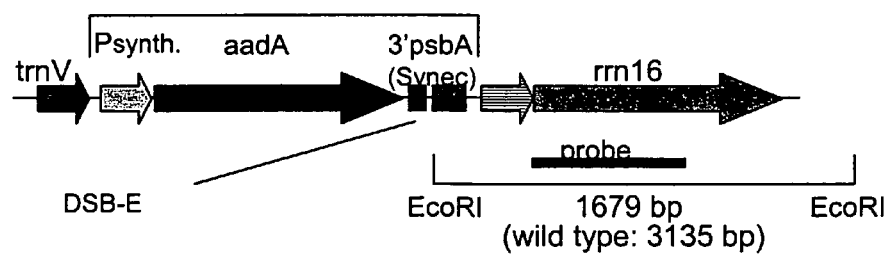

12. FIG. 12:
A: wild-type and predominantly homotransplastomic master plants were analyzed in a Southern analysis with regard to the modification (introduction of one of the I-PpoI DSB recognition sequence; cf. Example 14.2). Owing to the modification, an approximately 1.7 kb band was detected in the DNA which had been treated here with EcoRI (TG; lanes 1 and 4 corresponding to lines CB456NTH-1 and -15), while an approximately 3.1 kb band was detected in the unmodified wild-type plant (WT; lane 6). (wt—unmodified wild-type plant; wild type—shows the expected fragment size in unmodified wild-type plants; transgenic—shows the expected fragment size in plants CB456NTH)
B: Schematic representation of the EcoRI fragment which was to be expected in A by hybridization with the probe in a modified plant CB456NTH. (trnV—gene encoding a tRNA-Val; rrn16—gene encoding the 16SrRNA; aada—gene encoding a selection marker; 3'psbA (Synec)—non-coding region upstream of the Synechocystis psbA-1 gene, here incorporated into the expression cassette for the selection marker aada; Psynth.—synthetic promoter derived from the consensus sequence for *E. coli* σ70 promoters; DSB-R: DSB recognition sequence).

The following examples illustrate embodiments of the invention, but should not be viewed as limiting the scope of the invention.

EXAMPLES

General Methods:

Oligonucleotides can be synthesized chemically for example in the known manner, using the phosphoamidite method (Voet, Voet, 2nd edition, Wiley Press New York, pages 896-897). The cloning steps carried out within the scope of the present invention such as, for example, restriction cleavages, agarose gel electrophoresis, purification of DNA fragments, transfer of nucleic acids to nitrocellulose and nylon membranes, linkage of DNA fragments, transformation of *E. coli* cells, bacterial cultures, propagation of phages, and the sequence analysis of recombinant DNA, are carried out as described by Sambrook et al. (1989) Cold Spring Harbor Laboratory Press; ISBN 0-87969-309-6. Recombinant DNA molecules are sequenced with an ALF-Express laser fluorescence DNA sequencer (Pharmacia, Uppsala, Sweden) following the method of Sanger (Sanger et al. (1977) Proc Natl Acad Sci USA 74:5463-5467).

Example 1

Generating a Basic Vector for the Transformation of Plastids

Initially, the selected target regions were cloned from the plastome of tobacco cv. SR1 by means of PCR. The left-hand target region was amplified using the primers p19 and p20.

p19: 5'-TAAGGCCCTCGGTAGCAACGG-3'   (SEQ ID NO: 16)

p20: 5'-GGGGTACCAAATCCAACTAG-3'   (SEQ ID NO: 17)

The primers p21 and p22 were used for amplifying the right-hand target region, the last-mentioned primer additionally introducing a spectinomycin resistance into the amplified part of the 16S rDNA, in addition to the SR1 resistance (binding-type marker).

(SEQ ID NO: 18)
p21: 5'-GGAGCTCGCTCCCCCGCCGTCGTTC-3'

(SEQ ID NO: 19)
p22: 5'-GATGCATGATGACTTGACGGCATCCTC-3'

The two amplified regions were cloned into pBluescript and pzeroBlunt, respectively, and sequenced. The left-hand and right-hand target regions were subsequently cloned into the backbone of the pUC19 vector. The cleavage sites EcoO109I and PvuII of the vector were used for this purpose. A multiple cloning site from pBluescript (from KpnI to SacI) was cloned between the left-hand and right-hand target region. This multiple cloning site resides between the two plastid-encoded genes trnv and rrnl6 in the basic vector for the transformation of plastids.

This basic vector for the transformation of plastids was named pCB42-94 (SEQ ID NO: 1). The vector-comprises the following sequence elements:
a) Position complementary to bp 55-1405: right-hand target region-with-the partial gene of the 16S rRNA (complementary to bp 56 to 1322). The latter comprises mutations for the streptomycin resistance (SR1, position bp 346) and spectinomycin resistance (SPC1, position bp 68).
b) Position complementary to bp 2374 to 1510: left-hand target region comprising ORF131 (bp 1729 to 2124) and trnv gene inter alia (complementary to bp 1613 to 1542).
c) Position bp 1404 to 1511: multiple cloning site
d) Position bp 2629 to 3417: ampicillin resistance in the vector backbone Example 2

Generation of a Vector (pCB199-3) for Introducing a Non-Naturally Occurring Recognition Region for the Homing Endonucleases I-PpoI into the Plastome of Tobacco Various elements were cloned one after the other into the multiple cloning site of the basic vector pCB42-94 (SEQ ID NO: 1) for the transformation of plastids:

a) frt recognition region (mutated, contains no XbaI cleavage site; complementary to 1307-1354)
b) expression cassette for expressing the marker gene aada, consisting of:
  i) promoter of the gene for 16S rRNA (complementary to 1191-1281)
  ii) 5'-untranslated region of the tobacco rbcL gene (complementary to 1167-1184) including mutated 5' portions of the rbcL gene (duplication of 6 AS of the rbcL gene, partly mutated, as the consequence of the cloning strategy so that a fusion encoding a total of 12 amino acids (complementary to 1131-1166) with the subsequent element, the aada gene, was formed)
  iii) aada gene (complementary to 336-1130)
  iv) the 3' region of the psbA gene (complementary to 232-323)
c) core recognition region for the homing endonuclease I-PpoI (complementary to. 176-190).

This vector, which is referred to as pCB199-3, comprises the abovementioned elements within the nucleic acid sequence with the SEQ ID NO: 2 instead of the multiple cloning site in the basic vector for the transformation of plastids. The sequence which replaces the complete MCS from KpnI to SacI is shown. However, there is no longer a KpnI cleavage site in the sequence shown, owing the cloning strategy.

Example 3

Generation of a Further Vector (pCB401-20) for Introducing a Non-Naturally Occurring Recognition region for the Homing Endonuclease I-PpoI into the Plastome of Tobacco In contrast to the vector pCB199-3 described in Example 2, the vector described herein comprises no promoter and 3'UTR linked directly to the selection marker aada. Rather, the expression of the aada gene is controlled starting from the promoter of the trnV gene which is localized in the plastidic genome or in the left-hand target region upstream of the aadA gene. The purpose of generating this vector was to avoid sequence duplication by exploiting regulatory regions from the tobacco plastidic genome. To this end, various elements were cloned one after the other into the multiple cloning site of the basic vector pCB42-94 for the transformation of plastids:
a) ribosome binding site (complementary to bp 1033 to 1050)
b) aada gene (complementary to bp 238 to 1032)
c) core recognition region for the homing endonuclease I-PpoI (complementary to bp 176 to 190)

The resulting vector also confers spectinomycin resistance in *E. coli*. This vector, which is referred to as pCB401-20, comprises the abovementioned elements within the nucleic acid sequence with the SEQ ID NO: 3 instead of the multiple cloning site in the basic vector pCB42-94 (SEQ ID NO: 1) for the transformation of plastids. Again, all of the sequence which replaces the MCS (from SacI to KpnI) is shown.

Example 4

Generation of Predominantly Homoplastomic Tobacco Master Plants Comprising a Non-Natural DSB Recognition Sequence The plasmid pCB199-3 was introduced into the plastids of tobacco (*Nicotiana tabacum* cv. Petit Havana) as described hereinbelow. The regenerated plants-were named CB199NTH. Independent lines were provided with different last numbers (for example CB199NTH-4).

The vector pCB401-20 is introduced analogously into the plastids of tobacco. Accordingly, the resulting plants are named CB401NTH.

First, leaf disks of diameter 2.0 to 2.5 cm were punched out of in-vitro-cultured plants, using a sterile cork borer, and placed upside-down on a Petri dish with bombardment medium [MS salts (Sigma-Aldrich): 4.3 g/l; sucrose: 30.0 g/l, Phyto-agar (Duchefa, P1003): 0.6% (w/v); pH 5.8; after autoclaving, 1.0 mg/l thiamine (Duchefa, T0614) and 0.1 g/l myo-inositol (Duchefa, I0609,) were added]. The underside of the leaf, which faced away from the agar, was subsequently bombarded using the particle gun. To this end, the plasmid DNA to be transformed (isolated from *E. coli* using Nucleobond AX100 Macherey & Nagel) was first applied to gold particles 0.6 μm in side by the following protocol ("coating"). First, 30 mg of powdered gold (BioRad) were taken up in ethanol. 60 μl of the gold suspension were transferred into a fresh Eppendorf tube and the gold particles were sedimented by centrifugation (for 10 seconds). The gold particles were washed twice in each case 200 μl of sterile water and, after a further centrifugation step, taken up in 55 μl of water. The following were added rapidly, with continuous mixing (vortexing):

5 μl plasmid DNA (1 μg/μl)

50 μl 2.5 M CaCl$_2$

20 μl 0.1 M spermidine

The suspension was subsequently vortexed for a further 3 minutes and subsequently centrifuged briefly. The gold/DNA complexes which had sedimented were washed once or twice in each case 200 μl of ethanol and, after a further centrifugation step, finally taken up in 63 μl of ethanol. 3.5 μl (corresponding to 100 μl of gold) of this suspension were applied to a macrocarrier for each bombardment.

The particle gun (BioRad, PDS1000He) was prepared in accordance with the manufacturer's instructions, and the leaf explants were bombarded with the gold/DNA complexes from a distance of 10 cm. The following parameters were used: vacuum: 27 inch Hg, pressure 1100 psi. After the bombardment, the explants were incubated for 2 days in controlled-evironment cabinets (24° C., 16 h light, 8 h darkness) and subsequently divided into segments approximately 0.5 cm$^2$ in size, using a surgical blade. These segments were then transferred to regeneration medium [bombardment medium supplemented with 1 mg/l 6-benzylaminopurine (BAP, Duchefa, B0904) and 0.1 mg/l naphthylacetic acid (NAA, Duchefa, N0903)] supplemented with 500 mg/l spectinomycin (Duchefa, S0188) and incubated for 10 to 14 days under the abovementioned conditions in a controlled-environment cabinet. After this period of time had elapsed, the leaf segments were transferred to fresh regeneration medium supplemented with 500 mg/l spectinomycin. This procedure was repeated until green shoots formed on the explants. The shoots were removed using a surgical blade and grown on growth medium (like bombardment medium, but with 10 g/l sucrose instead of 30 g/l sucrose) supplemented with 500 mg/l spectinomycin.

To obtain as predominantly homoplastomic plants as possible, it is optionally possible to excise explants from the regenerated plants themselves and to place them on regeneration medium with 1000 mg/l spectinomycin. Regenerating shoots are transferred into glass containers with growth medium supplemented with 500 to 1000 mg/l spectinomycin. After the plants have rooted, they are transferred into the greenhouse, where they are grown in soil until the seeds have matured.

When the transformation was carried out with the plasmid pCB199-3, 8 plants with resistance to spectinomycin were obtained. PCR and Southern analyses proved that three of these lines (lines CB199NTH-4, -6 and -8) have indeed incorporated the aada gene into the plastidic genome.

To perform a Southern analysis of the transplastomic plants, total DNA from leaves was isolated from transformed and untransformed plants with the aid of the GenElute Plant Genomic DNA Kit (Sigma). The DNA was taken up in 200 μl of eluate. 86 μl portions of this were treated with in each case 10 μl of 10× restriction puffer and 40 U of restriction endonuclease and incubated for 4 to 8 hours at the temperature recommended for the restriction enzyme. The DNA was subsequently precipitated with ethanol in the manner known to the skilled worker and the precipitate was subsequently taken up in 20 μl of water. The samples were subsequently separated on agarose gel by methods known to the skilled worker, and the DNA was denatured in the gel and transferred to a nylon membrane by means of a capillary blot.

A suitable probe for the radioactive hybridization was generated with the aid of the HighPrime (Roche) system. First, the membrane was prehybridized for 1 hour at 65° C. with Hyb buffer (1% (w/v)) bovine-serum-albumin; 7% (w/v) SDS; 1 mM EDTA; 0.5 M sodium phosphate buffer, pH 7.2). The heat-denatured probe was subsequently added and left to hybridize overnight at 65° C. The blots were subsequently washed as follows: one rinse with 2×SSPE/0.1% SDS; washing for 15 minutes at 65° C. with 2×SSPE/0.1% SDS; washing for 15 minutes at 65° C. with 1×SSPE/0.1% SDS; if appropriate, the last step was repeated again (20×SSPE is 3 M NaCl; 0.2 M NaH$_2$PO$_4$; 0.5 M EDTA; pH 7.4).

The hybridization was subsequently analyzed with the aid of a phosphoimager (Molecular Imager FX, BioRad).

For example, PstI-cut total DNA from different plants which had been regenerated after transformation with pCB199-3 were hybridized with the aadA gene as radiolabeled probe (793 bp PstI/NcoI fragment from pCB199-3). Here, it was found that the lines CB199NTH-4, -6 and -8 had indeed incorporated the aadA gene into the DNA. Moreover, EcoRI- and XhoI-cut total DNA from CB199NTH-4, -6 and -8 was hybridized with a radiolabeled probe (1082 bp Bsp120I/SacI fragment from pCB199-3), which hybridizes with part of the 16S rDNA. While, as expected, an approximately 3100 bp band was detected in the wild type (untransformed plant), mostly a band at 1750 bp was detected in the transplastomic lines, as the result of the insertion of the insertion sequence from pCB199-3 into the plastome (FIG. 9). The resulting plants can be considered as being predominantly homotransplastomic.

Example 5

Generation of Transformation Vectors which can be used for Transforming the Plastids of Master Plants CB199NTH by Means of the Artificial Homing Process 5.1 Cloning of the Homing Endonuclease I-PpoI The homing endonuclease I-PpoI was generated from 26 synthetic oliogonucleotides by means of PCR, following a modification of the method of Stemmer WPC et al. (1995) Gene 164: 49-53 (SEQ ID NO: 11). The basic sequence was derived from the published sequence (Accession No. M38131 nucleotides 86 to 577). Here, a few mutations were introduced to remove restriction endonuklease recognition sites from the gene; however, these mutations did not involve an altered amino acid sequence. The following elements were subsequently combined one after the other in a pBluescript KS (Stratagene) vector backbone in order to generate an I-PpoI expression cassette. The sequence is flanked by the cleavage sites KpnI and SacI.
a) Posit-ion 21 to 111: Prrn promoter
b) Position 118 to 135: 5'-untranslated region of the rbcL gene followed by 18 bp encoding 6 amino acids of the rbcL protein (bp 136-152)
c) Position 154 to 645: Nucleic acid sequence encoding I-PpoI.
d) Position 688-779: 3'-untranslated region of the psbA gene.

The resulting plasmid was named pCB289-13. Despite the expression of the enzyme I-PpoI, which was expected to take place in *E. coli*, no adverse effects on the growth were observed. The sequence described by SEQ ID NO: 4 resulted from the KpnI cleavage site to the SacI cleavage site (vector backbone remains that of pBluescript KS).

5.2 Generation of a Transformation Vector for Artificial Homing with Homologous Regions Flanking the Insertion Sequence Bilaterally I) Without I-PpoI in the Insertion Sequence Regions around the I-PpoI recognition region from pCB199-3 were excised using PstI and SacI and ligated into the PstI and SacI cleavage sites of pBluescript. Thereafter, cleavage sites which ere not required were removed from this vector by linearizing it with PstI and Bsp120I and, following treatment with Klenow fragment, recircularizing the vector. With the aid of commercially available enzyme I-PpoI (PROMEGA GmbH, Mannheim, Germany), the corresponding recognition region was cleaved in the resulting vector, and further cleavage sites were inserted therein by means of the synthetic oligos p190 and p191.

```
Oligo p190: 5'-GTCGACAGATCTTTAA-3'    (SEQ ID NO: 20)

Oligo p191: 5'-AGATCTGTCGACTTAA-3'    (SEQ ID NO: 21)
```

An expression cassette consisting of the following elements was introduced in the form of.a BglII/XhoI fragment (SEQ ID NO: 6) into the cleavage sites SalI and BglII, which had thus been introduced:
a) Prps16 promoter (complementary to 1033-1139)
b) 5'rbcL (complementary to 1007-1024) with 18 bp encoding the 6 AAs (complementary to 989-1006)
c) nptII gene (complementary-to 185-988)
d) 3'rbcL (complementary to 6-143)

The resulting vector was named pCB304-25 and also conferred kanamycin resistance to *E. coli* cells. This vector is no longer linearized by commercially available I-PpoI. All of the insert of the vector pCB304-25 (backbone pBluescript; replacing the MCS accordingly from SacI to KpnI) is described by SEQ ID NO: 62 and thus comprises the following elements:
a) Position bp 19 to 110: 3'psbA from tobacco
b) Position bp 149 to 160: nonfunctional "half" of the I-PpoI recognition sequence
c) Position bp 171 to 277: Prps16 promoter
d) Position bp 286 to 303: 5'rbcL sequence followed by 18 bp encoding the first 6 amino acids of the rbcL protein (bp 304-321)
e) Position bp 322 to 1125: nptII
f) Position bp 1167 to 1304: 3'rbcL
g) Position bp 1310 to 1319: nonfunctional "half" of the I-PpoI recognition sequence II) With I-PpoI in the Insertion Sequence A BglII/MunI fragment which encoded a 5'psbA -1-PpoI fusion was additionally introduced into the vector pCB304-25 with the aid of the BamHI and EcoRI cleavage sites. The resulting vector pCB320-192 thus expressed the nptII gene and I-PpoI homing endonuclease under the control of the Prps16 promoter. The Bgl II/Mun I fragment is represented by SEQ ID NO: 63 and comprises the following elements:
a) Position bp 6 to 82: 5'psbA
b) Position bp 83 to 574: I-PpoI 5.3 Generation of a Transformation Vector for Artificial Homing with a Homologous Region Flanking the Insertion Sequence Unilaterally The elements located upstream of the Prps16 promoter and which are homologous to those in the master plants CB199NTH were removed from the vector pCB320-192 by restriction with KpnI and BglII. Instead, a BstXI cleavage site was introduced therein by means of synthetic oligonucleotides p199 and p200.

```
p199 5'-GATCTCCAGTTAACTGGGGTAC-3'    (SEQ ID NO: 22)

p200 5'-CCCAGTTAACTGGA-3'            (SEQ ID NO: 23)
```

DNA ends which are compatible with those originating by restriction with I-PpoI can now be generated by cleaving with BstXI. The resulting vector was renamed pCB322-1. A fragment which, at its one side, has an end which is compatible with DNA which had been cleaved with I-PpoI at its core recognition region and, at its other side, homology with plastome sequences of the master plants CB199NTH can be obtained from this vector for example using the enzymes BstXI and SacI.

5.4 Generation of a Transformation Vector for Artificial Homing Without Homologous Regions Around the Insertion Sequence The remaining portion, which is homologous with recombinant plastid sequences of the master plants CB199NTH, was removed from the vector pCB322-1 using SacI and BspTI. Simultaneously, a BstXI cleavage site which, after cleavage with BstXI generates DNA ends which are compatible with I-PpoI-cut DNA, was generated here by introducing synthetic oligonucleotides p218 and p219. The resulting vector was named pCB347-33.

```
                                      (SEQ ID NO: 24)
p218 5'-TTAAGCCAGTTAACTGGGCGGAGCT-3'

(SEQ ID NO: 25)
p219 5'-CCGCCCAGTTAACTGGC-3'
```

A fragment with bilateral DNA ends which are compatible with the DNA ends generated by the I-PpoI enzyme at its core recognition region can be isolated from this vector using the enzyme BstXI.

Example 6

Use of the Master Plants CB199NTH for Plastid Transformation by Means of DSB Induction 6.1 Using the Vectors Generated in 5.1 and 5.2 for Transforming the Master Plants CB199NTH by using the DSBI enzyme I-PpoI The plasmid pCB304-24 and the plasmid pCB289-13 were simultaneously applied to gold particles as described in Example 4 and used to bombard explants of the master plants CB199NTH, which explants had been treated analogously to what has been said in Example 4. However, the procedure differed from the decription in Example 4 insofar as incubation is first carried out for 10 days on the regeneration medium without antibiotics; later, kanamycin is used in a concentration of 50 mg/l (in contrast to the 500 mg/l spectinomycin stated in Example 4).

The plasmid pCB320-192 was applied to gold particles as described in Example 4. After the ethanol washing step, 20 U of commercially available I-PpoI enzyme (Promega) were additionally added. Further treatment was as described above.

Also, in a different batch, 0.5 µg of a transcript generated in vitro with the aid of the T7 polymerase was applied simultaneously with the plasmid pCB320-192 to the gold particles.

The template for the in-vitro transcription was HindIII-linearized DNA of the plasmid pCB289-13. The transcript generated thus therefore encodes I-PpoI. After the bombardment, the treatment of the explants of the master plants continues as described above.

6.2 Using the Vectors Generated in 5.1 and 5.3 for Transforming the Master Plants CB199NTH by Utilizing the DSBI Enzyme I-PpoI and Homologous Regions which are only Unilaterally Present A fragment excised from the plasmid pCB322-1 with BstXI and SacI was eluted from an agarose gel. This fragment was subsequently applied to gold particles simultaneously with 1 µg of in-vitro transcript of HindIII-linearized plasmid pCB289-13 (cf. Example 6.1). After the explants of the master plants CB199NTH have been bombarded, the rest of the treatment is as described for Example 6.1.

6.3 Using the Vectors Generated in 5.1 and 5.4 for Transforming the Master Plants CB199NTH by Utilizing the DSBI Enzyme I-PpoI Without Homologous Regions The insertion sequence was excised from the plasmid pCB347-33 by means of BstXI and eluted from an agarose gel. This fragment was applied to gold particles simultaneously with 1 µg of in-vitro transcript of the HindIII-linearized plasmid pCB289-13. The bombardment and the rest of the treatment are as detailed in Example 6.1.

Example 7

Identification of Naturally Occurring, Endogenous Recognition Regions for Homing Endonucleases in Plastomes of Different Plant Species Although no homing enconucleases are known to occur in the plastids of higher plants, known plastome sequences were tested for the presence of recognition regions for homing endonucleases. This was done with the aid of the computer program SeqMan II (DNASTAR Inc.). The recognition regions which were identified in this manner are compiled in Table 1.

Based on the computer analysis, it was not possible to tell whether I-SceI has a recognition region in the plastidic genome or not. The region which is most likely to be able to act as recognition region was generated synthetically and integrated into the XbaI and XhoI cleavage site of pBluescript in the form of oligonucleotides p276 and p277. The resulting plasmid pCB414-1 was subsequently analyzed with the aid of a commercially available enzyme I-SceI (Roche) for the presence of a functional cleavage site. The plasmid was indeed linearized by I-SceI. This leads to the conclusion that I-SceI which is expressed in lastids likewise recognizes, and cleaves, this sequence. A further endogenous DSB recognition sequence for a DSBI enzyme has thus been identified.

```
                                              (SEQ ID NO: 26)
    p276 5'-TCGAGAAGATCAGCCTGTTATCCCTAGAGTAACT-3'

(SEQ ID NO: 27)
    p277 5'-CTAGAGTTACTCTAGGGATAACAGGCTGATCTTC-3'
```

Example 8

Cloning Homologous Regions from the Tobacco Plastome which Flank the Endogenous Recognition Region for the Homing Endonuclease I-CpaI DNA fragments from the 23S rDNA of the tobacco plastome were amplified by means of PCR upstream and downstream of the I-CpaI recognition region using the primers p93 and p97, and p98 and p95, respectively.

```
                                              (SEQ ID NO: 64)
    p93:  AAAGATCTCCTCACAAAGGGGTCG (SEQ ID NO: 65)
    p97:  TCGAAGACTTAGGACCGTTATAG (SEQ ID NO: 66)
    p98:  AGGAAGACCTTGTCGGGTAAGTTCCG (SEQ ID NO: 67)
    p95:  CTCAATTGGGGTCTCTCTGTCCAGGTGCAGG
```

The resulting fragments were used for constructing the vector pCB270-1. The fragment from BssHII to BssHII of the pBlueScript vector (SEQ ID NO: 8) is shown, the 5' end of the sequence indicated being located at the BssHII cleavage site which is closer to the 3' end of the lacZ gene.

Two BpiI cleavage sites were introduced between the DNA fragments located upstream and downstream of the I-CpaI recognition regions. BpiI generates overhangs which are outside their recognition region. This procedure ensured that the vector pCB270-1 could likewise be used for the subsequent ingegration of various introns. To this end, simple overhangs which are compatible with the ends generated by BpiI in the vector pCB270-1 are generated at the introns to be cloned. Moreover, the respective nucleotides which are absent between the two fragments of the 23S rDNA in the vector pCB270-1 are added onto the introns. The selected regions are so highly conserved that there is no need to amplify new regions from other plant species. Furthermore, a point mutation in the 23S rDNA, as has also been found in lincomycin-resistant mutants, has been introduced into the sequence downstream of the I-CpaI recognition region via PCR strategy. The sequence of the vector pCB270-1 which has been inserted into the pBluescript vector is shown in SEQ ID NO: 8. The sequence comprises the following elements:

Fragment of the 23S rDNA upstream of the I-CpaI recognition region: nucleotides 37 to 194

Fragment of the 23SrDNA upstream of the I-CpaI recognition region: nucleotides 237 to 359

Point mutation for lincomycin resistance: 352 (A being native at this point)

Vector pCB234-1 is constructed just as vector pCB270-1, but additionally has a recognition region for each of the restriction enconucleases XhoI and SacI downstream of the sequence shown hereinbelow.

Example 9

Cloning of the CpLSU2 Intron Including the Homing Endonuclease I-CpaI

The CpLSU2 intron (SEQ ID NO: 15) was amplified from the DNA of the alga *Chlamydomonas* pallidostigmatica (Culture Collection of Algae at the University of Gbttingen, SAG Number 9.83, *Chlamydomonas segnis*, authentic strain of *Chlamydomonas* pallidostigmatica King) by means of PCR using the oligonucleotides p91 and p92.

```
p91 5'-AGAAGACGATCCTAAGG-3'         (SEQ ID NO: 28)

p92 5'-TGAAGACTTGACAAGGAATTTCGC-3'  (SEQ ID NO: 29)
```

The oligonucleotides were chosen in such a way that cloning into the BpiI cleavage sites of the vector pCB234-1 was possible, as described above. The sequence comprises the following elements:
- Position 9-17—portion of the tobacco 23S rDNA which is absent in pCB234-1
- CpLSU2 intron: position 18-893
- I-CpaI ORF: position 377-835
- Position 894-909—portion of the tobacco 23S rDNA which is absent in pCB234-1

This fragment, which comprises the CpLSU2 intron, was cloned into the backbone of the vector pGEMTeasy (Promega) (vector pCB141-3). The entire fragment was excised from this vector using BpiI and cloned into the BpiI-linearized vector pCB234-1. The resulting vector was named pCB254-2.

Example 10

Nuclear LSU-rRNA Intron from *Tetrahymena thermophila*

10.1 Cloning the LSU-rRNA Intron from *Tetrahymena thermophila*

The LSU-rRNA intron was amplified from the organism Tetrahymena thermophila by means of PCR. Again, the oligonucleotides p102 and p103 were chosen in such a way that the nucleotides of the tobacco 23S rDNA, which are absent in pCB234-1, were added onto the intron to be amplified.

```
p102 (SEQ ID NO: 30):
5'-AGAAGACGATCCTAAATAGCAATATTTACCTTTGGGACCAAAAGTTA
TCAGGCATG-3' p103 (SEQ ID NO: 31):
5'TGAAGACTTGACAAGGAATTTCGCTACCTTCGAGTACTCCAAAACTAA
TC-3'
```

Moreover, the internal guide sequence (underlined in p102) is mutated in such a way over the wild type, owing to the choice of the oligonucleotide p102, that splicing of this intron-at the desired position in the tobacco 23S rDNA is possible. The sequence shown in SEQ ID NO: 7—the PCR fragment from the BpiI to BpiI cleavage site is shown—was cloned into the backbone of the vector pGEMTeasy. The resulting vector was named pCB220-17. The sequence comprises the following elements:
- Position 9-12—portion of the tobacco 23S rDNA which is absent in pCB234-1
- LSU intron: position 13-425
- Position 426-446—portion of the tobacco 23S rDNA which is absent in pCB234-1

The *Tetrahymena* LSU intron including the added, flanking sequences, was excised from the vector pCB220-17 using BpiI and inserted into the BpiI cleavage sites of the vector pCB234-1. The resulting product was named pCB255-1.

10.2 Indirect Detection of the Splicing Activity of the *Tetrahymena* LSU Intron in *E. coli*

To prove indirectly that the modified intron is indeed capable of splicing in the predetermined environment within the I-CpaI cleavage site, the modified Tetrahymena intron from pCB220-17 together with a portion which surrounds the I-CpaI recognition region from the tobacco 23S rDNA was cloned in such a way into the lacZ gene of pBluescript that, if this intron is spliced into *E. coli* (strain XL1-Blue), a functional lacZ peptide can be formed. The expression of the latter can be detected in suitable strains by methods with which the skilled worker is familiar by converting the substance 5-bromo-4-chloro-3-indolyl-$\beta_D$-galactopyranoside (X-Gal) in the medium into a blue pigment. This vector was named pCB315-1. The lacZ gene including the introns in the vector pCB315-1 is described by SEQ ID NO: 9. The vector backbone is identical with pBluescript. The sequence comprises the following elements:
- lacZ-5' portion: complementary (789-765)
- multiple cloning site from pBluescript: complementary (764-692)
- 23S rDNA fragment upstream and including the I-CpaI recognition region: complementary (691-682)
- modified *Tetrahymena* intron: complementary (681-269)
- 23S rDNA fragment upstream and including the I-CpaI recognition region: complementary (268-244)
- multiple cloning site from pBluescript: complementary (243-168)
- lacZ-5' portion: complementary (167-1)

A plasmid which corresponds to pCB315-1, but which plasmid (PCB305-1) lacks the element for the modified Tetrahymena intron, was generated for control purposes. pCB305-1 thus acted as positive control to demonstrate that lacZ, with the tobacco plastome 23S rDNA nucleotides incorporated in the reading frame is still functional. This reflects the situation after correct splicing of the Tetrahymena intron. XL1-Blue competent cells were transformed with the plasmids pCB315-1 and pCB305-1 by means of a method with which the skilled worker is familiar. In each case one individual colony was incubated on LB (Bactotryptone: 10 g/l, yeast extract: 5 g/l, NaCl: 10 g/l, pH 7.5) plates comprising 15 g/l Bacto agar, 40 µg/l ampicillin, 75 µg/l IPTG (isopropyl-$\beta_D$-thiogalactopyranoside) and 80 µg/l X-Gal overnight at 37° C. In fact, both clones turned blue, which suggests that the modified Tetrahymena intron was spliced in the non-natural environment of the tobacco 23S rDNA in the heterologous organismus *E. coli*.

10.3: Introduction of Further Sequences into the Tetrahymena LSU Intron

In addition to the experiments in Example 10.2, the possibility of incorporating further elements into the modified *Tetrahymena* intron without destroying the splicing activity was studied. To this end, pCB315-1 was linearized with BglII and the overhangs were filled up with the aid of Klenow fragment. Then, an XhoI-SacI fragment as is found in pCB199-3 was therefore cloned into this vector, likewise after treatment with Klenow fragment. A 229 bp fragment was thus inserted into the modified intron by this cloning step. This fragment comprises an I-PpoI recognition region. Independently of the orientation in which the 229 bp fragment inserted into the *Tetrahymena* intron, a blue coloration was detected in the test as described in Example 10.2. This suggests that the *Tetrahymena* intron is capable both of splicing at the desired region in the 23S rDNA and of incorporating additional genetic information while nevertheless retaining a splicing activity.

10.4 Transformation of a Natural Master Plant and Destruction of the Endogenous I-CpaI Recognition Region with the Modified *Tetrahymena* Intron The modified *Tetrahymena* intron was excised from the vector pCB220-17 using BpiI and cloned into the BpiI linearized vector pCB234-1 as described in principle in Example 8. The resulting vector was named pCB255-1.

pCB255-1 is applied to gold particles simultaneously with in vitro transcript of pCB262-5 (linearized with SalI, using T7 polymerase) by the method described in Example 4. These gold particles are subsequently used to bombard tobacco plants cv. Petit Havana analogously to the method described in Example 4. If appropriate, the explants can be selected on lincomycin (250 to 500 mg/l).

Example 11

Ll.LtrB Intron from *Lactococcus* lactis

The Ll.LtrB intron including few bases of the flanking exon sequences was amplified from *Lactococcus* lactis by means of PCR using the primers p207 and p208. The PCR product was cloned into the vector pCR2.1TA (Invitrogen) (pCB345-34) and sequenced (SEQ ID NO: 10). Few deviations in comparison with the published sequence were found.

```
                                            (SEQ ID NO: 32)
p207 5'-GAGAAGACATTCCTAACACATCCATAACGTGCG-3'

(SEQ ID NO: 33)
p208 5'-TGAAGACTTGACATTTGATATGGTGAAGTAGG-3'
```

The cloned fragment in pCB345-34 (from the EcoRI cleavage site to the EcoRI cleavage site of the pCR2.1TA vector) is represented in SEQ ID NO: 10. The remainder of the vector is identical with the backbone of pCR2.1TA. The sequence comprises the following elements:
  Portion of the natural 5' exon: complementary (2540-2527)
  Intron Ll.LtrB: complementary (2526-35)
  ORF in the intron: complementary (1953-154)
  Portion of the natural 3' exon: complementary (34-28)

Example 12

Generation of a Further Derivative of the *Tetrahymena* LSU Intron, and Incorporation of a Foreign Gene into this Intron Derivative, and Transformation into Natural Master Plants In accordance with a preferred embodiment of the present invention, an artificial intron was generated, which intron can be incorporated into the plastidic genome at precisely the position where the natural intron belonging to the DSB recognition sequence under investigation resides. In the present example, the *Tetrahymena* LSU intron was modified in such a way that it is capable of splicing at the position marked "^" at the recognition site, identified within the scope of the present invention, for the DSBI enzyme I-CpaI in the plastidic genome of higher plants: CGATCCTAAGGT^AGCGAAAT-TCA.

The gene encoding I-CpaI including an RBS was subsequently incorporated into the intron. This gave rise to an intron which has splicing activity, bears a foreign gene and which can be incorporated, by means of the process found within the scope of the present invention, into the plastids of a natural master plant within an essential gene (encoding the 23S rRNA).

12.1: Generation of a Further *Tetrahymena* LSU Intron Derivative

To obtain a functional intron derivative at a predefined insertion site, the internal guide sequence (IGS) must be adapted in such a way that it is capable of undergoing base pairing with the 5' and the 3' exon. FIG. 10 illustrates how this adaptation was carried out in the present example in order to generate a Tetrahymena intron derivative which is capable of splicing at the natural insertion site of the CpLSU5 intron within the I-CpaI recognition region. An adaptation to any desired insertion site can be carried out analogously. The intron generated within the scope of the present example was named TetIVS2a and is described by SEQ ID NO: 73.

12.2: Indirect Detection of the Splicing Activity of the TetIVS2a Intron in *E. coli*

TetIVS2a was incorporated into the lacz gene of pBluescript analogously to Example 10.2. After suitable incubation of *E. coli* XL1-blue cells which comprised the plasmid pCB459-1, a blue coloration indicated the splicing activity of the TetIVS2a intron at the desired position.

Components of the insert from plasmid pCB459-1 (SEQ ID NO: 74; backbone corresponds to pBluescript)
  lacZ-3' portion including parts of the multiple cloning site from pBluescript (complementary to position 1-254)
  Sequence from the I-CpaI recognition region (complementary to position 254-265)
  TetIVS2a (complementary to position 266-678)
  Sequence from the I-CpaI recognition region (complementary to position 679-687)
  lacZ-5' portion including parts of the multiple cloning site from pBluescript (complementary to position 688-791)

12.3: Introduction of further Genetic Information into the TetIVS2a Intron and Detection of the Splicing Activity in *E. coli*

In this example, the gene encoding the DSBI enzyme I-CpaI is introduced into TetIVS2a without the latter losing its splicing activity at said position within the I-CpaI recognition region.

To this end, a BclI cleavage site was first introduced, by PCR, into the sequence segment of TetIVS2a which corresponds to loop L8 in the *Tetrahymena* LSU intron. A nonfunctional derivative of the gene encoding I-CpaI was then incorporated into this BclI cleavage site. Since the expression of 1-CpaI in *E. coli* is toxic, it was necessary to use, for the splice test in *E. coli*, a nonfunctional gene which had previously been generated by linearizing the gene in question at the EcoRI cleavage site, making the overhangs blunt-ended by Klenow treatment and subsequently religating the gene segments. This resulted in a reading-frame shift in the gene. Incorporation of said intron with the nonfunctional gene into the lacZ gene of pBluescript gave rise to the plasmid pCB478-3 and, again, it was possible to detect the splicing activity of this intron in *E. coli* at the desired position within the I-CpaI recognition site by means of the blue coloration of colonies in question, analogously to Example 12.2. Since the functional gene encoding I-CpaI differs from the nonfunctional gene used in pCB478-3 by only 4 bases, it can be assumed that the intron retains the desired splicing activity, even after the functional, instead of the nonfunctional, I-CpaI gene has been incorporated.

Components of the insert of plasmid pCB478-3 (SEQ ID NO: 75; backbone corresponds to pBluescript)
- lacZ-3' portion including parts of the multiple cloning site from pBluescript (complementary to position 1-265)
- Sequence from the I-CpaI recognition region (complementary to position 256-265)
- TetIVS2a (complementary to position 266-1178), comprising a nonfunctional gene for I-CpaI (complementary to position 399-861) and an RSB upstream of the nonfunctional I-CpaI gene (complementary to 866-870)
- Sequence from the I-CpaI recognition region (complementary to position 1179-1187)
- lacZ-5' portion including parts of the multiple cloning site from pBluescript (complementary to position 1179-1291)

12.4: Transformation of a Self-disseminating, Artificial Intron in a Natural Master Plant After it had been demonstrated that the TetIVS2a intron is capable of splicing at the desired position and of simultaneously incorporating further genetic information without losing this splicing activity, a construct was generated which is intended to make possible that the I-CpaI gene can be introduced into the plastidic genome by means of the method described within the scope of the present invention in the form of a foreign gene without using a selection marker. To this end, the vector pCB492-25, which comprises an insert with the following elements was first generated (SEQ ID NO: 76; backbone corresponds to that of pBluescript; sequence from BssHII to BssHII in pBluescript is indicated, the BssHII cleavage site indicated here at the 5' end is the BssHII cleavage site in pBluescript which is localized closer to the 3' end of the lacZ gene):
- 23S rDNA fragment upstream of and including the I-CpaI recognition region (position 37-203)
- TetIVS2a (position 204-1112) with inserted gene encoding I-CpaI (position 521-979) and RBS (position 512-516)
- 23S rDNA fragment downstream of and including the I-CpaI recognition region (position 1113-1247)

To ensure expression of I-CpaI directly after the introduction into plastids of natural master plants, a promoter was added in vitro upstream of said intron Cpa construct by means of PCR. The primers p396 and p95 and, as template, pCB492-25 were used for this purpose.

p396 (SEQ ID NO: 77):
5'-TAGTAAATGACAATTTTCCTCTGAATTATATAATTAACATGGCGACT
GTTTACCAAAAAC-3 p95 (SEQ ID NO: 78):
5'-CTCAATTGGGGTCTCTCTGTCCAGGTGCAGG-3'

The resulting PCR product was named Prom-TetIVS2a-Cpa, is described by SEQ ID NO: 79 and comprised the following elements:
- synthetic promoter (position 8-40)
- tobacco 23S rDNA upstream of and including portions of the I-CpaI recognition region (position 41-207)
- TetIVS2a (position 208-1116) comprising gene encoding I-CpaI (position 525-983) and RBS (position 516-520)
- tobacco 23S rDNA downstream of and including portions of the I-CpaI recognition region (position 1117-1243)

The plasmid pCB492-25 was applied to gold particles simultaneously with the above-described PCR product Prom-TetIVS2a-Cpa as described in Example 4 and subsequently used to bombard wild-type tobacco. By expression of the I-CpaI enzyme, it was intended to bring about a double-strand break in the 23S rDNA, which double-strand break is repaired by the PCR product which has been introduced or by the insertion sequence, of the plasmid pCB492-25, which has been introduced. The I-CpaI recognition region, which is naturally present, is thereby inactivated in the transformed plastome copies. Plants were regenerated without any selection pressure, and these plants are tested by PCR for the presence of the insertion sequence in the plastome.

Example 13

Dissemination of the Modified *Tetrahymena* LSU Intron from pCB255-1 in a Natural Master Plant by Expression of the DSBI Enzyme I-CpaI in trans This example shows how a DSBI enzyme can be expressed in the plastids of master plants in order to efficiently disseminate an insertion sequence in the copies of the master plant.

13.1: Generation of a Vector for the Transformation of Plastids which Permits the Expression of the Homing Endonuclease I-CpaI in Plastids First, a vector which encodes the selection marker aadA and the DSBI enzyme I-CpaI was generated. Since expression of the I-CpaI enzyme is lethal in *E. coli*, the accD promoter was chosen in order to allow for the expression of this enzyme in the plastids, but to prevent the expression in *E. coli*. Thus, it was possible to generate and amplify this vector in a conventional manner with *E. coli* as the host organism. The resulting vector was named pCB435-45 and comprised an insert as shown in SEQ ID NO: 80 with the following elements:
- Right-hand target region (as in pCB42-94, see above; complementary to position 66-1403)
- promoter PaccD (position 1422-1478)
- RBS (position 1500-1504)
- Gene encoding I-CpaI (position 1509-1967)
- Expression cassette for the marker gene aadA consisting of:
    the 3' region of the psbA gene (complementary to position 2065-1974)
- aadA gene (complementary to position 2872-2078)
- 5'-untranslated regions of the tobacco rbcL gene (complementary to position 2890-2873), partly mutated
- Promoter of the gene for the 16S rRNA (complementary to position 2987 to 2897)
- Left-hand target region (as in pCB42-94, see above; complementary to position 3863-3007)
- Portions of the pBluescript (including origin of replication; positions 3864-4746 and 1-65)

13.2 Cotransformation of pCB435-45 and pCB255-1 into Natural Master Plants

The plasmids pCB435-45 and pCB255-1 were applied simultaneously to gold particles as detailed in Example 4 and then introduced into plastids of tobacco leaves by means of the particle gun. Transplastomic plants were selected on regeneration medium supplemented with 500 mg/l spectinomycin as described in Example 4. As soon as plantlets had formed, they were transferred to growth medium supplemented with 500 mg/l spectinomycin, and leaf material was harvested. This leaf material was analyzed by Southern analysis using the Dig-Easy Hyb® (Roche Diagnostics; Mannheim) for the incorporation of the two plasmids into the plastidic genome. A probe with a sequence as shown in SEQ ID NO: 81 was used to determine the percentage of plastome copies which were transgenic with regard to the insertion sequence from pCB435-45 (probe directed against portions of the 16S rDNA).

A probe with a sequence as shown in SEQ ID NO: 82 was used to determine the percentage of plastome copies which were transgenic with regard to the insertion sequence from pCB255-1 (probe directed against portions of the 23S rDNA).

FIG. 11 shows that, in this experiment, 2 lines (CB255+ 435NTH-19 and -20) were identified which are transgenic with regard to both the insertion sequence of pCB435-45 and that from pCB255-1. It was furthermore demonstrated in this manner that, surprisingly, the insertion sequence from pCB255-1 (modified *Tetrahymena* LSU intron) had already been disseminated into more copies of the plastidic genome than the insertion sequence from pCB435-45, even though the selection had been carried for the event of the insertion of the insertion sequence from pCB435-45 (aadA marker gene resides in pCB435-45). The efficiency of the method described within the present invention—viz. the insertion and rapid dissemination of an insertion sequence in the plastidic genome without selecting for the presence of this insertion sequence by utilizing DSBI enzymes and suitable recognition sites—has thus been demonstrated for said lines in the present example.

Example 14

Generation of Further Master Plants with a DSB Recognition Region which does not Naturally Occur in Plastids, and Transformation of these Plants Utilizing the DSBI Enzyme I-PpoI 14.1: Generation of a Further Vector (pCB456-2) for Introducing a Non-naturally-occurring Recognition Region for the Homing Endonuclease I-PpoI into the Plastome of Tobacco The purpose of this approach was (analogously to Example 3) to generate a further vector for the transformation of plastids, which vector has no extensive homologies with sequences in the plastidic genome.

In this plasmid, the selection marker aadA is under the control of a synthetic promoter which is derived from the consensus sequence for *E. coli* σ70 promoters. A region downstream of the *Synechocystis* 3'psbA-1 gene was used as the 3' end. In contrast to the vector pCB199-3 which has already been described, the DSB recognition sequence was here introduced into the molecule immediately downstream of the aadA gene, but upstream of the Synechocystis 3'psbA-1 sequence. An operon can be generated thereby with the aid of a DSBI enzyme following insertion of an insertion sequence. The genes on the insertion sequence can then be optionally inserted on the insertion sequence without promoter. After the insertion, suitable genes of the insertion sequence then also come under the control of the synthetic promoter upstream of the aadA gene in the master plant. An operon structure consisting of the aadA and the subsequently introduced genes can thereby optionally be generated in the plastome.

Various elements were cloned one after the other into the basic vector pCB42-94 in order to generate the plasmid pCB456-2:

Synthetic promoter (complementary to bp 1226-1260)
Ribosome binding site (complementary to bp 1214-1218)
aadA gene (complementary to bp 414-1208)
Core recognition region for the homing endonuclease I-PpoI (complementary to bp 331-345)
3'psbA-1 from Synechocystis (complementary to bp 19-155)

The vector thus obtained also confers spectinomycin resistance in *E. coli*. This vector, which is named pCB456-2, comprises the abovementioned elements within the nucleic acid sequence with the SEQ ID NO: 83, instead of the multiple cloning site in the basic vector pCB42-94 for the transformation of plastids. Again, all of the sequence which replaces MCS (from SacI to KpnI) is indicated.

14.2: Generation of Predominantly Homotransplastomic Master Plants which Comprise a Nonnatural DSB Recognition Sequence The vector pCB456-2 was introduced into the plastids of tobacco analogously to pCB199-3 in Example 4. However, as opposed to the description in Example 4, the shoots obtained were grown on growth medium comprising 30 g/l sucrose (instead of the 10 g/l stated in Example 4). The resulting plants were named CB456NTH. 2 lines which have the insertion sequence from pCB456-2 incorporated into their plastome (CB456NTH-1 and -15, cf. FIG. 12) were identified among the spectinomycin-resistant plants obtained after the transformation, using Southern hybridization. A probe which was directed against a fragment of the 16S rDNA was employed in the Southern experiment (cf. Example 13.2 above). This probe was suitable for detecting an approx. 3.1 kb fragment from EcoRI-digested DNA corresponding to the wild type. In contrast, an approx. 1.7 kb fragment was detected when the insertion sequence from pCB456-2 had been incorporated into the corresponding plastome copies.

14.3: Generation of a Transformation Vector for Artificial Homing in the Master Plants CB456NTH First, an operon structure consisting of the elements RBS—nptII (encoding an enzyme which confers kanamycin resistance)—RBS—I-PpoI (encoding a DSBI enzyme) was generated. This cassette was surrounded with BstXI cleavage sites which, after exposure to the enzyme BstXI, generate DNA ends which are compatible with the DNA ends generated by the enzyme I-PpoI. The resulting vector (backbone corresponds to that of pBluescript) was named pCB528-2 and comprises an insert as shown in SEQ ID NO: 84 with the following elements:

RBS (position 28-32)
nptII (position 27-840)
RBS (position 849-853)
Gene encoding I-PpoI (position 859-1350)

The 1360 bp fragment was subsequently excised from pCB528-2 using BstXI and ligated into the I-PpoI cleavage site in the vector pCB456-2. Clones with kanamycin resistance were selected from those obtained after the ligation products had been transformed into *E. coli*. It was thereby ensured that said insert in the clone in question was inserted in the vector in such a way that the nptII and I-PpoI cassettes had the same orientation as the aadA cassette. This was also verified by the restriction analysis method, with which the skilled worker is familiar. The vector in question was named pCB535-11.

14.4: Transformation of pCB535-11 into Master Plants CB456NTH pCB535-11 was Applied to Gold Particles as Described for pCB456-2 in Example 14.2 and Subsequently Introduced into Plastids of the Master Plant CB456NTH-1 Using the Particle Gun.

Some of the explants were incubated on regeneration medium without any selection pressure. Resulting plants were transferred to growth medium (again without selection pressure). Thereafter, the plants are analyzed by PCR for the presence of the RBS—nptII—RBS—I-PpoI cassette.

Other explants were incubated on regeneration medium supplemented with 15 or 30 mg/l kanamycin. After 2 weeks, the plants are transferred to fresh regeneration medium and the kanamycin concentration increased stepwise to 50 and 80 mg/l, respectively.

I claim:

1. A method for integration of a DNA sequence into a plastid DNA of a plant or plant cell, said method comprising:
   a) combining a transformation construct comprising an insertion sequence with at least one enzyme suitable for directed induction of DNA double-strand breaks at a recognition sequence of the plastid DNA in at least one plastid of a plant or plant cell, wherein the plastid DNA comprises at least one recognition sequence for the directed induction of DNA double-strand breaks;
   b) inducing DNA double-strand breaks at the recognition sequence; and
   c) inserting the insertion sequence into the recognition sequence of the plastid DNA at the DNA double-strand breaks, wherein functionality of the recognition sequence for the directed induction is deactivated and said recognition sequence is no longer capable of being cleaved by the at least one enzyme;
   wherein the at least one enzyme is expressed in the plastid of a plant or plant cell or expressed in the nucleus and transported to the plastid of a plant or plant cell.

2. The method of claim 1, wherein the recognition sequence and the insertion sequence are flanked at least unilaterally by sequences with sufficient length and sufficient homology to ensure homologous recombination with each other.

3. The method of claim 1, wherein the transformation construct encompasses at least one element selected from the group consisting of:
   i) an expression cassette for an enzyme suitable for the induction of DNA double-strand breaks at the recognition sequence for the directed induction of DNA double-strand breaks;
   ii) a positive selection marker;
   iii) a negative selection marker;
   iv) a reporter gene;
   v) a replication origin;
   vi) a multiple cloning region;
   vii) a sequence which makes possible homologous recombination or insertion into the genome of a host organism; and
   viii) combinations thereof.

4. The method of claim 1, wherein the enzyme is selected from the group consisting of restriction endonucleases and homing endonucleases.

5. The method of claim 1, wherein the at least one enzyme is selected from the group of homing endonucleases consisting of F-SceI, F-SceII, F-SuvI, F-TevI, F-TevII, I-AmaI, I-AniI, I-CeuI, I-CeuAIIP, I-ChuI, I-CmoeI, I-CpaI, I-CpaII, I-CreI, I-CrepsbIP, I-CrepsbIIP, I-CrepsbIIIP, I-CrepsbIVP, I-CsmI, I-CvuI, I-CvuAIP, I-DdiII, I-DirI, I-DmoI, I-HspNIP, I-LlaI, I-MsoI, I-NaaI, I-NanI, I-NclIP, I-NgrIP, I-NitI, I-NjaI, I-Nsp2361P, I-PakI, I-Pbo1P, I-PcuIP, I-PcuAI, I-PcuVI, I-PgrIP, I-PobIP, I-PorI, I-PorIIP, I-PpbIP, I-PpoI, I-SPBetaIP, I-ScaI, I-SceI, I-SceII, I-SceIII, I-SceIV, I-SceV, I-SceVI, I-SceVII, I-SexIP, I-SneIP, I-SpomCP, I-SpomIP, I-SpomIIP, I-SquIP, I-Ssp6803I, I-SthPhiJP, I-SthPhiST3P, I-SthPhiS3bP, I-Tde1P, I-TevI, I-TevII, I-TevIII, I-UarAP, I-UarHGPA1P, I-UarHGPA13P, I-VinIP, I-ZbiIP, PI-MtuI, PI-MtuHIP, PI-MtuHIIP, PI-PfuI, PI-PfuII, PI-PkoI, PI-PkoII, PI-PspI, PI-Rma43812IP, PI SPBetaIP, PI-SceI, PI-TfuI, PI-TfuII, PI-ThyI, PI-TliI, and PI-TliII.

6. The method of claim 1, wherein the at least one enzyme is selected from the group consisting of enzymes that contain the amino acid sequence of SEQ ID NO: 5, 12, 14 or 71.

7. The method of claim 1, wherein the at least one enzyme is expressed from an expression cassette.

8. The method of claim 1, wherein the plastid DNA is derived from a cell of a multi-celled plant.

9. The method of claim 1, further comprising isolating a plant or plant cell in which the insertion sequence has been inserted into the plastid DNA in at least one plastid of the plant or plant cell.

10. The method of claim 9, further comprising selecting a predominantly homotranspiastomic plant cell containing the insertion sequence inserted into its plastid DNA.

11. A multi-celled plant formed from the predominantly homotransplastomic plant cell selected by the method of claim 10.

12. The multi-celled plant of claim 11, further comprising an expression cassette inserted into the plastid DNA.

13. The multi-celled plant of claim 11, further comprising an expression cassette inserted into the nuclear DNA of said plant cell.

14. The multi-celled plant of claim 11, wherein the plant is selected from the group consisting of Arabidopsis thaliana, tobacco, Tagetes, wheat, rye, barley, oats, oilseed rape, maize, potato, sugar beet, soybean, sunflower, pumpkin/squash and peanut.

15. A cell culture, organ, tissue, part or transgenic propagation material derived from the multi-celled plant of claim 11, wherein the cell culture, organ, tissue, part or transgenic propagation material comprises the insertion sequence.

16. A pharmaceutical, fine chemical, food, feed or seed, comprising the cell culture, organ, part or transgenic propagation material of claim 15.

* * * * *

UNITED STATES PATENT AND TRADEMARK OFFICE
CERTIFICATE OF CORRECTION

PATENT NO. : 7,462,758 B2
APPLICATION NO. : 10/499518
DATED : December 9, 2008
INVENTOR(S) : Christian Biesgen It is certified that error appears in the above-identified patent and that said Letters Patent is hereby corrected as shown below:

In claim 10, in column 168, on line 34, "predominantly homotranspiastomic plant cell containing the" should read -- predominantly homotransplastomic plant cell containing the --.

Signed and Sealed this

Second Day of June, 2009

JOHN DOLL
*Acting Director of the United States Patent and Trademark Office*

SEQUENCE LISTING

<160> NUMBER OF SEQ ID NOS: 159

<210> SEQ ID NO 1
<211> LENGTH: 4363
<212> TYPE: DNA
<213> ORGANISM: Artificial sequence
<220> FEATURE:
<223> OTHER INFORMATION: Description of the artificial sequence: plastid
      transformation plasmid pCB42-94
<220> FEATURE:
<221> NAME/KEY: misc_feature
<222> LOCATION: (55)..(1405)
<223> OTHER INFORMATION: right targeting region
<220> FEATURE:
<221> NAME/KEY: mutation
<222> LOCATION: (346)
<223> OTHER INFORMATION: mutation causing streptomycin resistance
<220> FEATURE:
<221> NAME/KEY: mutation
<222> LOCATION: (68)
<223> OTHER INFORMATION: mutation causing spectinomycin resistance
<220> FEATURE:
<221> NAME/KEY: misc_feature
<222> LOCATION: (1404)..(1511)
<223> OTHER INFORMATION: multiple cloning site
<220> FEATURE:
<221> NAME/KEY: misc_feature
<222> LOCATION: (2629)..(3417)
<223> OTHER INFORMATION: Ampicillin resistance

<400> SEQUENCE: 1

```
gcgcccaata cgcaaaccgc ctctccccgc gcgttggccg attcattaat gcagtgatga      60
cttgacggca tcctcacctt cctccggctt atcaccggca gtctgttcag ggttccaaac     120
tcaacgatgg caactaaaca cgagggttgc gctcgttgcg ggacttaacc caacaccttt     180
cggcacgagc tgacgacagc catgcaccac ctgtgtccgc gttcccgaag caccccctct     240 cttttcaagag gattcgcggc atgtcaagcc tggtaaggt tcttcgcttt gcatcgaatt     300
aaaccacatg ctccaccgct tgtgcgggcc ccgtcaatt ccttttagtt tcattcttgc      360
gaacgtactc cccaggcggg atacttaacg cgttagctac agcactgcac gggtcgatac     420
gcacagcgcc tagtatccat cgtttacggc taggactact ggggtatcta atcccattcg     480
ctcccctagc tttcgtctct cagtgtcagt gtcggcccag cagagtgctt tcgccgttgg     540
tgttctttcc gatctctacg catttcaccg ctccaccgga aattccctct gccctaccg     600 tactccagct tggtagtttc caccgccgt ccagggttga gccctgggat tgacgcgcgg    660
acttaaaaag ccacctacag acgctttacg cccaatcatt ccggataacg cttgcatcct    720
ctgtattacc gcggctgctg gcacagagtt agccgatgct tattccccag ataccgtcat    780
tgcttcttct ccgggaaaag aagttcacga cccgtgggcc ttctacctcc acgcggcatt    840
gctccgtcag gctttcgccc attgcggaaa attccccact gctgcctccc gtaggagtct    900
gggccgtgtc tcagtcccag tgtggctgat catcctctcg gaccagctac tgatcatcgc    960
cttggtaagc tattgcctca ccaactagct aatcagacgc gagcccctcc tcgggcggat   1020 tcctccttt gctcctcagc ctacggggta ttagcagccg tttccagctg ttgttcccct   1080
cccaagggca ggttcttacg cgttactcac ccgtccgcca ctggaaacac cacttcccgt   1140
ccgacttgca tgtgttaagc atgccgccag cgttcatcct gagccaggat cgaactctcc   1200
atgagattca tagttgcatt acttatagct tccttgttcg tagacaaagc ggattcggaa   1260
ttgtctttca ttccaaggca taacttgtat ccatgcgctt catattcgcc cggagttcgc   1320
```

| | |
|---|---|
| tcccagaaat atagccatcc ctgcccctc acgtcaatcc cacgagcctc ttatccattc | 1380 |
| tcattgaacg acggcggggg agcgagctcc accgcgtgg cggccgctct agaactagtg | 1440 |
| gatcccccgg gctgcaggaa ttcgatatca agcttatcga taccgtcgac ctcgaggggg | 1500 |
| ggcccggtac caaatccaac tagaaaaact cacattgggc ttagggataa tcaggctcga | 1560 |
| actgatgact tccaccacgt caaggtgaca ctctaccgct gagttatatc ccttccccgc | 1620 |
| cccatcgaga aatagaactg actaatccta agtcaaggg tcgagaaact caacgccact | 1680 |
| attcttgaac aacttggagc cgggccttct tttcgcacta ttacggatat gaaaataatg | 1740 |
| gtcaaaatcg gattcaattg tcaactgccc ctatcgaaaa taggattgac taccgattcc | 1800 |
| gaaggaactg gagttacatc tcttttccat tcaagagttc ttatgcgttt ccacgcccct | 1860 |
| ttgagacccc gaaaaatgga caaattcctt ttcttaggaa cacatacaag attcgtcact | 1920 |
| acaaaaagga taatggtaac cctaccatta actacttcat ttatgaattt catagtaata | 1980 |
| gaaatacatg tcctaccgag acagaatttg aacttgcta tcctcttgcc tagcaggcaa | 2040 |
| agatttacct ccgtggaaag gatgattcat tcggatcgac atgagagtcc aactacattg | 2100 |
| ccagaatcca tgttgtatat ttgaaagagg ttgacctcct tgcttctctc atggtacact | 2160 |
| cctcttcccg ccgagcccct tttctcctcg gtccacagag acaaaatgta ggactggtgc | 2220 |
| caacaattca tcagactcac taagtcggga tcactaacta atactaatct aatataatag | 2280 |
| tctaatatat ctaatataat agaaaatact aatataatag aaaagaactg tcttttctgt | 2340 |
| atactttccc cggttccgtt gctaccgagg gcctcgtgat acgcctattt ttataggtta | 2400 |
| atgtcatgat aataatggtt tcttagacgt caggtggcac ttttcgggga aatgtgcgcg | 2460 |
| gaacccctat ttgtttattt ttctaaatac attcaaatat gtatccgctc atgagacaat | 2520 |
| aaccctgata aatgcttcaa taatattgaa aaaggaagag tatgagtatt caacatttcc | 2580 |
| gtgtcgccct tattccctt tttgcggcat tttgccttcc tgttttgct cacccagaaa | 2640 |
| cgctggtgaa agtaaaagat gctgaagatc agttgggtgc acgagtgggt tacatcgaac | 2700 |
| tggatctcaa cagcggtaag atccttgaga gttttcgccc cgaagaacgt tttccaatga | 2760 |
| tgagcacttt taaagttctg ctatgtggcg cggtattatc ccgtattgac gccgggcaag | 2820 |
| agcaactcgg tcgccgcata cactattctc agaatgactt ggttgagtac tcaccagtca | 2880 |
| cagaaaagca tcttacggat ggcatgacag taagagaatt atgcagtgct gccataacca | 2940 |
| tgagtgataa cactgcggcc aacttacttc tgacaacgat cggaggaccg aaggagctaa | 3000 |
| ccgcttttt gcacaacatg ggggatcatg taactcgcct tgatcgttgg aaccggagc | 3060 |
| tgaatgaagc cataccaaac gacgagcgtg acaccacgat gcctgtagca atggcaacaa | 3120 |
| cgttgcgcaa actattaact ggcgaactac ttactctagc ttcccggcaa caattaatag | 3180 |
| actggatgga ggcggataaa gttgcaggac cacttctgcg ctcggccctt ccggctggct | 3240 |
| ggtttattgc tgataaatct ggagccggtg agcgtgggtc tcgcggtatc attgcagcac | 3300 |
| tggggccaga tggtaagccc tcccgtatcg tagttatcta cacgacgggg agtcaggcaa | 3360 |
| ctatggatga acgaaataga cagatcgctg agataggtgc ctcactgatt aagcattggt | 3420 |
| aactgtcaga ccaagtttac tcatatatac tttagattga tttaaaactt catttttaat | 3480 |
| ttaaaaggat ctaggtgaag atcctttttg ataatctcat gaccaaaatc ccttaacgtg | 3540 |
| agttttcgtt ccactgagcg tcagaccccg tagaaaagat caaggatct tcttgagatc | 3600 |
| cttttttct gcgcgtaatc tgctgcttgc aaacaaaaaa accaccgcta ccagcggtgg | 3660 |
| tttgtttgcc ggatcaagag ctaccaactc tttttccgaa ggtaactggc ttcagcagag | 3720 |

| | |
|---|---|
| cgcagatacc aaatactgtc cttctagtgt agccgtagtt aggccaccac ttcaagaact | 3780 |
| ctgtagcacc gcctacatac ctcgctctgc taatcctgtt accagtggct gctgccagtg | 3840 |
| gcgataagtc gtgtcttacc gggttggact caagacgata gttaccggat aaggcgcagc | 3900 |
| ggtcgggctg aacggggggt tcgtgcacac agcccagctt ggagcgaacg acctacaccg | 3960 |
| aactgagata cctacagcgt gagctatgag aaagcgccac gcttcccgaa gggagaaagg | 4020 |
| cggacaggta tccggtaagc ggcagggtcg gaacaggaga gcgcacgagg gagcttccag | 4080 |
| ggggaaacgc ctggtatctt tatagtcctg tcgggtttcg ccacctctga cttgagcgtc | 4140 |
| gattttgtg atgctcgtca gggggcgga gcctatggaa aaacgccagc aacgcggcct | 4200 |
| ttttacggtt cctggccttt tgctggcctt ttgctcacat gttctttcct gcgttatccc | 4260 |
| ctgattctgt ggataaccgt attaccgcct ttgagtgagc tgataccgct cgccgcagcc | 4320 |
| gaacgaccga gcgcagcgag tcagtgagcg aggaagcgga aga | 4363 |

```
<210> SEQ ID NO 2
<211> LENGTH: 1359
<212> TYPE: DNA
<213> ORGANISM: Artificial sequence
<220> FEATURE:
<223> OTHER INFORMATION: Description of the artificial sequence: Insert
      of vector pCB199-3

<400> SEQUENCE: 2
```

| | |
|---|---|
| gagctctgat cacggaagat agctttggca aaaaaagcaa aaagcattta ccttgattga | 60 |
| gatgttaatt gtgttggcaa ttatcagtat tttaattttg cttttttgtgc caaatttgat | 120 |
| actagagctt cgggtgccag ggcgtgccct tgggctcccc gggcgcgtac tcgacgctac | 180 |
| cttaagagag tcaagcttct atattaccct gttatcccta gcgtactcga aaaaaaaga | 240 |
| aaggagcaat agcaccctct tgatagaaca agaaaatgat tattgctcct ttcttttcaa | 300 |
| aacctcctat agactaggcc aggaattatc tgcagttatt tgccaactac cttagtgatc | 360 |
| tcgcctttca cgtagtggac aaattcttcc aactgatctg cgcgcgaggc caagcgatct | 420 |
| tcttcttgtc caagataagc ctgtctagct tcaagtatga cgggctgata ctgggccggc | 480 |
| aggcgctcca ttgcccagtc ggcagcgaca tccttcggcg cgattttgcc ggttactgcg | 540 |
| ctgtaccaaa tgcgggacaa cgtaagcact acatttcgct catcgccagc ccagtcgggc | 600 |
| ggcgagttcc atagcgttaa ggtttcattt agcgcctcaa atagatcctg ttcaggaacc | 660 |
| ggatcaaaga gttcctccgc cgctggacct accaaggcaa cgctatgttc tcttgctttt | 720 |
| gtcagcaaga tagccagatc aatgtcgatc gtggctggct cgaagatacc tgcaagaatg | 780 |
| tcattgcgct gccattctcc aaattgcagt tcgcgcttag ctggataacg ccacggaatg | 840 |
| atgtcgtcgt gcacaacaat ggtgacttct acagcgcgga gaatctcgct ctctccaggg | 900 |
| gaagccgaag tttccaaaag gtcgttgatc aaagctcgcc gcgttgtttc atcaagcctt | 960 |
| acggtcaccg taaccagcaa atcaatatca ctgtgtggct tcaggccgcc atccactgcg | 1020 |
| gagccgtaca aatgtacggc cagcaacgtc ggttcgagat ggcgctcgat gacgccaact | 1080 |
| acctctgata gttgagttga tacttcggcg ataaccgctt cacgagccat ggctgtttgt | 1140 |
| ggtgtcatgc tgtttgtgg tgtcatgaat ccctccctac aactagatcc tcgcccggag | 1200 |
| ttcgctccca gaaatatagc catccctgcc ccctcacgtc aatcccacga gcctcttatc | 1260 |
| cattctcatt gaacgacggc gtcgaggggg ggcccggtac gtcgacgaag ttcctattcc | 1320 |
| gaagttccta ttctcaagaa agtataggaa cttcgtacc | 1359 |

<210> SEQ ID NO 3
<211> LENGTH: 1070
<212> TYPE: DNA
<213> ORGANISM: Artificial sequence
<220> FEATURE:
<223> OTHER INFORMATION: Description of the artificial sequence: insert
of vector pCB401-20

<400> SEQUENCE: 3

```
gagctctgat cacggaagat agctttggca aaaaaagcaa aaagcattta ccttgattga    60
gatgttaatt gtgttggcaa ttatcagtat tttaattttg cttttttgtgc caaatttgat   120
actagagctt cgggtgccag ggcgtgccct tgggctcccc gggcgcgtac tcgacgctac   180
cttaagagag tcaagcttct atattaccct gttatcccta gcgtactcga gctgcagtta   240
tttgccaact accttagtga tctcgccttt cacgtagtgg acaaattctt ccaactgatc   300
tgcgcgcgag gccaagcgat cttcttcttg tccaagataa gcctgtctag cttcaagtat   360
gacgggctga tactgggccg gcaggcgctc cattgcccag tcggcagcga catccttcgg   420
cgcgattttg ccggttactg cgctgtacca atgcgggac aacgtaagca ctacatttcg    480
ctcatcgcca gcccagtcgg gcggcgagtt ccatagcgtt aaggtttcat ttagcgcctc   540
aaatagatcc tgttcaggaa ccggatcaaa gagttcctcc gccgctggac ctaccaaggc   600
aacgctatgt tctcttgctt tgtcagcaa gatagccaga tcaatgtcga tcgtggctgg   660
ctcgaagata cctgcaagaa tgtcattgcg ctgccattct ccaaattgca gttcgcgctt   720
agctggataa cgccacggaa tgatgtcgtc gtgcacaaca atggtgactt ctacagcgcg   780
gagaatctcg ctctctccag gggaagccga agtttccaaa aggtcgttga tcaaagctcg   840
ccgcgttgtt tcatcaagcc ttacggtcac cgtaaccagc aaatcaatat cactgtgtgg   900
cttcaggccg ccatccactg cggagccgta caaatgtacg gccagcaacg tcggttcgag   960
atggcgctcg atgacgccaa ctacctctga tagttgagtt gatacttcgg cgataaccgc  1020
ttcacgagcc atggttccct ccctacaacg tcgagggggg gcccggtacc              1070
```

<210> SEQ ID NO 4
<211> LENGTH: 804
<212> TYPE: DNA
<213> ORGANISM: Artificial sequence
<220> FEATURE:
<223> OTHER INFORMATION: Description of the artificial sequence: insert
of vector pCB289-13
<220> FEATURE:
<221> NAME/KEY: CDS
<222> LOCATION: (154)..(642)
<223> OTHER INFORMATION: sequence coding for I-PpoI homing-endonuclease

<400> SEQUENCE: 4

```
ggtaccgggc ccccctcga cgccgtcgtt caatgagaat ggataagagg ctcgtgggat    60
tgacgtgagg gggcagggat ggctatattt ctgggagcga actccgggcg aggatctagt  120
tgtagggagg gattcatgac accacaaaca gcc atg gcg ctc acc aat gct caa  174
                                    Met Ala Leu Thr Asn Ala Gln
                                      1               5
atc ttg gct gtg att gac agt tgg gaa gaa aca gtc ggt cag ttt cca   222
Ile Leu Ala Val Ile Asp Ser Trp Glu Glu Thr Val Gly Gln Phe Pro
         10                  15                  20
gtg ata acg cac cat gta cca tta ggt ggc ggt ctg caa gga acg ctc   270
Val Ile Thr His His Val Pro Leu Gly Gly Gly Leu Gln Gly Thr Leu
     25                  30                  35
```

```
cat tgt tac gag atc ccc cta gca gct cct tat ggg gtt ggc ttt gct      318
His Cys Tyr Glu Ile Pro Leu Ala Ala Pro Tyr Gly Val Gly Phe Ala
 40                  45                  50                  55 aag aat ggg cct acc cgc tgg caa tac aaa cgg aca atc aat caa gtc      366
Lys Asn Gly Pro Thr Arg Trp Gln Tyr Lys Arg Thr Ile Asn Gln Val
                 60                  65                  70 gtc cac aga tgg ggg tcc cac aca gtc cct ttt cta tta gaa ccg gat      414
Val His Arg Trp Gly Ser His Thr Val Pro Phe Leu Leu Glu Pro Asp
             75                  80                  85 aac atc aac ggc aaa acc tgc aca gca tcg cac cta tgt cat aat act      462
Asn Ile Asn Gly Lys Thr Cys Thr Ala Ser His Leu Cys His Asn Thr
         90                  95                 100 cga tgc cac aat ccc ttg cac ttg tgc tgg gag tca cta gac gac aac      510
Arg Cys His Asn Pro Leu His Leu Cys Trp Glu Ser Leu Asp Asp Asn
    105                 110                 115 aaa ggc aga aac tgg tgc ccc ggt ccc aac ggg gga tgt gtc cat gcg      558
Lys Gly Arg Asn Trp Cys Pro Gly Pro Asn Gly Gly Cys Val His Ala
120                 125                 130                 135 gtg gtt tgt tta agg cag ggt ccg ttg tac ggc cca ggg gcg act gtg      606
Val Val Cys Leu Arg Gln Gly Pro Leu Tyr Gly Pro Gly Ala Thr Val
                140                 145                 150 gca ggt cct caa caa agg ggc agt cac ttt gtg gta taactgcaga           652
Ala Gly Pro Gln Gln Arg Gly Ser His Phe Val Val
            155                 160 agcttcaatt gcatgctcta gatgatcaaa gaattcctgg cctagtctat aggaggtttt    712
gaaaagaaag gagcaataat catttctctg ttctatcaag agggtgctat tgctcctttc    772 ttttttttctc gagaggggta cgtaccgagc tc                                 804

<210> SEQ ID NO 5
<211> LENGTH: 163
<212> TYPE: PRT
<213> ORGANISM: Artificial sequence
<220> FEATURE:
<223> OTHER INFORMATION: Description of the artificial sequence: insert
      of vector pCB289-13

<400> SEQUENCE: 5

Met Ala Leu Thr Asn Ala Gln Ile Leu Ala Val Ile Asp Ser Trp Glu
 1               5                  10                  15

Glu Thr Val Gly Gln Phe Pro Val Ile Thr His His Val Pro Leu Gly
             20                  25                  30

Gly Gly Leu Gln Gly Thr Leu His Cys Tyr Glu Ile Pro Leu Ala Ala
         35                  40                  45

Pro Tyr Gly Val Gly Phe Ala Lys Asn Gly Pro Thr Arg Trp Gln Tyr
     50                  55                  60

Lys Arg Thr Ile Asn Gln Val Val His Arg Trp Gly Ser His Thr Val
 65                  70                  75                  80

Pro Phe Leu Leu Glu Pro Asp Asn Ile Asn Gly Lys Thr Cys Thr Ala
                 85                  90                  95

Ser His Leu Cys His Asn Thr Arg Cys His Asn Pro Leu His Leu Cys
            100                 105                 110

Trp Glu Ser Leu Asp Asp Asn Lys Gly Arg Asn Trp Cys Pro Gly Pro
        115                 120                 125

Asn Gly Gly Cys Val His Ala Val Val Cys Leu Arg Gln Gly Pro Leu
    130                 135                 140

Tyr Gly Pro Gly Ala Thr Val Ala Gly Pro Gln Gln Arg Gly Ser His
145                 150                 155                 160
```

Phe Val Val

<210> SEQ ID NO 6
<211> LENGTH: 1150
<212> TYPE: DNA
<213> ORGANISM: Artificial sequence
<220> FEATURE:
<223> OTHER INFORMATION: Description of the artificial sequence:
    XhoI / Bgl II  fragment for construction of
    vector  pCB304-25

<400> SEQUENCE: 6

```
ctcgagtatt cggctcaatc cttttagtaa aagattgggc cgagtttaat tgcaattcaa     60
ttaagagaac gaaggataat tacttgagtt ctttctcctt atccttcttt atttcctgct    120
aatttatctg ctaatgtcta ctgaattcaa gcttggatcc gcggccgcct agcttgggtc    180
ccgctcagaa gaactcgtca agaaggcgat agaaggcgat gcgctgcgaa tcgggagcgg    240
cgataccgta aagcacgagg aagcggtcag cccattcgcc gccaagctct tcagcaatat    300
cacgggtagc caacgctatg tcctgatagc ggtccgccac acccagccgg ccacagtcga    360
tgaatccaga aaagcggcca ttttccacca tgatattcgg caagcaggca tcgccatggg    420
tcacgacgag atcctcgccg tcgggcatgc gcgccttgag cctggcgaac agttcggctg    480
gcgcgagccc ctgatgctct tcgtccagat catcctgatc gacaagaccg gcttccatcc    540
gagtacgtgc tcgctcgatg cgatgtttcg cttggtggtc gaatgggcag gtagccggat    600
caagcgtatg cagccgccgc attgcatcag ccatgatgga tactttctcg gcaggagcaa    660
ggtgagatga caggagatcc tgccccggca cttcgcccaa tagcagccag tcccttcccg    720
cttcagtgac aacgtcgagc acagctgcgc aaggaacgcc cgtcgtggcc agccacgata    780
gccgcgctgc ctcgtcctgc agttcattca gggcaccgga caggtcggtc ttgacaaaaa    840
gaaccgggcg cccctgcgct gacagccgga acacggcggc atcagagcag ccgattgtct    900
gttgtgccca gtcatagccg aatagcctct cacccaagc ggccggagaa cctgcgtgca    960
atccatcttg ttcaatccaa gctcccatgg ctgtttgtgg tgtcatgaat ccctccctac   1020
aactagatcc tatatactat agagataggt ggataaatat ttttctttag taagacccca   1080
tcgctaatat taatttatct aacatattaa ttaatattta atatataaat atatatagag   1140
tcgagatcta                                                           1150
```

<210> SEQ ID NO 7
<211> LENGTH: 454
<212> TYPE: DNA
<213> ORGANISM: Artificial sequence
<220> FEATURE:
<223> OTHER INFORMATION: Description of the artificial sequence: insert
    of vector pCB220-17

<400> SEQUENCE: 7

```
gaagacgatc ctaaatagca atatttacct ttgggaccaa aagttatcag gcatgcacct     60
ggtagctagt ctttaaacca atagattgca tcggtttaaa aggcaagacc gtcaaattgc    120
gggaaagggg tcaacagccg ttcagtacca agtctcaggg gaaactttga gatggccttg    180
caaagggtat ggtaataagc tgacggacat ggtcctaacc acgcagccaa gtcctaagtc    240
aacagatctt ctgttgatat ggatgcagtt cacagactaa atgtcggtcg gggaagatgt    300
attcttctca taagatatag tcggacctct ccttaatggg agctagcgga tgaagtgatg    360
caacactgga gccgctggga actaatttgt atgcgaaagt atattgatta gttttggagt    420
```

-continued

```
actcgaaggt agcgaaattc cttgtcaagt cttc                              454
```

<210> SEQ ID NO 8
<211> LENGTH: 498
<212> TYPE: DNA
<213> ORGANISM: Artificial sequence
<220> FEATURE:
<223> OTHER INFORMATION: Description of the artificial sequence: insert
      of vector pCB270-1

<400> SEQUENCE: 8

```
gcgcgcgtaa tacgactcac tatagggcga attggggggcg actgtttacc aaaaacacag    60
gtctccgcaa agtcgtaaga ccatgtatgg gggctgacgc ctgcccagtg ccggaaggtc   120
aaggaagttg gtgacctgat gacaggggag ccggcgaccg aagccccggt gaacggcggc   180
cgtaactata acggtcctaa gtcttcgaat cgaattcact agtgatagga agaccttgtc   240
gggtaagttc cgacccgcac gaaaggcgta acgatctggg cactgtctcg gagagaggct   300
cggtgaaata gacatgtctg tgaagatgcg gactacctgc acctggacag agagacccca   360
attcctggcc tagtctatag gaggttttga aagaaaagga gcaataatca tttctttgtt    420
ctatcaagag ggtgctattg ctcctttctt ttttttctcga ccagcttttg ttcccttag   480 tgagggttaa ttgcgcgc                                                 498
```

<210> SEQ ID NO 9
<211> LENGTH: 789
<212> TYPE: DNA
<213> ORGANISM: Artificial sequence
<220> FEATURE:
<223> OTHER INFORMATION: Description of the artificial sequence: lacZ
      gene with inserted intron to demonstrate splicing
      (from vector pCB315-1)

<400> SEQUENCE: 9

```
acaatttcca ttcgccattc aggctgcgca actgttggga agggcgatcg gtgcgggcct     60
cttcgctatt acgccagctg gcgaaagggg gatgtgctgc aaggcgatta agttgggtaa   120
cgccagggtt ttcccagtca cgacgttgta aaacgacggc cagtgagcgc gcgtaatacg   180
actcactata gggcgaattg ggtaccgggc cccccctcga ggtcgacggt atcgataagc   240
ttgacccgac aaggaatttc gctaccttcg agtactccaa aactaatcaa tatactttcg   300
catacaaatt agttcccagc ggctccagtg ttgcatcact tcatccgcta gctcccatta   360
aggagaggtc cgactatatc ttatgagaag aatacatctt ccccgaccga catttagtct   420
gtgaactgca tccatatcaa cagaagatct gttgacttag acttggctg cgtggttagg   480 accatgtccg tcagcttatt accataccct ttgcaaggcc atctcaaagt ttcccctgag   540
acttggtact gaacggctgt tgacccctt cccgcaattt gacggtcttg ccttttaaac    600
cgatgcaatc tattggttta aagactagct accaggtgca tgcctgataa cttttggtcc   660
caaaggtaaa tattgctatt taggaccgtt aggatccact agttctagag cggccgccac   720
cgcggtggag ctccagcttt tgttcccttt agtgagggtt aattgcgcgc ttggcgtaat   780
catggtcat                                                          789
```

<210> SEQ ID NO 10
<211> LENGTH: 2566
<212> TYPE: DNA
<213> ORGANISM: Artificial sequence
<220> FEATURE:
<223> OTHER INFORMATION: Description of the artificial sequence: Ll.LtrB
      intron from vector pCB345-34.

<400> SEQUENCE: 10

```
gaattcgccc tttgaagact tgacatttga tatggtgaag tagggaggta ccgccttgtt      60
cacattactg tgactggttt gcaccaccct cttcggaac cgtacgtacc cctctcggag      120
tatacggctc tgttattgtt cgttcgtaaa aattcacttg tgtttatgaa tcacgtgacg      180
atgacaatga aagcatacaa caagagtttt acgttgtttc gctatcattg ccatttccca      240
ttttctttg cctttaagat ttttgacctt attgacatgg tgaatttcat aggaagtatt      300
ttcatcagat gttccacata attcacaaca tttagctttt aacctgtttt caagagtatt      360
ccgggcatag ccatacaata caggagcttg acttatctta tccgtaaatt gataagggga      420
tttacattca ctaaaatttg caaaataacg gcgctgctta ccttgcttta tctcatacgg      480
gatgccccac gaaccacttc catctttaaa catggaaatg ttttttgaaa gtgttccctt      540
atgtttggag gctatcgttt ttagacagct gtattccata agataagcaa ataattgag       600
ctggttaaaa ttacttgcta gaccgtagta attacaaatc cctcttaatt cagaattata      660
aattgtgatg atttctaagt ctgttgaacg aataagatat ttcctgtgaa ctggaaacca      720
tgagctatct ttcttttgga tagctatttt cttgtcaaaa ataaattgac gaattttgtc      780
ttgaagagga ataaggagtt ctacactccc attgagtgtt ctcttttga ctttaccaga      840
tcgttttatc gttccacttc tccttactcg tatatcatat cccagaaaac gagcgggttg      900
actgctatgt gtgatgagtg tttttcttc actcaattcc attttagct tgttatgaat       960
aaaaagtttt aattgttctt ttatccattg acagtcctct ttgcttcctt taacagagat     1020
aatgaagtcg tccgcatacc ggacgtattt caatacttta tttgtctgtg aggtacaggg     1080
gagtgtgggt aatcttttac gttttcttg atattctaaa agaactttag cttttcttc      1140
accctccaac ttcttgagac ggtgagaaat tcttttatc tcattgtgaa gttcccgata     1200
ttcaggtgtt attcttctg gactttctcg gtcaaacttc attttgagtt gtaaaacaaa      1260
cttatccaat tcatgaagat agatgttggc caaagagga gatagaattc caccttgagg     1320
tgttccgctg taagttttgt gatactgcca gttttccaga taacctgctt ttagaaattt     1380
ataaatcaat tggctcattt tcatatcttt gattttaaga ttgatgagtc caatgagtgt     1440
aacgtggtct atattatcga agcagccttt tatatctccc tccacaaacc atcttgcgcc     1500
gccaaactct cttttgattg ttttcaaagc cgtgtgacag cttcgttgag gtctaaaacc     1560
gtgagacaca tcttcgaata ccggttcata gatagattca agaattattc tcacagcttc     1620
ttggatcaat ttatctgtga agttggaat tcctaaaggt ctcatctttt tagaattctt     1680
ttttgcaata tacattcttc gtacaggttg aggatagtaa gttccgtctt ttaaagattg     1740
aataatcttt tttatttttt cttcactaaa gccatccgct gtatcatcta atattccttt     1800
tgtggaagct cctttattgg aatataaatt ttgatacgcc acgtaataaa tatctggacg     1860
taaaagataa cgataaagtc ttgtaaaaac ttcgtctata ttttcttgtg aatttttact     1920
gattctttct aaaattgcca ttgttggttt cattttgagg ttttcctccc taatcaattt     1980
ttaattttag tacacaataa ctgtacccct ttgccatgta aagggcgtta cccttctcag     2040
actactacga gtactccgta cccttgcaag atttttcaagc tctagtgcta tagccttttt     2100
cctccttttct attaggcatt cttgtttagg gtatcccag ttagtgttaa gtcttggtaa     2160
attcagattc tcggcatcgc tttcgtttcg ttcccatagg ttctcctaca gattgtacaa     2220
atgtggtgat aacagataag tccacaacca taacttacct ttctttgtac tagaggtttc     2280
```

```
agacactttc ctctatcgac acataaccga aattagaaac ttgckttcag taaacacaac    2340
ttatacctta tatctgatta acattgcgac tcagtcgtac ccgattgtct ttaggtaact    2400
catcgctttc caaccgtgct ctgttcccgt atcagctttc gcttttcggt taggttggct    2460
gttttctgtg ttatcttaca gagtagtacc ttaaactact tgacttaaca ccctatctgg    2520
gcgcacgtta tggatgtgtt aggaatgtct tctcaagggc gaattc                    2566
```

```
<210> SEQ ID NO 11
<211> LENGTH: 520
<212> TYPE: DNA
<213> ORGANISM: Artificial sequence
<220> FEATURE:
<223> OTHER INFORMATION: Description of the artificial sequence:
      synthetic sequence coding for I-Ppo I homing-endonuclease
<220> FEATURE:
<221> NAME/KEY: CDS
<222> LOCATION: (16)..(504)

<400> SEQUENCE: 11
gcatatgaga tctcc atg gcg ctc acc aat gct caa atc ttg gct gtg att       51
                Met Ala Leu Thr Asn Ala Gln Ile Leu Ala Val Ile
                  1               5                  10 gac agt tgg gaa gaa aca gtc ggt cag ttt cca gtg ata acg cac cat        99
Asp Ser Trp Glu Glu Thr Val Gly Gln Phe Pro Val Ile Thr His His
            15                  20                  25 gta cca tta ggt ggc ggt ctg caa gga acg ctc cat tgt tac gag atc       147
Val Pro Leu Gly Gly Gly Leu Gln Gly Thr Leu His Cys Tyr Glu Ile
     30                  35                  40 ccc cta gca gct cct tat ggg gtt ggc ttt gct aag aat ggg cct acc       195
Pro Leu Ala Ala Pro Tyr Gly Val Gly Phe Ala Lys Asn Gly Pro Thr
 45                  50                  55                  60 cgc tgg caa tac aaa cgg aca atc aat caa gtc gtc cac aga tgg ggg       243
Arg Trp Gln Tyr Lys Arg Thr Ile Asn Gln Val Val His Arg Trp Gly
                 65                  70                  75 tcc cac aca gtc cct ttt cta tta gaa ccg gat aac atc aac ggc aaa       291
Ser His Thr Val Pro Phe Leu Leu Glu Pro Asp Asn Ile Asn Gly Lys
             80                  85                  90 acc tgc aca gca tcg cac cta tgt cat aat act cga tgc cac aat ccc       339
Thr Cys Thr Ala Ser His Leu Cys His Asn Thr Arg Cys His Asn Pro
         95                 100                 105 ttg cac ttg tgc tgg gag tca cta gac gac aac aaa ggc aga aac tgg       387
Leu His Leu Cys Trp Glu Ser Leu Asp Asp Asn Lys Gly Arg Asn Trp
     110                 115                 120 tgc ccc ggt ccc aac ggg gga tgt gtc cat gcg gtg gtt tgt tta agg       435
Cys Pro Gly Pro Asn Gly Gly Cys Val His Ala Val Val Cys Leu Arg
125                 130                 135                 140 cag ggt ccg ttg tac ggc cca ggg gcg act gtg gca ggt cct caa caa       483
Gln Gly Pro Leu Tyr Gly Pro Gly Ala Thr Val Ala Gly Pro Gln Gln
                145                 150                 155 agg ggc agt cac ttt gtg gta taactgcagc tcgagg                          520
Arg Gly Ser His Phe Val Val
            160
```

```
<210> SEQ ID NO 12
<211> LENGTH: 163
<212> TYPE: PRT
<213> ORGANISM: Artificial sequence
<220> FEATURE:
<223> OTHER INFORMATION: Description of the artificial sequence:
      synthetic sequence coding for I-Ppo I homing-endonuclease

<400> SEQUENCE: 12
```

-continued

```
Met Ala Leu Thr Asn Ala Gln Ile Leu Ala Val Ile Asp Ser Trp Glu
 1               5                  10                  15

Glu Thr Val Gly Gln Phe Pro Val Ile Thr His His Val Pro Leu Gly
                 20                  25                  30

Gly Gly Leu Gln Gly Thr Leu His Cys Tyr Glu Ile Pro Leu Ala Ala
             35                  40                  45

Pro Tyr Gly Val Gly Phe Ala Lys Asn Gly Pro Thr Arg Trp Gln Tyr
         50                  55                  60

Lys Arg Thr Ile Asn Gln Val Val His Arg Trp Gly Ser His Thr Val
 65                  70                  75                  80

Pro Phe Leu Leu Glu Pro Asp Asn Ile Asn Gly Lys Thr Cys Thr Ala
                 85                  90                  95

Ser His Leu Cys His Asn Thr Arg Cys His Asn Pro Leu His Leu Cys
            100                 105                 110

Trp Glu Ser Leu Asp Asp Asn Lys Gly Arg Asn Trp Cys Pro Gly Pro
            115                 120                 125

Asn Gly Gly Cys Val His Ala Val Val Cys Leu Arg Gln Gly Pro Leu
130                 135                 140

Tyr Gly Pro Gly Ala Thr Val Ala Gly Pro Gln Gln Arg Gly Ser His
145                 150                 155                 160

Phe Val Val
```

<210> SEQ ID NO 13
<211> LENGTH: 481
<212> TYPE: DNA
<213> ORGANISM: Chlamydomonas pallidostigmatica
<220> FEATURE:
<221> NAME/KEY: CDS
<222> LOCATION: (4)..(459)
<223> OTHER INFORMATION: ORF coding for I-Cpa I homing endonuclease

<400> SEQUENCE: 13

```
acc atg gac att aat cct caa tgg att aca ggt ttc gta gat ggg gaa        48
    Met Asp Ile Asn Pro Gln Trp Ile Thr Gly Phe Val Asp Gly Glu
      1               5                  10                  15 ggt tgt ttt agt gta agt ata ctt aga aat aat tcg ttg cgc tat ggc        96
Gly Cys Phe Ser Val Ser Ile Leu Arg Asn Asn Ser Leu Arg Tyr Gly
                 20                  25                  30 cat cag ctt caa cca gaa ttc gta gtg acc caa cat aaa tta gat gca       144
His Gln Leu Gln Pro Glu Phe Val Val Thr Gln His Lys Leu Asp Ala
             35                  40                  45 aat gtt tta tat gca tta aaa gac tac ttt aaa gtt gga tca gtc gtt       192
Asn Val Leu Tyr Ala Leu Lys Asp Tyr Phe Lys Val Gly Ser Val Val
         50                  55                  60 gtg aat cat ggg gaa cgg ctt tgc tat aaa gtc aaa aat att gat cac       240
Val Asn His Gly Glu Arg Leu Cys Tyr Lys Val Lys Asn Ile Asp His
 65                  70                  75 ttt ata acc gtc att ata cca ttt ttc gaa aaa cat gag cta aaa aca       288
Phe Ile Thr Val Ile Ile Pro Phe Phe Glu Lys His Glu Leu Lys Thr
 80                  85                  90                  95 aaa aga aga att gaa ttt ctt cga ttt cga aaa atc tgc ttg ctg tta       336
Lys Arg Arg Ile Glu Phe Leu Arg Phe Arg Lys Ile Cys Leu Leu Leu
                100                 105                 110 aaa gca ggt aga cat tta gaa tcg cag gaa gga ttc gag aaa gtg ttg       384
Lys Ala Gly Arg His Leu Glu Ser Gln Glu Gly Phe Glu Lys Val Leu
            115                 120                 125 gat tta gca aaa aaa ctc cgt atc aat gag aaa aac tac cag gaa tct       432
Asp Leu Ala Lys Lys Leu Arg Ile Asn Glu Lys Asn Tyr Gln Glu Ser
130                 135                 140
```

```
atc aaa cgt ttt gaa gaa act ggc gag taactcgaga gtatagagct cc      481
Ile Lys Arg Phe Glu Glu Thr Gly Glu
    145                 150

<210> SEQ ID NO 14
<211> LENGTH: 152
<212> TYPE: PRT
<213> ORGANISM: Chlamydomonas pallidostigmatica

<400> SEQUENCE: 14

Met Asp Ile Asn Pro Gln Trp Ile Thr Gly Phe Val Asp Gly Glu Gly
 1               5                  10                  15

Cys Phe Ser Val Ser Ile Leu Arg Asn Asn Ser Leu Arg Tyr Gly His
                20                  25                  30

Gln Leu Gln Pro Glu Phe Val Thr Gln His Lys Leu Asp Ala Asn
         35                  40                  45

Val Leu Tyr Ala Leu Lys Asp Tyr Phe Lys Val Gly Ser Val Val Val
     50                  55                  60

Asn His Gly Glu Arg Leu Cys Tyr Lys Val Lys Asn Ile Asp His Phe
 65                  70                  75                  80

Ile Thr Val Ile Ile Pro Phe Phe Glu Lys His Glu Leu Lys Thr Lys
                 85                  90                  95

Arg Arg Ile Glu Phe Leu Arg Phe Arg Lys Ile Cys Leu Leu Leu Lys
            100                 105                 110

Ala Gly Arg His Leu Glu Ser Gln Glu Gly Phe Glu Lys Val Leu Asp
        115                 120                 125

Leu Ala Lys Lys Leu Arg Ile Asn Glu Lys Asn Tyr Gln Glu Ser Ile
    130                 135                 140

Lys Arg Phe Glu Glu Thr Gly Glu
145                 150

<210> SEQ ID NO 15
<211> LENGTH: 917
<212> TYPE: DNA
<213> ORGANISM: Chlamydomonas pallidostigmatica
<220> FEATURE:
<221> NAME/KEY: intron
<222> LOCATION: (18)..(893)
<223> OTHER INFORMATION: CPLSU2 Intron

<400> SEQUENCE: 15
gaagacgatc ctaaggttaa ttgctagctt tagtaaaact gaactatatg ctggaaaatc      60
ctcgggcctc ttctttcccc agttgcactt cgtgctaaag cgggcagatg aaactataaa     120
gcaaaaagag gctcatcact ttttttttacc ggaactccgt tccggcttaa agtgatgaaa    180 agatgtctt gtacgtctcg tattttgcca cgagccgtga taatcaagcg tacatgggga      240
caatcagcag ggaaggatgt ttgatacacg cagagtagaa ctggcagtct agaatcggtc     300
ggtatcgcta aacataaccc tcagagacta tacgttcgga agtcttaata atcataataa     360
taggaggaaa ttgaaaatgg acattaatcc tcaatggatt acaggtttcg tagatggggga    420 aggttgtttt agtgtaagta tacttagaaa taattcgttg cgctatggcc atcagcttca     480
accagaattc gtagtgaccc aacataaatt agatgcaaat gttttatatg cattaaagaa    540
ctactttaaa gttggatcag tcgttgtgaa tcatgggga cggctttgct ataaagtcaa     600
aaatattgat cactttataa ccgtcattat accatttttc gaaaacatg agctaaaaac     660 aaaaagaaga attgaattcc ttcgatttcg aaaaatctgc ttgctgttaa aagcaggtag    720
```

-continued

```
acatttagaa tcgcaggaag gattcgagaa agtgttggat ttagcaaaaa aactccgtat      780
caatgagaaa aactaccagg aatctatcaa acgttttgaa gaaactggcg agtaaaaaaa      840
ataagattta agatagagtc cagcctattt tgaagaaaaa tggggtaaat ctgagcgaaa      900
ttccttgtca agtcttc                                                    917
```

```
<210> SEQ ID NO 16
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 16
taaggccctc ggtagcaacg g                                                21

<210> SEQ ID NO 17
<211> LENGTH: 20
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 17
ggggtaccaa atccaactag                                                  20

<210> SEQ ID NO 18
<211> LENGTH: 25
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 18
ggagctcgct cccccgccgt cgttc                                            25

<210> SEQ ID NO 19
<211> LENGTH: 27
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 19
gatgcatgat gacttgacgg catcctc                                          27

<210> SEQ ID NO 20
<211> LENGTH: 16
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 20
gtcgacagat ctttaa                                                      16

<210> SEQ ID NO 21
<211> LENGTH: 16
<212> TYPE: DNA
<213> ORGANISM: Artificial sequence
<220> FEATURE:
```

-continued

```
<223> OTHER INFORMATION: Description of the artificial sequence:
      oligonucleotide primer

<400> SEQUENCE: 21
agatctgtcg acttaa                                                    16

<210> SEQ ID NO 22
<211> LENGTH: 22
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 22
gatctccagt taactggggt ac                                             22

<210> SEQ ID NO 23
<211> LENGTH: 14
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 23
cccagttaac tgga                                                      14

<210> SEQ ID NO 24
<211> LENGTH: 25
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 24
ttaagccagt taactgggcg gagct                                          25

<210> SEQ ID NO 25
<211> LENGTH: 17
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 25
ccgcccagtt aactggc                                                   17

<210> SEQ ID NO 26
<211> LENGTH: 34
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 26
tcgagaagat cagcctgtta tccctagagt aact                                34

<210> SEQ ID NO 27
<211> LENGTH: 34
<212> TYPE: DNA
<213> ORGANISM: Artificial sequence
<220> FEATURE:
<223> OTHER INFORMATION: Description of the artificial sequence:
``` oligonucleotide primer

<400> SEQUENCE: 27
ctagagttac tctagggata acaggctgat cttc                                34

<210> SEQ ID NO 28
<211> LENGTH: 17
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 28
agaagacgat cctaagg                                                   17

<210> SEQ ID NO 29
<211> LENGTH: 23
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 29
tgaagacttg acaaggaatt tcg                                            23

<210> SEQ ID NO 30
<211> LENGTH: 56
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 30
agaagacgat cctaaatagc aatatttacc tttgggacca aaagttatca ggcatg        56

<210> SEQ ID NO 31
<211> LENGTH: 50
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 31
tgaagacttg acaaggaatt tcgctacctt cgagtactcc aaaactaatc               50

<210> SEQ ID NO 32
<211> LENGTH: 33
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 32
gagaagacat tcctaacaca tccataacgt gcg                                 33

<210> SEQ ID NO 33
<211> LENGTH: 32
<212> TYPE: DNA
<213> ORGANISM: Artificial sequence
<220> FEATURE:
<223> OTHER INFORMATION: Description of the artificial sequence:
      oligonucleotide primer

```
<400> SEQUENCE: 33
tgaagacttg acatttgata tggtgaagta gg                                    32

<210> SEQ ID NO 34
<211> LENGTH: 175
<212> TYPE: DNA
<213> ORGANISM: Pisum sativum
<220> FEATURE:
<221> NAME/KEY: CDS
<222> LOCATION: (1)..(174)
<223> OTHER INFORMATION: plastid translocalization sequence

<400> SEQUENCE: 34 atg gct tct atg ata tcc tct tca gct gtg act aca gtc agc cgt gct      48
Met Ala Ser Met Ile Ser Ser Ser Ala Val Thr Thr Val Ser Arg Ala
  1               5                  10                  15 tct acg gtg caa tcg gcc gcg gtg gct cca ttc ggc ggc ctc aaa tcc      96
Ser Thr Val Gln Ser Ala Ala Val Ala Pro Phe Gly Gly Leu Lys Ser
             20                  25                  30 atg act gga ttc cca gtt aag aag gtc aac act gac att act tcc att     144
Met Thr Gly Phe Pro Val Lys Lys Val Asn Thr Asp Ile Thr Ser Ile
         35                  40                  45 aca agc aat ggt gga aga gta aag tgc atg c                           175
Thr Ser Asn Gly Gly Arg Val Lys Cys Met
     50                  55

<210> SEQ ID NO 35
<211> LENGTH: 58
<212> TYPE: PRT
<213> ORGANISM: Pisum sativum

<400> SEQUENCE: 35

Met Ala Ser Met Ile Ser Ser Ser Ala Val Thr Thr Val Ser Arg Ala
  1               5                  10                  15

Ser Thr Val Gln Ser Ala Ala Val Ala Pro Phe Gly Gly Leu Lys Ser
             20                  25                  30

Met Thr Gly Phe Pro Val Lys Lys Val Asn Thr Asp Ile Thr Ser Ile
         35                  40                  45

Thr Ser Asn Gly Gly Arg Val Lys Cys Met
     50                  55

<210> SEQ ID NO 36
<211> LENGTH: 84
<212> TYPE: PRT
<213> ORGANISM: Nicotiana tabacum
<220> FEATURE:
<221> NAME/KEY: TRANSIT
<222> LOCATION: (1)..(84)
<223> OTHER INFORMATION: plastidic translocalisation signal derived from
      plastidic transketolase

<400> SEQUENCE: 36

Met Ala Ser Ser Ser Ser Leu Thr Leu Ser Gln Ala Ile Leu Ser Arg
  1               5                  10                  15

Ser Val Pro Arg His Gly Ser Ala Ser Ser Gln Leu Ser Pro Ser
             20                  25                  30

Ser Leu Thr Phe Ser Gly Leu Lys Ser Asn Pro Asn Ile Thr Thr Ser
         35                  40                  45

Arg Arg Arg Thr Pro Ser Ser Ala Ala Ala Ala Val Val Arg Ser
     50                  55                  60

Pro Ala Ile Arg Ala Ser Ala Ala Thr Glu Thr Ile Glu Lys Thr Glu
```

Thr Ala Gly Ser

<210> SEQ ID NO 37
<211> LENGTH: 258
<212> TYPE: DNA
<213> ORGANISM: Nicotiana tabacum
<220> FEATURE:
<221> NAME/KEY: transit_peptide
<222> LOCATION: (1)..(258)
<223> OTHER INFORMATION: plastidic translocalisation signal derived from plastidic transketolase (frame 1)

<400> SEQUENCE: 37

```
ggtaccatgg cgtcttcttc ttctctcact ctctctcaag ctatcctctc tcgttctgtc    60
cctcgccatg gctctgcctc ttcttctcaa ctttcccctt cttctctcac ttttccggc    120
cttaaatcca atcccaatat caccacctcc cgccgccgta ctccttcctc cgccgccgcc    180
gccgccgtcg taaggtcacc ggcgattcgt gcctcagctg caaccgaaac catagagaaa    240
actgagactg cgggatcc                                                  258
```

<210> SEQ ID NO 38
<211> LENGTH: 260
<212> TYPE: DNA
<213> ORGANISM: Nicotiana tabacum
<220> FEATURE:
<221> NAME/KEY: transit_peptide
<222> LOCATION: (1)..(260)
<223> OTHER INFORMATION: plastidic translocalisation signal derived from plastidic transketolase (frame 2)

<400> SEQUENCE: 38

```
ggtaccatgg cgtcttcttc ttctctcact ctctctcaag ctatcctctc tcgttctgtc    60
cctcgccatg gctctgcctc ttcttctcaa ctttcccctt cttctctcac ttttccggc    120
cttaaatcca atcccaatat caccacctcc cgccgccgta ctccttcctc cgccgccgcc    180
gccgccgtcg taaggtcacc ggcgattcgt gcctcagctg caaccgaaac catagagaaa    240
actgagactg cgctggatcc                                                260
```

<210> SEQ ID NO 39
<211> LENGTH: 259
<212> TYPE: DNA
<213> ORGANISM: Nicotiana tabacum
<220> FEATURE:
<221> NAME/KEY: transit_peptide
<222> LOCATION: (1)..(259)
<223> OTHER INFORMATION: plastidic translocalisation signal derived from plastidic transketolase (frame 3)

<400> SEQUENCE: 39

```
ggtaccatgg cgtcttcttc ttctctcact ctctctcaag ctatcctctc tcgttctgtc    60
cctcgccatg gctctgcctc ttcttctcaa ctttcccctt cttctctcac ttttccggc    120
cttaaatcca atcccaatat caccacctcc cgccgccgta ctccttcctc cgccgccgcc    180
gccgccgtcg taaggtcacc ggcgattcgt gcctcagctg caaccgaaac catagagaaa    240
actgagactg cggggatcc                                                 259
```

<210> SEQ ID NO 40
<211> LENGTH: 63
<212> TYPE: PRT
<213> ORGANISM: Arabidopsis thaliana
<220> FEATURE:

```
<221> NAME/KEY: TRANSIT
<222> LOCATION: (1)..(63)
<223> OTHER INFORMATION: plastidic translocalisation signal derived from
      plastidic  isopentenylpyrophosphate isomerase-2
      (IPP-2)

<400> SEQUENCE: 40

Met Ser Ala Ser Ser Leu Phe Asn Leu Pro Leu Ile Arg Leu Arg Ser
 1               5                  10                  15

Leu Ala Leu Ser Ser Ser Phe Ser Ser Phe Arg Phe Ala His Arg Pro
                20                  25                  30

Leu Ser Ser Ile Ser Pro Arg Lys Leu Pro Asn Phe Arg Ala Phe Ser
            35                  40                  45

Gly Thr Ala Met Thr Asp Thr Lys Asp Gly Ser Arg Val Asp Met
        50                  55                  60

<210> SEQ ID NO 41
<211> LENGTH: 205
<212> TYPE: DNA
<213> ORGANISM: Arabidopsis thaliana
<220> FEATURE:
<221> NAME/KEY: transit_peptide
<222> LOCATION: (1)..(205)
<223> OTHER INFORMATION: plastidic translocalisation signal derived from
      plastidic  isopentenylpyrophosphate isomerase-2
      (IPP-2)  (frame 1)

<400> SEQUENCE: 41
gatatccaca ccaacaccaa tgtctgcttc ttctttattt aatctcccat tgattcgcct      60
cagatctctc gctctttcgt cttctttttc ttctttccga tttgcccatc gtcctctgtc     120
atcgatttca ccgagaaagt taccgaattt tcgtgctttc tctggtaccg ctatgacaga    180
tactaaagat ggatcccggg tcgac                                          205

<210> SEQ ID NO 42
<211> LENGTH: 207
<212> TYPE: DNA
<213> ORGANISM: Arabidopsis thaliana
<220> FEATURE:
<221> NAME/KEY: transit_peptide
<222> LOCATION: (1)..(207)
<223> OTHER INFORMATION: plastidic translocalisation signal derived from
      plastidic  isopentenylpyrophosphate isomerase-2
      (IPP-2)  (frame 2)

<400> SEQUENCE: 42
gatatccaca ccaacaccaa tgtctgcttc ttctttattt aatctcccat tgattcgcct      60
cagatctctc gctctttcgt cttctttttc ttctttccga tttgcccatc gtcctctgtc     120
atcgatttca ccgagaaagt taccgaattt tcgtgctttc tctggtaccg ctatgacaga    180
tactaaagat ctggatcccg ggtcgac                                        207

<210> SEQ ID NO 43
<211> LENGTH: 206
<212> TYPE: DNA
<213> ORGANISM: Arabidopsis thaliana
<220> FEATURE:
<221> NAME/KEY: transit_peptide
<222> LOCATION: (1)..(206)
<223> OTHER INFORMATION: plastidic translocalisation signal derived from
      plastidic  isopentenylpyrophosphate isomerase-2
      (IPP-2)  (frame 3)

<400> SEQUENCE: 43
gatatccaca ccaacaccaa tgtctgcttc ttctttattt aatctcccat tgattcgcct      60
```

-continued

```
cagatctctc gctctttcgt cttcttttc ttctttccga tttgcccatc gtcctctgtc      120
atcgatttca ccgagaaagt taccgaattt tcgtgctttc tctggtaccg ctatgacaga      180
tactaaagat gggatcccgg gtcgac                                           206

<210> SEQ ID NO 44
<211> LENGTH: 44
<212> TYPE: DNA
<213> ORGANISM: Nicotiana tabacum
<220> FEATURE:
<221> NAME/KEY: promoter
<222> LOCATION: (1)..(44)
<223> OTHER INFORMATION: plastidic promoter PrbcL

<400> SEQUENCE: 44
gttgcgctat atatatgaaa gagtatacaa taatgatgta tttg                      44

<210> SEQ ID NO 45
<211> LENGTH: 64
<212> TYPE: DNA
<213> ORGANISM: Nicotiana tabacum
<220> FEATURE:
<221> NAME/KEY: promoter
<222> LOCATION: (1)..(64)
<223> OTHER INFORMATION: plastidic promoter Prps16-107

<400> SEQUENCE: 45
tagcgatggg gtcttactaa agaaaaatat ttatccacct atctctatag tatatagata      60
taga                                                                   64

<210> SEQ ID NO 46
<211> LENGTH: 91
<212> TYPE: DNA
<213> ORGANISM: Nicotiana tabacum
<220> FEATURE:
<221> NAME/KEY: promoter
<222> LOCATION: (1)..(91)
<223> OTHER INFORMATION: plastidic promoter Prrn16

<400> SEQUENCE: 46
cgccgtcgtt caatgagaat ggataagagg ctcgtgggat tgacgtgagg gggcagggat      60
ggctatattt ctgggagcga actccgggcg a                                    91

<210> SEQ ID NO 47
<211> LENGTH: 71
<212> TYPE: DNA
<213> ORGANISM: Nicotiana tabacum
<220> FEATURE:
<221> NAME/KEY: promoter
<222> LOCATION: (1)..(71)
<223> OTHER INFORMATION: plastidic promoter PaccD-129

<400> SEQUENCE: 47
gtcgacatat tatttaaat aatataaagg gggttccaac atattaatat atagtgaagt       60
gttccggatc c                                                           71

<210> SEQ ID NO 48
<211> LENGTH: 27
<212> TYPE: DNA
<213> ORGANISM: Nicotiana tabacum
<220> FEATURE:
<221> NAME/KEY: promoter
<222> LOCATION: (1)..(27)
<223> OTHER INFORMATION: plastidic promoter PclpP-53
```

<400> SEQUENCE: 48
agacaataaa aaaaattgtt acgtttc                                          27

<210> SEQ ID NO 49
<211> LENGTH: 65
<212> TYPE: DNA
<213> ORGANISM: Nicotiana tabacum
<220> FEATURE:
<221> NAME/KEY: promoter
<222> LOCATION: (1)..(65)
<223> OTHER INFORMATION: plastidic promoter Prrn-62

<400> SEQUENCE: 49
gagcgaactc cgggcgaata tgaagcgcat ggatacaagt tatgccttgg aatgaaagac      60
aattc                                                                  65

<210> SEQ ID NO 50
<211> LENGTH: 107
<212> TYPE: DNA
<213> ORGANISM: Nicotiana tabacum
<220> FEATURE:
<221> NAME/KEY: promoter
<222> LOCATION: (1)..(107)
<223> OTHER INFORMATION: plastidic promoter Prps16

<400> SEQUENCE: 50
tctatatata tttatatatt aaatattaat taatatgtta gataaattaa tattagcgat      60
ggggtcttac taaagaaaaa tatttatcca cctatctcta tagtata                   107

<210> SEQ ID NO 51
<211> LENGTH: 47
<212> TYPE: DNA
<213> ORGANISM: Nicotiana tabacum
<220> FEATURE:
<221> NAME/KEY: promoter
<222> LOCATION: (1)..(47)
<223> OTHER INFORMATION: plastidic promoter PatpB/E-290

<400> SEQUENCE: 51
agaaatagaa aataaagttc aggttcgaat tccatagaat agataat                    47

<210> SEQ ID NO 52
<211> LENGTH: 25
<212> TYPE: DNA
<213> ORGANISM: Nicotiana tabacum
<220> FEATURE:
<221> NAME/KEY: promoter
<222> LOCATION: (1)..(25)
<223> OTHER INFORMATION: plastidic promoter PrpoB-345

<400> SEQUENCE: 52
aatgtgtatt atcataataa tggta                                            25

<210> SEQ ID NO 53
<211> LENGTH: 35
<212> TYPE: DNA
<213> ORGANISM: Artificial sequence
<220> FEATURE:
<223> OTHER INFORMATION: Description of the artificial sequence:
      consensus sequence of E.coli sigma70 promoter

<400> SEQUENCE: 53
ttgacattca ctcttcaatt atctataatg ataca                                 35

<210> SEQ ID NO 54

```
<211> LENGTH: 80
<212> TYPE: DNA
<213> ORGANISM: Nicotiana tabacum
<220> FEATURE:
<221> NAME/KEY: misc_feature
<222> LOCATION: (1)..(80)
<223> OTHER INFORMATION: 5'-untranslated region of psbA gene (incl. NcoI
      site)

<400> SEQUENCE: 54
tccattttct attttgattt gtagaaaact agtgtgcttg ggagtccctg atgattaaat        60
aaaccaagat tttaccatgg                                                   80

<210> SEQ ID NO 55
<211> LENGTH: 40
<212> TYPE: DNA
<213> ORGANISM: Nicotiana tabacum
<220> FEATURE:
<221> NAME/KEY: misc_feature
<222> LOCATION: (1)..(40)
<223> OTHER INFORMATION: 5'-untranslated region of rbcL gene

<400> SEQUENCE: 55
agttgtaggg agggattcat gacaccacaa acagccatgg                             40

<210> SEQ ID NO 56
<211> LENGTH: 22
<212> TYPE: DNA
<213> ORGANISM: Nicotiana tabacum
<220> FEATURE:
<221> NAME/KEY: misc_feature
<222> LOCATION: (1)..(22)
<223> OTHER INFORMATION: 5'-untranslated region of rbcLs gene (modified)

<400> SEQUENCE: 56
agttgtaggg agggattcat ga                                                22

<210> SEQ ID NO 57
<211> LENGTH: 127
<212> TYPE: DNA
<213> ORGANISM: Synechocystis sp.
<220> FEATURE:
<221> NAME/KEY: misc_feature
<222> LOCATION: (1)..(127)
<223> OTHER INFORMATION: 3'-untranslated region of synechcystis psbA-1
      gene

<400> SEQUENCE: 57
tgccattgcc ataactgctt tcggttagac ttcgtttcat ttggttaatc aagggcactc        60
tcgcaatggg gtgcctttta tggtccaagg ttaaagttaa gccagtacta tttctagggt       120
gaaatgt                                                                127

<210> SEQ ID NO 58
<211> LENGTH: 90
<212> TYPE: DNA
<213> ORGANISM: Nicotiana tabacum
<220> FEATURE:
<221> NAME/KEY: misc_feature
<222> LOCATION: (1)..(90)
<223> OTHER INFORMATION: 3'-untranslated region of tobacco psbA gene

<400> SEQUENCE: 58
cctggcctag tctataggag gttttgaaaa gaaaggagca ataatcattt tcttgttcta        60
tcaagagggt gctattgctc ctttctttt                                         90
```

```
<210> SEQ ID NO 59
<211> LENGTH: 136
<212> TYPE: DNA
<213> ORGANISM: Nicotiana tabacum
<220> FEATURE:
<221> NAME/KEY: misc_feature
<222> LOCATION: (1)..(136)
<223> OTHER INFORMATION: 3'-untranslated region of tobacco rbcL gene

<400> SEQUENCE: 59
agtagacatt agcagataaa ttagcaggaa ataaagaagg ataaggagaa agaactcaag      60
taattatcct tcgttctctt aattgaattg caattaaact cggcccaatc ttttactaaa    120
aggattgagc cgaata                                                    136

<210> SEQ ID NO 60
<211> LENGTH: 13
<212> TYPE: DNA
<213> ORGANISM: Artificial sequence
<220> FEATURE:
<223> OTHER INFORMATION: Description of the artificial sequence:
      synthetic ribosome binding site (RBS)
<220> FEATURE:
<221> NAME/KEY: misc_feature
<222> LOCATION: (6)..(10)
<223> OTHER INFORMATION: n is a, c, g, or t

<400> SEQUENCE: 60
ggaggnnnnn atg                                                        13

<210> SEQ ID NO 61
<211> LENGTH: 13
<212> TYPE: DNA
<213> ORGANISM: Artificial sequence
<220> FEATURE:
<223> OTHER INFORMATION: Description of the artificial sequence:
      synthetic ribosome binding site (RBS)

<400> SEQUENCE: 61
ggaggatctc atg                                                        13

<210> SEQ ID NO 62
<211> LENGTH: 1494
<212> TYPE: DNA
<213> ORGANISM: Artificial sequence
<220> FEATURE:
<223> OTHER INFORMATION: Description of the artificial sequence:
      complete insert of vector pCB304-25

<400> SEQUENCE: 62
ggtaccgggc cgataattcc tggcctagtc tataggaggt tttgaaaaga aaggagcaat      60
aatcattttc ttgttctatc aagagggtgc tattgctcct ttctttttt ctcgagtacg     120 ctagggataa cagggtaata tagaagcttg actctcttaa agatctcgac tctatatata    180
tttatatatt aaatattaat taatatgtta gataaattaa tattagcgat ggggtcttac    240
taaagaaaaa tatttatcca cctatctcta tagtatatag gatctagttg tagggaggga    300
ttcatgacac cacaaacagc catgggagct tggattgaac aagatggatt gcacgcaggt    360
tctccggccg cttgggtgga gaggctattc ggctatgact gggcacaaca gacaatcggc    420
tgctctgatg ccgccgtgtt ccggctgtca gcgcaggggc gcccggttct ttttgtcaag    480
accgacctgt ccggtgccct gaatgaactg caggacgagg cagcgcggct atcgtggctg    540
gccacgacgg gcgttccttg cgcagctgtg ctcgacgttg tcactgaagc gggaagggac    600
tggctgctat tgggcgaagt gccggggcag gatctcctgt catctcacct tgctcctgcc    660
```

```
gagaaagtat ccatcatggc tgatgcaatg cggcggctgc atacgcttga tccggctacc    720
tgcccattcg accaccaagc gaaacatcgc atcgagcgag cacgtactcg gatggaagcc    780
ggtcttgtcg atcaggatga tctggacgaa gagcatcagg gctcgcgcc agccgaactg     840 ttcgccaggc tcaaggcgcg catgcccgac ggcgaggatc tcgtcgtgac ccatggcgat    900
gcctgcttgc cgaatatcat ggtggaaaat ggccgctttt ctggattcat cgactgtggc    960
cggctgggtg tggcggaccg ctatcaggac atagcgttgg ctacccgtga tattgctgaa   1020
gagcttggcg gcgaatgggc tgaccgcttc ctcgtgcttt acggtatcgc cgctcccgat   1080
tcgcagcgca tcgccttcta tcgccttctt gacgagttct tctgagcggg acccaagcta   1140
ggcggccgcg gatccaagct tgaattcagt agacattagc agataaatta gcaggaaata   1200 agaaggata aggagaaaga actcaagtaa ttatccttcg ttctcttaat tgaattgcaa    1260
ttaaactcgg cccaatcttt tactaaaagg attgagccga atactcgact taaggtagcg   1320
tcgagtacgc gcccggggag cccaagggca cgccctggca ccgaagctc tagtatcaaa    1380 tttggcacaa aaagcaaaat taaaatactg ataattgcca acacaattaa catctcaatc   1440
aaggtaaatg cttttttgctt tttttgccaa agctatcttc cgtgatcaga gctc         1494

<210> SEQ ID NO 63
<211> LENGTH: 592
<212> TYPE: DNA
<213> ORGANISM: Artificial sequence
<220> FEATURE:
<223> OTHER INFORMATION: Description of the artificial sequence: BglII
      / MunI fragment from  vector pCB320-192

<400> SEQUENCE: 63
agatcttcca ttttctattt tgatttgtag aaaactagtg tgcttgggag tccctgatga      60
ttaaataaac caagatttta ccatggcgct caccaatgct caaatcttgg ctgtgattga    120
cagttgggaa gaaacagtcg gtcagtttcc agtgataacg caccatgtac cattaggtgg    180
cggtctgcaa ggaacgctcc attgttacga gatcccccta gcagctcctt atggggttgg    240
ctttgctaag aatgggccta cccgctggca atacaaacgg acaatcaatc aagtcgtcca    300
cagatggggg tcccacacag tccctttct attagaaccg gataacatca acggcaaaac    360
ctgcacagca tcgcacctat gtcataatac tcgatgccac aatcccttgc acttgtgctg    420
ggagtcacta gacgacaaca aaggcagaaa ctggtgcccc ggtcccaacg ggggatgtgt    480
ccatgcggtg gtttgtttaa ggcagggtcc gttgtacggc ccaggggcga ctgtggcagg    540
tcctcaacaa agggcagtc actttgtggt ataactgcag aagcttcaat tg             592

<210> SEQ ID NO 64
<211> LENGTH: 25
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 64
aaagatctcc tcacaaaggg ggtcg                                            25

<210> SEQ ID NO 65
<211> LENGTH: 23
<212> TYPE: DNA
<213> ORGANISM: Artificial sequence
<220> FEATURE:
```

```
<223> OTHER INFORMATION: Description of the artificial sequence:
      oligonucleotide primer

<400> SEQUENCE: 65
tcgaagactt aggaccgtta tag                                              23

<210> SEQ ID NO 66
<211> LENGTH: 26
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 66
aggaagacct tgtcgggtaa gttccg                                           26

<210> SEQ ID NO 67
<211> LENGTH: 31
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 67
ctcaattggg gtctctctgt ccaggtgcag g                                     31

<210> SEQ ID NO 68
<211> LENGTH: 672
<212> TYPE: DNA
<213> ORGANISM: Artificial sequence
<220> FEATURE:
<223> OTHER INFORMATION: Description of the artificial sequence:
      artificial fusion protein of I-Ppo I homing endonuclease and
      plastidic transit peptide
<220> FEATURE:
<221> NAME/KEY: CDS
<222> LOCATION: (1)..(669)

<400> SEQUENCE: 68 atg tct gct tct tct tta ttt aat ctc cca ttg att cgc ctc aga tct        48
Met Ser Ala Ser Ser Leu Phe Asn Leu Pro Leu Ile Arg Leu Arg Ser
  1               5                  10                  15 ctc gct ctt tcg tct tct ttt tct tct ttc cga ttt gcc cat cgt cct        96
Leu Ala Leu Ser Ser Ser Phe Ser Ser Phe Arg Phe Ala His Arg Pro
                 20                  25                  30 ctg tca tcg att tca ccg aga aag tta ccg aat ttt cgt gct ttc tct       144
Leu Ser Ser Ile Ser Pro Arg Lys Leu Pro Asn Phe Arg Ala Phe Ser
             35                  40                  45 ggt acc gct atg aca gat act aaa gat ggg atc ccc atg gcg ctc acc       192
Gly Thr Ala Met Thr Asp Thr Lys Asp Gly Ile Pro Met Ala Leu Thr
         50                  55                  60 aat gct caa atc ttg gct gtg att gac agt tgg gaa gaa aca gtc ggt       240
Asn Ala Gln Ile Leu Ala Val Ile Asp Ser Trp Glu Glu Thr Val Gly
 65                  70                  75                  80 cag ttt cca gtg ata acg cac cat gta cca tta ggt ggc ggt ctg caa       288
Gln Phe Pro Val Ile Thr His His Val Pro Leu Gly Gly Gly Leu Gln
                 85                  90                  95 gga acg ctc cat tgt tac gag atc ccc cta gca gct cct tat ggg gtt       336
Gly Thr Leu His Cys Tyr Glu Ile Pro Leu Ala Ala Pro Tyr Gly Val
                100                 105                 110 ggc ttt gct aag aat ggg cct acc cgc tgg caa tac aaa cgg aca atc       384
Gly Phe Ala Lys Asn Gly Pro Thr Arg Trp Gln Tyr Lys Arg Thr Ile
            115                 120                 125
```

```
aat caa gtc gtc cac aga tgg ggg tcc cac aca gtc cct ttt cta tta    432
Asn Gln Val Val His Arg Trp Gly Ser His Thr Val Pro Phe Leu Leu
    130                 135                 140 gaa ccg gat aac atc aac ggc aaa acc tgc aca gca tcg cac cta tgt    480
Glu Pro Asp Asn Ile Asn Gly Lys Thr Cys Thr Ala Ser His Leu Cys
145                 150                 155                 160 cat aat act cga tgc cac aat ccc ttg cac ttg tgc tgg gag tca cta    528
His Asn Thr Arg Cys His Asn Pro Leu His Leu Cys Trp Glu Ser Leu
                165                 170                 175 gac gac aac aaa ggc aga aac tgg tgc ccc ggt ccc aac ggg gga tgt    576
Asp Asp Asn Lys Gly Arg Asn Trp Cys Pro Gly Pro Asn Gly Gly Cys
            180                 185                 190 gtc cat gcg gtg gtt tgt tta agg cag ggt ccg ttg tac ggc cca ggg    624
Val His Ala Val Val Cys Leu Arg Gln Gly Pro Leu Tyr Gly Pro Gly
        195                 200                 205 gcg act gtg gca ggt cct caa caa agg ggc agt cac ttt gtg gta taa    672
Ala Thr Val Ala Gly Pro Gln Gln Arg Gly Ser His Phe Val Val
    210                 215                 220

<210> SEQ ID NO 69
<211> LENGTH: 223
<212> TYPE: PRT
<213> ORGANISM: Artificial sequence
<220> FEATURE:
<223> OTHER INFORMATION: Description of the artificial sequence:
      artificial fusion protein of I-Ppo I homing endonuclease and
      plastidic transit peptide

<400> SEQUENCE: 69

Met Ser Ala Ser Ser Leu Phe Asn Leu Pro Leu Ile Arg Leu Arg Ser
  1               5                  10                  15

Leu Ala Leu Ser Ser Ser Phe Ser Ser Phe Arg Phe Ala His Arg Pro
             20                  25                  30

Leu Ser Ser Ile Ser Pro Arg Lys Leu Pro Asn Phe Arg Ala Phe Ser
         35                  40                  45

Gly Thr Ala Met Thr Asp Thr Lys Asp Gly Ile Pro Met Ala Leu Thr
     50                  55                  60

Asn Ala Gln Ile Leu Ala Val Ile Asp Ser Trp Glu Glu Thr Val Gly
 65                  70                  75                  80

Gln Phe Pro Val Ile Thr His His Val Pro Leu Gly Gly Gly Leu Gln
                 85                  90                  95

Gly Thr Leu His Cys Tyr Glu Ile Pro Leu Ala Ala Pro Tyr Gly Val
            100                 105                 110

Gly Phe Ala Lys Asn Gly Pro Thr Arg Trp Gln Tyr Lys Arg Thr Ile
        115                 120                 125

Asn Gln Val Val His Arg Trp Gly Ser His Thr Val Pro Phe Leu Leu
    130                 135                 140

Glu Pro Asp Asn Ile Asn Gly Lys Thr Cys Thr Ala Ser His Leu Cys
145                 150                 155                 160

His Asn Thr Arg Cys His Asn Pro Leu His Leu Cys Trp Glu Ser Leu
                165                 170                 175

Asp Asp Asn Lys Gly Arg Asn Trp Cys Pro Gly Pro Asn Gly Gly Cys
            180                 185                 190

Val His Ala Val Val Cys Leu Arg Gln Gly Pro Leu Tyr Gly Pro Gly
        195                 200                 205

Ala Thr Val Ala Gly Pro Gln Gln Arg Gly Ser His Phe Val Val
    210                 215                 220
```

```
<210> SEQ ID NO 70
<211> LENGTH: 558
<212> TYPE: DNA
<213> ORGANISM: Physarum polycephalum
<220> FEATURE:
<221> NAME/KEY: CDS
<222> LOCATION: (1)..(555)
<223> OTHER INFORMATION: coding for long version of I-PpoI

<400> SEQUENCE: 70 atg gcg aaa tcc aac caa gct cgg gta aac ggc ggt agt aac tat gac        48
Met Ala Lys Ser Asn Gln Ala Arg Val Asn Gly Gly Ser Asn Tyr Asp
 1               5                  10                  15 tct ctc acc ccc tta aat atg gcg ctc acc aat gct caa atc ttg gct        96
Ser Leu Thr Pro Leu Asn Met Ala Leu Thr Asn Ala Gln Ile Leu Ala
             20                  25                  30 gtg att gac agc tgg gaa gaa aca gtc ggt cag ttt cca gtg ata acg       144
Val Ile Asp Ser Trp Glu Glu Thr Val Gly Gln Phe Pro Val Ile Thr
         35                  40                  45 cac cat gta cca tta ggt ggc ggt ctg caa gga acg ctc cat tgt tac       192
His His Val Pro Leu Gly Gly Gly Leu Gln Gly Thr Leu His Cys Tyr
     50                  55                  60 gag atc ccc cta gca gct cct tat ggg gtt ggc ttt gct aag aat ggg       240
Glu Ile Pro Leu Ala Ala Pro Tyr Gly Val Gly Phe Ala Lys Asn Gly
 65                  70                  75                  80 cct acc cgc tgg caa tac aaa cgg aca atc aat caa gtc gtc cac aga       288
Pro Thr Arg Trp Gln Tyr Lys Arg Thr Ile Asn Gln Val Val His Arg
                 85                  90                  95 tgg gga tcc cac aca gtc cct ttt cta tta gaa ccg gat aac atc aac       336
Trp Gly Ser His Thr Val Pro Phe Leu Leu Glu Pro Asp Asn Ile Asn
            100                 105                 110 ggc aaa acc tgc aca gca tcg cac cta tgt cat aat act cga tgc cac       384
Gly Lys Thr Cys Thr Ala Ser His Leu Cys His Asn Thr Arg Cys His
        115                 120                 125 aat ccc ttg cac ttg tgc tgg gag tca cta gac gac aac aaa ggc aga       432
Asn Pro Leu His Leu Cys Trp Glu Ser Leu Asp Asp Asn Lys Gly Arg
    130                 135                 140 aac tgg tgc ccg ggt ccc aac ggg gga tgt gtc cat gcg gtg gtt tgt       480
Asn Trp Cys Pro Gly Pro Asn Gly Gly Cys Val His Ala Val Val Cys
145                 150                 155                 160 tta agg cag ggt ccg ttg tac ggc ccg ggg gcg act gtg gca ggt cct       528
Leu Arg Gln Gly Pro Leu Tyr Gly Pro Gly Ala Thr Val Ala Gly Pro
                165                 170                 175 caa caa agg ggc agt cac ttt gtg gta taa                               558
Gln Gln Arg Gly Ser His Phe Val Val
            180                 185

<210> SEQ ID NO 71
<211> LENGTH: 185
<212> TYPE: PRT
<213> ORGANISM: Physarum polycephalum

<400> SEQUENCE: 71

Met Ala Lys Ser Asn Gln Ala Arg Val Asn Gly Gly Ser Asn Tyr Asp
 1               5                  10                  15

Ser Leu Thr Pro Leu Asn Met Ala Leu Thr Asn Ala Gln Ile Leu Ala
             20                  25                  30

Val Ile Asp Ser Trp Glu Glu Thr Val Gly Gln Phe Pro Val Ile Thr
         35                  40                  45

His His Val Pro Leu Gly Gly Gly Leu Gln Gly Thr Leu His Cys Tyr
     50                  55                  60
```

```
Glu Ile Pro Leu Ala Ala Pro Tyr Gly Val Gly Phe Ala Lys Asn Gly
 65                  70                  75                  80

Pro Thr Arg Trp Gln Tyr Lys Arg Thr Ile Asn Gln Val Val His Arg
             85                  90                  95

Trp Gly Ser His Thr Val Pro Phe Leu Leu Glu Pro Asp Asn Ile Asn
            100                 105                 110

Gly Lys Thr Cys Thr Ala Ser His Leu Cys His Asn Thr Arg Cys His
        115                 120                 125

Asn Pro Leu His Leu Cys Trp Glu Ser Leu Asp Asp Asn Lys Gly Arg
    130                 135                 140

Asn Trp Cys Pro Gly Pro Asn Gly Gly Cys Val His Ala Val Val Cys
145                 150                 155                 160

Leu Arg Gln Gly Pro Leu Tyr Gly Pro Gly Ala Thr Val Ala Gly Pro
                165                 170                 175

Gln Gln Arg Gly Ser His Phe Val Val
            180                 185

<210> SEQ ID NO 72
<211> LENGTH: 34
<212> TYPE: DNA
<213> ORGANISM: Escherichia coli
<220> FEATURE:
<221> NAME/KEY: promoter
<222> LOCATION: (1)..(34)
<223> OTHER INFORMATION: coding for promoter derived from consensus of
      sigma70 E.coli promoters

<400> SEQUENCE: 72
ttgacaattt tcctctgaat tatataatta acat                                    34

<210> SEQ ID NO 73
<211> LENGTH: 413
<212> TYPE: DNA
<213> ORGANISM: Artificial sequence
<220> FEATURE:
<223> OTHER INFORMATION: Description of the artificial sequence:
      artificial intron TetIVS2a

<400> SEQUENCE: 73
aaatagcaat attttcgtt gccttaaaaa gttatcaggc atgcacctgg tagctagtct          60
ttaaaccaat agattgcatc ggtttaaaag gcaagaccgt caaattgcgg gaaagggtc        120 aacagccgtt cagtaccaag tctcagggga actttgaga tggccttgca aagggtatgg        180
taataagctg acggacatgg tcctaaccac gcagccaagt cctaagtcaa cagatcttct       240
gttgatatgg atgcagttca cagactaaat gtcggtcggg gaagatgtat tcttctcata      300
agatatagtc ggacctctcc ttaatgggag ctagcggatg aagtgatgca acactggagc      360
cgctgggaac taatttgtat gcgaaagtat attgattagt tttggagtac tcg             413

<210> SEQ ID NO 74
<211> LENGTH: 791
<212> TYPE: DNA
<213> ORGANISM: Artificial sequence
<220> FEATURE:
<223> OTHER INFORMATION: Description of the artificial sequence: insert
      of plasmid pCB459-1

<400> SEQUENCE: 74
ttacaatttc cattcgccat tcaggctgcg caactgttgg gaagggcgat cggtgcgggc        60
ctcttcgcta ttacgccagc tggcgaaagg gggatgtgct gcaaggcgat taagttgggt      120
```

```
aacgccaggg ttttcccagt cacgacgttg taaaacgacg ccagtgagc gcgcgtaata      180 cgactcacta tagggcgaat tgggtaccgg gcccccctc gaggtcgacg gtatcgataa      240
gcttgacccg acaaggaatt tcgctcgagt actccaaaac taatcaatat actttcgcat     300
acaaattagt tcccagcggc tccagtgttg catcacttca tccgctagct cccattaagg     360
agaggtccga ctatatctta tgagaagaat acatcttccc cgaccgacat ttagtctgtg     420
aactgcatcc atatcaacag aagatctgtt gacttaggac ttggctgcgt ggttaggacc    480
atgtccgtca gcttattacc atacccttg caaggccatc tcaaagtttc ccctgagact     540
tggtactgaa cggctgttga cccctttccc gcaatttgac ggtcttgcct tttaaaccga    600
tgcaatctat tggtttaaag actagctacc aggtgcatgc ctgataactt tttaaggcaa    660
cgaaaaatat tgctatttac cttaggaccg ttaggatcca ctagttctag agcggccgcc    720
accgcggtgg agctccagct tttgttccct ttagtgaggg ttaattgcgc gcttggcgta    780
atcatggtca t                                                         791

<210> SEQ ID NO 75
<211> LENGTH: 1291
<212> TYPE: DNA
<213> ORGANISM: Artificial sequence
<220> FEATURE:
<223> OTHER INFORMATION: Description of the artificial sequence: insert
      of vector  pCB478-3

<400> SEQUENCE: 75
ttacaatttc cattcgccat tcaggctgcg caactgttgg gaagggcgat cggtgcgggc     60
ctcttcgcta ttacgccagc tggcgaaagg gggatgtgct gcaaggcgat taagttgggt    120
aacgccaggg ttttcccagt cacgacgttg taaaacgacg ccagtgagc gcgcgtaata     180 cgactcacta tagggcgaat tgggtaccgg gcccccctc gaggtcgacg gtatcgataa     240
gcttgacccg acaaggaatt tcgctcgagt actccaaaac taatcaatat actttcgcat    300
acaaattagt tcccagcggc tccagtgttg catcacttca tccgctagct cccattaagg    360
agaggtccga ctatatctta tgagaagaat tttgatcctt actcgccagt tcttcaaaa    420 cgtttgatag gttcctggta gttttttctca ttgatacgga gttttttgc taaatccaac    480 actttctcga atccttcctg cgattctaaa tgtctacctg cttttaacag caagcagatt    540
tttcgaaatc gaagaaattc aattcttctt tttgttttta gctcatgttt ttcgaaaaat    600
ggtataatga cggttataaa gtgatcaata tttttgactt tatagcaaag ccgttcccca    660
tgattcacaa cgactgatcc aactttaaag tagtctttta atgcatataa aacatttgca    720
tctaatttat gttgggtcac tacgaattaa ttctggttga agctgatggc catagcgcaa    780
cgaattattt ctaagtatac ttacactaaa acaaccttcc ccatctacga aacctgtaat    840
ccattgagga ttaatgtcca tggtccctcc ctacaacgtc tgcagatcaa acatcttccc    900
cgaccgacat ttagtctgtg aactgcatcc atatcaacag aagatctgtt gacttaggac    960
ttggctgcgt ggttaggacc atgtccgtca gcttattacc atacccttg caaggccatc    1020 tcaaagtttc ccctgagact tggtactgaa cggctgttga cccctttccc gcaatttgac    1080
ggtcttgcct tttaaaccga tgcaatctat tggtttaaag actagctacc aggtgcatgc    1140
ctgataactt tttaaggcaa cgaaaaatat tgctatttac cttaggaccg ttaggatcca    1200
ctagttctag agcggccgcc accgcggtgg agctccagct tttgttccct ttagtgaggg    1260
ttaattgcgc gcttggcgta atcatggtca t                                   1291
```

<210> SEQ ID NO 76
<211> LENGTH: 1386
<212> TYPE: DNA
<213> ORGANISM: Artificial sequence
<220> FEATURE:
<223> OTHER INFORMATION: Description of the artificial sequence: insert
      of vector pCB492-25

<400> SEQUENCE: 76

| | | | | | |
|---|---|---|---|---|---|
| gcgcgcgtaa | tacgactcac | tatagggcga | attgggggcg | actgtttacc | aaaaacacag | 60 |
| gtctccgcaa | agtcgtaaga | ccatgtatgg | gggctgacgc | ctgcccagtg | ccggaaggtc | 120 |
| aaggaagttg | gtgacctgat | gacagggag | ccggcgaccg | aagccccggt | gaacggcggc | 180 |
| cgtaactata | acggtcctaa | ggtaaatagc | aatattttc | gttgccttaa | aaagttatca | 240 |
| ggcatgcacc | tggtagctag | tctttaaacc | aatagattgc | atcggtttaa | aaggcaagac | 300 |
| cgtcaaattg | cgggaaaggg | gtcaacagcc | gttcagtacc | aagtctcagg | ggaaactttg | 360 |
| agatggcctt | gcaaagggta | tggtaataag | ctgacggaca | tggtcctaac | cacgcagcca | 420 |
| agtcctaagt | caacagatct | tctgttgata | tggatgcagt | tcacagacta | aatgtcggtc | 480 |
| ggggaagatg | tttgatctgc | agacgttgta | gggagggacc | atggacatta | atcctcaatg | 540 |
| gattacaggt | ttcgtagatg | gggaaggttg | ttttagtgta | agtatactta | gaaataattc | 600 |
| gttgcgctat | ggccatcagc | ttcaaccaga | attcgtagtg | acccaacata | aattagatgc | 660 |
| aaatgtttta | tatgcattaa | aagactactt | taaagttgga | tcagtcgttg | tgaatcatgg | 720 |
| ggaacggctt | tgctataaag | tcaaaaatat | tgatcacttt | ataaccgtca | ttataccatt | 780 |
| tttcgaaaaa | catgagctaa | aaacaaaaag | aagaattgaa | tttcttcgat | tcgaaaaat | 840 |
| ctgcttgctg | ttaaaagcag | gtagacattt | agaatcgcag | gaaggattcg | agaaagtgtt | 900 |
| ggatttagca | aaaaaactcc | gtatcaatga | gaaaaactac | caggaatcta | tcaaacgttt | 960 |
| tgaagaaact | ggcgagtaag | gatcaaaatt | cttctcataa | gatatagtcg | acctctcct | 1020 |
| taatgggagc | tagcggatga | agtgatgcaa | cactggagcc | gctgggaact | aatttgtatg | 1080 |
| cgaaagtata | ttgattagtt | ttggagtact | cgagcgaaat | tccttgtcgg | gtaagttccg | 1140 |
| acccgcacga | aaggcgtaac | gatctgggca | ctgtctcgga | gagaggctcg | gtgaaataga | 1200 |
| catgtctgtg | aagatgcgga | ctacctgcac | ctggacagag | agaccccaat | tcctggccta | 1260 |
| gtctatagga | ggttttgaaa | agaaaggagc | aataatcatt | tcttgttct | atcaagaggg | 1320 |
| tgctattgct | cctttctttt | tttctcgacc | agcttttgtt | ccctttagtg | agggttaatt | 1380 |
| gcgcgc | | | | | | 1386 |

<210> SEQ ID NO 77
<211> LENGTH: 60
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 77
tagtaaatga caattttcct ctgaattata taattaacat ggcgactgtt taccaaaaac   60

<210> SEQ ID NO 78
<211> LENGTH: 31
<212> TYPE: DNA
<213> ORGANISM: Artificial sequence
<220> FEATURE:

<223> OTHER INFORMATION: Description of the artificial sequence:
      oligonucleotide primer

<400> SEQUENCE: 78
ctcaattggg gtctctctgt ccaggtgcag g                                       31

<210> SEQ ID NO 79
<211> LENGTH: 1258
<212> TYPE: DNA
<213> ORGANISM: Artificial sequence
<220> FEATURE:
<223> OTHER INFORMATION: Description of the artificial sequence: PCR
      product Prom-TetIVS2a-Cpa

<400> SEQUENCE: 79
tagtaaatga caattttcct ctgaattata taattaacat ggcgactgtt taccaaaaac     60
acaggtctcc gcaaagtcgt aagaccatgt atgggggctg acgcctgccc agtgccggaa    120
ggtcaaggaa gttggtgacc tgatgacagg ggagccggcg accgaagccc cggtgaacgg    180
cggccgtaac tataacggtc ctaaggtaaa tagcaatatt tttcgttgcc ttaaaaagtt    240
atcaggcatg cacctggtag ctagtctttta aaccaataga ttgcatcggt ttaaaaggca    300
agaccgtcaa attgcgggaa agggtcaac agccgttcag taccaagtct caggggaaac     360
tttgagatgg ccttgcaaag ggtatggtaa taagctgacg gacatggtcc taaccacgca    420
gccaagtcct aagtcaacag atcttctgtt gatatggatg cagttcacag actaaatgtc    480
ggtcggggaa gatgtttgat ctgcagacgt tgtagggagg gaccatggac attaatcctc    540
aatggattac aggtttcgta gatggggaag gttgttttag tgtaagtata cttagaaata    600
attcgttgcg ctatggccat cagcttcaac cagaattcgt agtgacccaa cataaattag    660
atgcaaatgt tttatatgca ttaaaagact actttaaagt tggatcagtc gttgtgaatc    720
atggggaacg gctttgctat aaagtcaaaa atattgatca cttttataacc gtcattatac    780 cattttttcga aaacatgag ctaaaaacaa aagaagaat tgaatttctt cgatttcgaa      840
aaatctgctt gctgttaaaa gcaggtagac atttagaatc gcaggaagga ttcgagaaag    900
tgttggattt agcaaaaaaa ctccgtatca atgagaaaaa ctaccaggaa tctatcaaac    960
gttttgaaga aactggcgag taaggatcaa aattcttctc ataagatata gtcggacctc   1020
tccttaatgg gagctagcgg atgaagtgat gcaacactgg agccgctggg aactaatttg   1080
tatgcgaaag tatattgatt agttttggag tactcgagcg aaattccttg tcgggtaagt   1140
tccgacccgc acgaaaggcg taacgatctg ggcactgtct cggagagagg ctcggtaaaa   1200
tagacatgtc tgtgaagatg cggactacct gcacctggac agagagaccc caattgag    1258

<210> SEQ ID NO 80
<211> LENGTH: 4746
<212> TYPE: DNA
<213> ORGANISM: Artificial sequence
<220> FEATURE:
<223> OTHER INFORMATION: Description of the artificial sequence: insert
      of vector pCB435-45

<400> SEQUENCE: 80
gcgcccaata cgcaaaccgc ctctccccgc gcgttggccg attcattaat gcagtgatga     60
cttgacggca tcctcacctt cctccggctt atcaccggca gtctgttcag ggttccaaac    120
tcaacgatgg caactaaaca cgagggttgc gctcgttgcg ggacttaacc caacacctta    180
cggcacgagc tgacgacagc catgcaccac ctgtgtccgc gttcccgaag gcacccctct    240

```
ctttcaagag gattcgcggc atgtcaagcc ctggtaaggt tcttcgcttt gcatcgaatt    300
aaaccacatg ctccaccgct tgtgcgggcc cccgtcaatt cctttagtt tcattcttgc    360 gaacgtactc cccaggcggg atacttaacg cgttagctac agcactgcac gggtcgatac    420
gcacagcgcc tagtatccat cgtttacggc taggactact ggggtatcta atcccattcg    480
ctcccctagc tttcgtctct cagtgtcagt gtcggcccag cagagtgctt tcgccgttgg    540
tgttctttcc gatctctacg catttcaccg ctccaccgga aattccctct gcccctaccg    600
tactccagct tggtagtttc caccgcctgt ccagggttga gccctgggat ttgacggcgg    660
acttaaaaag ccacctacag acgctttacg cccaatcatt ccggataacg cttgcatcct    720
ctgtattacc gcggctgctg gcacagagtt agccgatgct tattcccag ataccgtcat     780 tgcttcttct ccgggaaaag aagttcacga cccgtgggcc ttctacctcc acgcggcatt    840
gctccgtcag gctttcgccc attgcggaaa attccccact gctgcctccc gtaggagtct    900
gggccgtgtc tcagtcccag tgtggctgat catcctctcg accagctac tgatcatcgc     960 cttggtaagc tattgcctca ccaactagct aatcagacgc gagcccctcc tcgggcggat   1020
tcctcctttt gctcctcagc ctacgggta ttagcagccg tttccagctg ttgttcccct    1080
cccaagggca ggttcttacg cgttactcac ccgtccgcca ctggaaacac cacttcccgt   1140
ccgacttgca tgtgttaagc atgccgccag cgttcatcct gagccaggat cgaactctcc   1200
atgagattca tagttgcatt acttatagct tccttgttcg tagacaaagc ggattcggaa   1260
ttgtctttca ttccaaggca taacttgtat ccatgcgctt catattcgcc cggagttcgc   1320
tcccagaaat atagccatcc ctgcccctc acgtcaatcc cacgagcctc ttatccattc    1380
tcattgaacg acggcggggg agcgcgggcc cccctcgac atatattta aataatataa     1440 agggggttcc aacatattaa tatatagtga agtgttccgg atccactagg acgttgtagg   1500
gagggaccat ggacattaat cctcaatgga ttacaggttt cgtagatggg gaaggttgtt   1560
ttagtgtaag tatacttaga ataaattcgt tgcgctatgg ccatcagctt caaccagaat   1620
tcgtagtgac ccaacataaa ttagatgcaa atgttttata tgcattaaaa gactacttta   1680
aagttggatc agtcgttgtg aatcatgggg aacggctttg ctataaagtc aaaaatattg   1740
atcactttat aaccgtcatt ataccatttt tcgaaaaaca tgagctaaaa acaaaaagaa   1800
gaattgaatt tcttcgattt cgaaaaatct gcttgctgtt aaaagcaggt agacatttag   1860
aatcgcagga aggattcgag aaagtgttgg atttagcaaa aaaactccgt atcaatgaga   1920
aaaactacca ggaatctatc aaacgttttg aagaaactgg cgagtaactc gagaaaaaaa   1980
gaaaggagca atagcaccct cttgatagaa caagaaaatg attattgctc ctttcttttc   2040
aaaacctcct atagactagg ccaggaatta tctgcagtta tttgccaact accttagtga   2100
tctcgccttt cacgtagtgg acaaattctt ccaactgatc tgcgcgcgag gccaagcgat   2160
cttcttcttg tccaagataa gcctgtctag cttcaagtat gacgggctga tactgggccg   2220
gcaggcgctc cattgcccag tcggcagcga catccttcgg cgcgattttg ccggttactg   2280
cgctgtacca aatgcgggac aacgtaagca ctacatttcg ctcatcgcca gcccagtcgg   2340
gcggcgagtt ccatagcgtt aaggtttcat ttagcgcctc aaatagatcc tgttcaggaa   2400
ccggatcaaa gagttcctcc gccgctggac ctaccaaggc aacgctatgt tctcttgctt   2460
ttgtcagcaa gatagccaga tcaatgtcga tcgtggctgg ctcgaagata cctgcaagaa   2520
tgtcattgcg ctgccattct ccaaattgca gttcgcgctt agctggataa cgccacggaa   2580
tgatgtcgtc gtgcacaaca atggtgactt ctacagcgcg gagaatctcg ctctctccag   2640
```

```
gggaagccga agtttccaaa aggtcgttga tcaaagctcg ccgcgttgtt tcatcaagcc      2700
ttacggtcac cgtaaccagc aaatcaatat cactgtgtgg cttcaggccg ccatccactg      2760
cggagccgta caaatgtacg gccagcaacg tcggttcgag atggcgctcg atgacgccaa      2820
ctacctctga tagttgagtt gatacttcgg cgataaccgc ttcacgagcc atgaatccct      2880
ccctacaact agatcctcgc ccggagttcg ctcccagaaa tatagccatc cctgccccct      2940
cacgtcaatc ccacgagcct cttatccatt ctcattgaac gacggcgtcg agggggggcc      3000
cggtaccaaa tccaactaga aaactcaca ttgggcttag ggataatcag gctcgaactg       3060
atgacttcca ccacgtcaag gtgacactct accgctgagt tatatccctt cccgccccca      3120
tcgagaaata gaactgacta atcctaagtc aaagggtcga gaaactcaac gccactattc      3180
ttgaacaact tggagccggg ccttcttttc gcactattac ggatatgaaa ataatggtca      3240
aaatcggatt caattgtcaa ctgcccctat cggaaatagg attgactacc gattccgaag      3300
gaactggagt tacatctctt ttccattcaa gagttcttat gcgtttccac gcccctttga      3360
gaccccgaaa aatggacaaa ttccttttct taggaacaca tacaagattc gtcactacaa      3420
aaaggataat ggtaaccta ccattaacta cttcatttat gaatttcata gtaatagaaa       3480
tacatgtcct accgagacag aatttggaac ttgctatcct cttgcctagc aggcaaagat      3540
ttacctccgt ggaaggatg attcattcgg atcgacatga gagtccaact acattgccag       3600
aatccatgtt gtatatttga agaggttga cctccttgct tctctcatgg tacactcctc       3660
ttcccgccga gcccctttc tcctcggtcc acagagacaa aatgtaggac tggtgccaac       3720
aattcatcag actcactaag tcgggatcac taactaatac taatctaata taatagtcta      3780
atatatctaa tataatagaa aatactaata taatagaaaa gaactgtctt ttctgtatac      3840
tttccccggt tccgttgcta ccgagggcct cgtgatacgc ctattttat aggttaatgt       3900 catgaccaaa atcccttaac gtgagttttc gttccactga cgtcagacc ccgtagaaaa       3960 gatcaaagga tcttcttgag atccttttt tctgcgcgta atctgctgct tgcaaacaaa       4020 aaaccaccg ctaccagcgg tggtttgttt gccggatcaa gagctaccaa ctctttttcc       4080
gaaggtaact ggcttcagca gagcgcagat accaaatact gtccttctag tgtagccgta      4140
gttaggccac cacttcaaga actcgtagc accgcctaca tacctcgctc tgctaatcct       4200
gttaccagtg gctgctgcca gtggcgataa gtcgtgtctt accgggttgg actcaagacg      4260
atagttaccg gataaggcgc agcggtcggg ctgaacgggg ggttcgtgca cacagcccag      4320
cttggagcga acgacctaca ccgaactgag atacctacag cgtgagctat gagaaagcgc      4380
cacgcttccc gaagggagaa aggcggacag gtatccggta agcggcaggg tcggaacagg      4440
agagcgcacg agggagcttc caggggggaaa cgcctggtat ctttatagtc ctgtcgggtt      4500
tcgccacctc tgacttgagc gtcgattttt gtgatgctcg tcaggggggc ggagcctatg      4560
gaaaaacgcc agcaacgcgg ccttttttacg gttcctggcc ttttgctggc cttttgctca      4620
catgttcttt cctgcgttat cccctgattc tgtggataac cgtattaccg cctttgagtg      4680
agctgatacc gctcgccgca gccgaacgac cgagcgcagc gagtcagtga gcgaggaagc      4740
ggaaga                                                                4746
```

<210> SEQ ID NO 81
<211> LENGTH: 1213
<212> TYPE: DNA
<213> ORGANISM: Artificial sequence
<220> FEATURE:

```
<223> OTHER INFORMATION: Description of the artificial sequence: probe
      for Southern blot analysis (16SrDNA)

<400> SEQUENCE: 81
ttatcaccgg cagtctgttc agggttccaa actcaacgat ggcaactaaa cacgagggtt      60
gcgctcgttg cgggacttaa cccaacacct tacggcacga gctgacgaca gccatgcacc     120
acctgtgtcc gcgttcccga aggcacccct ctctttcaag aggattcgcg gcatgtcaag     180
ccctggtaag gttcttcgct tgcatcgaa ttaaaccaca tgctccaccg cttgtgcggg      240
cccccgtcaa ttccttttag tttcattctt gcgaacgtac tccccaggcg ggatacttaa     300
cgcgttagct acagcactgc acgggtcgat acgcacagcg cctagtatcc atcgtttacg     360
gctaggacta ctggggtatc taatcccatt cgctcccta gctttcgtct ctcagtgtca      420
gtgtcggccc agcagagtgc tttcgccgtt ggtgttcttt ccgatctcta cgcatttcac     480
cgctccaccg gaaattccct ctgccctac cgtactccag cttggtagtt tccaccgcct      540
gtccagggtt gagccctggg atttgacggc ggacttaaaa agccacctac agacgcttta     600
cgcccaatca ttccggataa cgcttgcatc ctctgtatta ccgcggctgc tggcacagag     660
ttagccgatg cttattcccc agataccgtc attgcttctt ctccgggaaa agaagttcac     720
gacccgtggg ccttctacct ccacgcggca ttgctccgtc aggctttcgc ccattgcgga     780
aaattcccca ctgctgcctc ccgtaggagt ctgggccgtg tctcagtccc agtgtggctg     840
atcatcctct cggaccagct actgatcatc gccttggtaa gctattgcct caccaactag     900
ctaatcagac gcgagcccct cctcgggcgg attcctcctt ttgctcctca gcctacgggg     960
tattagcagc cgtttccagc tgttgttccc ctcccaaggg caggttctta cgcgttactc    1020
acccgtccgc cactggaaac accacttccc gtccgacttg catgtgttaa gcatgccgcc    1080
agcgttcatc ctgagccagg atcgaactct ccatgagatt catagttgca ttacttatag    1140
cttccttgtt cgtagacaaa gcggattcgg aattgtcttt cattccaagg cataacttgt    1200
atccatgcgc ttc                                                       1213

<210> SEQ ID NO 82
<211> LENGTH: 949
<212> TYPE: DNA
<213> ORGANISM: Artificial sequence
<220> FEATURE:
<223> OTHER INFORMATION: Description of the artificial sequence: probe
      for Southern blot (23SrDNA)

<400> SEQUENCE: 82
catcgtcgag agggaaacag cccggatcac cagctaaggc ccctaaatga tcgctcagtg      60
ataaaggagg tagggtgca gagacagcca ggaggtttgc ctagaagcag ccacccttga      120
aagagtgcgt aatagctcac tgatcgagcg ctcttgcgcc gaagatgaac ggggctaagc     180
gatctgccga agctgtggga tgtaaaaata catcggtagg ggagcgttcc gccttagaga     240
gaagcctccg cgcgagcggt ggtggacgaa gcggaagcga gaatgtcggc ttgagtaacg     300
caaacattgg tgagaatcca atgccccgaa aacctaaggg ttcctccgca aggttcgtcc     360
acggagggtg agtcagggcc taagatcagg ccgaaaggcg tagtcgatgg acaacaggtg     420
aatattcctg tactgcccct tgttggtccc gagggacgga ggaggctagg ttagccgaaa     480
gatggttatc ggttcaagaa cgtaaggtgt ccctgctttg tcagggtaag aaggggtaga     540
gaaaatgcct cgagccaatg ttcgaatacc aggcgctacg gcgctgaagt aacccatgcc     600
atactcccag gaaaagctcg aacgactttg agcaagaggg tacctgtacc cgaaaccgac     660
```

```
acaggtgggt aggtagagaa tacctagggg cgcgagacaa ctctctctaa ggaactcggc      720
aaaatagccc cgtaacttcg ggagaagggg tgcctcctca caaagggggt cgcagtgacc      780
aggcccgggc gactgtttac caaaaacaca ggtctccgca aagtcgtaag accatgtatg      840
ggggctgacg cctgcccagt gccggaaggt caaggaagtt ggtgacctga tgacaggggga    900 gccggcgacc gaagcccgg tgaacggcgg ccgtaactat aacggtcct                  949
```

<210> SEQ ID NO 83
<211> LENGTH: 1287
<212> TYPE: DNA
<213> ORGANISM: Artificial sequence
<220> FEATURE:
<223> OTHER INFORMATION: Description of the artificial sequence: insert
    of vector pCB456-2

<400> SEQUENCE: 83

```
gagctctcag tactcgagac atttcaccct agaaatagac ttaaacttta ctggcttaac      60
tttaaccttg gaccataaaa ggcaccccat tgcgagagtg cccttgatta accaaatgaa     120
acgaagtcta accgaaagca gttatggcaa tggcagaatt ctgatcacgg aagatagctt    180
tggcaaaaaa agcaaaaagc atttaccttg attgagatgt taattgtgtt ggcaattatc    240
agtattttaa ttttgctttt tgtgccaaat ttgatactag agcttcgggt gccagggcgt    300
gcccttgggc tccccgggcg cgtactcgac gctaccttaa gagagtcaag ctaattctaa    360
tctgcagtct agcgtgcggc cgctctagaa ctagtggatc ccccgggctg cagttatttg    420
ccaactacct tagtgatctc gcctttcacg tagtggacaa attcttccaa ctgatctgcg    480
cgcgaggcca agcgatcttc ttcttgtcca agataagcct gtctagcttc aagtatgacg    540
ggctgatact gggccggcag gcgctccatt gcccagtcgg cagcgacatc cttcggcgcg    600
attttgccgg ttactgcgct gtaccaaatg cgggacaacg taagcactac atttcgctca   660
tcgccagccc agtcgggcgg cgagttccat agcgttaagg tttcatttag cgcctcaaat    720
agatcctgtt caggaaccgg atcaaagagt tcctccgccg ctggacctac caaggcaacg    780
ctatgttctc ttgcttttgt cagcaagata gccagatcaa tgtcgatcgt ggctggctcg    840
aagatacctg caagaatgtc attgcgctgc cattctccaa attgcagttc gcgcttagct    900
ggataacgcc acggaatgat gtcgtcgtgc acaacaatgg tgacttctac agcgcggaga    960
atctcgctct ctccagggga agccgaagtt tccaaaaggt cgttgatcaa agctcgccgc    1020
gttgtttcat caagccttac ggtcaccgta accagcaaat caatatcact gtgtggcttc    1080
aggccgccat ccactgcgga gccgtacaaa tgtacggcca gcaacgtcgg ttcgagatgg    1140
cgctcgatga cgccaactac ctctgatagt tgagttgata cttcggcgat aaccgcttca    1200
cgagccatga gatcctccag atccatgtat cattatagat aattgaagag tgaatgtcaa    1260
gtcgacctcg agggggggcc cggtacc                                        1287
```

<210> SEQ ID NO 84
<211> LENGTH: 1387
<212> TYPE: DNA
<213> ORGANISM: Artificial sequence
<220> FEATURE:
<223> OTHER INFORMATION: Description of the artificial sequence: insert
    of vector pCB528-2

<400> SEQUENCE: 84

```
ggtaccccag ttaactggag atctcgagga ggtcacatgg gagcttggat tgaacaagat     60
```

```
ggattgcacg caggttctcc ggccgcttgg gtggagaggc tattcggcta tgactgggca      120
caacagacaa tcggctgctc tgatgccgcc gtgttccggc tgtcagcgca ggggcgcccg      180 gttcttttg tcaagaccga cctgtccggt gccctgaatg aactgcagga cgaggcagcg       240
cggctatcgt ggctggccac gacgggcgtt ccttgcgcag ctgtgctcga cgttgtcact      300
gaagcgggaa gggactggct gctattgggc gaagtgccgg ggcaggatct cctgtcatct      360
caccttgctc ctgccgagaa agtatccatc atggctgatg caatgcggcg gctgcatacg      420
cttgatccgg ctacctgccc attcgaccac caagcgaaac atcgcatcga gcgagcacgt      480
actcggatgg aagccggtct tgtcgatcag gatgatctgg acgaagagca tcaggggctc      540
gcgccagccg aactgttcgc caggctcaag gcgcgcatgc ccgacggcga ggatctcgtc      600
gtgacccatg gcgatgcctg cttgccgaat atcatggtgg aaaatggccg cttttctgga      660
ttcatcgact gtggccggct gggtgtggcg gaccgctatc aggacatagc gttggctacc      720
cgtgatattg ctgaagagct tggcggcgaa tgggctgacc gcttcctcgt gctttacggt      780
atcgccgctc ccgattcgca gcgcatcgcc ttctatcgcc ttcttgacga gttcttctga      840
tctagatagg aggtcatcat ggcgctcacc aatgctcaaa tcttggctgt gattgacagt      900
tgggaagaaa cagtcggtca gtttccagtg ataacgcacc atgtaccatt aggtggcggt      960
ctgcaaggaa cgctccattg ttacgagatc cccctagcag ctccttatgg ggttggcttt     1020
gctaagaatg ggcctacccg ctggcaatac aaacggacaa tcaatcaagt cgtccacaga     1080
tgggggtccc acacagtccc ttttctatta gaaccggata acatcaacgg caaaacctgc     1140
acagcatcgc acctatgtca taatactcga tgccacaatc ccttgcactt gtgctgggag     1200
tcactagacg acaacaaagg cagaaactgg tgccccggtc ccaacggggg atgtgtccat     1260
gcggtggttt gtttaaggca gggtccgttg tacgcccag gggcgactgt ggcaggtcct      1320
caacaaaggg gcagtcactt tgtggtataa ctgcagaagc tttaagccag ttaactgggc     1380
ggagctc                                                               1387

<210> SEQ ID NO 85
<211> LENGTH: 30
<212> TYPE: DNA
<213> ORGANISM: Artificial Sequence
<220> FEATURE:
<223> OTHER INFORMATION: Description of the artificial sequence: I-DmoI
      recognition sequence

<400> SEQUENCE: 85
atgcgcgccg gaacttaccc ggcaaggcat                                        30

<210> SEQ ID NO 86
<211> LENGTH: 23
<212> TYPE: DNA
<213> ORGANISM: Artificial Sequence
<220> FEATURE:
<223> OTHER INFORMATION: Description of the artificial sequence: I-CpaI
      recognition sequence

<400> SEQUENCE: 86
cgatcctaag gtagcgaaat tca                                               23

<210> SEQ ID NO 87
<211> LENGTH: 29
<212> TYPE: DNA
<213> ORGANISM: Artificial Sequence
<220> FEATURE:
<223> OTHER INFORMATION: Description of the artificial sequence: I-CeuI
      recognition sequence
```

```
<400> SEQUENCE: 87
cgtaactata acggtcctaa ggtagcgaa                                              29

<210> SEQ ID NO 88
<211> LENGTH: 30
<212> TYPE: DNA
<213> ORGANISM: Artificial Sequence
<220> FEATURE:
<223> OTHER INFORMATION: Description of the artificial sequence: I-ChuI
      recognition sequence

<400> SEQUENCE: 88
gaaggtttgg cacctcgatg tcggctcatc                                             30

<210> SEQ ID NO 89
<211> LENGTH: 20
<212> TYPE: DNA
<213> ORGANISM: Artificial Sequence
<220> FEATURE:
<223> OTHER INFORMATION: Description of the artificial sequence: I-CpaII
      recognition sequence

<400> SEQUENCE: 89
cccggctaac tctgtgccag                                                        20

<210> SEQ ID NO 90
<211> LENGTH: 30
<212> TYPE: DNA
<213> ORGANISM: Artificial Sequence
<220> FEATURE:
<223> OTHER INFORMATION: Description of the artificial sequence: I-CreI
      recognition sequence

<400> SEQUENCE: 90
ctgggttcaa aacgtcgtga gacagtttgg                                             30

<210> SEQ ID NO 91
<211> LENGTH: 24
<212> TYPE: DNA
<213> ORGANISM: Artificial Sequence
<220> FEATURE:
<223> OTHER INFORMATION: Description of the artificial sequence: I-SceI
      recognition sequence

<400> SEQUENCE: 91
taccctgtta tccctagcgt aact                                                   24

<210> SEQ ID NO 92
<211> LENGTH: 30
<212> TYPE: DNA
<213> ORGANISM: Artificial Sequence
<220> FEATURE:
<223> OTHER INFORMATION: Description of the artificial sequence: I-DmoI,
      in plastome

<400> SEQUENCE: 92
gtgcgggtcg gaacttaccc gacaaggaat                                             30

<210> SEQ ID NO 93
<211> LENGTH: 23
<212> TYPE: DNA
<213> ORGANISM: Artificial Sequence
<220> FEATURE:
<223> OTHER INFORMATION: Description of the artificial sequence: I-CpaI,
      in plastome

<400> SEQUENCE: 93
cggtcctaag gtagcgaaat tcc                                                    23
```

<210> SEQ ID NO 94
<211> LENGTH: 29
<212> TYPE: DNA
<213> ORGANISM: Artificial Sequence
<220> FEATURE:
<223> OTHER INFORMATION: Description of the artificial sequence: I-CeuI,
      in plastome

<400> SEQUENCE: 94
cgtaactata acggtcctaa ggtagcgaa                                         29

<210> SEQ ID NO 95
<211> LENGTH: 30
<212> TYPE: DNA
<213> ORGANISM: Artificial Sequence
<220> FEATURE:
<223> OTHER INFORMATION: Description of the artificial sequence: I-ChuI,
      in plastome

<400> SEQUENCE: 95
gaaggtttgg cacctcgatg tcggctcttc                                        30

<210> SEQ ID NO 96
<211> LENGTH: 20
<212> TYPE: DNA
<213> ORGANISM: Artificial Sequence
<220> FEATURE:
<223> OTHER INFORMATION: Description of the artificial sequence: I-CpaII,
      in plastome

<400> SEQUENCE: 96
atcggctaac tctgtgccag                                                   20

<210> SEQ ID NO 97
<211> LENGTH: 30
<212> TYPE: DNA
<213> ORGANISM: Artificial Sequence
<220> FEATURE:
<223> OTHER INFORMATION: Description of the artificial sequence: I-CreI,
      in plastome

<400> SEQUENCE: 97
ctgggttcag aacgtcgtga gacagttcgg                                        30

<210> SEQ ID NO 98
<211> LENGTH: 24
<212> TYPE: DNA
<213> ORGANISM: Artificial Sequence
<220> FEATURE:
<223> OTHER INFORMATION: Description of the artificial sequence: I-SceI,
      in plastome

<400> SEQUENCE: 98
cagcctgtta tccctagagt aact                                              24

<210> SEQ ID NO 99
<211> LENGTH: 13
<212> TYPE: DNA
<213> ORGANISM: Arabidopsis sp.

<400> SEQUENCE: 99
ggcctttatg gcc                                                          13

<210> SEQ ID NO 100
<211> LENGTH: 13
<212> TYPE: DNA

<213> ORGANISM: Nicotiana tabacum

<400> SEQUENCE: 100
ggcctttatg gcc                                                        13

<210> SEQ ID NO 101
<211> LENGTH: 13
<212> TYPE: DNA
<213> ORGANISM: Triticum aestivum

<400> SEQUENCE: 101
ggcccagggg gcc                                                        13

<210> SEQ ID NO 102
<211> LENGTH: 39
<212> TYPE: DNA
<213> ORGANISM: Aspergillus nidulans
<220> FEATURE:
<221> NAME/KEY: misc_feature
<222> LOCATION: (25)..(39)
<223> OTHER INFORMATION: n is a, c, g, or t

<400> SEQUENCE: 102
ttgaggaggt ttctctgtaa ataannnnnn nnnnnnnn                              39

<210> SEQ ID NO 103
<211> LENGTH: 30
<212> TYPE: DNA
<213> ORGANISM: Chlorella vulgaris

<400> SEQUENCE: 103
ctgggttcaa aacgtcgtga gacagtttgg                                       30

<210> SEQ ID NO 104
<211> LENGTH: 30
<212> TYPE: DNA
<213> ORGANISM: Chlamydomonas smithii

<400> SEQUENCE: 104
gtactagcat ggggtcaaat gtctttctgg                                       30

<210> SEQ ID NO 105
<211> LENGTH: 18
<212> TYPE: DNA
<213> ORGANISM: Chlamydomonas moewusii

<400> SEQUENCE: 105
tcgtagcagc tcacggtt                                                    18

<210> SEQ ID NO 106
<211> LENGTH: 30
<212> TYPE: DNA
<213> ORGANISM: Chlamydomonas reinhardtii

<400> SEQUENCE: 106
ctgggttcaa aacgtcgtga gacagtttgg                                       30

<210> SEQ ID NO 107
<211> LENGTH: 30
<212> TYPE: DNA
<213> ORGANISM: Chlamydomonas humicola

<400> SEQUENCE: 107
gaaggtttgg cacctcgatg tcggctcatc                                       30

<210> SEQ ID NO 108
<211> LENGTH: 23
<212> TYPE: DNA
<213> ORGANISM: Chlamydomonas pallidostigmatica

<400> SEQUENCE: 108
cgatcctaag gtagcgaaat tca                                            23

<210> SEQ ID NO 109
<211> LENGTH: 20
<212> TYPE: DNA
<213> ORGANISM: Chlamydomonas pallidostigmatica

<400> SEQUENCE: 109
cccggctaac tctgtgccag                                                20

<210> SEQ ID NO 110
<211> LENGTH: 29
<212> TYPE: DNA
<213> ORGANISM: Chlamydomonas eugametos

<400> SEQUENCE: 110
cgtaactata acggtcctaa ggtagcgaa                                      29

<210> SEQ ID NO 111
<211> LENGTH: 30
<212> TYPE: DNA
<213> ORGANISM: Desulfurococcus mobilis

<400> SEQUENCE: 111
atgccttgcc gggtaagttc cggcgcgcat                                     30

<210> SEQ ID NO 112
<211> LENGTH: 30
<212> TYPE: DNA
<213> ORGANISM: Saccharomyces cerevisiae

<400> SEQUENCE: 112
agttacgcta gggataacag ggtaatatag                                     30

<210> SEQ ID NO 113
<211> LENGTH: 18
<212> TYPE: DNA
<213> ORGANISM: Saccharomyces cerevisiae

<400> SEQUENCE: 113
tagggataac agggtaat                                                  18

<210> SEQ ID NO 114
<211> LENGTH: 29
<212> TYPE: DNA
<213> ORGANISM: Saccharomyces cerevisiae

<400> SEQUENCE: 114
ttttgattct ttggtcaccc tgaagtata                                      29

<210> SEQ ID NO 115
<211> LENGTH: 29
<212> TYPE: DNA
<213> ORGANISM: Saccharomyces cerevisiae

<400> SEQUENCE: 115

```
attggaggtt ttggtaacta tttattacc                                  29

<210> SEQ ID NO 116
<211> LENGTH: 29
<212> TYPE: DNA
<213> ORGANISM: Saccharomyces cerevisiae

<400> SEQUENCE: 116
tcttttctct tgattagccc taatctacg                                  29

<210> SEQ ID NO 117
<211> LENGTH: 24
<212> TYPE: DNA
<213> ORGANISM: Saccharomyces cerevisiae

<400> SEQUENCE: 117
aataattttc ttcttagtaa tgcc                                       24

<210> SEQ ID NO 118
<211> LENGTH: 24
<212> TYPE: DNA
<213> ORGANISM: Saccharomyces cerevisiae

<400> SEQUENCE: 118
gttatttaat gttttagtag ttgg                                       24

<210> SEQ ID NO 119
<211> LENGTH: 28
<212> TYPE: DNA
<213> ORGANISM: Saccharomyces cerevisiae

<400> SEQUENCE: 119
tgtcacattg aggtgcacta gttattac                                   28

<210> SEQ ID NO 120
<211> LENGTH: 30
<212> TYPE: DNA
<213> ORGANISM: Saccharomyces cerevisiae

<400> SEQUENCE: 120
atctatgtcg ggtgcggaga aagaggtaat                                 30

<210> SEQ ID NO 121
<211> LENGTH: 24
<212> TYPE: DNA
<213> ORGANISM: Saccharomyces cerevisiae

<400> SEQUENCE: 121
gatgctgtag gcataggctt ggtt                                       24

<210> SEQ ID NO 122
<211> LENGTH: 20
<212> TYPE: DNA
<213> ORGANISM: Saccharomyces cerevisiae

<400> SEQUENCE: 122
ctttccgcaa cagtaaaatt                                            20

<210> SEQ ID NO 123
<211> LENGTH: 24
<212> TYPE: DNA
<213> ORGANISM: Lactococcus lactis

<400> SEQUENCE: 123
```

```
cacatccata accatatcat tttt                                          24

<210> SEQ ID NO 124
<211> LENGTH: 30
<212> TYPE: DNA
<213> ORGANISM: Monomastix species

<400> SEQUENCE: 124
ctgggttcaa aacgtcgtga gacagtttgg                                    30

<210> SEQ ID NO 125
<211> LENGTH: 21
<212> TYPE: DNA
<213> ORGANISM: Naegleria andersoni

<400> SEQUENCE: 125
aagtctggtg ccagcacccg c                                             21

<210> SEQ ID NO 126
<211> LENGTH: 21
<212> TYPE: DNA
<213> ORGANISM: Naegleria italica

<400> SEQUENCE: 126
aagtctggtg ccagcacccg c                                             21

<210> SEQ ID NO 127
<211> LENGTH: 21
<212> TYPE: DNA
<213> ORGANISM: Naegleria jamiesoni

<400> SEQUENCE: 127
aagtctggtg ccagcacccg c                                             21

<210> SEQ ID NO 128
<211> LENGTH: 30
<212> TYPE: DNA
<213> ORGANISM: Pseudendoclonium akinetum

<400> SEQUENCE: 128
ctgggttcaa aacgtcgtga gacagtttgg                                    30

<210> SEQ ID NO 129
<211> LENGTH: 25
<212> TYPE: DNA
<213> ORGANISM: Pyrobaculum organotrophum

<400> SEQUENCE: 129
gcgagcccgt aagggtgtgt acggg                                         25

<210> SEQ ID NO 130
<211> LENGTH: 29
<212> TYPE: DNA
<213> ORGANISM: Physarum polycephalum

<400> SEQUENCE: 130
taactatgac tctcttaagg tagccaaat                                     29

<210> SEQ ID NO 131
<211> LENGTH: 28
<212> TYPE: DNA
<213> ORGANISM: Saccharomyces capensis
```

```
<400> SEQUENCE: 131
tgtcacattg aggtgcacta gttattac                                           28

<210> SEQ ID NO 132
<211> LENGTH: 19
<212> TYPE: DNA
<213> ORGANISM: Synechocystis sp.

<400> SEQUENCE: 132
gtcgggctca tacccgaa                                                       19

<210> SEQ ID NO 133
<211> LENGTH: 30
<212> TYPE: DNA
<213> ORGANISM: Pyrococcus furiosus Vc1

<400> SEQUENCE: 133
gaagatggga ggagggaccg gactcaactt                                          30

<210> SEQ ID NO 134
<211> LENGTH: 29
<212> TYPE: DNA
<213> ORGANISM: Pyrococcus furiosus Vc1

<400> SEQUENCE: 134
acgaatccat gtggagaaga gcctctata                                           29

<210> SEQ ID NO 135
<211> LENGTH: 19
<212> TYPE: DNA
<213> ORGANISM: Pyrococcus kodakaraensis KOD1

<400> SEQUENCE: 135
gattttagat ccctgtacc                                                      19

<210> SEQ ID NO 136
<211> LENGTH: 15
<212> TYPE: DNA
<213> ORGANISM: Pyrococcus kodakaraensis KOD1

<400> SEQUENCE: 136
cagtactacg gttac                                                          15

<210> SEQ ID NO 137
<211> LENGTH: 30
<212> TYPE: DNA
<213> ORGANISM: Pyrococcus sp.

<400> SEQUENCE: 137
aaaatcctgg caaacagcta ttatgggtat                                          30

<210> SEQ ID NO 138
<211> LENGTH: 26
<212> TYPE: DNA
<213> ORGANISM: Thermococcus fumicolans

<400> SEQUENCE: 138
tagattttag gtcgctatat ccttcc                                              26

<210> SEQ ID NO 139
<211> LENGTH: 22
<212> TYPE: DNA
<213> ORGANISM: Thermococcus fumicolans
```

```
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 139
taygcngaya cngacggytt yt                                              22

<210> SEQ ID NO 140
<211> LENGTH: 22
<212> TYPE: DNA
<213> ORGANISM: Thermococcus hydrothermalis
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 140
taygcngaya cngacggytt yt                                              22

<210> SEQ ID NO 141
<211> LENGTH: 22
<212> TYPE: DNA
<213> ORGANISM: Thermococcus litoralis
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 141
taygcngaya cngacggytt yt                                              22

<210> SEQ ID NO 142
<211> LENGTH: 30
<212> TYPE: DNA
<213> ORGANISM: Thermococcus litoralis

<400> SEQUENCE: 142
aaattgcttg caaacagcta ttacggctat                                      30

<210> SEQ ID NO 143
<211> LENGTH: 24
<212> TYPE: DNA
<213> ORGANISM: Bacteriophage T4

<400> SEQUENCE: 143
agtggtatca acgctcagta gatg                                            24

<210> SEQ ID NO 144
<211> LENGTH: 30
<212> TYPE: DNA
<213> ORGANISM: Bacteriophage T4

<400> SEQUENCE: 144
gcttatgagt atgaagtgaa cacgttattc                                      30
```

```
<210> SEQ ID NO 145
<211> LENGTH: 38
<212> TYPE: DNA
<213> ORGANISM: Bacteriophage T4
<220> FEATURE:
<221> NAME/KEY: misc_feature
<222> LOCATION: (25)..(38)
<223> OTHER INFORMATION: n is a, c, g, or t

<400> SEQUENCE: 145
gaaacacaag aaatgtttag taaannnnnn nnnnnnnn                         38

<210> SEQ ID NO 146
<211> LENGTH: 29
<212> TYPE: DNA
<213> ORGANISM: Bacteriophage T4

<400> SEQUENCE: 146
tttaatcctc gcttcagata tggcaactg                                   29

<210> SEQ ID NO 147
<211> LENGTH: 16
<212> TYPE: DNA
<213> ORGANISM: Zea mays

<400> SEQUENCE: 147
cattatcata gtggat                                                 16

<210> SEQ ID NO 148
<211> LENGTH: 16
<212> TYPE: DNA
<213> ORGANISM: Zea mays

<400> SEQUENCE: 148
cattattata gtggat                                                 16

<210> SEQ ID NO 149
<211> LENGTH: 22
<212> TYPE: DNA
<213> ORGANISM: Artificial Sequence
<220> FEATURE:
<223> OTHER INFORMATION: DSB recognition site of I-CpaI

<400> SEQUENCE: 149
cggtcctaag gtagcgaaat tc                                          22

<210> SEQ ID NO 150
<211> LENGTH: 22
<212> TYPE: DNA
<213> ORGANISM: Artificial Sequence
<220> FEATURE:
<223> OTHER INFORMATION: synthetic

<400> SEQUENCE: 150
cggtcctaag gtagcgaaat tc                                          22

<210> SEQ ID NO 151
<211> LENGTH: 12
<212> TYPE: DNA
<213> ORGANISM: Artificial Sequence
<220> FEATURE:
<223> OTHER INFORMATION: synthetic

<400> SEQUENCE: 151
tcgctacctt ag                                                     12
```

```
<210> SEQ ID NO 152
<211> LENGTH: 11
<212> TYPE: DNA
<213> ORGANISM: Artificial Sequence
<220> FEATURE:
<223> OTHER INFORMATION: EBS1 region and downstream

<400> SEQUENCE: 152
ttatggttgt g                                                              11

<210> SEQ ID NO 153
<211> LENGTH: 12
<212> TYPE: DNA
<213> ORGANISM: Arabidopsis thaliana

<400> SEQUENCE: 153
cgctacctta gg                                                             12

<210> SEQ ID NO 154
<211> LENGTH: 11
<212> TYPE: DNA
<213> ORGANISM: Arabidopsis thaliana

<400> SEQUENCE: 154
aatgttaaaa a                                                              11

<210> SEQ ID NO 155
<211> LENGTH: 15
<212> TYPE: DNA
<213> ORGANISM: Nicotiana tabacum

<400> SEQUENCE: 155
aaagacccta tgaag                                                          15

<210> SEQ ID NO 156
<211> LENGTH: 15
<212> TYPE: DNA
<213> ORGANISM: Nicotiana tabacum

<400> SEQUENCE: 156
ggagacccta tgaag                                                          15

<210> SEQ ID NO 157
<211> LENGTH: 15
<212> TYPE: DNA
<213> ORGANISM: Nicotiana tabacum

<400> SEQUENCE: 157
ggaaggtgag gatgc                                                          15

<210> SEQ ID NO 158
<211> LENGTH: 11
<212> TYPE: DNA
<213> ORGANISM: Nicotiana tabacum

<400> SEQUENCE: 158
gaatgaaact a                                                              11

<210> SEQ ID NO 159
<211> LENGTH: 29
<212> TYPE: DNA
<213> ORGANISM: Zea mays
```

```
<400> SEQUENCE: 159
ctgggttcag aacgtcgtga gacgttcgg                                          29
```